United States Patent [19]
Duncia et al.

[11] Patent Number: 5,545,651
[45] Date of Patent: Aug. 13, 1996

[54] IMIDAZOLE 5-POSITION SUBSTITUTED ANGIOTENSIN II ANTAGONISTS

[75] Inventors: John J. V. Duncia, Wilmington; Carol L. Ensinger, Newark; Richard E. Olson, Wilmington; Mimi L. Quan, Newark, all of Del.; Joseph B. Santella, III, Springfield, Pa.; Mary K. Vanatten, Wilmington, Del.

[73] Assignee: The DuPont Merck Pharmaceutical Company, Wilmington, Del.

[21] Appl. No.: 348,843

[22] Filed: Nov. 28, 1994

Related U.S. Application Data

[62] Division of Ser. No. 72,977, Jun. 10, 1993, Pat. No. 5,395,844.

[51] Int. Cl.$^6$ .................... C07D 401/14; A61K 31/415
[52] U.S. Cl. .................. 514/381; 514/235.8; 514/307; 514/314; 514/326; 514/333; 514/341; 514/359; 514/383; 514/397; 514/398; 514/399; 514/400; 544/139; 546/148; 546/174; 546/176; 546/180; 546/210; 546/256; 546/272.4; 546/272.7; 546/274.4; 546/274.7; 546/275.1; 546/22; 546/23; 546/24; 548/253; 548/255; 548/261; 548/266.2; 548/315.1; 548/335.1; 548/341.1; 548/343.1; 548/343.5; 548/346.1; 548/314.7
[58] Field of Search .................... 546/207, 210, 546/256, 276, 148, 180, 174, 176; 548/387, 253, 315.1, 319.7, 335.1, 341.1, 343.5, 346.1, 255, 261, 266.2, 343.1; 514/326, 333, 341, 381, 396, 398, 399, 400, 397, 235.8, 307, 314, 383, 359; 544/139

[56] References Cited

U.S. PATENT DOCUMENTS 5,138,069  8/1992  Carini et al. .................... 548/253

FOREIGN PATENT DOCUMENTS 479479  9/1991  European Pat. Off. ........... 548/337
503785  9/1992  European Pat. Off. ........... 548/253

OTHER PUBLICATIONS

P. C. Wong, et al., *Cardiovascular Drug Reviews* 1991; 9:317–339; Trends in Endocrinol. Metal. 1992; 3:211–217).
Carini et al, J. Med. Chem, vol. 34, No. 8, 1991, pp. 2525–2547.
Chiu et al, Biochem. Biophys. Res. Comm, vol. 188, No. 3, Nov. 16, 1992, pp. 1030–1039.

*Primary Examiner*—Zinna Northington Davis

[57] ABSTRACT

Novel substituted imidazoles of Formula (I), which are useful as angiotensin II antagonists, are disclosed:

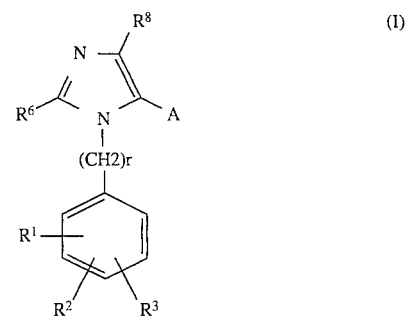

5 Claims, No Drawings

IMIDAZOLE 5-POSITION SUBSTITUTED ANGIOTENSIN II ANTAGONISTS

This is a division of application Ser. No. 08/072,977, filed Jun. 10, 1993, now U.S. Pat. No. 5,395,844.

BACKGROUND OF THE INVENTION

Field of the Invention

This invention relates to novel imidazole 5-position substituted angiotensin II antagonists. The invention also relates to pharmaceutical compositions containing these novel imidazoles and pharmaceutical methods using them, alone and in conjugation with other drugs, especially diuretics, angiotensin converting enzyme (ACE) inhibitors, and non-steroidal anti-inflammatory drugs (NSAIDS).

The compounds of this invention inhibit the action of the hormone angiotensin II (AII) and am useful therefore in alleviating angiotensin induced hypertension. The enzyme renin acts on a blood plasma a2-globulin, angiotensinogen, to produce angiotensin I, which is then converted by ACE to AII. The latter substance is a powerful vasopressor agent which has been implicated as a causative agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a NSAID can prevent renal failure which sometimes results from administration of a NSAID.

Several peptide analogs of AII are known to inhibit the effects of this hormone by competitively blocking the receptors, but their experimental and clinical applications have been limited by their partial agonist activity and lack of oral absorption (M. Antonaccio, *Clin. Exp. Hypertens.*, 1982, A4, 27–46; D. H. P. Streeten and G. H. Anderson, Jr.—*Handbook of Hypertension, Clinical Pharmacology of Antihypertensive Drugs*, ed., A. E. Doyle, Vol. 5, pages 246–271, Elsevier Science Publisher, Amsterdam, The Netherlands, 1984).

Several non-peptide antagonists of angiotensin II, including some biphenylmethyl imidazoles, have been disclosed. U.S. Pat. Nos. 5,137,902 and 5,138,069 disclose biphenylmethylimidazoles (A) where $R^1$ may be a

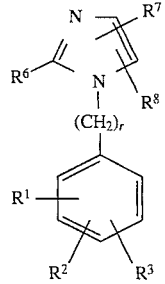

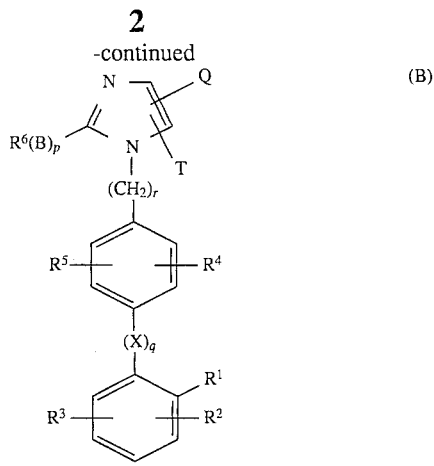

phenyl substituted in the 2'-position with acidic functional groups, such as carboxy and tetrazole, and where imidazole substitutent $R^7$ may be alkyl or optionally substituted phenyl, and where $R^8$ may be formyl, acyl, carboxy, alkoxycarbonyl, aminocarbonyl, alkoxyalkyl and hydroxyalkyl. U.S. Applications Ser. No. 90/03683 and Ser. No. 07/545302 disclose substituted imidazoles of the same basic structure where $R^7$ may be optionally substituted aryl or heteroaryl. European Application EP401,030 (Merck) describes imidazoles of structure (B), where Q represents various nitrogenous functional groups, T may be carboxy, alkoxycarbonyl or aminocarbonyl, r may be 1, $(X)q$ can represent a single bend, $R^6(B)_p$ may represent alkyl and $R^1$ may be $SO_2NHR^9$, $SO_2NH$-heteroaryl, $SO_2NHCOR^{25}$ or $SO_2NHCONHR^{25}$, where $R^9$ is H, alkyl, phenyl or benzyl, and where $R^{25}$ is aryl, heteroaryl, cycloalkyl or optionally substituted alkyl.

Australian Application AU-A-80163/91 (EP465,368, Roussel-Uclaf) discloses substituted imidazoles (C) where $R^1$ may be alkyl, m may be 1, either $R^2$ or $R^3$ is $OR^4$, or a sulfurous group of structure $—S(O)_nR^4$,

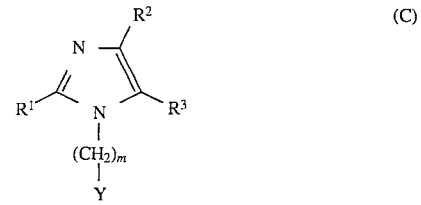

$—SO(R^4)=NS(O)_nX'$ or $—SSR^4$, where $R^4$ represents a variety of optionally substituted alkyl, alkenyl, alkynyl, acyl or nitrogenous or sulfurous radicals. The imidazole nitrogen substituent $(CH_2)_m\text{-}Y$ may represent a biphenylmethyl group, which may be substituted in the 2'-position by acidic groups, such as $—(CH_2)_{m1}—S(O)_{m2}\text{-}X\text{-}R^{10}$, in which m1 may be 0–4, m2 may be 0–2, X may be a single bond, $—NH—$, $—NH—CO—$, or $—NH—CO—NH—$ and $R^{10}$ is an optionally substituted alkyl, alkenyl, aryl or heteroaryl radical. European Application EP479,479 (Merck) discloses biphenylmethyl imidazoles (D) where $R^1B$ may represent alkyl, $R^3$ may be H, alkyl, alkenyl or alkynyl, perfluoroalkyl, halogen, $—NO_2$, $—CN$ or optionally substituted phenyl, $R^4$ includes formyl, acyl, carboxy, alkoxycarbonyl, aminocarbonyl, alkoxyalkyl and hydroxyalkyl, X may be a single bond, and $R^5$ includes $—SO_2NH$-heteroaryl, $—SO_2NHCOR^{12}$ and $—SO_2NHCONR^2R^{12}$, in which $R^2$ is H or alkyl, and $R^{12}$ is aryl, heteroaryl, cycloalkyl, perfluoroalkyl or optionally substituted C1–C4 alkyl, where the alkyl substituents include aryl, heteroaryl, alkyl, OH, SH, alkoxy, thioalkoxy, halo, carboxy, alkoxycarbonyl, $—NO_2$, optionally substituted amino and various phosphoryl radicals.

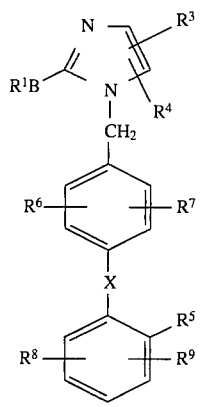

European patent application number EPA 503, 162, (published Sep. 16, 1992, Hoechst Aktiengesellschaft) describes compounds of structure (E) wherein Z can be nitrogen, and X and Y are independently $CR^2$. $R^1$ can be alkyl, alkenyl, alkynyl, cycloalkyl, cycloalkylalkyl, cycloalkylalkenyl, cycloalkylalkynyl, or benzyl. $R^2$ can be H, halogen, nitro perfluoroalkyl, pentafluorophenyl, cyano, phenyl, phenylalkyl, alkyl, alkenyl, phenylalkenyl, imidazolylalkyl, triazolylalkyl, tetrazolylalkyl, ethers, esters, thioethers, sulfides, sulfoxides, sulfones, amides and other groups as well. L-(O)q-A may represent a biphenylmethyl group which may be substituted in the 2' position with an acidic radical.

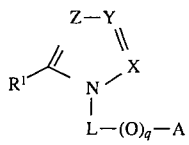

None of the above publications disclose the imidazole biphenylsulfonyl carbamates of the present invention. It is well known that two types of angiotensin II receptors are widely distributed in various mammalian tissues (P. C. Wong et al., *Cardiovascular Drug Reviews* 1991; 9:. 317–339; *Trends in Endoctocrinol. Metab.* 1992; 3: 211–217). The angiotensin II receptor most directly involved in the mediation of blood pressure is termed the $AT_1$ receptor, and is characterized by high sensitivity to the non-peptide antagonist DuP 753. A second angiotensin II receptor, designated $AT_2$, is sensitive to another class of non-peptide AII antagonists, represented by PD 123177 (ibid.), and to the peptide CGP42112A. Angiotensin II has approximately equal affinity for both receptor subtypes.

Recent evidence suggests that the $AT_2$ receptor may have a role in mediating the synthesis and breakdown of cardiac connective tissues. For example, Matsubara et

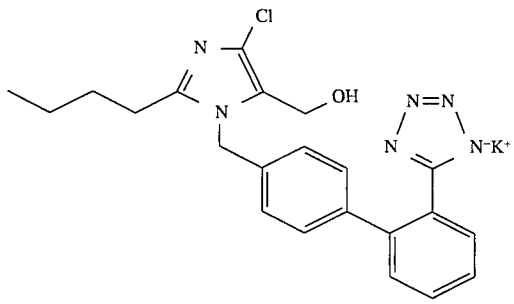

DuP 753

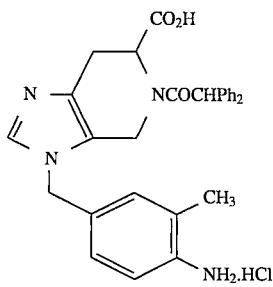

PD123177

CGP42112A = nicotinic acid-Tyr-(Na-benzyloxy-carbonyl-Arg)Lys—His—Pro—Ile—OH al. (The FASEB *Journal* 6, 4: A941, 1992) have reported that PD123177, but not DuP 753, blocks the AII-stimulated inhibition of collagenase in cultured cardiac fibroblasts. Both PD123177 and DuP 753 are reported by Zhou et al. to block the AII-stimulated increase in collagen synthesis in cardiac fibroblasts (The FASEB *Journal* 6, 4: A1914, 1992).

Tsutsumi and Saavedra have found $AT_2$ receptors in cerebral arteries (*Am. J. Physiol.* 261: H667-H670, 1991). An analog of PD123177, PD123319, has been reported by Brix and Haberl (The FASEB *Journal* 6, 4: A1264, 1992) to block the pial artery dilation induced by angiotensin II in a rat cranial window preparation monitored by intravital microscopy. This suggests that the $AT_2$ receptor may have a role in modifying cerebral blood flow.

The $AT_2$ selective antagonist CGP42112A has been reported by LeNoble et al. (*The FASEB Journal* 6, 4: A937, 1992) to block the increase in microvascular density induced by angiotensin II in the chick chorioallantoic membrane, suggesting that angiotensin II may in some contexts mediate angiogenesis through $AT_2$ receptors.

As noted above, DuP 753, disclosed in U.S. Pat. No. 5,138,069, is a selective $AT_1$ antagonist, having extremely low affinity for the $AT_2$ receptor. No data is presented in U.S. Pat. No. 5,138,069 or the other references above which suggests that any of the compounds disclosed possess high $AT_2$ affinity.

In addition to potent $AT_1$ antagonist and antihypertensive properties, the imidazole compounds of the present invention possess potent $AT_2$ antagonist properties. Since $AT_1$ antagonism leads to increased levels of circulating angiotensin II in vivo (Y. Christen et al., *Am. J. Hypertension*, 1991; 4: 350S-353S), and the $AT_2$-mediated consequences, if any, of higher AII levels are unknown, simultaneous $AT_1/AT_2$ antagonism may prove desirable during $AT_1$-targeted therapy.

SUMMARY OF THE INVENTION

This invention pertains to novel angiotensin II blocking imidazole compounds of the following Formula (I):

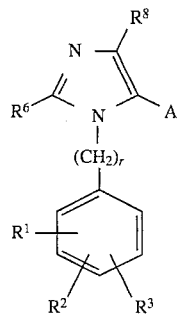  (I)

wherein
R¹ is in the meta or para position and is
(a) 4-$CO_2H$,
(b) —$CH_2CO_2H$,
(c) —$C(CF_3)_2OH$,
(d) —$CONHNHSO_2CF_3$,
(e) 4-$CONHCH(CO_2H)CH_2C_6H_5$ (L-isomer),
(f) 4-$CONHOR^{12}$,
(g) —$CONHSO_2R^{10}$,
(h) —$CONHSO_2NHR^9$,
(i) —$C(OH)R^9PO_3H_2$,
(j) —$NHCOCF_3$,
(k) —$NHCONHSO_2R^{10}$,
(l) —$NHPO_3H_2$,
(m) 4-$NHSO_2R^{10}$,
(n) —$NHSO_2NHCOR^{10}$,
(o) —$OPO_3H_2$,
(p) —$OSO_3H$,
(q) —$PO_3H_2$,
(r) —$PO(OH)R^9$,
(s) —$SO_3H$,
(t) —$SO_2NHR^9$,
(u) —$SO_2NHCOR^{10}$,
(v) —$SO_2NHCONHR^9$,

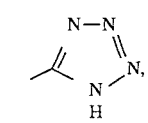 (w)

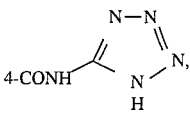 (x)

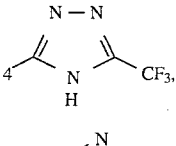 (y)

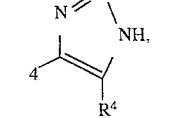 (z)

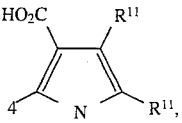 (aa)

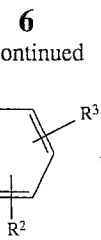

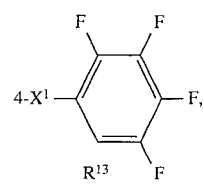 (bb)

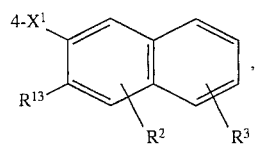 (cc)

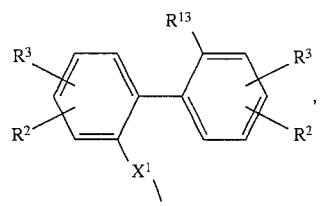 (dd)

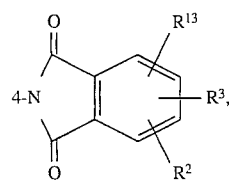 (ee)

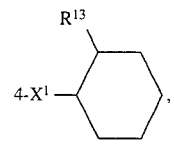 (ff)

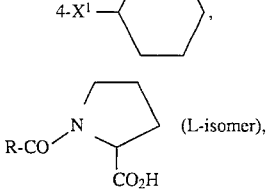 (gg)

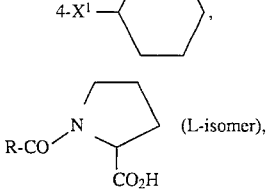

(hh)

(ii) —$SO_2NHCO_2R^{10}$;
R² is independently
(a) H,
(b) halo (F, Cl, Br, I),
(c) $C_1$–$C_4$-alkyl,
(d) $C_1$–$C_4$-alkoxy,
(e) $C_1$–$C_4$-acyloxy,
(f) $C_1$–$C_4$-alkylthio,
(g) $C_1$–$C_4$-alkylsulfinyl,
(h) $C_1$–$C_4$-alkylsulfonyl,
(i) —($C_1$–$C_4$-alkyl)-OH,
(j) —($C_1$–$C_4$) alkyl-aryl,
(k) —$CO_2H$,
(l) —CN,
(m) tetrazol-5-yl,
(n) —$CONHOR_{12}$,
(o) —$SO_2NHR^9$,
(p) —$NH_2$,
(q) $C_1$–$C_4$-alkylamino,
(r) $C_1$—$C_4$-dialkylamino,
(s) —$NHSO_2R^{10}$, (t) —NO$_2$,
(u) furyl,
(v) phenyl or phenyl optionally substituted with one or two substituents selected from the group consisting of halo, C$_1$–C$_4$-alkyl, C$_1$–C$_4$-alkoxy, —NO$_2$, —CF$_3$, C$_1$–C$_4$-alkylthio, —OH, —NH$_2$, C$_1$–C$_4$-alkylamino, C$_1$–C$_4$-dialkylamino, —CN, —CO$_2$R$^{12}$, acetyl;

R$^3$ is independently
(a) H,
(b) halo,
(c) C$_1$–C$_4$-alkyl,
(d) C$_1$–C$_4$-alkoxy, or
(e) —C$_1$–C$_4$-alkyl-(C$_1$–C$_4$-alkoxy);

R$^4$ is
(a) —CN,
(b) —NO$_2$, or
(c) —CO$_2$R$^{11}$;

R$^5$ is
(a) H,
(b) C$_1$–C$_6$-alkyl,
(c) C$_3$–C$_6$-cycloalkyl,
(d) C$_2$–C$_4$-alkenyl, or
(e) C$_2$–C$_4$-alkynyl;

R$^6$ is
(a) C$_1$–C$_{10}$-alkyl,
(b) C$_3$–C$_{10}$-alkenyl,
(c) C$_3$–C$_{10}$-alkynyl,
(d) C$_3$–C$_8$-cycloalkyl,
(e) C$_3$–C$_8$-cycloalkenyl,
(f) —C$_1$–C$_3$-alkyl-(C$_3$–C$_8$-cycloalkyl),
(g) —C$_1$–C$_3$-alkenyl-(C$_5$–C$_{10}$-cycloalkyl),
(h) —C$_1$–C$_3$-alkynyl-(C$_5$–C$_{10}$-cycloalkyl),
(i) —(CH$_2$)$_s$S(CH$_2$)$_m$R$^5$, or
(j) benzyl, optionally substituted on the phenyl ring with 1–2 substituents selected from the group consisting of halo, C$_1$–C$_4$-alkyl, C$_1$–C$_4$-alkoxy or —NO$_2$;

R$^7$ is
(a) C$_1$–C$_6$-alkyl,
(b) C$_3$–C$_6$-cycloalkyl,
(c) aryl, or
(d) benzyl, optionally substituted on the phenyl ring with 1–2 substituents selected from the group consisting of halo, C$_1$–C$_4$-alkyl, C$_1$–C$_4$-alkoxy or —NO$_2$;

R$^8$ is
(a) H,
(b) halogen (F,Cl, Br, I),
(c) phenyl, or phenyl optionally substituted with halogen (F, Cl, Br, I), C$_1$–C$_4$-alkyl, —OH, C$_1$–C$_4$-alkoxy, —NO$_2$, —NR$_{26}$R$^{27}$, —NR$^{26}$COR$^{11}$, —NR$^{26}$CO$_2$R$^7$, —S(O)$_r$R$^{10}$, —SO$_2$NR$^{26}$R$^{27}$, —NR$^{26}$SO$_2$R$^{10}$, —CF$_3$,
(d) C$_1$–C$_6$-alkyl, optionally substituted with
i) OR$^{25}$,
ii) S(O)$_r$R$^{10}$,
iii) NR$^{23}$R$^{24}$,
iv) NR$^{26}$COR$^{11}$,
v) NR$^{26}$CO$_2$R$^7$,
vi) NR$^{26}$CONR$^{23}$R$^{24}$,
vii) OCONR$^{23}$R$^{24}$,
viii) OCOR$^{11}$,
ix) aryl,
(e) C$_2$–C$_6$-alkenyl,
(f) —C$_1$–C$_4$-alkyl-aryl,
(h) C$_1$–C$_4$-alkoxy,
(i) C$_v$F$_{2v+1}$ where v=1 to 3,
(j) —S(O)$_r$R$^{10}$,
(k) —S(O)$_2$NR$^{23}$R$^{24}$,
(l) —CONR$^{23}$R$^{24}$,
(m) —COR$^7$, or
(n) —CO$_2$R$^{12}$;

R$^9$ is
(a) H,
(b) C$_1$–C$_5$-alkyl,
(c) aryl,
(d) —(C$_1$–C$_4$-alkyl)-aryl,
(e) heteroaryl, or
(f) C$_3$–C$_5$-cycloalkyl;

R$^{10}$ is
(a) aryl,
(b) C$_3$–C$_7$-cycloalkyl,
(c) C$_1$–C$_4$-perfluoroalkyl,
(d) C$_1$–C$_4$-alkyl, optionally substituted with a substituent selected from the group consisting of aryl, heteroaryl, —OH, —SH, C$_1$C$_4$-alkyl, C$_1$–C$_4$-alkoxy, C$_1$–C$_4$-alkylthio, —CF$_3$, halo, —NO$_2$, —CO$_2$R$^{12}$, —NH$_2$, C$_1$–C$_4$-alkylamino, C$_1$–C$_4$-dialkylamino, —PO$_3$H$_2$, or
(e) heteroaryl;

R$^{11}$, R$^{11a}$ and R$^{11b}$ are independently
(a) H,
(b) C$_1$–C$_6$-alkyl,
(c) C$_3$–C$_6$-cycloalkyl,
(d) aryl,
(e) —(C$_1$–C$_5$-alkyl)-aryl, or
(f) heteroaryl;

R$^{12}$ is
(a) H,
(b) methyl, or
(c) benzyl, optionally substituted on the phenyl ring with 1–2 substituents selected from the group consisting of halo, C$_1$–C$_4$-alkyl, C$_1$–C$_4$-alkoxy or —NO$_2$;

R$^{13}$ is
(a) —CO$_2$H,
(b) —CH$_2$CO$_2$H,
(c) —C(CF$_3$)$_2$OH,
(d) —CONHNHSO$_2$CF$_3$,
(e) —CONHOR$^{12}$,
(f) —CONHSO$_2$R$^{10}$,
(g) —CONHSO$_2$NHR$_9$,
(h) —C(OH)R$_9$PO$_3$H$_2$,
(i) —NHCOCF$_3$,
(j) —NHCONHSO$_2$R$^{10}$,
(k) —NHPO$_3$H$_2$,
(l) —NHSO$_2$R$^{10}$,
(m) —NHSO$_2$NHCOR$^{10}$,
(n) —OPO$_3$H$_2$,
(o) —OSO$_3$H,
(p) —PO(OH)R$^9$,
(q) —PO$_3$H$_2$,
(r) —SO$_3$H,
(s) —SO$_2$NHR$^9$,
(t) —SO$_2$NHCOR$^{10}$,
(u) —SO$_2$NHCONHR$^9$,
(v) —SO$_2$NHCO$_2$R$^{10}$,

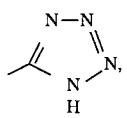 (w)

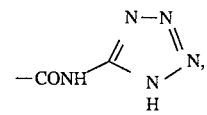 (x)

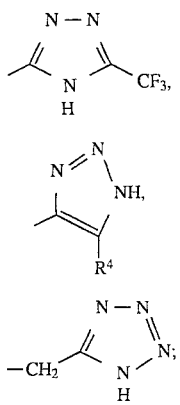

(y)

(z)

(aa)

$R^{14}$ is
(a) H,
(b) $C_1$–$C_6$-alkyl,
(c) —$CH_2CH$=$CH_2$, or
(d) benzyl, optionally substituted on the phenyl ring with 1–2 substituents selected from the group consisting of halo, $C_1$–$C_4$-alkyl, $C_1$–$C_4$-alkoxy or —$NO_2$;

$R^{15}$ is
(a) H,
(b) $C_1$–$C_8$-alkyl,
(c) $C_1$–$C_8$-perfluoroalkyl,
(d) $C_3$–$C_6$-cycloalkyl,
(e) aryl, or
(f) benzyl, optionally substituted on the phenyl ring with 1–2 substituents selected from the group consisting of halo, $C_1$–$C_4$-alkyl, $C_1$–$C_4$-alkoxy or —$NO_2$;

$R^{16}$ is
(a) H,
(b) $C_1$–$C_6$-alkyl, or
(c) benzyl, optionally substituted on the phenyl ring with 1–2 substituents selected from the group consisting of halo, $C_1$–$C_4$-alkyl, $C_1$–$C_4$-alkoxy or —$NO_2$;

$R^{17}$ is
(a) H,
(b) $C_1$–$C_6$-alkyl,
(c) $C_3$–$C_6$-cycloalkyl,
(d) aryl, or
(e) benzyl, optionally substituted on the phenyl ring with 1–2 substituents selected from the group consisting of halo, $C_1$–$C_4$-alkyl, $C_1$–$C_4$-alkoxy or —$NO_2$;

$R^{18}$ is
(a) —$NR^{19}R^{20}$,
(b) —$NHCONH_2$,
(c) —$NHCSNH_2$, or
(d) —$NHSO_2$-$C_6H_5$;

$R^{19}$ and $R^{20}$ are independently
(a) H,
(b) $C_1$–$C_5$-alkyl, or
(c) aryl;

$R^{21}$ and $R^{22}$ are independently
(a) $C_1$–$C_4$-alkyl,
or taken together are
(b) —$(CH_2)_q$—;

$R^{23}$ and $R^{24}$ are, independently
(a) H,
(b) $C_1$–$C_6$-alkyl,
(c) aryl, or
(d) —($C_1$–$C_4$-alkyl)-aryl, or
(e) $R^{23}$ and $R^{24}$ when taken together constitute a pyrrolidine, piperidine or morpholine ring;

$R^{25}$ is (a) H,
(b) $C_1$–$C_6$-alkyl,
(c) aryl,
(d) —($C_1$–$C_4$-alkyl)-aryl,
(e) $C_3$–$C_6$-alkenyl, or
(f) —($C_3$–$C_6$-alkenyl)-aryl;

$R^{26}$ and $R^{27}$ are independently
(a) H,
(b) $C_1$–$C_4$-alkyl,
(c) aryl, or
(d) —$CH_2$-aryl;

$R^{28}$ is
(a) aryl, or
(b) heteroaryl;

$R^{29}$ is
(a) —CHO,
(b) —$CONH_2$,
(c) —NHCHO,
(d) —CO-($C_1$–$C_6$ perfluomalkyl),
(e) —$S(O)_r$-($C_1$–$C_6$ perfluoroalkyl),
(f) —O-($C_1$–$C_6$ perfluoroalkyl), or
(g) —$NR^{11a}$-($C_1$–$C_6$ perfluoroalkyl);

$R^{30}$ is
(a) —CHO,
(b) —$SO_2$-($C_1$–$C_6$ perfluoroalkyl), or
(c) —CO-($C_1$–$C_6$ perfluoroalkyl);

A is
(a) —$(CH_2)_n$-$L^1$-B-$(T)_y$-$(B)_y$-$X^2$-$(B)_y$-$R^{28}$,
(b) —$(CH_2)_n$-$L^1$-B-T-$(B)_y$-$R^{28}$,
(c) —$(CH_2)_n$-$L^1$-B-$(T)_y$-$(B)_y$-$X^2$-B,
(d) —$(CH_2)_n$-$L^1$-B-T-$(B)_y$-$R^{29}$,
(e) —$(CH_2)_n$-$L^1$-T-$(B)_y$-$X^2$-$(B)_y$-$R^{28}$,
(f) —$(CH_2)_n$-$L^1$-T-$(B)_y$-$R^{28}$,
(g) —$(CH_2)_n$-$L^1$-T-$(B)_y$-$X^2$-B,
(h) —$(CH_2)_n$-$L^1$-($CR^{19}R^{20}$)-D-$(T)_y$-$(B)y$-$X^3$-$(B)_y$-$R^{28}$,
(i) —$(CH_2)_n$-$L^1$-($OR^{19}R^{20}$)-D-T-$(B)_y$-$R^{28}$,
(j) —$(CH_2)_n$-$L^1$-($CR^{19}R^{20}$)-D-$(T)_y$-$(B)_y$-$X^3$-B,
(k) —$(CH_2)_n$-$L^1$-($CR^{19}R^{20}$)-D-T-$(B)_y$-$R^{29}$,
(l) —$(CH_2)_n$-$L^1$-($CR^{19}R^{20}$)-D-T-$(B)_y$-$X^4$-$(B)_y$-$R^{28}$,
(m) —$(CH_2)_n$-$L^1$-($CR^{19}R^{20}$)-D-B-$X^4$-$(B)_y$-$R^{28}$,
(n) —$(CH_2)_n$-$L^1$-($CR^{19}R^{20}$)-D-T-$(B)_y$-$X^4$-B,
(o) —$(CH_2)_n$-$L^1$-($CR^{19}R^{20}$)-D-B-$X^4$-B,
(p) —$(CH_2)_n$-$L^2$-B-$(T)_y$-$(B)_y$-$X^2$-$(B)_y$-$R^{28}$,
(q) —$(CH_2)_n$-$L^2$-B-T-$(B)_y$-$R^{28}$,
(r) —$(CH_2)_n$-$L^2$-B-$(T)_y$-$(B)_y$-$X_2$-B,
(s) —$(CH_2)_n$-$L^2$-B-T-$(B)_y$-$R^{29}$,
(t) —$(CH_2)_n$-$L^2$-T-$(B)_y$-$X^2$-$(B)_y$-$R^{28}$,
(u) —$(CH_2)_n$-$L^2$-T-$(B)_y$-$R^{28}$,
(v) —$(CH_2)_n$-$L^2$-T-$(B)_y$-$X^2$-B,
(w) —$(CH_2)_n$-$L^2$-D-$(T)_y$-$(B)_y$-$X^3$-$(B)_y$-$R^{28}$,
(x) —$(CH_2)_n$-$L^2$-D-T-$(B)_y$-$R^{28}$,
(y) —$(CH_2)_n$-$L^2$-D-$(T)_y$-$(B)_y$-$X^3$-B,
(z) —$(CH_2)_n$-$L^2$-D-T-$(B)_y$-$R^{29}$,
(aa) —$(CH_2)_n$-$L^2$-D-T-$(B)_y$-$X^4$-$(B)_y$-$R^{28}$,
(bb) —$(CH^2)_n$-$L^2$-D-B-$X^4$-$(B)_y$-$R^{28}$,
(cc) —$(CH_2)_n$-$L^2$-D-T-$(B)_y$-$X^4$-B,
(dd) —$(CH_2)_n$-$L^2$-D-B-$X^4$-B,
(ee) —$(CH_2)_m$-$L^3$-B-$(T)_y$-$(B)_y$-$X^2$-$(B)_y$-$R^{28}$,
(ff) —$(CH_2)_m$-$L^3$-B-T-$(B)_y$-$R^{28}$,
(gg) —$(CH_2)_m$-$L^3$-B-$(T)_y$-$(B)_y$-$X^2$-B,
(hh) —$(CH_2)_m$-$L^3$-B-T-$(B)_y$-$R^{29}$,
(ii) —$(CH_2)_m$-$L^3$-T-$(B)_y$-$X^2$-$(B)_y$-$R^{28}$,
(jj) —$(CH_2)_m$-$L^3$-T-$(B)_y$-$R^{28}$,
(kk) —$(CH_2)_m$-$L^3$-T-$(B)_y$-$X^2$-B,
(ll) —$(CH_2)_m$-$L^3$-($CR^{19}R^{20}$)-D-$(T)_y$-$(B)_y$-$X^3$-$(B)_y$-$R^{28}$,
(mm) —$(CH_2)_m$-$L^3$-($CR^{19}R^{20}$)-D-T-$(B)_y$-$R^{28}$,
(nn) —$(CH_2)_m$-$L^3$-($CR^{19}R^{20}$)-D-$(T)_y$-$(B)_y$-$X^3$-B, (oo) —(CH$_2$)$_m$-L$^3$-(CR$^{19}$R$^{20}$)-D-T-(B)$_y$-R$^{29}$,
(pp) —(CH$_2$)$_m$-L$^3$-(CR$^{19}$R$^{20}$)-D-T-(B)$_y$-X$^4$-(B)$_y$-R$^{28}$,
(qq) —(CH$_2$)$_m$-L$^3$-(CR$^{19}$R$^{20}$)-D-(B)$_y$-X$^4$-(B)$_y$-R$^{28}$,
(rr) —(CH$_2$)$_m$-L$^3$-(CR$^{19}$R$^{20}$)-D-T-(B)$_y$-X$^4$-B,
(ss) —(CH$_2$)$_m$-L$^3$-(CR$^{19}$R$^{20}$)-D-B-X$^4$-B,

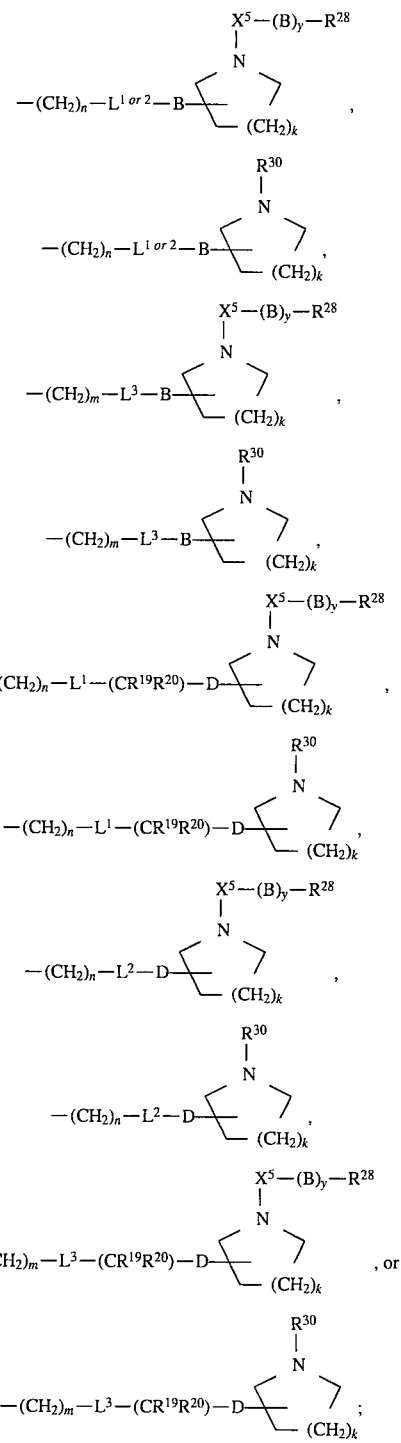

(tt)
(uu)
(vv)
(ww)
(xx)
(yy)
(zz)
(aaa)
(bbb)
(ccc)

L$^1$ is
(a) —CO$_2$—,
(b) —CONR$^{11a}$—,
(c) —NR$^{11a}$CO$_2$—, or
(d) —NR$^{11a}$CONR$^{11b}$—;
L$^2$ is
(a) —CO—,
(b) NR$^{11a}$CO—, or (c) —O$_2$C—;
L3 is
(a) —O—,
(b) —SO—, or
(c) —NR$^{11a}$—;
B is C$_1$–C$_6$ alkyl;
D is C$_2$–C$_8$ alkenyl or C$_2$–C$_8$ alkynyl;
T is
(a) arylene, , or
(b) heteroarylene
X$^1$ is
(a) a carbon-carbon single bond,
(b) —CO—,
(c) —C(R$^{19}$)(R$^{20}$)—,
(d) —O—,
(e) —S—,
(f) —SO—,
(g) —SO$_2$—,
(h) —NR$^{14}$—,
(i) —CONR$_{16}$—,
(j) —NR$^{16}$CO—,
(k) —OC(R$^{19}$)(R$^{20}$)—,
(l) —C(R$^{19}$)(R$^{20}$)O—,
(m) —SC(R$^{19}$)(R$^{20}$)—,
(n) —C(R$^{19}$)(R$^{20}$)S—,
(o) —NHC(R$^{19}$)(R$^{20}$)—,
(p) —C(R$^{19}$)(R$^{20}$)NH—,
(q) —NR$^{16}$SO$_2$—,
(r) —SO$_2$N R$^{16}$—,
(s) —CH=CH—,
(t) —CF=CF—,
(u) —CF=CH—,
(v) —CH=CF—,
(w) —CF$_2$CF$_2$—,
(x) —CH(OR$^{15}$)—,
(y) —CH(OCOR$^{17}$)—,
(z) —C(=NR$^{18}$)—,
(aa) —C(OR$^{21}$)(OR$^{22}$)—,
(bb) 1,2-cyclopropyl, or
(cc) 1,1-cyclopropyl;
X$^2$ is
(a) —CO—,
(b) —O—,
(c) —S(O)$_r$—,
(d) —(C$_1$–C$_4$-alkylene)—,
(e) —NR$^{11a}$CONR$^{11b}$—,
(f) —CONR$^{11a}$—,
(g) —NR$^{11a}$CO—,
(h) —SO$_2$NR$^{16}$—,
(i) —NR$^{16}$SO$_2$—,
(j) —OCONR$^{11a}$SO$_2$—,
(k) —SO$_2$NR$^{11a}$CO—,
(l) —SO$_2$NR$^{11a}$CO—,
(m) —OCONR$^{11a}$SO$_2$—,
(n) —SO$_2$NR$^{11a}$CONR$^{11b}$—,
(o) —NR$^{11a}$CONR$^{11b}$SO$_2$—,
(p) —SO$_2$NR$^{11a}$SO$_2$—,
(q) —CONR$^{11a}$SO$_2$NR$^{11b}$—, or
(r) —NR$^{11a}$SO$_2$NR$^{11b}$CO—;
X$^3$ is
(a) —CO—,
(b) —SO—,
(c) —SO$_2$—,
(d) single bond,
(e) —CONR$^{11a}$—,
(f) —SO$_2$NR$^{16}$—,
(g) —CONR$^{11a}$SO$_2$—, (h) —$SO_2NR^{11a}CO$—,
(i) —$SO_2NR^{11a}CO_2$—,
(j) —$SO_2NR^{11a}CONR^{11b}$—,
(k) —$SO_2NR^{11a}SO_2$—, or
(l) —$CONR^{11a}SO_2NR^{11b}$—;

$X^4$ is
(a) —$NR^{11a}CONR^{11b}$-,
(b) —$OCONR^{11a}SO_2$—,
(c) —$NR^{16}SO_2$—,
(d) —$OCONR^{11a}SO_2$—,
(e) —$NR^{11a}CONR^{11b}SO_2$—, or
(f) —$NR^{11a}SO_2NR^{11b}CO$—;

$X^5$ is
(a) —CO—,
(b) —$SO_2$—,
(c) —COO—, or
(d) —$CONR^{11a}$—;

Z is
(a) —O—,
(b) —S—, or
(c) —$NR^{11}$—;

k is 1 or 2;
m is 1 to 5;
n is 0 to 2;
q is 2 to 3;
r is 0 to 2;
s is 0 to 5;
t is 0 to 3;
u is 2 to 5;
y is 0 or 1;

and pharmaceutically acceptable salts of these compounds.

Preferred compounds of this invention are those of formula (I) wherein

A is
(a) —$(CH_2)_n$-$L^1$-S-$(T)_y$-$(S)_y$-$X^2$-$(S)_y$-$R^{28}$,
(b) —$(CH_2)_n$-$L^1$-B-T-$(B)_y$-$R^{28}$,
(c) —$(CH_2)_n$-$L^1$-B-$(T)_y$-$(B)_y$-$X^2$-B,
(d) —$(CH_2)_n$-$L^1$-B-T-$(B)_y$-$R^{29}$
(e) —$(CH_2)_n$-$L^2$-B-$(T)_y$-$(B)_y$-$X^2$-$(B)_y$-$R^{28}$,
(f) —$(CH_2)_n$-$L^2$-B-$(T)_y$-$(B)_y$-$R^{28}$, or
(g) —$(CH_2)_n$-$L^2$-B-$(T)_y$-$(B)_y$-$X^2$-B,
(h) —$(CH_2)_n$-$L^2$-B-T-$(B)_y$-$R^{29}$;

One embodiment of the preferred invention above is a compound of formula II

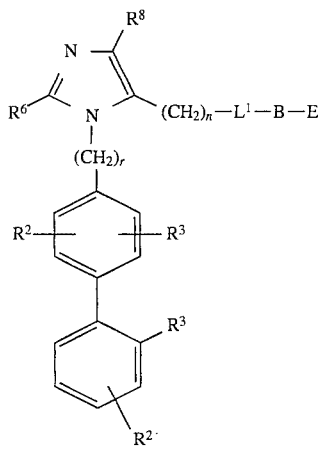

(II)

wherein
$R^2$ is independently
(a) H,
(b) halo (F, Cl, Br, I), or
(c) $C_1$–$C_4$-alkyl;

$R^3$ is
(a) H, or
(b) halo (F, Cl, Br, I);

$R^6$ is
(a) $C_1$–$C_{10}$ alkyl,
(b) $C_3$–$C_{10}$ alkenyl, or
(c) $C_3$–$C_{10}$ alkynyl;

R9 is
(a) H,
(b) $C_1$–$C_5$-alkyl,
(c) aryl,
(d) —($C_1$–$C_4$-alkyl)-aryl, or
(e) heteroaryl;

$R^{10}$ is
(a) aryl,
(b) $C_3$–$C_7$-cycloalkyl,
(c) $C_1$–$C_4$-perfluoroalkyl,
(d) $C_1$–$C_4$-alkyl, optionally substituted with a substituent selected from the group consisting of aryl, heteroaryl, —OH, —SH, $C_1$–$C_4$-alkyl, $C_1$–$C_4$-alkoxy, $C_1$–$C_4$-alkylthio, —$CF_3$, halo, —$NO_2$, —$CO_2R^{12}$, —$NH_2$, $C_1$–$C_4$-alkylamino, $C_1$–$C_4$-dialkylamino, —$PO_3H_2$, or
(e) heteroaryl;

$R^{11}$, $R^{11a}$ and $R^{11b}$ are independently
(a) H,
(b) $C_1$–$C_6$-alkyl,
(c) $C_3$–$C_6$-cycloalkyl,
(d) aryl,
(e) —($C_1$–$C_5$-alkyl)-aryl, or
(f) heteroaryl;

$R^{13}$ is
(a) —$CO_2H$,
(b) —$CONHSO_2R^{10}$,
(c) —$CONHSO_2NHR^9$,
(d) —$NHCONHSO_2R^{10}$,
(e) —$NHSO_2R^{10}$,
(f) —$NHSO_2NHCOR^{10}$,
(g) —$SO_2NHR^9$,
(h) —$SO_2NHCOR^{10}$,
(i) —$SO_2NHCONHR^9$,
(j) —$SO_2NHCO_2R^{10}$, or (k)

$R^{16}$ is
(a) H,
(b) $C_1$–$C_6$-alkyl, or
(c) benzyl, optionally substituted on the phenyl ring with 1–2 substituents selected from the group consisting of halo, $C_1$–$C_4$-alkyl, $C_1$–$C_4$-alkoxy or —$NO_2$;

$R^{28}$ is
(a) aryl, or
(b) heteroaryl;

$R^{29}$ is
(a) —CHO,
(b) —$CONH_2$,
(c) —NHCHO,
(d) —CO-($C_1$–$C_6$ perfluoroalkyl),
(e) —S(O)$_r$-($C_1$–$C_6$ perfluoroalkyl), E is
(a) —$(T)_y$-$(B)_y$-$X_2$-$(B)_y$-$R^{28}$,
(b) —T-$(B)_y$-$R^{28}$,
(c) —$(T)_y$-$(B)_y$-$X^2$-B or,
(d) —T-$(B)_y$-$R^{29}$;

$L^1$ is
(a) —$CO_2$—, (b) —CONR$^{11a}$—,
(c) —NR$^{11a}$CO$_2$—,
(d) —NR$^{11a}$CONR$^{11b}$—;

B is $C_1$–$C_6$ alkyl;

$X^2$ is
(a) —CO—,
(b) —O—,
(c) —S(O)$_r$—,
(d) —($C_1$–$C_4$-alkylene)-,
(e) —NR$^{11a}$CONR$^{11b}$—,
(f) —CONR$^{11a}$—,
(g) —NR$^{11a}$CO—,
(h) —SO$_2$NR$^{16}$—,
(i) —NR$^{16}$SO$_2$—,
(j) —CONR$^{11a}$SO$_2$—,
(k) —SO$_2$NR$^{11a}$CO—,
(l) —SO$_2$NR$^{11a}$CO$_2$—,
(m) —OCONR$^{11a}$SO$_2$—,
(n) —SO$_2$NR$^{11a}$CONR$^{11b}$—,
(o) —NR$^{11a}$CONR$^{11b}$SO$_2$—,
(p) —SO$_2$NR$^{11a}$SO$_2$—,
(q) —CONR$_{11a}$SO$_2$NR$^{11b}$—, or
(r) —NR$^{11a}$SO$_2$NR$^{11b}$CO— and pharmaceutically acceptable salts of these compounds.

Another embodiment of the preferred invention is a compound of Formula III

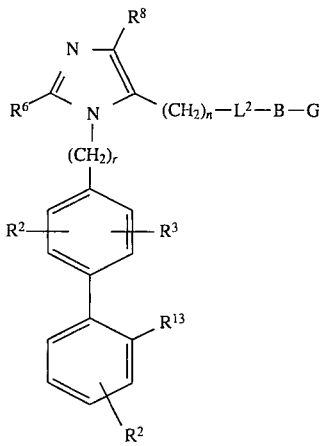

(III)

wherein
$R^2$ is independently
(a) H,
(b) halo (F, Cl, Br, I), or
(c) $C_1$–$C_4$-alkyl;

$R^3$ is
(a) H, or
(b) halo (F, Cl, Br, I);

$R^6$ is
(a) $C_1$–$C_{10}$ alkyl,
(b) $C_3$–$C_{10}$ alkenyl, or
(c) $C_3$–$C_{10}$ alkynyl;

$R^9$ is
(a) H,
(b) $C_1$–$C_5$-alkyl,
(c) aryl
(d) —($C_1$–$C_4$-alkyl)-aryl, or
(e) heteroaryl;

$R^{10}$ is
(a) aryl,
(b) $C_3$–$C_7$-cycloalkyl,
(c) $C_1$–$C_4$-perfluoroalkyl,
(d) $C_1$–$C_4$-alkyl, optionally substituted with a substituent selected from the group consisting of aryl, heteroaryl, —OH, —SH, $C_1$–$C_4$-alkyl, $C_1$–$C_4$-alkoxy, $C_1$–$C_4$-alkylthio, —CF$_3$, halo, —NO$_2$, —CO$_2$R$^{12}$, —NH$_2$, $C_1$–$C_4$-alkylamino, $C_1$–$C_4$-dialkylamino, —PO$_3$H$_2$, or
(e) heteroaryl;

$R^{11}$, $R^{11a}$ and $R^{11b}$ are independently
(a) H,
(b) $C_1$–$C_6$-alkyl,
(c) $C_3$–$C_6$-cycloalkyl,
(d) aryl,
(e) —($C_1$–$C_5$-alkyl)-aryl, or
(f) heteroaryl;

$R^{13}$ is
(a) —CO$_2$H,
(b) —CONHSO$_2$R$^{10}$,
(c) —CONHSO$_2$NHR$^9$,
(d) —NHCONHSO$^2$R$^{10}$,
(e) —NHSO$^2$R$^{10}$,
(f) —NHSO$_2$NHCOR$^{10}$,
(g) —SO$_2$NHR$^9$,
(h) —SO$_2$NHCOR$^{10}$,
(i) —SO$_2$NHCONHR$^9$,
(j) —SO$_2$NHCO$_2$R$^{10}$, or

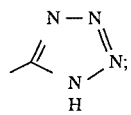 (k)

$R^{16}$ is
(a) H,
(b) $C_1$–$C_6$-alkyl, or
(c) benzyl, optionally substituted on the phenyl ring with 1–2 substituents selected from the group consisting of halo, $C_1$–$C_4$-alkyl, $C_1$–$C_4$-alkoxy or —NO$_2$;

$R^{28}$ is
(a) aryl, or
(b) heteroaryl;

$R^{29}$ is
(a) —CHO,
(b) —CONH$_2$,
(c) —NHCHO,
(d) —CO-($C_1$–$C_6$ perfluomalkyl),
(e) —S(O)$_r$-($C_1$–$C_6$ perfluoroalkyl), G is
(a) —(T)$_y$-(B)$_y$-X$^2$-(B)$_y$-R$^{28}$,
(b) —T-(B)$_y$-R$^{28}$,
(c) —(T)$_y$-(B)$_y$-X$^2$-B, or
(d) —T-(B)$_y$-R$^{29}$;

$L^2$ is —CO—, —NR$^{11a}$CO— or —O$_2$C—;

B is $C_1$–$C_6$ alkyl;

$X^2$ is
(a) —CO—,
(b) —O—,
(c) —S(O)$_r$—,
(d) —($C_1$–$C_4$-alkylene)—,
(e) —NR$^{11a}$CO, —NR$^{11a}$CONR$^{11b}$—,
(f) —CONR$^{11a}$—,
(g) —NR$^{11a}$CO—,
(h) —SO$_2$NR$^{16}$—,
(i) —NR$^{16}$SO$_2$—,
(j) —SO$_2$NR$^{11a}$SO$_2$—,
(k) —SO$_2$NR$^{11a}$CO$_2$—,
(l) —SO$_2$NR$^{11a}$CO$_2$—,
(m) —OCONR$^{11a}$SO$_2$—,
(n) —SO$_2$NR$^{11a}$CONR$^{11b}$—,
(o) —NR$^{11a}$CONR$^{11b}$SO$_2$—,
(p) —SO$_2$NR$^{11a}$SO$_2$—,
(q) —CONR$^{11a}$SO$_2$NR$^{11b}$—, or (r) —NR$^{11a}$SO$_2$NR$^{11b}$CO— and pharmaceutically acceptable salts of these compounds.

Illustrative of the preferred compounds of the invention are the following:

1-((2'-((i-Amyloxycarbonylamino)sulfonyl)-3-fluoro-(1,1'-biphenyl)- 4-yl)methyl)-5-[2-(N-benzoyl-N-phenylamino)ethylcarbonyl]-4-ethyl-2-propyl- 1H-imidazole 1-((2'-((n-Butyloxycarbonylamino)sulfonyl)-3-fluoro-(1,1'-biphenyl)- 4-yl)methyl)-5-[2-(N-benzoyl-N-phenylamino)ethylcarbonyl]-4-ethyl-2-propyl- 1H-imidazole 1-((2'-((n-Propyloxycarbonylamino)sulfonyl)-3-fluoro-(1,1'-biphenyl)- 4-yl)methyl)-5-[2-(N-benzoyl-N-phenylamino)ethylcarbonyl]-4-ethyl-2-propyl- 1H-imidazole 1-((2'-((n-Butyloxycarbonylamino)sulfonyl)-3-fluoro-(1,1'-biphenyl)- 4-yl)methyl)-5-[2-(N-benzoyl-N-butylamino)ethylcarbonyl]-4-ethyl-2-propyl- 1H-imidazole 1-((2'-((n-Butyloxycarbonylamino)sulfonyl)-3-fluoro-(1,1'-biphenyl )- 4-yl)methyl)-5-[2-(N-benzoyl-N-propylamino)ethylcarbonyl]-4-ethyl-2-propyl- 1H-imidazole 1-((2'-((n-Butyloxycarbonylamino)sulfonyl)-3-fluoro-(1,1'-biphenyl)- 4-yl)methyl)-5-[2-(N-butyryl-N-propylamino)ethylcarbonyl]-4-ethyl-2-propyl- 1H-imidazole 1-((2'-((n-Butyloxycarbonylamino)sulfonyl)-3-fluoro-(1,1'-biphenyl)- 4-yl)methyl)-5-[2-(N-butyryl-N-phenylamino)ethylcarbonyl]-4-ethyl-2-propyl- 1H-imidazole 1-((2'-((i-Amyloxycarbonylamino)sulfonyl)-3-fluoro-(1,1'-biphenyl)- 4-yl)methyl)-5-[2-(N-butyryl-N-phenylamino)ethylcarbonyl]-4-ethyl-2-propyl- 1H-imidazole 1-((2'-((i-Amyloxycarbonylamino)sulfonyl)-3-fluoro-(1,1'-biphenyl)- 4-yl)methyl)-5-[2-(N-isonicotinoyl-N-pyridin-3-ylamino)ethylcarbonyl]-4-ethyl- 2-propyl-1H-imidazole 1-((2'-((n-Butyloxycarbonylamino)sulfonyl)-3-fluoro-(1,1'-biphenyl)- 4-yl)methyl)-5-[2-(N-isonicotinoyl-N-pyridin-3-ylamino )ethylcarbonyl]-4-ethyl- 2-propyl-1H-imidazole 1-((2'-((n-Butyloxycarbonylamino)sulfonyl)-3-fluoro-(1,1'-biphenyl)- 4-yl)methyl)-5-[2-(N-nicotinoyl-N-pyridin-3-ylamino )ethylcarbonyl]-4-ethyl- 2-propyl-1H-imidazole 1-((2'-((i-Amyloxycarbonylamino)sulfonyl)-3-fluoro-(1,1'-biphenyl)- 4-yl)methyl)-5-[2-(N-nicotinoyl-N-pyridin-3-ylamino)ethylcarbonyl]-4-ethyl- 2-propyl-1H-imidazole 1-((2'-((i-Amyloxycarbonylamino)sulfonyl)-3-fluoro-(1,1'-biphenyl)- 4-yl)methyl)-5-[2-(N-nicotinoyl-N-pyridin-2-ylamino )ethylcarbonyl]-4-ethyl- 2-propyl-1H-imidazole 1-((2'-((i-Amyloxycarbonylamino)sulfonyl)-3-fluoro-(1,1'-biphenyl)- 4-yl)methyl)-5-[2-(N-isonicotinoyl-N-phenylamino)ethylcarbonyl]-4-ethyl- 2-propyl-1H-imidazole 1-((2'-((i-Amyloxycarbonylamino)sulfonyl)-3-fluoro-(1,1'-biphenyl)- 4-yl)methyl)-5-[2-(N-butyryl-N-pyridin-3-ylamino)ethylcarbonyl]-4-ethyl- 2-propyl-1H-imidazole 1-((2'-((i-Amyloxycarbonylamino)sulfonyl)-3-fluoro-(1,1'-biphenyl)- 4-yl)methyl)-5-[2-(N-isobutyryl-N-pyridin-3-ylamino )ethylcarbonyl]-4-ethyl- 2-propyl-1H-imidazole 1-((2'-((n-Butyloxycarbonylamino)sulfonyl)-3-fluoro-(1,1'-biphenyl)- 4-yl)methyl)-5-[2-(N-acetyl-N-pyridin-3-ylamino)ethylcarbonyl]-4-ethyl- 2-propyl-1H-imidazole 1-((2'-((i-Amyloxycarbonylamino)sulfonyl)-3-fluoro-(1,1'-biphenyl)- 4-yl)methyl)-5-[2-(N-butyryl-N-pyridin-2-ylamino )ethylcarbonyl]-4-ethyl- 2-propyl-1H-imidazole 1-((2'-((i-Amyloxycarbonylamino)sulfonyl)-(1,1'-biphenyl)-4-yl)methyl)-5-[2-(N-butyryl-N-pyridin-3-ylamino) ethylcarbonyl]-2-butyl-4-chloro-1H-imidazole 1-((2'-((i-amyloxycarbonylamino)sulfonyl)-3-fluoro-(1,1'-biphenyl)- 4-yl)methyl)-5-[2-(N-propionyl-N-pyridin-3-ylamino)ethylcarbonyl]-4-ethyl- 2-propyl-1H-imidazole 1-((2'-((i-Amyloxycarbonylamino)sulfonyl)(1,1'-biphenyl)-4-yl)methyl)-5-[2-(N-nicotinoyl-N-pyridin-3-ylamino)ethylcarbonyl]-4-ethyl-2-propyl-1H-imidazole 1-((2'-((i-Amyloxycarbonylamino)sulfonyl)(1,1'-biphenyl)-4-yl)methyl)-5-[2(N-butyryl-N-pyridin-3-ylamino)ethylcarbonyl]-4-ethyl-2-propyl-1H-imidazole 1-((2'-((n-Butyloxycarbonyl-amino)sulfonyl)-3-fluoro-(1, 1'-biphenyl)- 4-yl)methyl)-4-ethyl-5-(2-(2-phenoxyphenyl)ethylcarbonyl)-2-propyl- 1H-imidazole 4-[((5-(2-Benzoylbenzyloxycarbonyl)-4-ethyl-2-n-propyl)imidazol- 1-yl)methyl]-3-fluoro-2'-n-butyloxycarbonylaminosulfonyl-1,1'-biphenyl 4-[((5-(2-Benzoylbenzyloxycarbonyl)-4-ethyl-2-n-propyl)imidazol- 1-yl)methyl]-3-fluoro-2'-((2-phenyl)ethyloxycarbonylaminosulfonyl)-1,1'-biphenyl 4-[((5-(2-Benzoylbenzyloxycarbonyl)-4-ethyl-2-n-propyl)imidazol- 1-yl)methyl]-2'-((2-phenyl)ethyloxycarbonylaminosulfonyl)-1,1'-biphenyl 4-[((5-(2-Benzoylbenzyloxycarbonyl)-4-ethyl-2-n-propyl)imidazol- 1-yl)methyl]-3-fluoro-2'-n-butyloxycarbonylaminosulfonyl-1,1'-biphenyl 4-[((5-(2-Benzoylbenzyloxycarbonyl)-4-ethyl-2-n-propyl)imidazol- 1-yl)methyl]-3-fluoro-2'-n-isoamyloxycarbonylaminosulfonyl-1,1'-biphenyl 4-[((5-(2-Benzoylbenzyloxycarbonyl)-4-ethyl-2-n-propyl)imidazol- 1-yl)methyl]-2'-n-isoamyloxycarbonylaminosulfonyl-1,1'-biphenyl 4-[((5-(2-Benzoylbenzyloxycarbonyl)-4-ethyl-2-n-propyl)imidazol- 1-yl)methyl]-3-fluoro-2'-n-propyloxycarbonylaminosulfonyl-1,1'-biphenyl 4-[((5-(2-Isoamyloxybenzyloxycarbonyl)-4-ethyl-2-n-propyl)imidazol- 1-yl)methyl]-3-fluoro-2'-n-butyloxycarbonylaminosulfonyl-1,1'-biphenyl 4-[((5-(2-Phenylaminocarbonyl)benzyloxycarbonyl-4-ethyl-2-n-propyl)imidazol- 1-yl)methyl]-3-fluoro-2'-n-butyloxycarbonylaminosulfonyl- 1,1'-biphenyl.

4-[((5-(2-Benzoylbenzyloxycarbonyl)-4-ethyl-2-n-propyl)imidazol- 1-yl)methyl]-3-fluoro-2'-(1 H-tetrazol-5-yl)-1,1'-biphenyl 4-[((5-)2-trifluorophenyl)methylaminocarbonyl)-4-ethyl-2-n-propyl)imidazol- 1-yl)methyl]-3-fluoro-2'-isoamyloxycarbonylaminosulfonyl-1,1'-biphenyl N-butyl, N-benzyl-2-(aminocarbonyl)ethynylmethyl 4-ethyl-2-propyl-1-[[2'-( 1H-tetrazol-5-yl)biphenyl-4-yl]methyl]imidazole-5-carboxylate N, N-diphenyl-2-(aminocarbonyl)ethynylmethyl 4-ethyl-2-propyl-1-[[2'-( 1H-tetrazol-5-yl)biphenyl-4-yl]methyl]imidazole-5-carboxylate N-phenyl-2-(aminocarbonyl)ethyl 4-ethyl-2-propyl-1-[[2'-(1H-tetrazol- 5-yl)biphenyl-4-yl]methyl]imidazole-5-carboxylate N-butyl, N-benzyl-4-(aminocarbonyl)propyl 4-ethyl-2-propyl-1-[[2'-( 1H-tetrazol-5-yl)biphenyl-4-yl]methyl]imidazole-5-carboxylate N, N-dipentyl-4-(aminocarbonyl)propyl 4-ethyl-2-propyl-1-[[2'-(tetrazol- 5-yl)biphenyl-4-yl]methyl]imidazole-5-carboxylate 4-[(5-((2-benzoyl)phenylcarbonyloxymethyl)-4-chloro-2-n-propylimidazol- 1-yl)methyl]-3-fluoro-2'-isoamyloxycarbonylaminosulfonylbiphenyl 1-((2'-((n-butyloxycarbonylamino)sulfonyl)-3-fluoro-(1,1'-biphenyl)- 4-yl)methyl)-2-(n-propyl)-4-ethyl-5-(2-(phenoxy)phenoxy)acetyl-1H-imidazole Note that throughout the text when an alkyl substituent is mentioned, the normal alkyl structure is meant (e.g. butyl is n-butyl) unless otherwise specified. However, in the definition of radicals above (e.g. $R^3$), both branched and straight chains are included in the scope of alkyl, alkenyl and alkynyl.

The term aryl is meant to include phenyl, biphenyl, napthyl, or fluorenyl group optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$. The term heteroaryl is meant to include unsubstituted, monosubstituted or disubstituted 5- to 10-membered mono- or bicyclic aromatic rings which can optionally contain from 1 to 3 heteroatoms selected from the group consisting of O, N, and S. Included in the definition of the group heteroaryl, but not limited to, are the following: pyridyl, pyridazinyl, pyrimidinyl, pyrazinyl, 1,3,5-triazinyl, furyl, thiophenyl, imidazolyl, oxazolyl, thiazolyl, benzofuranyl, benzothiophenyl, benzimidazolyl, benzoxazolyl, benzothiazolyl, indolin-2-onyl, indolinyl, indolyl, pyrrolyl, quinonlinyl and isoquinolinyl. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$. The term arylene is meant to include a phenyl, biphenyl, napthyl, or fluorenyl group which is used as a link for two groups to form a chain. Included in the definition of arylene, but not limited to, are the following isomeric linkers: 1,2-phenyl, 1,3-phenyl, 1,4-phenyl; 4,4'-biphenyl, 4,3'-biphenyl, 4,2'-biphenyl, 2,4'-biphenyl, 2,3'-biphenyl, 2,2'-biphenyl, 3,4'-biphenyl, 3,3'-biphenyl, 3,2'-biphenyl,; 1,2-napthyl, 1,3-napthyl, 1,4-napthyl, 1,5-napthyl, 1,6-napthyl, 1,7-napthyl, 1,8-napthyl, 2,6-napthyl, 2,3-napthyl; 1,4-fluorenyl. Particularly preferred are 1,2-phenyl, 1,3-phenyl, 1,4-phenyl, 4,4'-biphenyl, 3,3'-biphenyl, and 2,2'-biphenyl optionally substituted with one to three substituents selected from the group consisting of —OH, —SH, $C_1$-$C_4$alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

The term heteroarylene is meant to include unsubstituted 5- to 10-membered aromatic ring which can optionally contain from 1 to 3 heteroatoms selected from the group consisting of O, N, and S which is used as a link for two groups to form a chain. Included in the definition of the group heteroaryl, but not limited to, are the following: 2,3-pyridyl, 2,4-pyridyl, 2,5-pyridyl, 2,6-pyridyl, 3,4-pyridyl, 3,5-pyridyl, 3,6-pyridyl; 2,3-furyl, 2,4-furyl, 2,5-furyl; 2,3-thiophenyl, 2,4-thiophenyl, 2,5-thiophenyl; 4,5-imidazolyl, 4,5-oxazolyl; 4,5-thiazolyl; 2,3-benzofuranyl; 2,3-benzothiophenyl; 2,3-benzimidazolyl; 2,3-benzoxazolyl; 2,3-benzothiazolyl; 3,4-indolin-2-onyl; 2,4-indolinyl; 2,4-indolyl; 2,4-pyrrolyl; 2,4-quinolinyl, 2,5-quinolinyl, 4,6-quinolinyl; 3,4-isoquinolinyl, 1,5-isoquinolinyl. Particularly preferred are 2,3-pyridyl, 3,4-pyridyl, 2,3-furyl, 3,4-furyl 2,3-thiophenyl, 3,4-thiophenyl, 2,3-quinolinyl, 3,4-quinolinyl and 1,4-isoquinolinyl optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N ($C_1$-$C_4$-alkyl)$_2$;

Pharmaceutically acceptable salts include both the metallic (inorganic) salts and organic salts; a non-exhaustive list of which is given in *Remington's Pharmaceutical Sciences* 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a novel compound of Formula (I), (II) or (III), and methods of using the novel compounds of Formula (I), (II) or (III), to treat hypertension and congestive heart failure. The pharmaceutical compositions can optionally contain one or more other therapeutic agents, such as a diuretic, an angiotensin I converting enzyme (ACE) inhibitor or a nonsteroidal antiinflammatory drug (NSAID). Also within the scope of this invention is a method of preventing renal failure resulting from administration of a NSAID which comprises administering a novel compound of Formula (I) in stepwise or physical combination with the NSAID. The compounds of this invention can also be used as diagnostic agents to test the renin angiotensin system.

It should be noted in the foregoing structural formula, when a radical can be a substituent in more than one previously defined radical, that first radical ($R^\#$, B or y) can be selected independently in each previously defined radical. For example, $R^1$ and $R^2$ can each be —$CONHOR^{12}$. $R^{12}$ need not be the same substituent in each of $R^1$ and $R^2$, but can be selected independently for each of them. Or if, for example, the same R group (let us take $R^2$, for instance) appears twice in a molecule, each of those R groups is independent of each other (one $R^2$ group may be —$CONHOR^{12}$, while the other $R^2$ group may be —CN).

It is understood that many of the compounds of the present invention contain one or more chiral centers and that these stereoisomers may possess distinct physical and biological properties. The present invention comprises all of the stereoisomers or mixtures thereof. If the pure enantiomers or diastereomers are desired, they may be prepared using starting materials with the appropriate stereochemistry, or may be separated from mixtures of undesired stereoisomers by standard techniques, including chiral chromatography and recrystallization of diastereomeric salts.

DETAILED DESCRIPTION OF THE INVENTION

Synthesis

The novel compounds of Formula (I), (II) or (III) may be prepared using the reactions and techniques described in this section. The reactions am performed in a solvent appropriate to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgement as to the order of synthetic steps, protecting groups required, and deprotection conditions. Throughout the following section, not all compounds of Formula (I), (II) or (III) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

The imidazole precursors in this application may be prepared as described in U.S. Pat. Nos. 5,137,902 and 5,138,069, in PCT U.S. Application 90/03683 and in European Application EP465,368 (see also Australian Patent AU-A-80163/91) and in U.S. Application (07/544557), which are hereby incorporated by reference.

When $L^1$ is —$CO_2$— and A is —$(CH_2)_n$-$L^1$-B-$(T)_y$-$(B)_y$-$X^2$-$(B)_y$-$R^{28}$ (subheading (a) of A in the scope of this application) then A may be synthesized by simply alkylating the corresponding free carboxylic acid A =—$(CH_2)_n$—COOH of structure (2) with X-B-$(T)_y$-$(B)_y$-$X^2$-$(B)_y$-$R^{28}$, where X is the corresponding chloride, bromide, tosylate or mesylate in an inert solvent in the presence of an acid scavenger such as potassium carbonate or triethylamine at room temperature to the reflux temperature of the solvent. Common inert solvents include THF, DMF, DMSO, etc. If B is longer than a methylene ($CH_2$), then to facilitate alkylation, it might be necessary to add some sodium iodide. An example of this alkylation is shown below when for A, subheading (a) and going from left to right, B=$CH_2$, T=Ph, y=1, y=0, $X^2$=(C=O), y=0 and $R^{28}$=Ph:

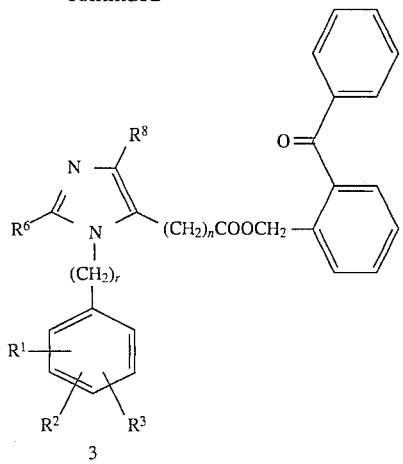

3

Or in general, the synthesis may be summarized as in Scheme 1:

Scheme 1

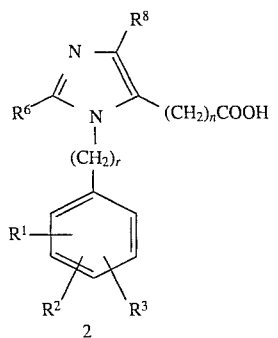

2

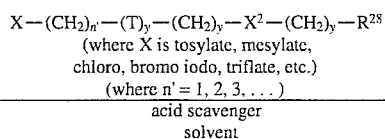

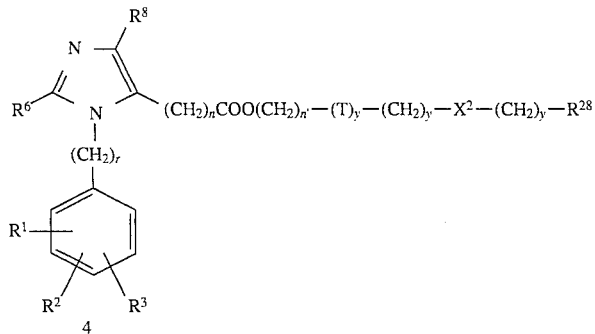

4

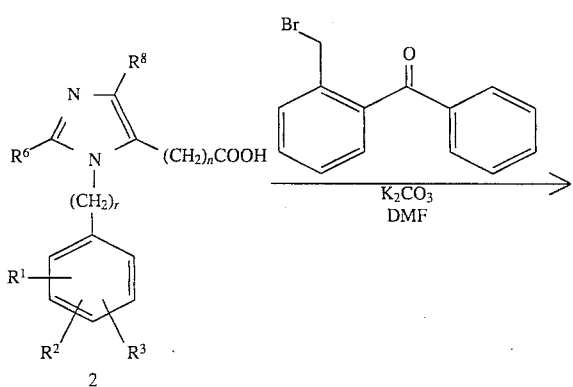

The entire side chain need not be fully elaborated in order to perform this alkylation. For example, instead of alkylating with X-B-$(T)_y$-$(B)_y$-$X^2$-$(B)_y$-$R^{28}$, one may alkylate with X-B-$(T)_y$-$(B)_y$-$X^{2'}$. $X^{2'}$ in this case must be a group which can be easily transformed into $X^2$-$(B)_y$-$R^{28}$ via condensation reactions. Therefore this synthetic route applies only where $X^2$ is a group such as one of the following: amides (—$CONR^{11a}$—, —$NR^{11a}CO$—), ureas (—$NR^{11a}CONR^{11b}$—), sulfonamides (—$SO_2NR^{16}$—, —$NR^{16}SO_2$—), acysulfonamides (—$SO_2NR^{11a}CO$—, —$CONR^{11a}SO_2$—), sulfonylcarbamates (—$OCONR^{11a}SO_2$—), sulfonylureas (—$SO_2NR^{11a}CONR^{11b}$—, —$NR^{11a}CONR^{11b}SO_2$-), sulfonylsulfonamides (—$SO_2NR^{11a}SO_2$—), and aminoacylsulfonamides (—$CONR^{11a}SO_2NR^{11b}$—,—$NR^{11a}SO_2NR^{11b}CO$—). All of the above groups or linkages may be formed via condensation reactions, which am exemplified in european patent application EPA 400 835, published Dec. 5, 1990. For example, if one were to synthesize $X^2$=—$CONR^{11a}$—, then one may alkylate the imidazole-5-carboxyl group with X-B-$(T)_y$-$(B)_y$-COO-CH$_2$Ph. Subsequent hydrogenation over palladium on carbon in an alcohol solvent yields the free carboxylic acid A=—$(CH_2)_n$-COO-B-$(T)_y$-$(B)_y$-COOH. Coupling with amine NHR$^{11a}$-$(B)_y$-R$^{28}$ using, for example, N,N'-diclohexylcarbodiimide in DMF or THF as solvent yields A=—$(CH_2)_n$-COO-B-$(T)_y$-$(B)_y$-CONR$^{11a}$-$(B)_y$-R$^{28}$. Similar types of synthetic schemes can be applied to the other $X^2$ group containing side-chains mentioned in this paragraph.

Amides wherein $L^1$=—CONR$^{11a}$, may be synthesized by the procedures shown in Scheme 2. Amine (5) is coupled to carboxylic acid (2) using a diimide coupling reagent such as N,N'-dicyclohexylcarbodiimide, etc., in an inert solvent such as DMF to yield amide (6). Another procedure involves converting carboxylic acid (2) into an acid chloride with for example thionyl chloride or oxallyl chloride, procedures familiar to one skilled in the art. This acid chloride is then coupled with amine (5) by simply mixing the two together in an inert solvent, such amide (6). Alternatively, The entire side chain need not be fully elaborated in order to perform this coupling. For example, instead of coupling with HR$^{11a}$N-B-$(T)_y$-$(B)_y$-$X^2$-$(B)_y$-R$^{28}$, one may couple with HR$^{11a}$N-B-$(T)_y$-$(B)_y$-$X^{2'}$. Thus coupling of carboxylic acid (2) with amine (7) under the above described coupling conditions yields amide (8) which can be subsequently elaborated into amide (6). This of course can only be done if the $X^2$ linker is one which can be formed by condensation reactions, as was described in the section under $L^1$=—COO—. Carbamates wherein $L^1$=—NR$^{11a}$CO$_2$— may be synthesized by the procedures shown in Scheme 3. Here amine (9) is reacted with chloroformate (10) either in the presence of aqueous base (Schotten-Baumann reaction: E. Baumann, *Ber. Deut. Chem. Ges.* 1886, 19, 3218.) or in the presence of an acid scavenger (either 1 equivalent or excess) such as pyridine, triethylamine, or Scheme 2

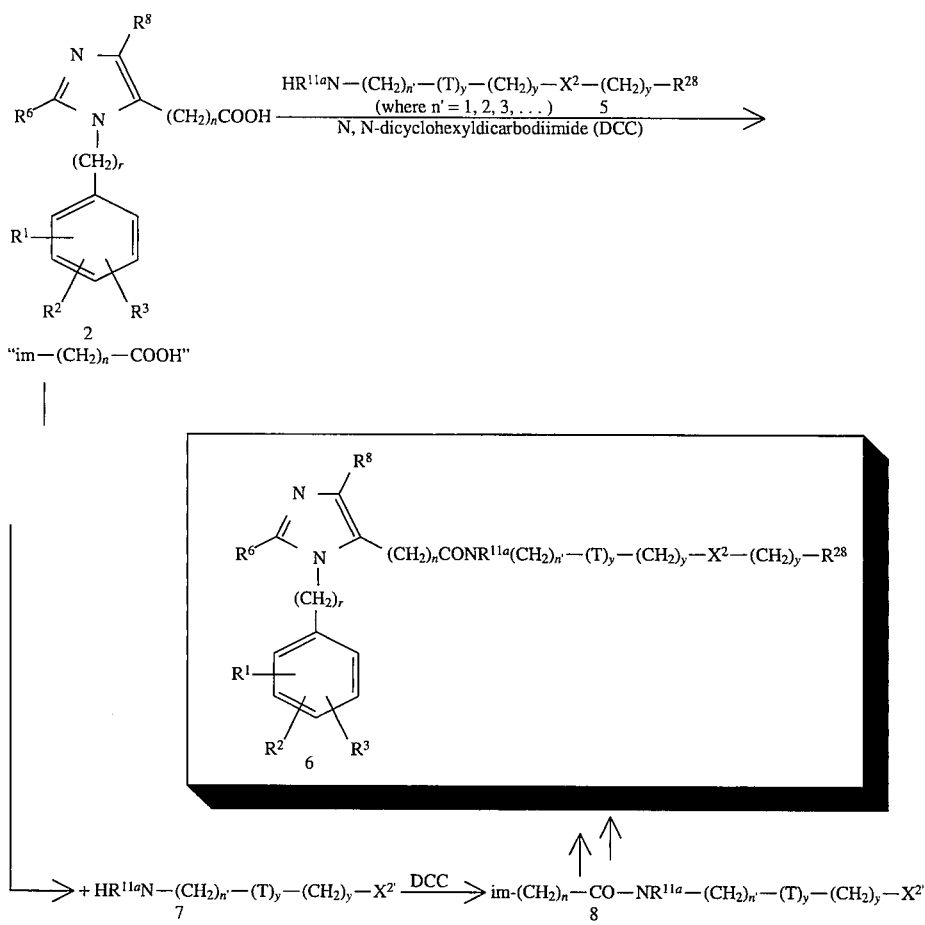

as methylene chloride over an acid scavenger such as potassium carbonate at 0° C. to room temperature to yield Scheme 3.

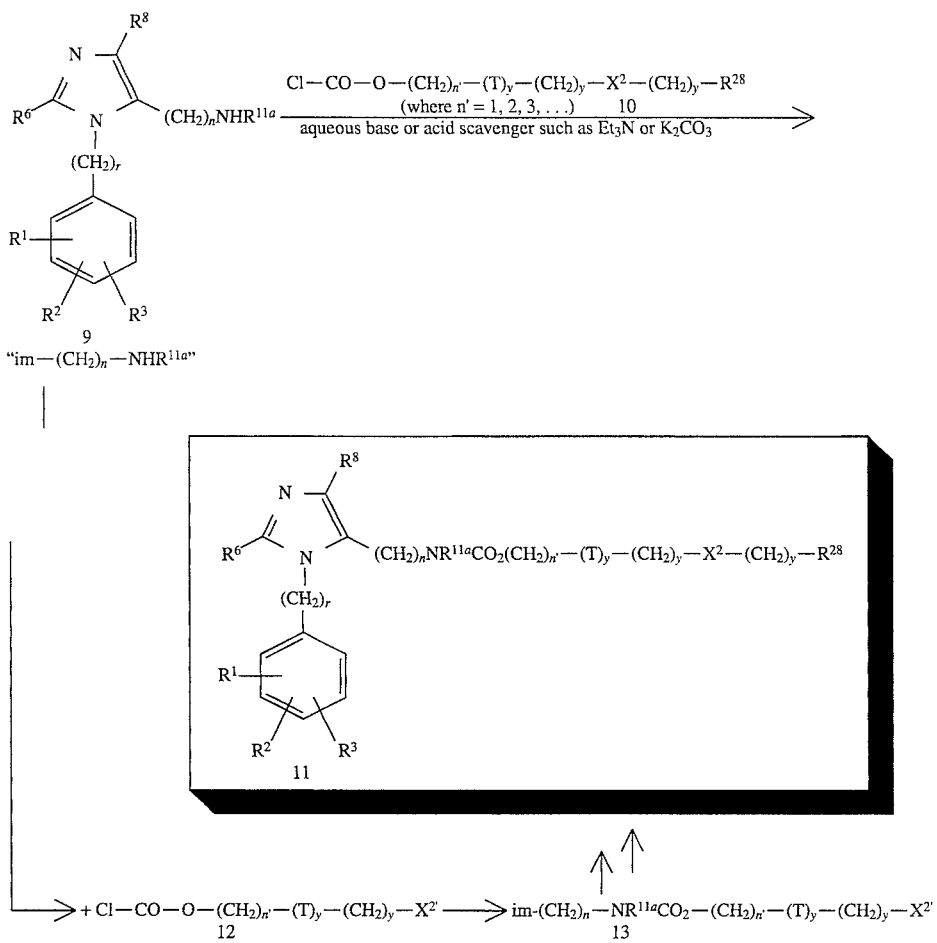

potassium carbonate to yield carbamate (11). If the reaction is sluggish, the chlorofomate might have to be activated with 4-N,N-dimethylaminopyridine, either catalytic or excess. The reaction is done in an inert solvent such as methylene chloride or THF, etc. at 0° C. or room temperature or higher. Likewise as seen earlier, the side-chain may be constructed in two steps, namely reaction of amine (9) with chloroformate (12) to yield carbamate (13) followed by elaboration to carbamate (11). This of course can only be done if the $X^2$ linker is one which can be formed by condensation reactions, as was described in the section under $L^1$=—COO—.

Another synthesis of carbamates $L^1$=—$NR^{11a}CO_2$, involves first reacting amine (9) ($R^{11a}$=H) (synthesis described in U.S. Pat. No. 5,138,069) with carbonyldiimidazole in an inert solvent such as THF or DMF at room temperature or with some heating to yield an isocyanate (14) as shown in Scheme 4. Further reaction with an alcohol (15) in an inert solvent with or without heat yields carbamate (11). Of course, as in Scheme 3, the synthesis of the side-chain can also be performed stepwise if $X^2$ can be formed via condensation reactions as was discussed earlier.

Scheme 4

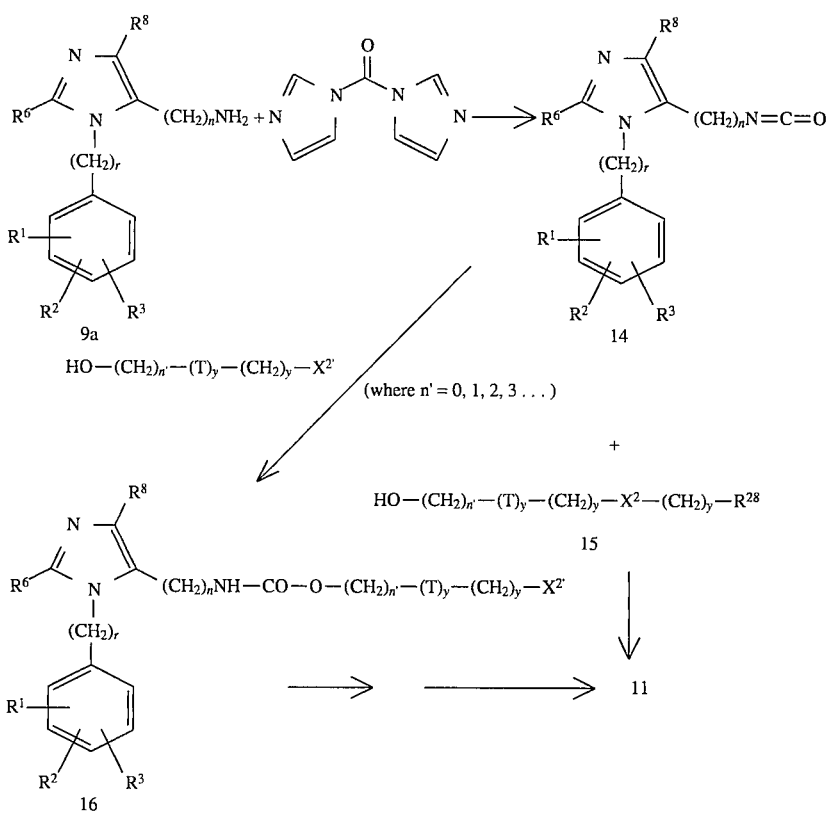

When n=0 in Schemes 3 and 4, then there is a carbamate group connected directly to the imidazole 5-position of (9) or (9a). The corresponding isocyanate starting material may be made by Curtius rearrangement (T. L. Capson, C. D. Poulter *Tet. Lett.* 1982, 25, 3515) of the corresponding acyl azide as shown in Scheme 5. Thus, carboxylic acid (17) (prepared as in U.S. Pat. No. 4,760,083) can be converted to its acid chloride by procedures familiar to one skilled in the art. Subsequent reaction with sodium azide yields acyl azide (19) which is heated to undergo Curtius rearrangement with nitrogen expulsion to yield isocyanate (14a). Heating acyl azide (19) in the presence of alcohol (15) will yield carbamate (11) directly (T. L. Capson, ibid.). If the alcohol is 2-trimethylsilylethanol, then the resulting carbamate (20) may be decomposed with fluoride ion (T. L. Capson, ibid.) to the amine (21) which can be used to make other carbamate side-chains (or ureas and amides, as seen subsequently). Amine (21) may undergo inductive amination by procedures familiar to one skilled in the art to yield alkylated amine (21a). The Curtius rearrangement may be performed in "one pot" by heating carboxylic acid (17) with diphenylphosphorylazide to yield isocyanate (14a) which again can be reacted in the same pot with an alcohol to yield a carbamate (T. Shiori, K. Ninomiya, S. Yamada *J. Am. Chem. Soc.* 1972, 94, 6203.

Yet another synthesis of amine (21) is shown below. Here an unsubstituted imidazole at the 5-position is nitrated with $HNO_3$ and $H_2SO_4$ under standard conditions. Then the nitro group is reduced with hydrogen over palladium on carbon in an alcohol solvent also under standard conditions to yield (21).

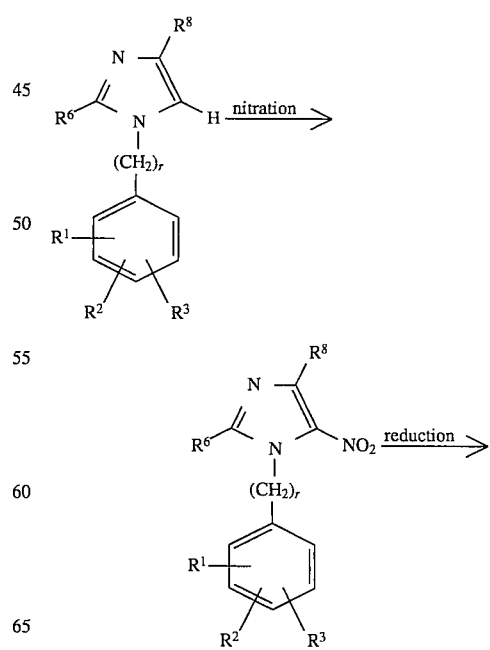

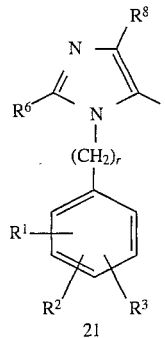

will yield urea (23) (Scheme 6). Likewise, primary amines (9) and (21) may be converted to the corresponding isocyanate as seen earlier and then reacted with an amine to yield urea (23). For example, reaction of isocyanate (14) with an amine such as (5) will yield urea (23). Conversely, amines (9), (9a), (21), or (21a) can be reacted with isocyanate (24) to yield urea (23). Of course, as in Scheme 3, the synthesis of the side-chains discussed in this paragraph can also be performed stepwise if $X^2$ can be formed via condensation reactions as was discussed earlier.

Scheme 5

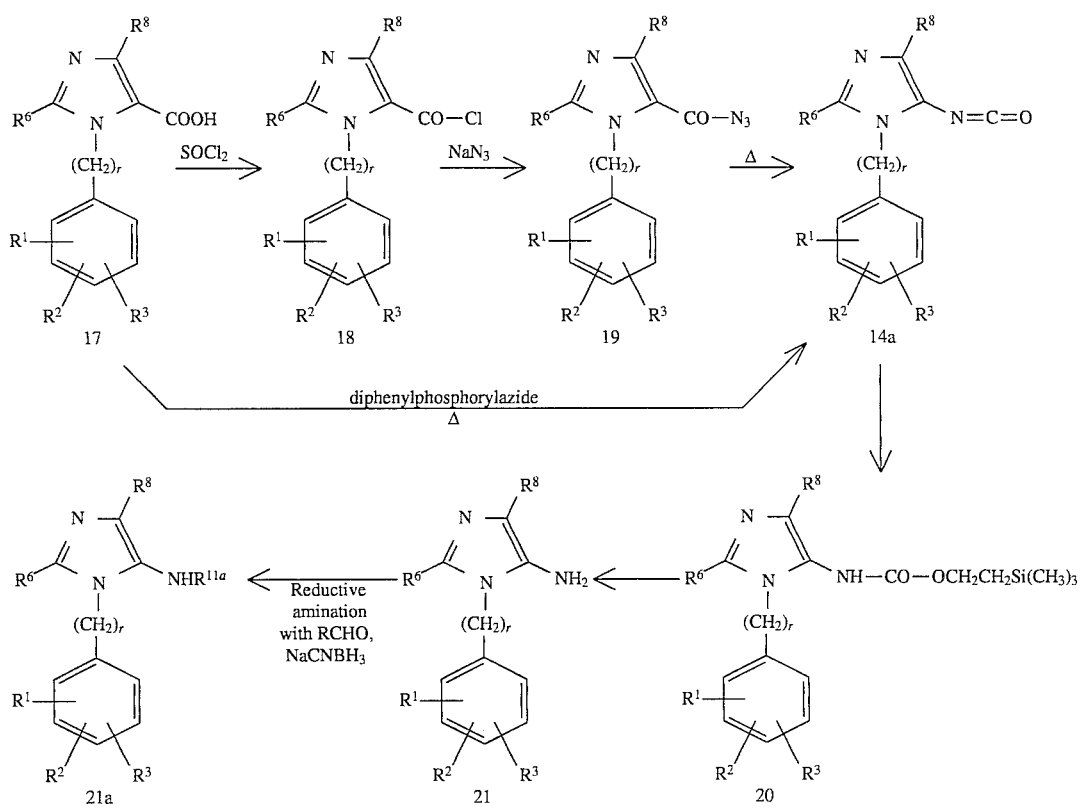

Taking amines (9), (9a), (21), or (21a) and reacting with carbamoyl chloride (22) (formed from phosgene and an amine: H. Hopif, H. Ohlinger *Angew. Chem.* 1949, 61, 183)

Scheme 6

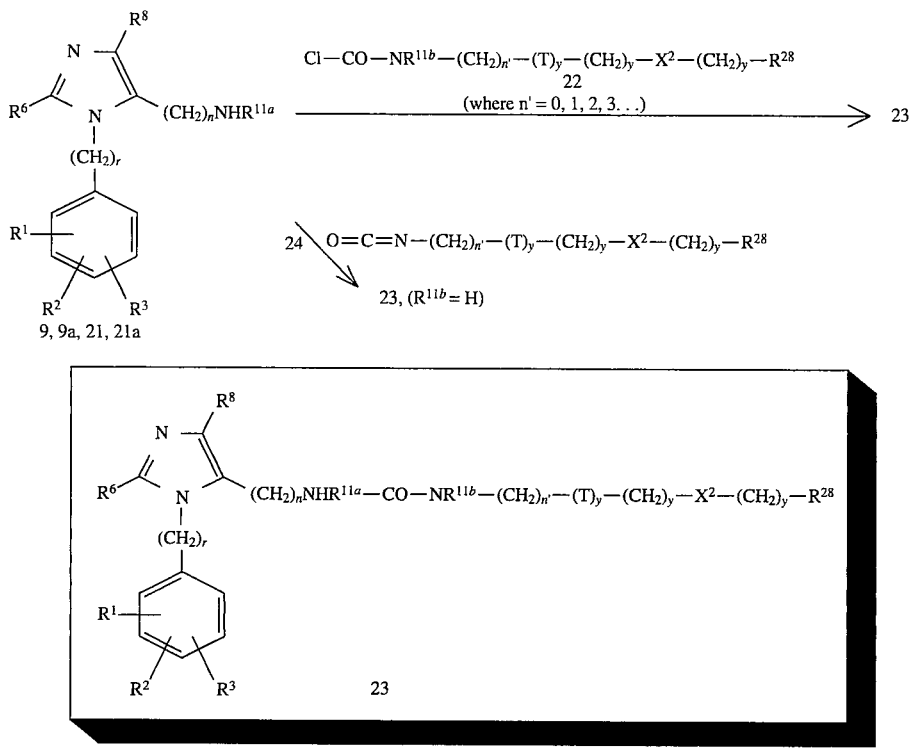

The synthesis of $-(CH_2)_n\text{-}L^1\text{-}B\text{-}(T)_y\text{-}(B)_y\text{-}X^2\text{-}(B)_y\text{-}R^{28}$ where $X^2$ is either a ketone, ether or thioether am summarized in Scheme 7. Aldehyde (25) may be reacted with Grignard reagent (26) in an inert solvent such as ether or THF at 0° C. to room temperature or with some heating to yield alcohol (27). Oxidation by a variety of methods familiar to one skilled in the art yields ketone (28). These methods include the use of PCC (pyridinium chlorochromate: E. J. Corey, J. W. Suggs *Tet. Lett.*, 1975, 47), pyridinium dichromate in methylene chloride (E. J. Corey, G. Schmidt *Tet. Lett.*, 1979, 399), the Swern oxidation using DMSO and trifluoroacetic anhydride (K. Omura, A. K. Sharma, D. Swern, *J. Org. Chem.*, 1976, 41, 957), the Dess-Martin Periodinane oxidation (D. B. Dess, J. C. Martin, *J. Org. Chem.* 1983, 48, 4156 and J. P. Burkhart, N. P. Peet, P. Bey, *Tet. Lett.* 1988, 29, 3433) or a Bobbitt oxidation using 4-acetylamino- 2,2,6,6-tetramethylpiperidinyl-1-oxyl and toluenesulfonic acid (Z. Ma, J. M. Bobbitt, *J. Org. Chem.*, 1991, 56, 6110). Metal alkoxide (29) is reacted with bromide (30) to undergo $S_N2$ displacement in an inert solvent such as DMF, DMSO, or THF, with or without the presence of an iodide salt, to yield ether (31). Likewise, the bromide and alkoxide moieties may be interchanged so that bromide (32) is reacted with alkoxide (33) to yield ether (31) under the same conditions. The oxygen atom may be replaced with sulfur to yield thioether products. Once the side-chain is synthesized, the THP group is removed using aqueous acid and the alcohol can be converted to the bromide via standard methods ($PBr_3$, $CBr_4$ & $Ph_3P$, etc.) or made into a leaving group such as a tosylate, mesylate or triflate by procedures familiar to one skilled in the art. These can be reacted further with sodium azide in DMSO to form the azide (J. M. Muchowski, *Can. J. Chem.* 1971, 49, 2023) which can be hydrogenated to the amine using hydrogen over palladium on carbon. Or the bromide, tosylate, mesylate or triflate may be reacted with ammonia to yield the amine directly.

Scheme 7

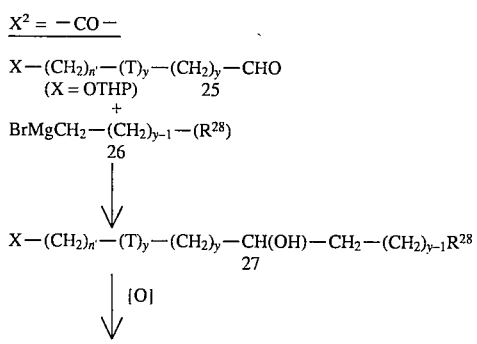

-continued
Scheme 7

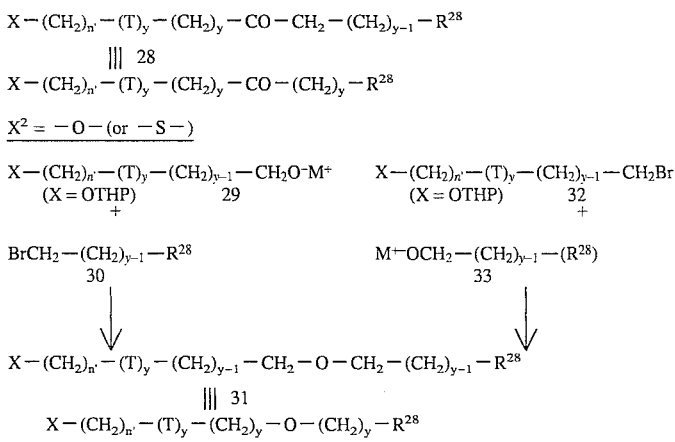

If any y is zero in $(CH_2)_y$ of (31), then they are aryl-ethers or -thioethers. These are synthesized employing variations of the Ullmann aryl ether synthesis (A. A. Moroz, M. S. Shvartssberg Russ. Chem. Rev., 1974, 43, 679).

Side-chains represented in the scope by A subheading (b) $(-(CH_2)_n-L^1-B-T-(B)_y-R_{28})$ may be synthesized by the methods described in A subheading (a). When y equals zero, then we have a biaryl, a heteroaryl-aryl, an aryl-heteroaryl, and biheteroaryl system. These compounds may be synthesized by employing aromatic cross-coupling reactions familiar to one skilled in the art. For example, there is the Stille Coupling (A. M. Echavarren, J. K. Stille, J. Am. Chem. Soc. 1987, 109, 5478; T. R. Bailey, Tet. Lett. 1986, 4407); Suzuki Coupling (N. Miyaura, T. Yanagi, A. Suzuki Syn. Comm. 1981, 11, 513; J.-m. Fu, V. Snieckus Tet. Lett. 1990, 31, 1665); Negishi Coupling (E. Negishi, A. O. King, N. Okukado J. Org. Chem. 1977, 42, 1821; A. S. Bell, D. A. Roberts, K. S. Ruddock, Tet. Lett. 1988, 29, 5013); Ullmann Coupling (W. J. Thompson, J. Gaudino J. Org. Chem. 1984, 49, 5237); and other reactions and references summarized in a review (V. N. Kalinin Synthesis 1992, 413). When y equals one, one can make the biaryl, heteroaryl-aryl, aryl-heteroaryl, and biheteroaryl methylene compounds ($B=CH_2$) via the Negishi coupling (ibid.). One can also make them from the corresponding ketones ($C=O$) by simply reducing the ketone to the methylene via hydrogenation over palladium on carbon. For y>1, one may employ the Wittig reaction (familiar to one skilled in the art) to make the corresponding biaryl substituted alkenes which can be reduced (hydrogenated over Pd on carbon) to the corresponding alkyl.

Side-chains represented in the scope by A subheading (c) may be synthesized by the methods described in A subheading (a). Side-chains represented in the scope by A subheading (d) may be synthesized by the methods described in A subheading (a) with the appropriate substitution on T to permit elaboration to $R^{29}$ (Scheme 8). For example, if T is substituted with a protected alcohol such as $CH_2(CH_2)_nOTHP$, where n=0–6, then the alcohol can be deprotected with aqueous acid or HCl in MeOH to yield the free alcohol. Subsequent oxidation, as with $MnO_2$ (if n =0), PCC (pyridinium chlorochromate: E. J. Corey, J. W. Suggs Tet. Lett., 1975, 2647), pyridinium dichromate in methylene chloride (E. J. Corey, G. Schmidt Tet. Lett., 1979, 399), Swern oxidation using DMSO and trifluoroacetic anhydride (K. Omura, A. K. Sharma, D. Swern, J. Org. Chem., 1976, 41, 957), Dess-Martin Periodinate oxidation (D. B. Dess, J. C. Martin, J. Org. Chem. 1983, 48, 4156 and J. P. Burkhart, N. P. Peet, P. Bey, Tet. Lett. 1988, 29, 3433) or a Bobbitt oxidation using 4-acetylamino- 2,2,6,6-tetramethylpiporidinyl-1-oxyl and toluenesulfonic acid (Z. Ma, J. M. Bobbitt, J. Org. Chem., 1991, 56, 6110) affords aldehyde (35). An amine can be protected, for example with 3,4-dimethoxybenzyl groups. Thus a carboxylic acid can be converted into its corresponding bis(3,4-dimethoxybenzyl)amine amide by coupling methods familiar to one skilled in the art. Subsequent hydrogenation or acid cleavage yields amide (36) (M. I. Jones, C. Froussios, D. A. Evans J. Chem. Soc. Chem. Comm., 1976, 472,). A nitro group is a latent amino functionality. Thus $R^{29'}=NO_2$ can be reduced by a variety of methods familiar to one skilled in the art, the easiest of which is simple hydrogenation over a noble metal catalyst to yield an amine. Subsequent refluxing with ethyl formate in an inert solvent yields formamide (37). $R^{29'}=S-C_vF_{2v+1}$ may be oxidized by one equivalent of hydrogen peroxide to yield sulfoxide (38) (r=1) or with excess peroxide to yield sulfone (38) (r=2) (R. L. Shriner, H. C. Struck, W. J. Jorison J. Am. Chem. Soc., 1930, 52, 2066; O. Hinsberg Chem. Ber. 1910, 43, 289). $R^{29'}=S-C_vF2v+1$ may be synthesized via $S_N2$ displacement chemistry by a sulfur nucleophile with an activated leaving group on the perfluoroalkyl group (L. M. Yagupolskii, et al. Synthesis 1978, 835). A variation of the preceding is an electochemical $S_N2$ displacement to yield S-perfluoroalkyl compounds (J. Pinson, J.-M. Saveant J. Am. Chem. Soc. 1991, 113, 6872). Another synthesis would be via reduction of the corresponding perfluoroalkylsulfone, with, for example, diisobutylaluminum hydride (Gardner, et al. Can. J. Chem. 1973, 51, 1419). Alkylsulfones are readily available from $S_N2$ displacement chemistry by sulfinic acid salts (Meek and Fowler J. Org. Chem. 1968, 33, 3422), in this case perfluoroalkylsulfinic acid salts. If the sulfide is directly attached to T, then a Friedel-Crafts reaction can be used to directly attach the perfluoroalkylsulfur group to T using $C_vF_{2v+1}$-S-Cl in the presence of $SnCl_4$ (A. Hass, V. Hellwig Chem. Ber. 1976, 109, 2475). This product in turn can be oxidized to the corresponding sulfoxides and sulfones, selectively. Perfluoroamide (39) may be made from the corresponding deprotected carboxylic acid as shown by diimide coupling methods familiar to one skilled in the art. $R^{29}=-CO-C_vF_{2v+1}$ and $O-\!\!-\!\!-C_vF_{2v+1}$ must be assembled before $L^1$, the linkage to the imidazole, is formed. For the other $R^{29}$ groups, one has the option of preassembling the side-chain before $L^1$ is formed or after it is formed. The $R^{29}=-CO-C_vF_{2v+1}$ and $-O-C_vF_{2v+1}$ groups can be prepared easily from commercially available starting materials, the procedures of which are familiar to one skilled in the art.

For example, a perfluoroalkanoyl-arene or -heteroarene may undergo Friedel-Crafts alkylation with $Cl(CH_2)_nCl$ to yield synthesis (Moroz and Schvartsberg *Russ. Chem. Rev.* 1974, 43, 679).

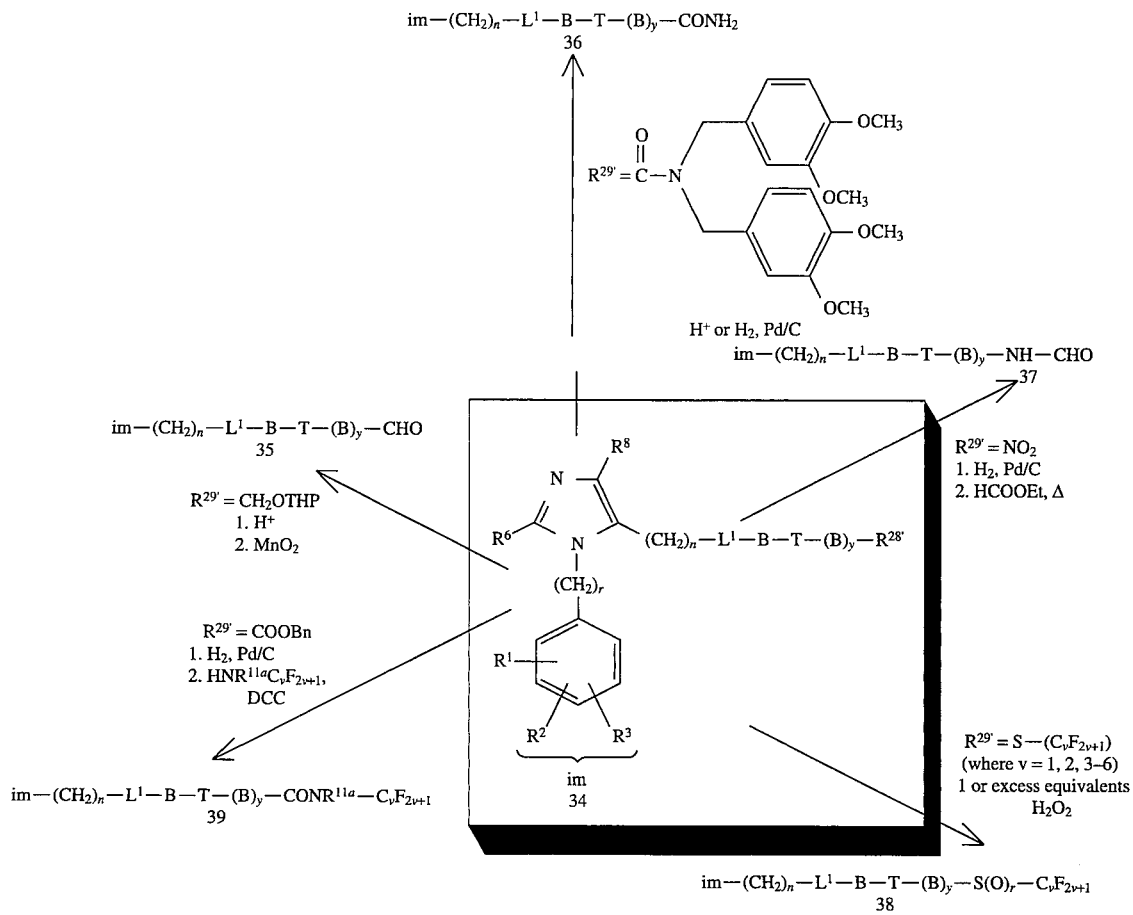

$Cl-(CH_2)_n-T-(B)_y-COC_vF_{2v+1}$. This in turn may be elaborated by any of a number of methods previously shown to yield imidazole (34) where $R^{29'}=R^{29}=-CO-C_vF_{2v+1}$. The same is true for elaborating perfluoroalkyloxy-arene or -heteroarene to $R^{29'}=R^{29}=-O-C_vF_{2v+1}$.

Grignard reagents will react with anhydrides of perfluoroalkanoic acids to yield perfluoroalkylketones (United Kingdom Patent, number 2,210,881, issued to Imperial Chemical Industries). Friedel-Crafts acylation of perfluoalkanoyl species directly onto T will also yield perfluoroalkanoyl ketones attached directly to T (T. R. Forbus, Jr. *J. Org. Chem.* 1979, 44, 313; J. W. Harbuck, H. Rapaport *J. Org. Chem.,* 1972, 37, 3618). Perfluoroalkoxyhalides will add across alkenes to yield perfluoroalkyl haloalkyl ethers (O. Lerman, et al. *J. Org. Chem.* 1980, 45, 4122; D. H. R. Barton, et al. *J. Chem. Soc. P. I,* 1977, 2604; L. R. Anderson *J. Org. Chem.* 1970, 35, 3730). Subsequent removal of the chlorine with tribuyltin hydride with a radical initiator will yield the perfluoroalkyl ether, familiar to one skilled in the art. If fluorine (or chlorine, for that matter) was used in the perfluoroalkoxyhalide, then subsequent dehydrofluorination with base followed by hydrogenation over a noble metal catalyst will yield the perfluoroalkyl alkyl ether, by procedures familiar to one skilled in the art. The perfluoroalkoxy group may be directly attached to T via the Ullmann ether When A is $-(CH_2)_n-L^1-(T)-(B)_y-X^2-(B)_y-R^{28}$ (subheading (e) of A in the scope of this application) then A may be synthesized by simply taking carboxylic acid (2) and coupling it with $HO-(T)-(B)_y-X^2-(B)_y-R^{28}$ to yield $L^1=-CO_2-$. This coupling is carried out via diimide coupling methods familiar to one skilled in the art (N,N-dicyclohexylcarbodiimide). Another way is via conversion of the carboxylic acid group of (2) to an acid chloride which can be reacted with the metal alkoxide of $HO-(T)-(B)_y-X^2-(B)_y-R^{28}$ formed from reaction with NaH or KH in DMF or another inert solvent, or with the free alcohol $HO-(T)-(B)_y-X^2-(B)_y-R^{28}$ using Schotten-Baumann conditions discussed previously. Likewise, the same procedures can be used with $HNR^{11a}-(T)-(B)_y-X^2-(B)_y-R^{28}$ to yield $L^1=-CONR^{11a}-$. Procedures in Schemes 3–6 can be used to synthesize $A=-(CH_2)_nNR^{11a}CO_2-(T)-(B)_y-X^2-(B)_y-R^{28}$ and $-(CH^2)_n-NR^{11a}CONR^{11b}-(T)-(B)_yX^2-(B)_y-R^{28}$. Of course, as in Scheme 3, the synthesis of the side-chain can also be performed stepwise if $X^2$ can be formed via condensation reactions as was discussed earlier. If $X^2$ cannot be formed by condensation reactions as when it is a ketone, ether, or thioether, then the syntheses of these side-chains follows basically the pathway described in Scheme 7. This is true for all of the $X^2$ containing side-chains described in the scope and listed under A.

Removal of $X^2$ from A subheading (e), the side-chain which was previously discussed above, leads to the side-chain described under A subheading (f), or namely —$(CH_2)_n$-$L^1$-(T)-$(B)_y$-$R^{28}$. This side-chain may be synthesized by the procedures described for A when A is —$(CH_2)_n$-$L^1$-(T)-$(B)_y$-$X^2$-$(B)_y$-$R^{28}$ (subheading (e)). When y=0, then any of the aryl cross-coupling reactions described previously may be used to synthesize the carbon-carbon bond between T and $R^{28}$. When y=1, then the Negishi coupling reaction may be used to synthesize the T-$CH_2$-$R^{28}$ unit. One can also make them from the corresponding ketones by simply reducing the ketone to the methylene via hydrogenation over palladium on carbon. For y>1, one may employ the Wittig reaction (familiar to one skilled in the art) to make the corresponding biaryl, or biheteroaryl or aryl-heteroaryl substituted alkenes which can be reduced to the corresponding alkyl to yield the T—$(CH_2)_n$-$R^{28}$ unit.

Removal of $R^{28}$ from the side-chain described in A, subheading (e), leads to the side-chain described under A subheading (g), or namely —$(CH_2)_n$-$L^1$-(T)-$(B)_y$-$X^2$-B. Here the synthesis is basically the same as described in A subheading (e).

A is —$(CH_2)_n$-$L^1$-($CR^{19}R^{20}$)-D-$(T)_y$-$(B)_y$-$X^3$—$(B)_y$-$R^{28}$ (subheading (h)) can be synthesized by the methods described in Schemes 9 and 10.

Scheme 9 describes the synthesis of D=alkenyl where the double bond is directly connected to $CR^{19}R^{20}$. A similar reaction sequence employing a Wittig reaction can be used to synthesize alkenes where the double bond is not connected directly to the $CR^{19}R^{20}$ methylene group. Only the appropriate aldehyde (analog of (43) must be used to place the double bond where necessary.

The synthetic scheme begins with the synthesis of (40). If $X^3$ cannot be made from condensation reactions as described previously, then $X^{3'}$ of (40) will be equal to $X^3$—$(CH_2)_y$-$R^{28}$. One may use the reaction sequences described in Scheme 7 to make these compounds. If $X^3$ can be made via condensation reactions, then a suitable precursor, $X^{3'}$ is present instead to make the synthesis easier. However, given the nature of the manipulations, sometimes the entire side-chain may be used where $X^3$-$(CH_2)_y$-$R^{28}$ is present instead of $X^{3'}$ and $X^3$ is made from condensation readtions. It is up to one familiar in the art to decide when to procede with the entire side-chain, or when to use a precursor containing $X^{3'}$.

Compound (40) may be synthesized by a number of routes, only some of which are disclosed in Scheme 9. For example, if n'=0 and y=1 of $(T)_y$, then the methanol side-chain may be alkylated onto the aryl group T (or heterocyclic group) by the methods shown using formaldehyde or its equivalents, for example paraformaldehyde (G. Olah Scheme 9

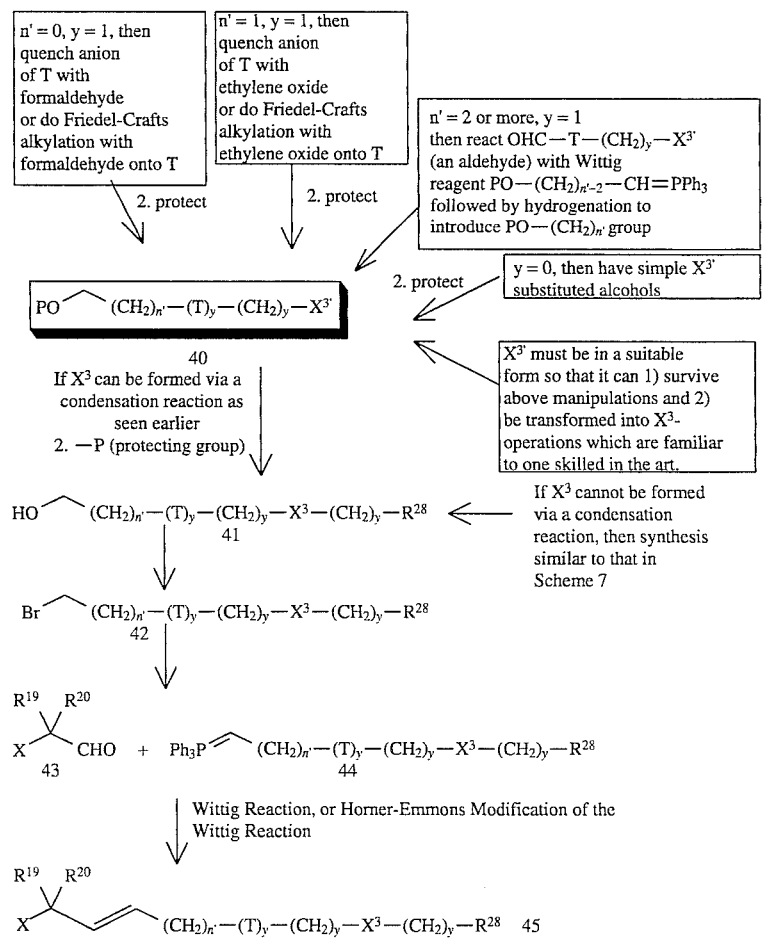

"Friedel-Crafts and Related Reactions," Interscience, New York, (1963) volume 2, pp. 597–640; N. S. Narasimhan, R.

S. Mall, B. S. Kulkarni *Tet. Lett.*, 1981,2797). When n'=1, then ethylene oxide or its equivalents may be used as shown in Scheme 9 (J. March "Advanced Organic Chemistry," Wiley-Interscience, 1985, 3rd ed., p. 480; H. A. Patel, D. B.

piece, both of which can be constructed by the chemistry mentioned in Scheme 9 and elsewhere in this disclosure.

The synthetic sequences leading to the incorporation of an alkynyl side-chain are summarized in scheme 10.

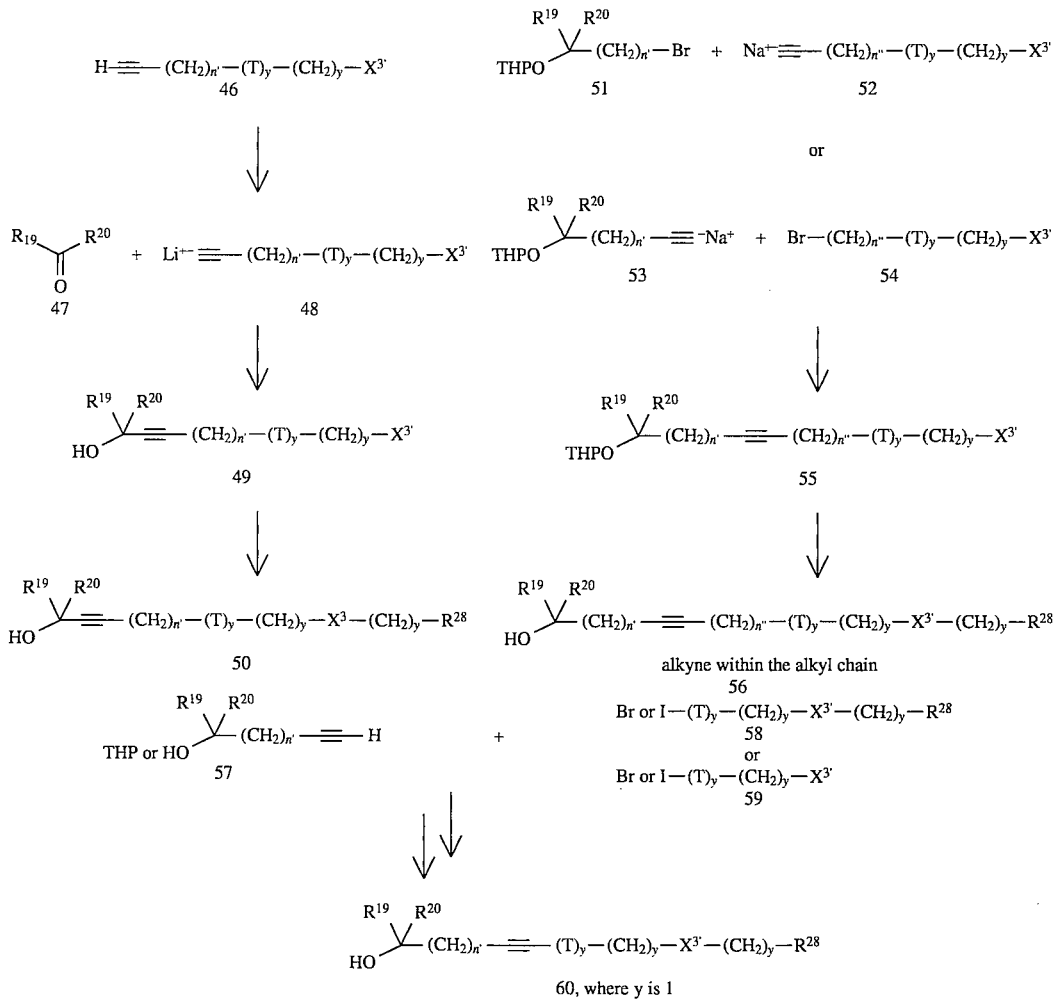

MacLean *Can. J. Chem.* 1983, 61, 7). When n'=2 or more, then the appropriate alkyl side-chain may be attached via a Wittig reaction (to make an intermediate alkene) followed by reduction to the alkane. If them is no T group (y=0), then one has simple $X^{3'}$ substituted alcohols, many of which are commercially available. $X^{3'}$ can be N-phthalimido, —NH-CBZ, carboxylic acid esters, —SO$_3$CH$_3$, —SO$_2$NH-t-Bu, -S-P where P is a protecting group, etc., all of which can be easily transformed later on into $X^3$ groups (or compound (41)), the transformations being familiar to one skilled in the art. The original protected alcohol is deprotected and converted to the bromide (42) as discussed elsewhere and previously. Conversion to the Wittig reagent (44) followed by reaction with aldehyde (43) (wherein X is a group suited for conversion later into L$^1$ such as a protected alcohol, halogen, a protected nitrogen, etc.) yields alkene (45) (for a summary of the Wittig reaction and the Horner-Emmons modification thereto, see J. March "Advanced Organic Chemistry," Wiley-Interscience, 1985, 3rd ed., p. 845–854). The sequence can also be reversed in that (43) could in theory be the Wittig reagent and (44) could be the aldehyde A terminal alkyne is reacted with either NaNH$_2$, Grignard reagents, or BuLi to form the metal acetylide (J. March "Advanced Organic Chemistry," Wiley-Interscience, 1985, 3rd ed., p. 545), in this case alkynyl lithium (46) using n-BuLi. Reaction of this anion with ketone or aldehyde (47) yields alcohol (49) (see Ziegenbein in Viehe, "Acetylenes" Marcel Dekker, New York, 1969, pp. 207–241; Ried, *Newer Methods Prep. Org. Chem.*, 1968, 4, 95). If $X^3$ can be formed via condensation reactions, then a suitable latent functionality $X^{3'}$ can be used instead as discussed previously. Subsequent elaboration yields $X^3$-containing alcohol (50). This alcohol may be esterified with im-(CH$_2$)$_n$-COOH (2) to yield sidechain A, subheading (h) where D is alkynyl. Likewise, as discussed previously to some extent, alcohol (49) may be esterified with carboxylic acid (2) followed by elaboration to the $X^3$-containing side-chain denoted in (50). Esterification procedures are familiar to one skilled in the art. However, one may use a Mitsunobu-type procedure for reacting alcohols (49) and (50) with carboxylic acid (2) under very mild conditions (O. Mitsunobu Synthesis 1981, 1) to yield the side-chain described in A, subheading (h), where D is alkynyl.

If the alkyne is not connected directly to $CR^{19}R^{20}$, but is found somewhere in the middle of the alkyl chain, then it may be synthesized by the route depicted in going from compounds (51) to (56). The metal acetylide (52) (in this case we have arbitrarily chosen sodium as the metal), may be alkylated with bromide (51). The opposite may also be done as shown with acetylide (53) reacting with bromide (54) to form acetylene (55). Intermediate (55) can then be deprotected and coupled to carboxylic acid (2). Or first, the $X^{3'}$ of (55) is elaborated to $X^3$, and then the alcohol deprotected to yield (56) which can be coupled to carboxylic acid (2) in a manner similar to that used for (50). In all of these syntheses, if $X^3$ cannot be formed by condensation reactions ($X^3$=CO, S,O, etc.) then the fully elaborated and protected (if necessary) side-chain must be used. Finally, if the acetylene portion is connected directly to T (y is 1), then the synthesis follows that of going from compound (57) to (60). Thus, acetylene (57) is coupled in the presence of a palladium catalyst to aryl or heteroaryl iodide or bromide (58) or (59) to yield the aryl or heteroaryl acetylene coupled product (W. Tao, S. Nesbitt, R. F. Heck *J. Org. Chem.* 1990, 55, 63; A. Walser, et al., *J. Med. Chem.* 1991, 34, 1440; T. Sakamoto, M. An-naka, Y. Kondo, H. Yamanaka *Chem. Pharm. Bull.* 1986, 34, 2754; N. A. Bumagin, V. V. Bykov, I. P. Beletskaya *Izv. Akad. Nauk. SSSR. Ser. Khim.* 1990, 2665; M. A. De la Rosa, E. Vlarde, A. Guzman *Syn. Comm.* 1990, 20, 2059;Y. Kondo, H. Yamanaka *Chem. Pharm. Bull.*, 1989, 37, 2933. Deprotection of the alcohol yields (60) which can be esterified as previously discussed.

Compounds where $L^1$ is amide, carbamate and urea may be made as discussed in Schemes 2–6 using the intermediates in Schemes 9 and 10.

Side-chains described in A, subheadings (i) through (o) may be made by the procedures described in Schemes 9 and 10 together with those mentioned in the previous discussion in this application.

Side-chains described in A, subheading (p), namely —$(CH_2)_n$-$L^2$-B-$(T)_y$-$(B)_y$-$X^2$-$(B)_y$-$R^{28}$, where $L^2$ is a ketone carbonyl ($L^2$=CO) may be synthesized by the methods shown in Scheme 11.

Scheme 11

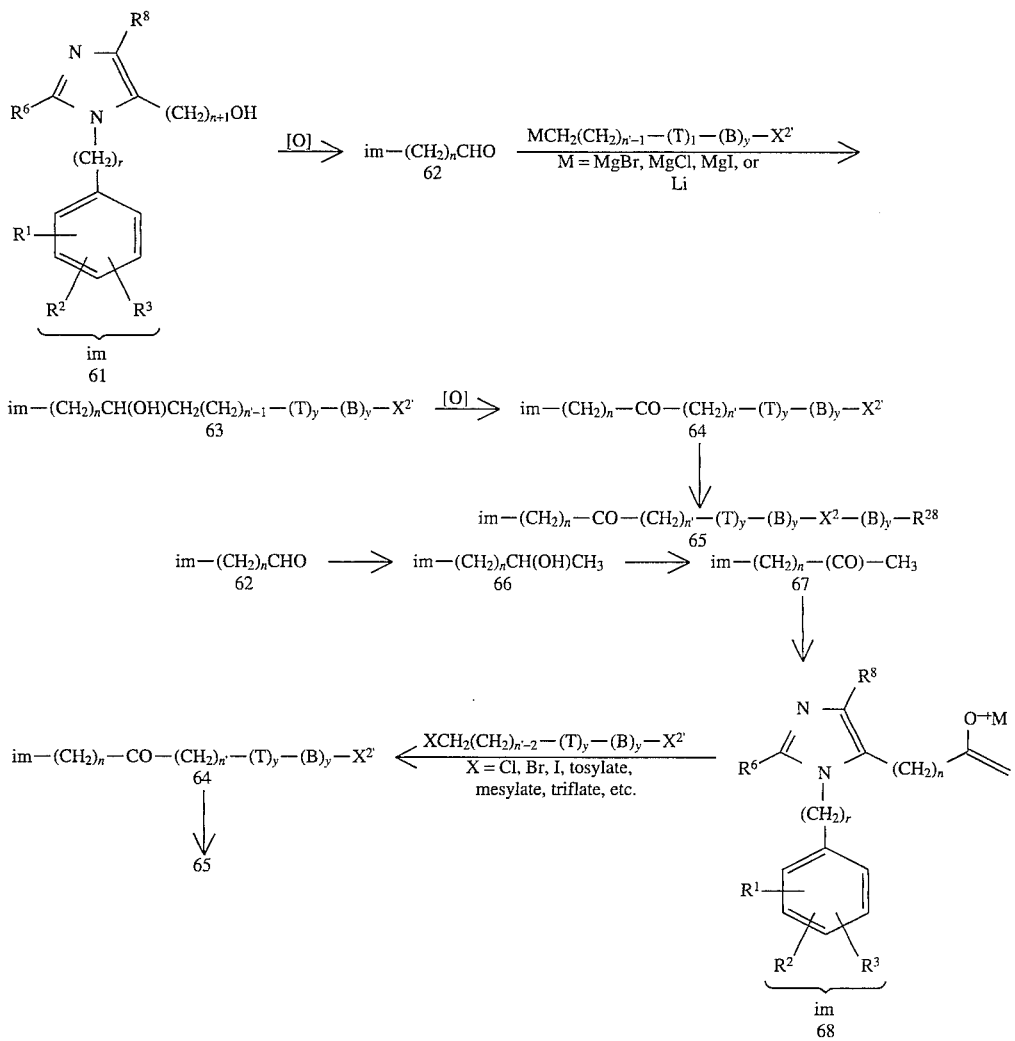

Alcohol (61) (described in U.S. Pat. No. 5,138,069) is oxidized by methods familiar to one skilled in the art to aldehyde (62). Some of these methods include $MnO_2$ if n+1=1;PCC (pyridinium chlorochromate: E. J. Corey, J. W. Suggs *Tet. Lett.*, 1975, 2647); pyridinium dichromate in methylene chloride: E. J. Corey, G. Schmidt *Tet. Lett.*, 1979, 399; Swern oxidation using DMSO and trifluoroacetic anhydride: K. Omura, A. K. Sharma, D. Swern, *J. Org. Chem.*, 1976, 4 1, 957; Dess-Martin Periodinane oxidation: D. B. Dess, J. C. Martin, *J. Org. Chem.* 1983, 48, 4156 and J. P. Burkhart, N. P. Peet, P. Bey, *Tet. Lett.* 1988, 29, 3433; and Bobbitt oxidation using 4-acetylamino-2,2,6,6-tetramethylpiperidinyl-1-oxyl and toluenesulfonic acid: Z. Ma, J. M. Bobbitt, *J. Org. Chem.*, 1991, 56, 6110. Subsequent reaction of aldehyde (62) with a Grignard reagent or a lithium reagent $MCH_2(CH_2)_{n'-1}$-$(T)_y$-$(B)_y$-$X^{2'}$ (obtained via halogen-metal exchange, for example) yields alcohol (63). Here, as discussed previously, $X^{2'}$ is a suitable precursor to the fully elaborated side-chain containing $X^2$, if $X^{2'}$ can be formed via condensation reaction chemistry. If $X^{2'}$ cannot be formed via condensation chemistry, then the whole side chain, namely $MCH_2(CH_2)_{n'-1}$-$(T)_y$-$(B)_y$-$X^2$-$(B)_y$-$R^{28}$, is used where $X^2$ is protected if necessary, with subsequent oxidation yielding ketone (65). Oxidation of alcohol (63) yields ketone (64) which may be elaborated as discussed previously to (65). Oxidation methods to the ketones include those mentioned in the synthesis of aldehyde (62).

Another method for making ketone (65) involves alkylating ketone (67) (formed in an analogous manner to ketone (64) but employing methyl Grignard or methyl lithium instead of $MCH_2(CH_2)_{n'-1}$-$(T)_y$—$(B)_y$-$X^{2'}$). Thus ketone (67) is reacted with lithium diisopropylamide (LDA) in THF at −78° C. to form enolate (68) where M=Li. This enolate is then alkylated in the same reaction flask with $XCH_2(CH_2)_{n'-2}$-$(T)_y$-$(B)_y$-$X^{2'}$ to yield ketone (64).

Side-chains described in A, subheading (p), namely —$(CH_2)_n$-$L^2$-B-$(T)_y$-$(B)_y$-$X^2$-$(B)_y$-$R^{28}$, where $L^2$ is an amide ($L^2$=—$NR^{11a}CO$—), may be synthesized as depicted in Scheme 12. Amine (9) may be reacted with acid chloride (69) under Schotten-Baumann conditions as discussed previously to Scheme 12

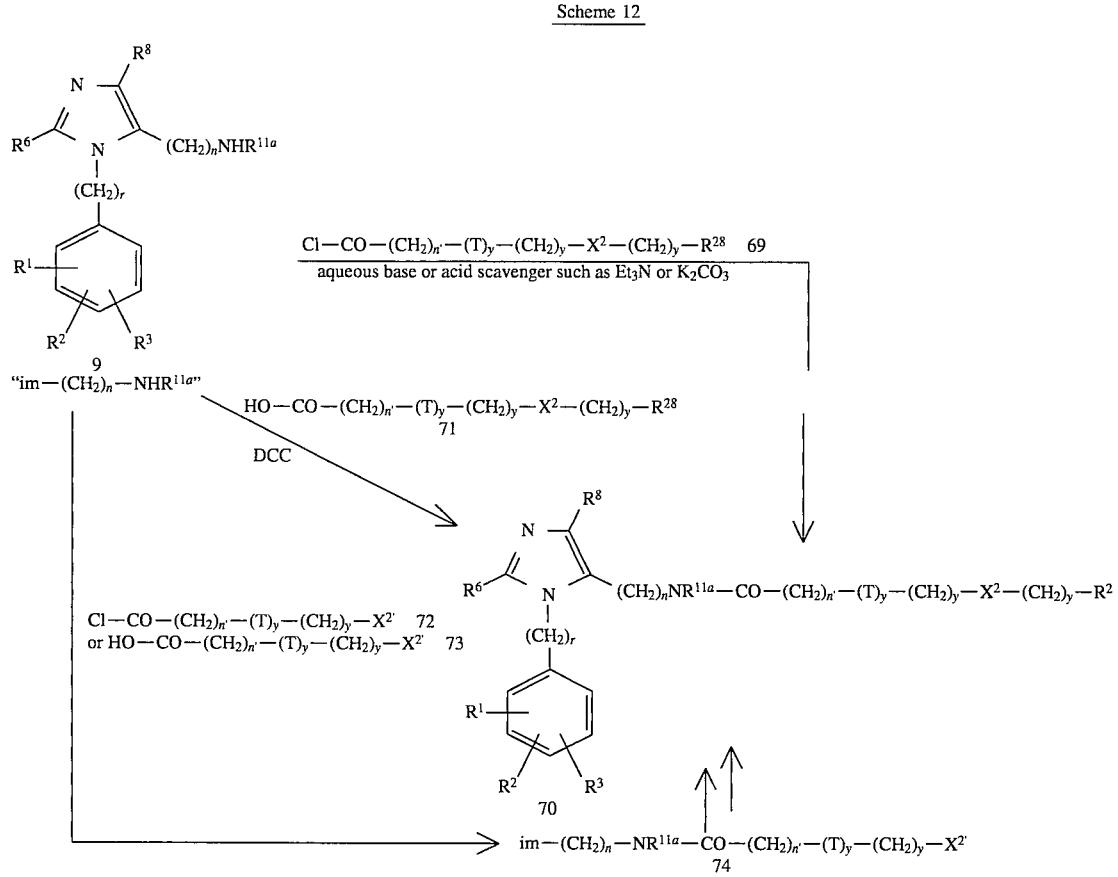

yield amide (70). Alternatively, diimide coupling of carboxylic acid (71) with amine (9) also yields amide (70), a procedure familiar to one skilled in the art, for example, the art of peptide synthesis. If $X^2$ can be made via condensation reactions, then the partial assembly of the side-chain may be carried out going through intermediates (72), (73) or (74) by the same procedures.

Scheme 13 shows the syntheses of amine (9) when n =0. Carboxylic acid (75) (prepared as in U.S. Pat. No. 5,138, 069) is decarboxylated in refluxing decane or another high boiling solvent to yield imidazole (76). Nitration under standard conditions yields nitroimidazole (77). Hydrogenation over palladium on carbon yields aminoimidazole (9a). Reductive amination to put on an $R^{11a}$ group yields imidazole (9b) (for a review on reductive amination reactions, see Klyuev and Khidekel, *Russ. Chem. Rev.*, 1980, 49, 14).

Scheme 13

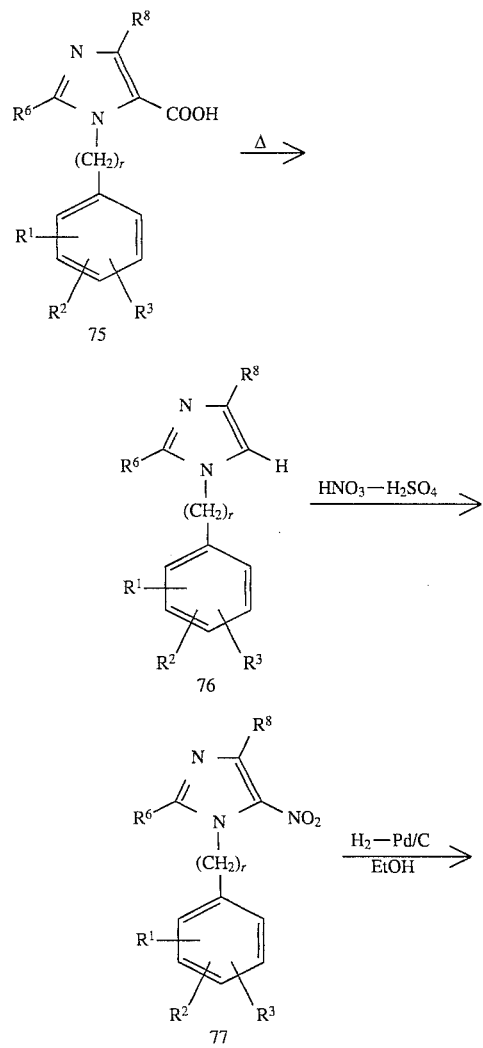

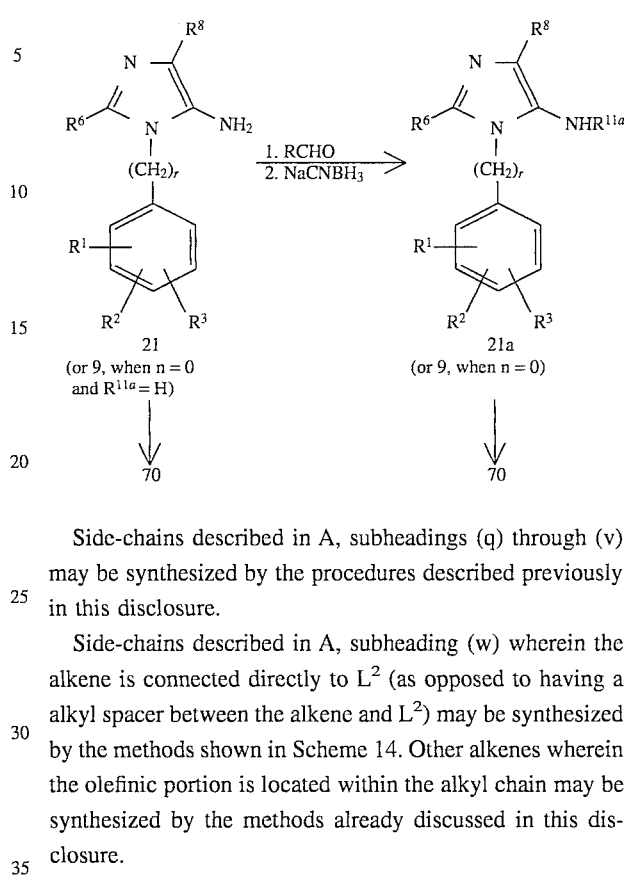

Side-chains described in A, subheadings (q) through (v) may be synthesized by the procedures described previously in this disclosure.

Side-chains described in A, subheading (w) wherein the alkene is connected directly to $L^2$ (as opposed to having a alkyl spacer between the alkene and $L^2$) may be synthesized by the methods shown in Scheme 14. Other alkenes wherein the olefinic portion is located within the alkyl chain may be synthesized by the methods already discussed in this disclosure.

Scheme 14

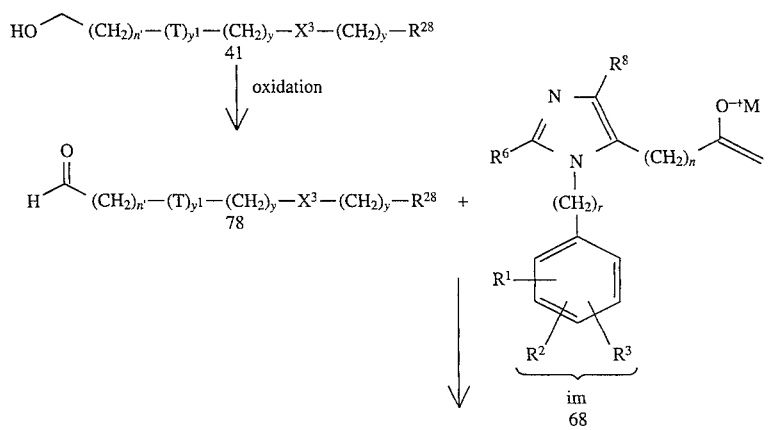

-continued
Scheme 14

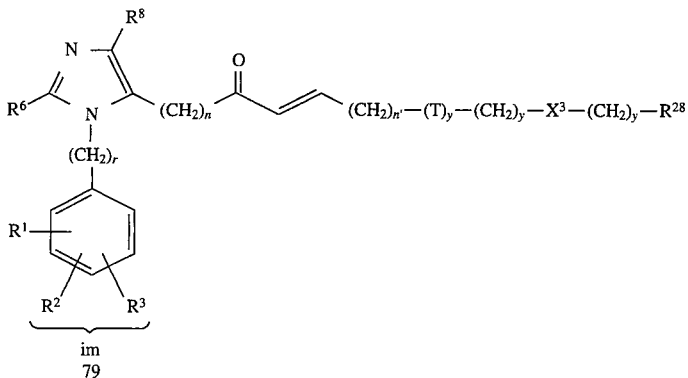

im
79

Alcohol (41) can be oxidized by a variety of methods discussed previously, such as the Swern oxidation, pyridinium chlorochromate, pyridinium dichromate, etc., to yield aldehyde (78). Reaction of this aldehyde with enolate (68) in an aldol reaction yields a,b-unsaturated ketone (79) (Aldol reaction: Nielsen and Houlihan, *Org. React.*, 1968, 16, 1-438). As discussed previously, if $X^3$ can be formed via condensation reactions, then the entire side-chain need not be fully elaborated as in aldehyde (78). Here, $X^{3'}$ can be substituted for $X^3$—$(CH_2)_y$-$R^{28}$, $X^{3'60}$ being a latent functionality, which after the aldol condensation may be converted into $X^3$—$(CH_2)_y$-$R^{28}$. Another synthesis of ketone (79) would involve a Wittig reaction between aldehyde (78) and Wittig reagent (80), mimicking the chemistry presented in Scheme 9.

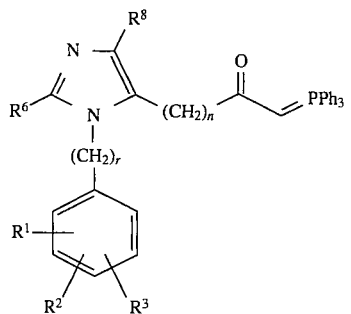

80

Compounds where $L^2$ is —$NR^{11a}CO$— may be synthesized by coupling (diimide coupling or Schotten-Baumann reaction, as discussed previously) amines 9, 9a, 21,21 a with a,b-unsaturated carboxylic acids (81) or (82) (or the corresponding acid chlorides), with subsequent elaboration if necessary.

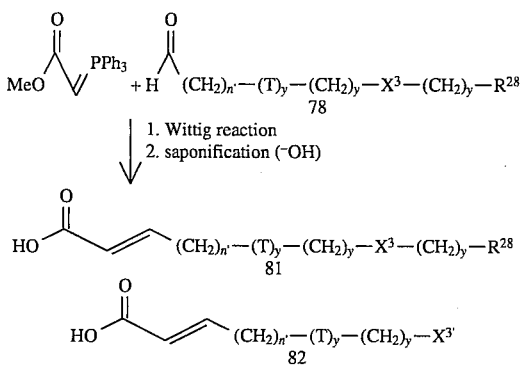

Alkynes described in A, subheading (w) wherein the alkyne portion is connected directly to the carbonyl group of $L^2$ in which $L^2$ is a ketone, may be synthesized by the methods shown in Scheme 15.

Scheme 15

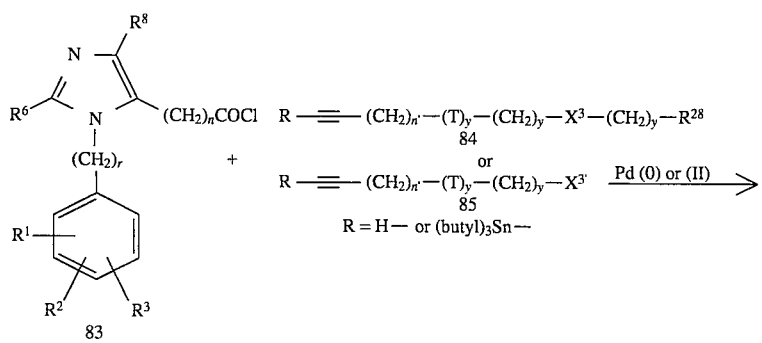

-continued
Scheme 15

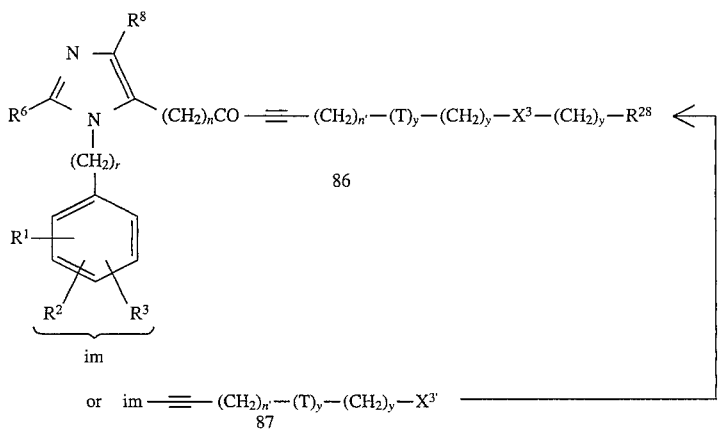

Acid chloride (83) (made from the corresponding carboxylic acid by simply stirring with thionyl chloride or oxallyl chloride in an inert solvent, procedures familiar to one skilled in the art and discussed previously) may be coupled with alkyne or alkynylstannane (84) or (85) in the presence of catalytic amounts of CuI-$(Ph_3P)_2PdCl_2$ and triethylamine (for (84)) or Pd(II) or Pd(O) complexes (for (85)) to yield alkynyl ketone (86) (Y. Tohda, K. Sonogashira, N. Hagihara *Synthesis* (1977) 777; M. W. Logue, K. Teng *J. Org. Chem.* (1982) 47, 2549). Other alkynes not directly connected to the ketone carbonyl can be synthesized by procedures already discussed previously.

Alkynes described in A. subheading (w) wherein the alkyne portion is connected directly to the carbonyl group of $L^2$ in which $L^2$ is —$NR^{11a}CO$—, may be synthesized by the methods shown in Scheme 16.

Scheme 16

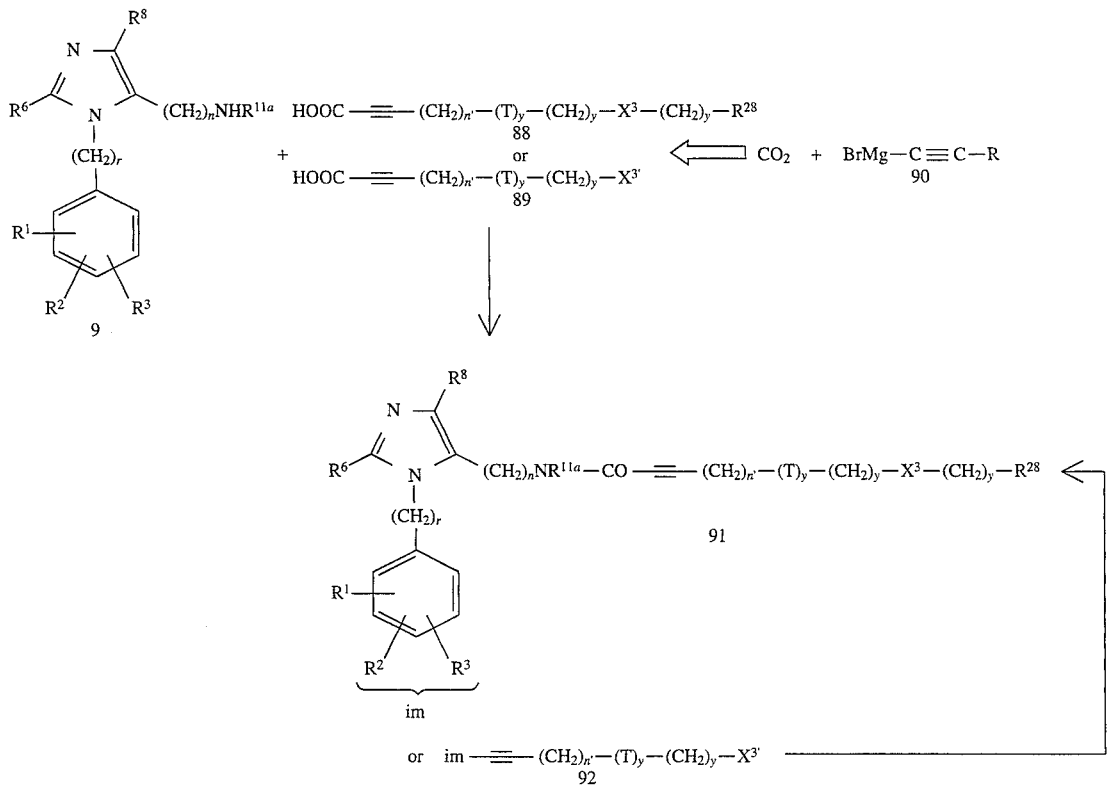

Amine (9) is coupled with alkynoic acids (88) or (89) to yield amide (91). Coupling methods include diimide, the Schotten-Baumann reaction with the corresponding acid chlorides, both of which were discussed previously. The alkynoic acids may be synthesized from the corresponding alkynes via metallation (in this case with a Grignard reagent to make alkynemagnesium bromide (90)) and quenching with carbon dioxide in an inert solvent such as THF (H.

Mayer *Helv. Chim. Acta* 1963, 46, 650; J. Wotiz, C. A. Hollingworth *J. Am. Chem. Soc.* 1956, 78, 1221). Intermediates in these metallations might have to be protected, in order for the reaction to succeed. For example, if $X^3$ is a ketone, then it must be protected, i.e., ketalized, a procedure familiar to one skilled in the art. Of course, intermediates like (92) and (87) (from Scheme 15) may be transformed to the fully elaborated side-chains as previously discussed. Compounds wherein $L^2$ is —$NR^{11a}CO$—, and the alkyne is located within the alkyl chain and not connected directly to the carbonyl group of $L^2$ may by synthesized by methods already discussed previously in this application.

Side-chains described in A, subheadings (x) through (dd) may be synthesized by the procedures described previously in this disclosure.

When A of compounds of Formula (I) contains $L^3$ (where $L^3$ is —O—, —SO—, —NH—, or —$NR^{11a}$—), imidazoles (61, 93, 95, 98, 99) can be used as starting materials in the synthesis of those side-chains. Such imidazoles can be prepared by the methods outlined in Scheme 17. Thus, treatment of alcohols (61,93) with thioacetic acid in the presence of a Lewis acid catalyst (e.g. $ZnI_2$) would provide (94), which upon saponification with hydroxide ion (e.g. NaOH or KOH) in aqueous or aqueous alcohol solution, would give thiol (95) (J. Y. Gauthier *Tet. Lett.* 1986, 15). Imidazoles (61,93) can be converted to the chloride derivatives (96) by treatment with $SOCl_2$, for example, either neat or in an inert solvent, such as benzene or dichloromethane, between room temperature and the reflux temperature of the mixture. In turn, (96) could be reacted with azide anion ($NaN_3$, $KN_3$) in a suitable sovent (DMSO, DMF, NMP), to give (97), which when reduced with $H_2$ in the presence of a catalyst, such as Pd/C, in alcohol solution, would generate amines (9, 9a, 99). These primary amines could, in turn, be converted to secondary amines (21,21a, 98) through reductive amination (a method well-known to those skilled in the art) with an aldehyde, RCHO, and a reducing agent, such as $NaCNBH_3$ or $NaBH(OAc)_3$ (A. F. Abdel-Magrid; C. A. Maryanoff; K. G. Carson, *Tet. Lett.* 1990, 31, 5595) in alcohol solution. Alternatively, these secondary amines could be generated directly from (96) by treatment with a primary amine, $R^{11a}NH_2$, in the presence of an acid scavenger (e.g. $K_2CO_3$, $Na_2CO_3$) in a suitable solvent (THF, DMF, $CH_2Cl_2$, benzene). The best route to (21, 21 a, 98) will be determined by the nature and availability of RCHO and $R^{11a}NH_2$, and the choice will be obvious to one skilled in the art.

Synthesis of imidazole (61) has been described here and elsewhere (U.S. Pat. No. 5,138,069). Imidazoles (93) may be prepared by methods shown in Scheme 18. In the cases where m of $(CH_2)_m$—OH is two or three, esterification of carboxylic acids (2, 100;U.S. Pat. No. 5,138,069) with an alcohol (e.g. MeOH, EtOH) in combination with a mineral acid (e.g. hydrochloric or sulfuric) between room temperature and the reflux point of the reaction mixture, followed by reduction with a hydride reducing agent ($LiAlH_4$, DIBAL-H, Red-Al®) in a suitable solvent (THF, ether) would yield (93, m=2, 3). On the other hand, Wittig reaction (a method known to one skilled in the art) of aldehyde (62) with a suitably protected phosphorane of the proper chain length (*Agric. Bid. Chem.* 1984, 48, 1731; *Synthesis* 1985, 12, 1161 ) would yield an olefin. Hydrogenation over a catalyst such as Pd/C, followed by removal of the protecting group with, for example, dilute mineral acid (HCl, $H_2SO_4$) or catalytic organic acid (p-TsOH, CSA) in a solvent such as THF or MeOH, would provide (93, m=3,4,5).

Scheme 17

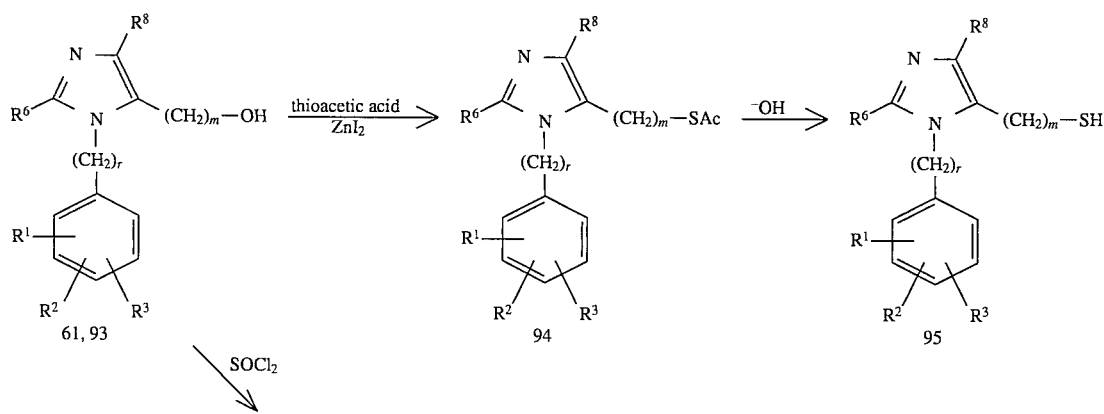

-continued
Scheme 17
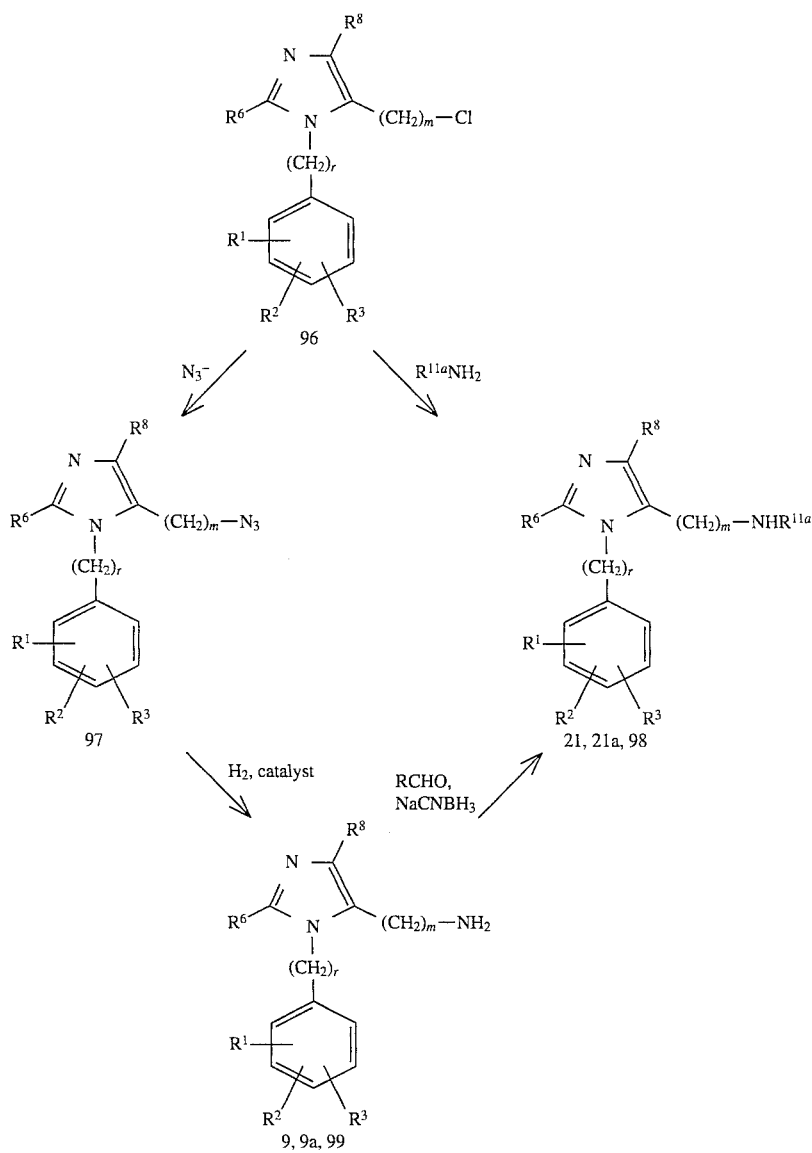
Scheme 18
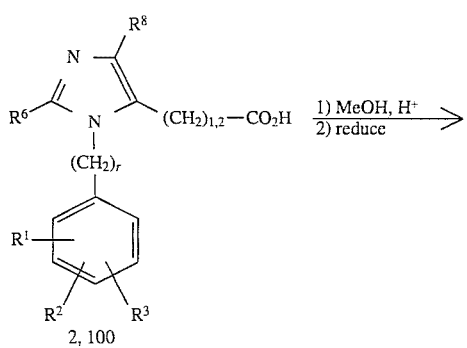
-continued
Scheme 18
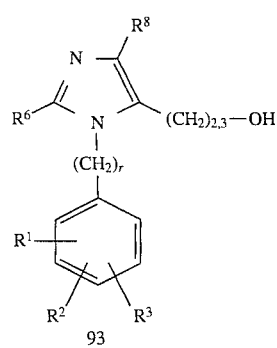

-continued
Scheme 18

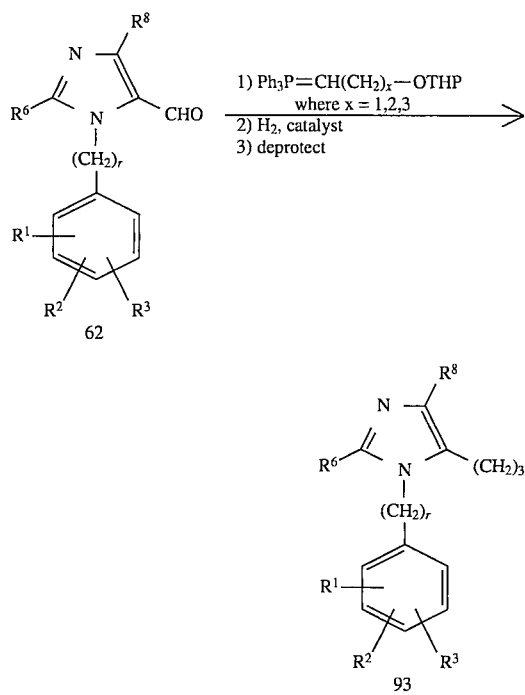

For subheadings (ee), (ff), (gg) and (hh), A may be synthesized by alkylating imidazole (61, 93, 95, 98, 99) with X—(CH$_2$)$_{n'}$-(T)$_y$—(CH$_2$)$_y$-X$^2$—(CH$_2$)$_y$-R$^{28}$, as in the specific case of (ee), as shown in Scheme 19. Likewise, for subheadings (if), (gg) and (hh), alkylation with the requisite alkylating agent would give A. In this alkylation, X would be a halide or sulfonate group, and the reaction would be run in an inert solvent such as THF, DMF, or DMSO between room temperature and the reflux temperature, in the presence of an acid scavenger, (e.g. Et$_3$N or K$_2$CO$_3$) or strong base (e.g. NaH or KH). In some cases, it may prove advantageous to add a source of iodide ion to the reaction (e.g. NaI, KI, or n-Bu$_4$N$^{+/-}$). Such cases would be obvious to one skilled in the art. After the alkylation, to convert L$^{3'}$=—S— to L$^3$=—SO—, an oxidant such as hydrogen peroxide (R. L. Shriner; H. C. Struck; W. J. Jorison *J. Am. Chem. Soc.*, 1930, 52, 2066) or sodium periodate (B. M. Trust, R. A. Kuns *J. Org. Chem.* 1974, 39, 2648), or an organic peracid (H. Richtzenhain; B. Alfredson *Chem. Ber.* 1953, 86, 142) or bromine/aqueous potassium hydrogen carbonate (J. Drabowicz; W. Midura; M. Mikolajczyk *Synthesis*, 1979, 39) can be used. As described previously in this disclosure, when X$^2$ in (ee) and (gg) is a condensable function, it may not be necessary to elaborate the entire side chain prior to alkylation.

Scheme 19

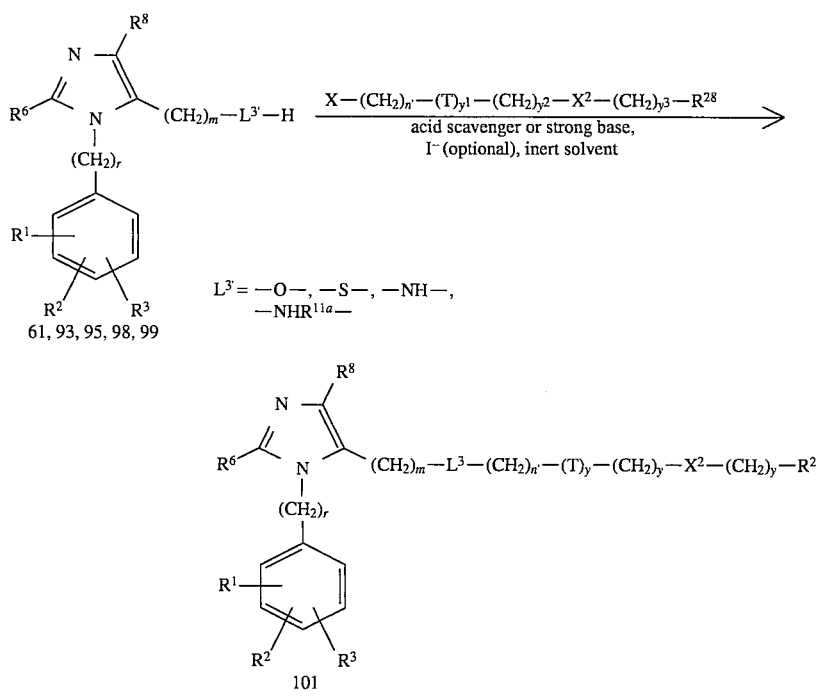

A general method for the preparation of A groups (ii), (jj), and (kk) is shown in Scheme 20 for the particular case of (ii). Alkylation of H-L$^{3'}$-T-(B)y-X$^2$-(B)y-R$^{28}$ (where H-L$^{3'}$ represents H-O-; H-S-, or H-NR$^{11a}$-) with chloride (96) in the presence of an acid scavenger or strong base in an inert solvent with or without added iodide ion, followed by oxidation (when L$^3$ is -SO-), would yield (102). When X$^2$ in (ii) and (kk) is a condensable function, it may not be necessary to elaborate the entire side chain prior to alkylation.

A possible method for preparation of A groups (ll) through (ss) is shown in Scheme 21 for the case of (ll). This method is analogous in all respects to that described above for subheadings (ee) through (hh). Following alkylation, oxidation (when L$^3$ is -SO-) would give (103). As above, when X$^6$ (subheadings (ll) and (nn)) is a condensable function or X$^7$ is present, it may not be necessary to elaborate the entire side chain prior to alkylation.

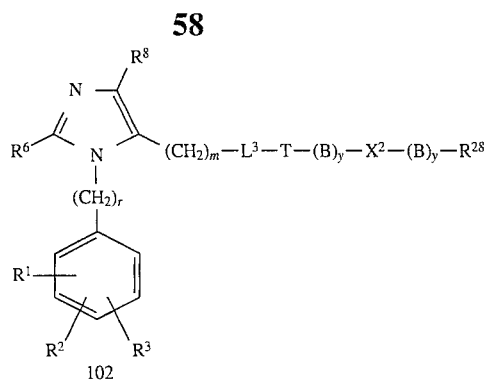

102

Scheme 21

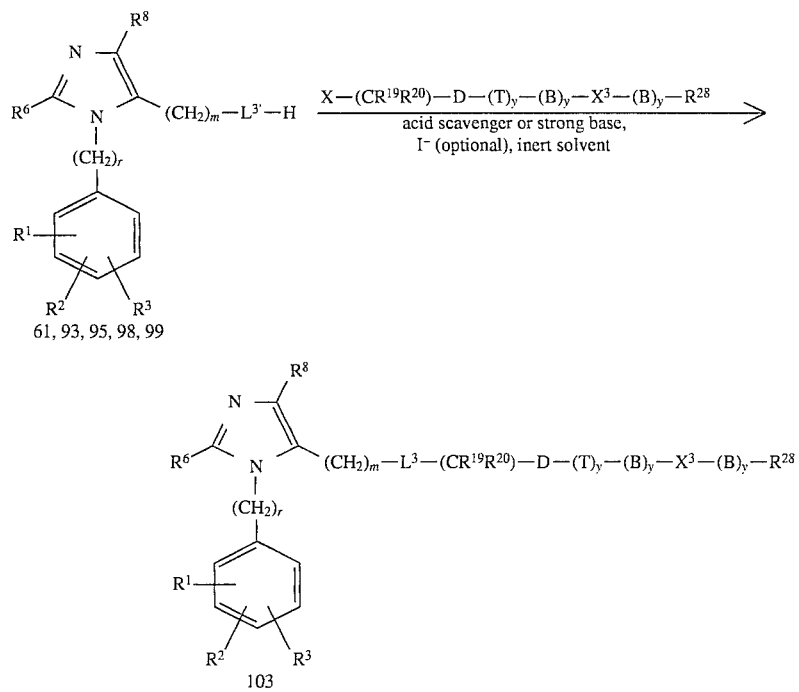

103

Side-chains described in A, subheading (tt) and (uu) may be made by the methods shown in Schemes 22 and 23.

Scheme 20

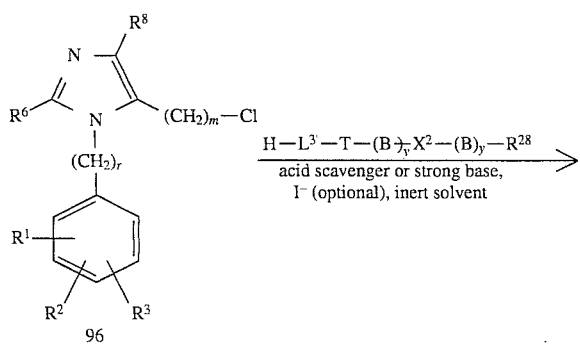

Scheme 22

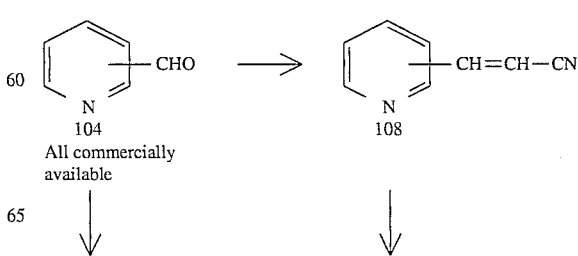

104
All commercially available 5,545,651
59
-continued
Scheme 22
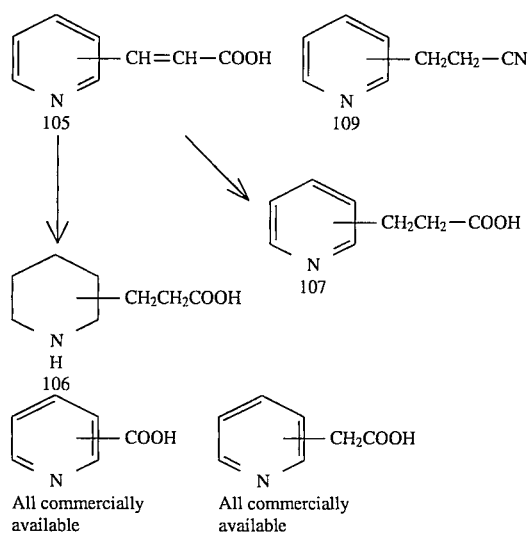
60
-continued
Scheme 22
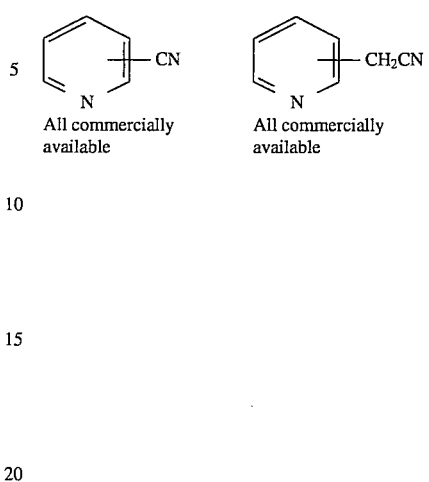
Scheme 23
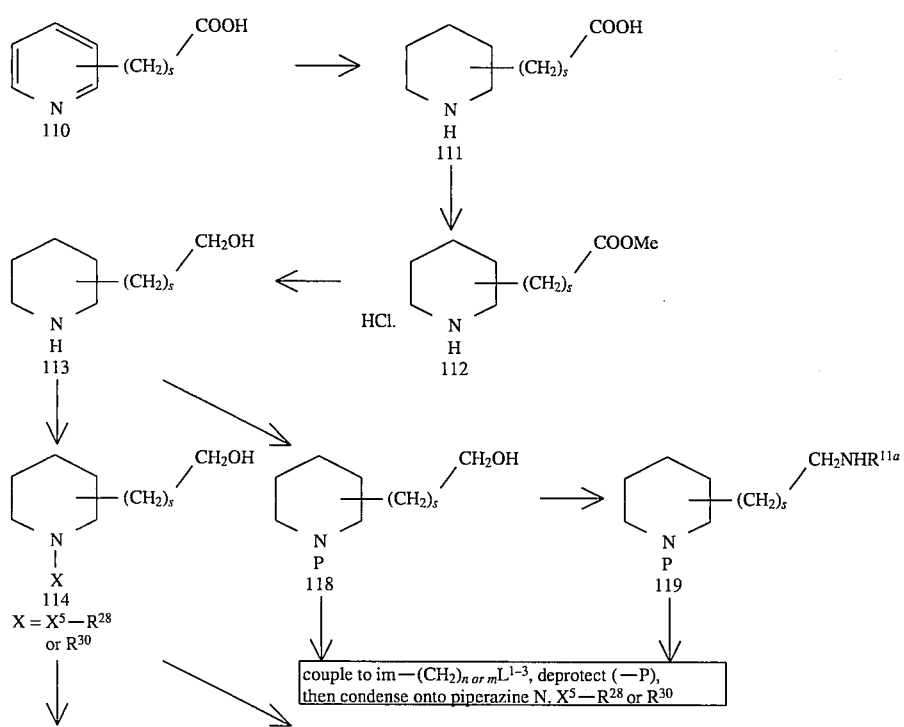

-continued
Scheme 23

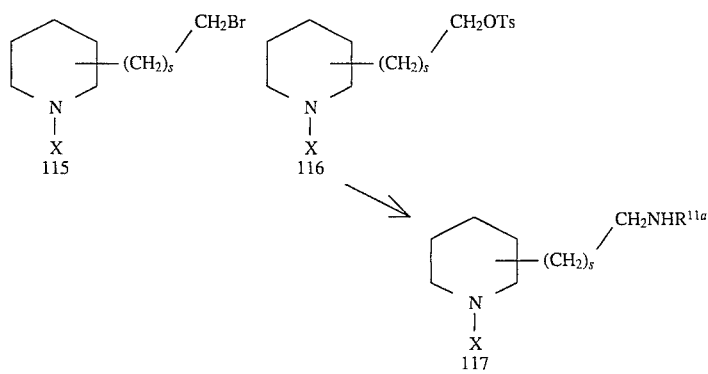

The 2-, 3-, and 4-pyridinecarboxylic acids, the 2-, 3-, and 4-pyridineacetic acids and the 2-, 3-, and 4-pyridinepropanoic acids are readily available from commercial sources or available with slight synthetic manipulation from commercial sources as shown in Scheme 22. For example, pyridinecarboxaldehydes (104) (commercially available) may undergo the Wittig reaction followed by saponification to yield pyridinepropenoic acids (105). Hydrogenation using palladium on carbon in an alcohol catalyst yields pyridinepropanoic acid (107). All of these types of reactions have been discussed previously. The pyridine alkanoic acids can then be hydrogenated with platinum oxide or rhodium on alumina (P. L. Ornstein, U.S. Pat. No. 4,968,678, issued Nov. 6, 1990) to yield the corresponding piperidine derivatives (111) (Scheme 23). Esterification by refluxing in methanol containing HCl (a procedure familiar to one skilled in the art) yields ester (112). Lithium aluminum hydride reduction yields alcohol (113) (P. L. Ornstein, ibid).

Condensing aminoalcohol (113) with the appropriately activated $R^{28}$-$X^5$ or $R^{30}$ group yields compound (114). In this step, the nitrogen is readily acylated or sulfonylated leaving the alcohol untouched, since it is more nucleophilic. For example, 4-(2-hydroxyethyl)piperidine, may be readily protected on the nitrogen exclusively with a carbamate ($X^5$=-CO-O-) such as a BOC group by simply reacting with $BOC_2O$ and triethylamine in DMF (M. E. Duggan, G. D. Hartman, N. Khle European Patent Application 512,829, published Nov. 11, 1992). Reaction of the aminoalcohol with alkyl- or arylchloroformates in the presence of an acid scavenger such as triethylamine at 0° C. also yields carbamates selectively (W. Wiegreve, et al., *Helv. Chim. Acta,* 1974, 57, 301; F. Schneider, *Helv. Chim. Acta,* 1974, 57, 434; S. Umezawa, *J. Antibiotics,* 1974, 27, 997). Amides ($X^9$=-CO-) may be made by simply stirring the amino alcohol with an appropriate ester (Y. Yamamoto, et al. *Agri. Bio. Chem.* 1985, 49, 1761) or with an acid chloride in the presence of an acid scavenger such as triethylamine at 0° C. (P. E. Sonnet et al., *J. Org. Chem.* 1980, 45, 3137) or with a carboxylic acid anhydride (D. A. Evans, J. M. Takacs *Tet. Lett.* 1980, 21, 4233; F. A. Davis, L. C. Vishwakarma *Tet. Lett.* 1985, 26, 3539). Sulfonamides ($X^5$=-$SO_2$-) may be made by stirring the aminoalcohol with a sulfonylchloride in the presence of an acid scavenger such as triethylamine at 0° C. (H. Takahashi, et al. *Chem. Pharm. Bull.,* 1991, 39, 260). Ureas ($X^5$=-CONH-) may be made by stirring the aminoalcohol with an isocyanate $R^{28}N$=C=O (J. W. Kobzina, U.S. Pat. No. 4,065,291, issued Dec. 27, 1977). Ureas ($X^9$=-CONH-) may also be made by stirring the aminoalcohol with a carbamyl chloride $R^{28}NR^{11a}COCl$ in the presence of an acid scavenger such as triethylamine at 0° C. (G. Hilgetag, A A. Martini "Preparative Organic Chemistry" John Wiley and Sons, New York, 1972, 469). The $R^{30}$ groups may be also attached to the amino group by the methods discussed above and previously using the appropriate starting material. Once again, all of these reactions selectively attach functionality to the nitrogen, but not to the alcohol.

The alcohol may be converted to a leaving group such as a tosylate or bromide or a $NR^{11a}$ group as shown by methods previously discussed elsewhere in this application. These radicals then may be attached to the $L^1$ or $L^2$ group to yield the side-chain described by A, subheading (tt) or (uu) by the same methods previously described in this application. In addition, the entire side-chain need not be elaborated before coupling it to the $L^1$ or $L^2$ group, but can be partially assembled as shown in the following discussion. Aminoalcohol (113) is selectively protected (for example, with a BOC group as described above) to yield (118) and then is coupled to the $L^1$ or $L^2$ group. Deprotection and then coupling with the activated $X^9$-$R^{28}$ or $R^{30}$ groups as previously described yields the side-chain described by A, subheading (tt) or (uu). Conversion of (118) to amine (119) by methods described previously followed by coupling to the $L^1$ or $L^2$ group, deprotection, and finally coupling with the activated $X^9$ or $R^{30}$ groups as previously described yields the side-chain described by A, subheading (tt) and (uu) wherein $L^1$=-$CONR^{11a}$-. Compounds represented by A, subheading (vv) to (ccc) may be synthesized by the procedures already described in this application from the appropriate starting material and by methods familiar to one skilled in the art.

The examples in Schemes 22 and 23 describe cases wherein v=2, or the heterocycles are all piperidines. For the pyrrolidine cases (v=1), the corresponding reactions can be performed on proline or betaproline (H. Yuki, Y. Okamoto, Y. Kobayashi *J. Polym Sci. Polym. Chem. Ed.* 1979, 7, 3867). Some starting materials, such as proline, are available in optically active form and the chirality can be carried through to the final product. If starting materials are racemic, then a resolution must be performed somewhere in the synthesis to obtain the product in enantiomeric form. Resolving methods include crystallization or chromatographic separation on a chiral column.

Schemes 24 and 25 show two ways in which the bottom phenyl ring of the molecules is attached. The first way as shown in Scheme 24 involves first, the connecting of the two phenyl rings together, in this case to form a biphenyl. This is then followed by the elaboration of A and finishing off with the elaboration of the acidic moiety, namely $R^{13}$. It is also possible to elaborate $R^{13}$ first, followed by A. It is also possible to partially elaborate A (we will refer to the precursor of A as A'), then $R^{13}$ and then finish with the final elaboration of A. All of these manipulations in relation to A have been previously described. The second way exemplified in Scheme 25 involves the alkylation of a benzyl onto the imidazole, followed by elaboration of A. Subsequent coupling of the second phenyl ring yields in this case a biphenyl system. Finally, the $R^{13}$ group is elaborated into its final form. Here as above, the A group does not have to be fully elaborated and its full elaboration can be put off to a later stage, depending on the compatability of the various groups in the molecule.

Scheme 24

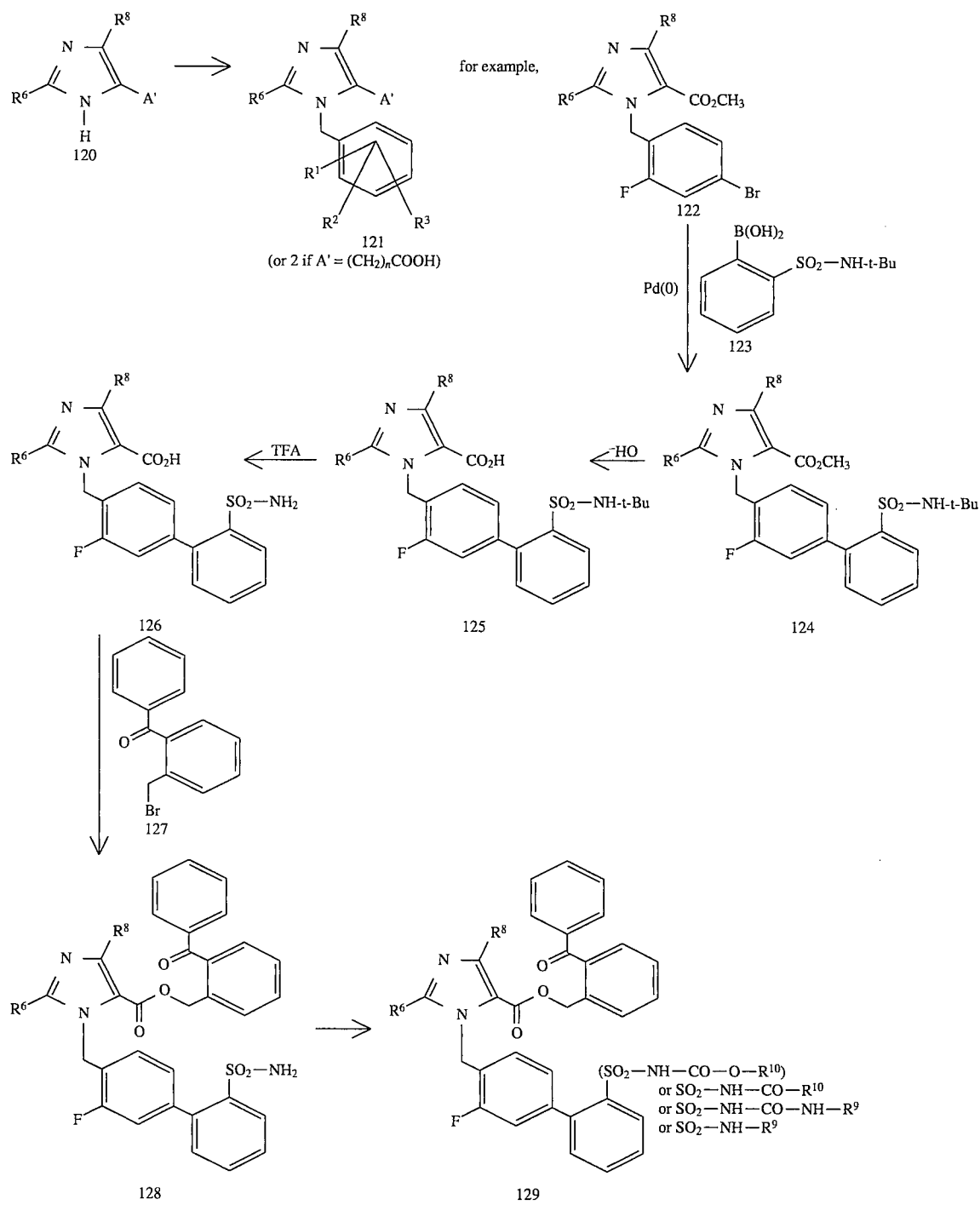

Scheme 25

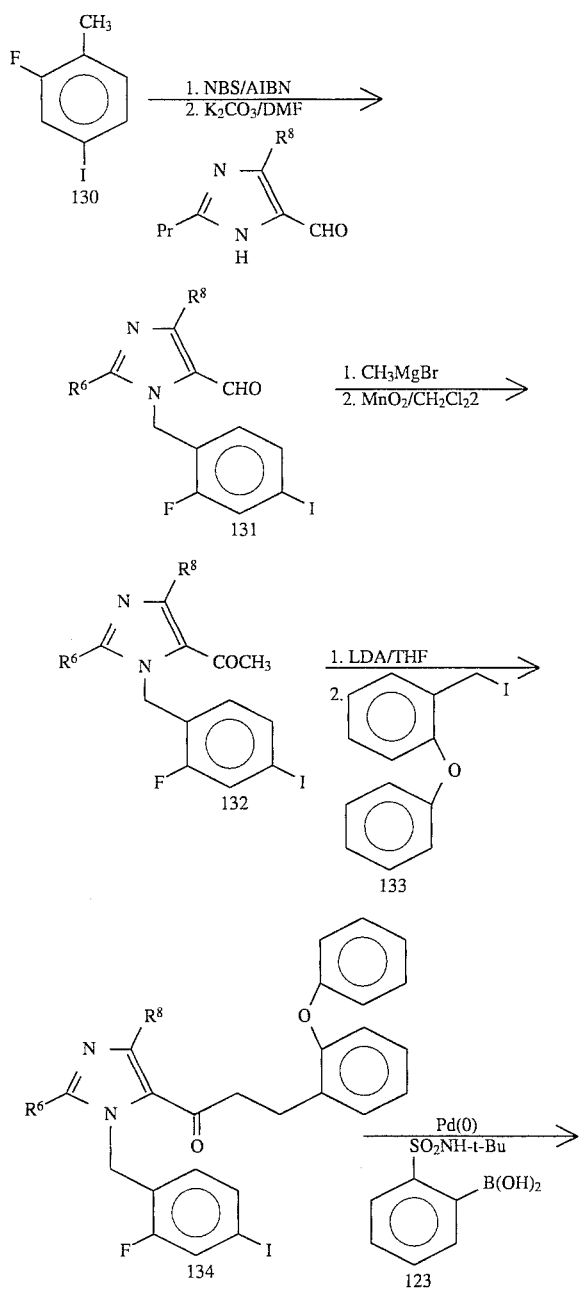

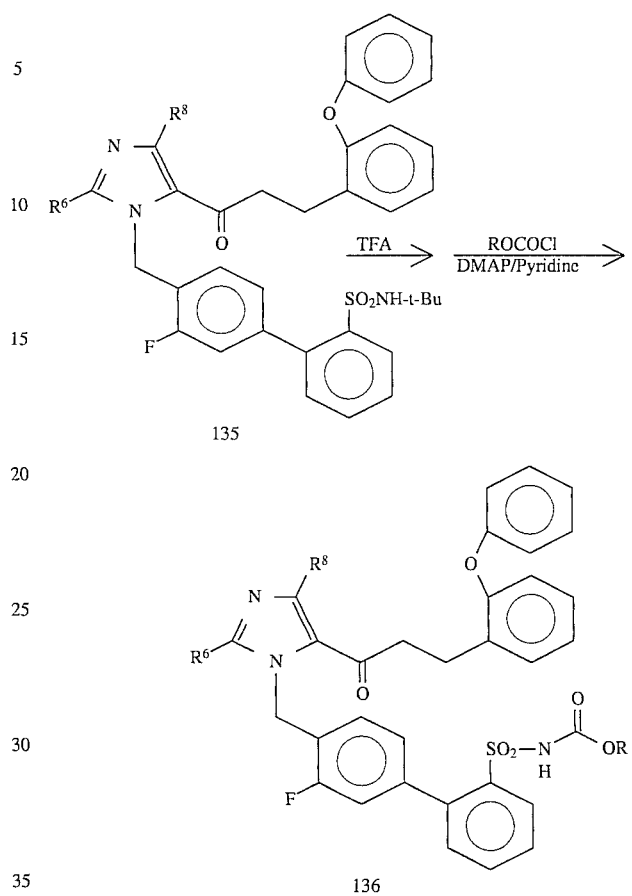

More specifically, we see in Scheme 24, that alkylation onto imidazole (120) (disclosed in U.S. Pat. No. 5,138,069, U.S. application Ser. No. 07/544557) with a benzyl halide, tosylate, mesylate, etc. in an inert solvent such as DMF in the presence of an acid scavenger such as $K_2CO_3$ yields benzylimidazole (121). The A' group can be further elaborated by methods familiar to one skilled in the art into $(CH_2)_n COOH$ to yield (2) which was seen earlier. However, for our present purposes, A' can equal $CO_2Me$ or compound (122). This ester group directs alkylation regioselectively as shown in U.S. application Ser. No. 07/544557. Suzuki coupling of bromobenzene (122) with boronic acid (123) (N. Miyaura, T. Yanagi, A. Suzuki, op. cit.) yields biphenyl (124). Note, that for simplicity, the phenylboronic acid (123) is unsubstituted but may be substituted with $R^2$ and $R^3$ groups as specified in the scope of this application. The synthesis of boronic acid (123) is shown in Scheme 26 and will be discussed later. Saponification of the ester yields (125). Removal of the t-butyl group with trifluoroacetic acid yields carboxylic acid-sulfonamide (126). Alkylation with bromide (127) in an inert solvent such as DMF in the presence of an acid scavenger such as $K_2CO_3$ yields ester (128). Sometimes, alkylation occurs both on the carboxylic acid and the sulfonamide. These two compounds are readily separated by chromatography. Finally acylation yields (129) as either a sulfonylcarbamate, acylsulfonamide, or sulfonylurea, depending on the acylating agent. For example, acylating with an alkyl- or arylchloroformate in an inert solvent such as THF or pyridine with or without the use of an activating agent such as 4-(N,N-dimethylamino)pyridine yields a sulfonylcarbamate ($SO_2$-NH-$CO_2R^{10}$). Doing the same with an acid chloride yields an acylsulfonamide ($SO_2$-NH-$COR^{10}$). Reacting sulfonamide (128) with an isocyanate yields a sulfonylurea ($SO_2$-NH-CO-$NHR^9$) ( Canadian patent application 2,058,198, published 1992/07/05, Hoechst Aktiengesellschaft). Finally, substitution with $R^9$-X where X is a leaving group yields a differently substituted sulfonamide ($SO_2$-NH-$R^9$), these substitution reactions being either $S_N2$ or aromatic or heteroaromatic substitution reactions, all of which are familiar to one skilled in the art. The synthesis of these and other carboxylic acid isosteres is summarized in a Merck patent application (European Patent Application 400974, Dec. 5, 1990).

In Scheme 25, we see that regioselective alkylation with the brominated analog of (130) onto the imidazole aldehyde yields benzylimidazole (131 ). The aldehyde directs regioselective alkylation (U.S. application Ser. No. 07/544557). Grignard additon followed by oxidation of the intermediate alcohol yields ketone (132). Deprotonation with LDA followed by alkylation with benzylbromide (133) yields (134) in which the A group is fully elaborated. Attachment of the bottom phenyl ring via Suzuki coupling (N. Miyaura, T. Yanagi, A. Suzuki, op. cit.) yields biphenyl (135). Cleavage of the t-butyl group with TFA and acylation yields sulfonylcarbamate (136). In a similar fashion, the acylsulfonamide, sulfonylurea, and differently substituted sulfonamide could have been made as described in the previous paragraph. Other carboxylic acid isosteres within the scope of $R^{13}$ can be substituted in place of the ones discussed in Schemes 24 and 25 using the Suzuki aryl coupling methodology or any other coupling strategy discussed previously employing the appropriate starting materials and the synthetic strategies outlined in Schemes 24 and 25. Again, the syntheses of these acid isosteres is discussed in a Merck patent application (European Patent Application 400974, Dec. 5, 1990). In the case where there is no bottom phenyl ring and therefore the imidazole is substituted by only a benzyl group and the benzyl group contains an acid isostere ($R^1$), then the synthetic strategy follows that of the biphenyl case with manipulations being performed in a similar fashion at A' and $R^1$ (instead of $R^{13}$).

The β-ketoamides listed in Table 3 can be prepared following the procedures outlined in Scheme 25a. Addition of vinyl Grignard to the benzylimidazole followed by oxidation of the intermediate alcohol yields the vinyl ketone. Michael addition of primary amine followed by acylation of the secondary amine with acyl chloride produces the β-ketoamide. Suzuki coupling of the aryl bromide with the boronic acid gives the biphenyl. The acylsulfonamides, sulfonylurea and sulfonyl carbamates can be made in a similar fashion as described previously in this section.

Scheme 25a

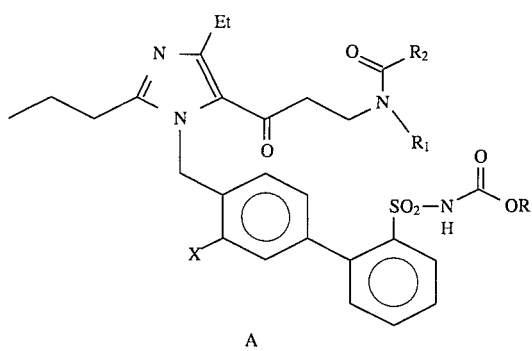

A

-continued
Scheme 25a
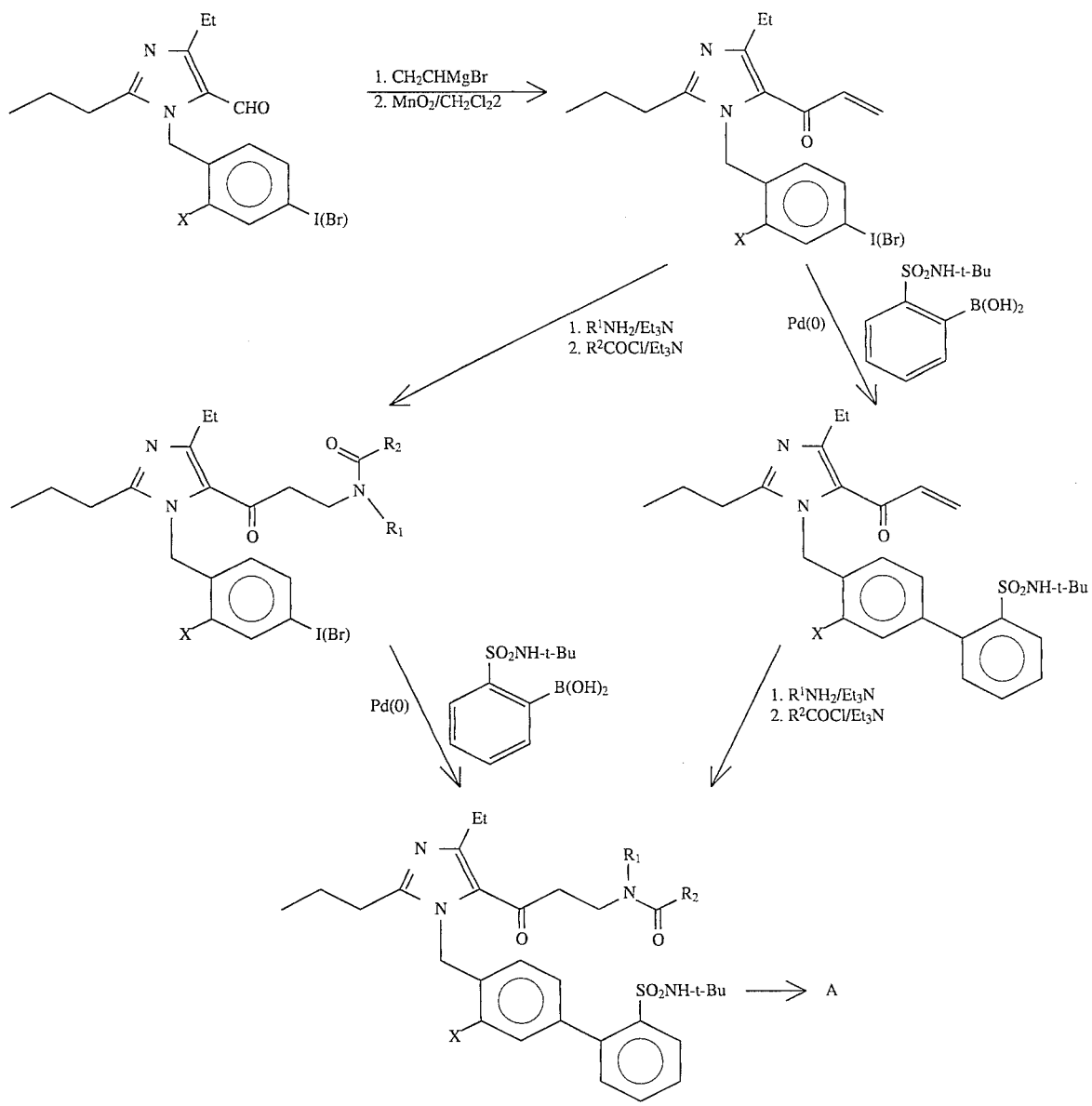
One may alkylate the imidazole nitrogen with a performed diaryl piece, such as the biphenyl moiety (37) shown in Scheme 26.
Scheme 26
-continued
Scheme 26
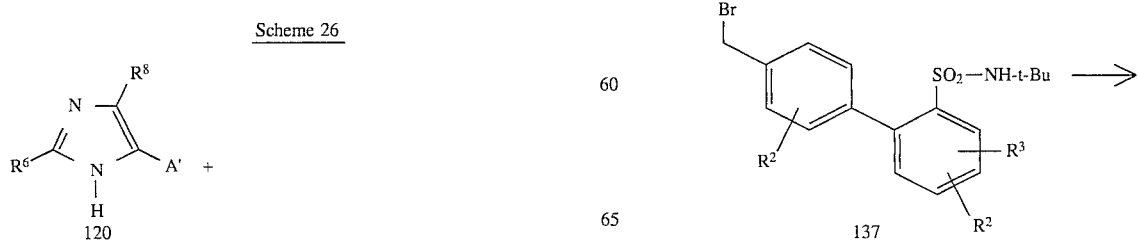

-continued
Scheme 26

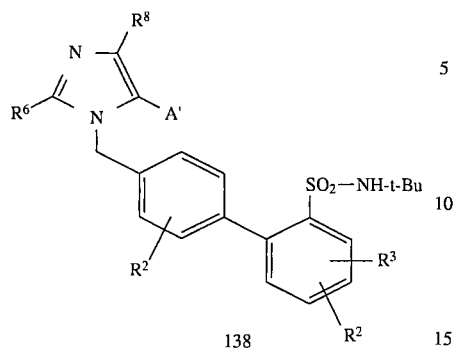

A' = CO₂Me; 124

Sulfonamidoboronic acids (140) may be prepared by ortho-lithiation of sulfonamide (139), followed by treatment with triisopropyl borate and hydrolysis, as shown in Scheme 27. The biphenyl sulfonamides (142) may be prepared as described in EP479,479 or by aromatic coupling chemistry (Suzuki coupling), shown in Scheme 27.

Scheme 27

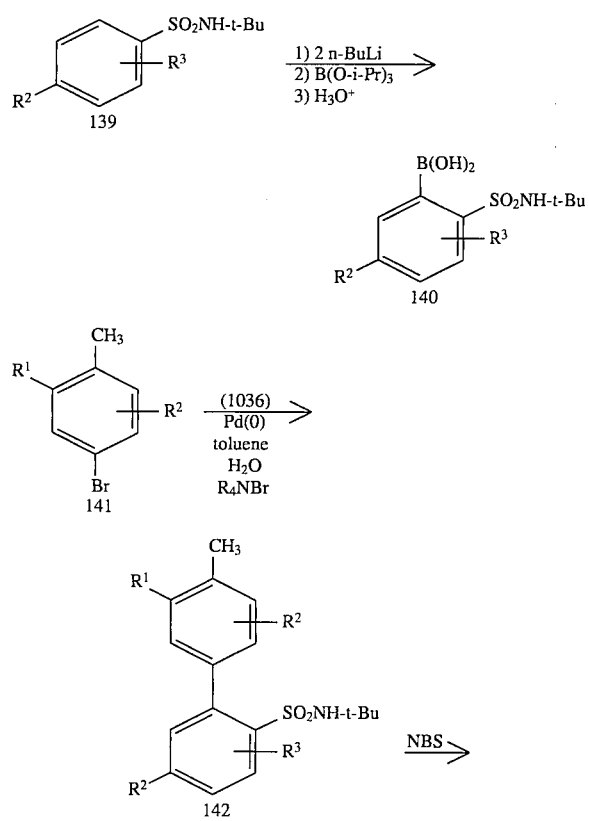

-continued
Scheme 27

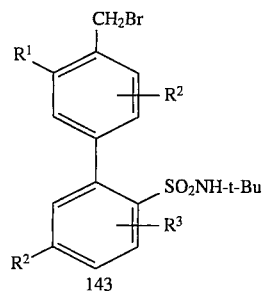

The imidazole precursors shown in Scheme 26 and elsewhere in this application may be prepared as described in U.S. Pat. Nos. 5,137,902 and 5,138,069, in PCT U.S. application Ser. No. 90/03683 and in European Application EP465,368 (see also Australian Patent AU-A-80163/91) and in U.S. application Ser. No. 07/544557, which are hereby incorporated by reference. Phenylimidazoles useful in preparing compounds of the Formula (I) where $R^8$ is phenyl can be obtained as shown in Scheme 28. Thus, phenylboronic acids, available using standard methods, can be coupled with iodoimidazoles (144) to yield phenylimidazoles (145). The boronic acids may contain substituents on the phenyl ring so as to allow convenient preparation of the compounds of the present invention where $R^8$ is a substituted phenyl.

Scheme 28

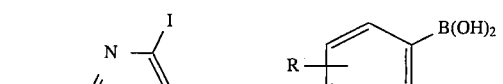

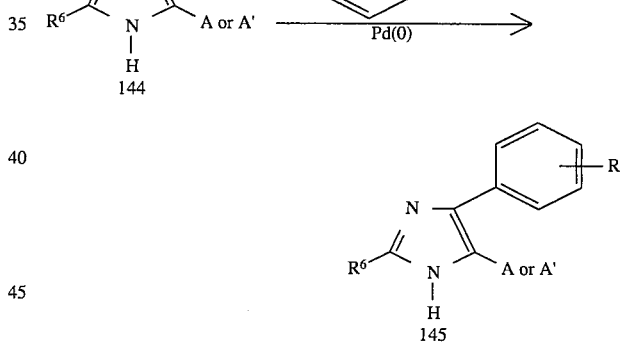

Compounds where $L^3$ is -O₂C- may be synthesized as shown in Scheme 29.

Scheme 29

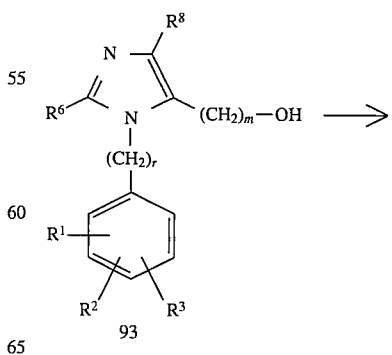

-continued
Scheme 29

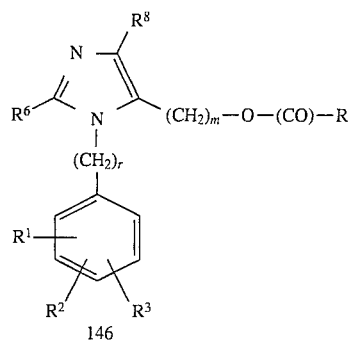

Thus, alcohol (93) may be acylated by a variety of methods familair to one skilled in the art to yield ester (146) where the R group represents any of the side-chains disclosed in A (ee) through (ss) and (vv), (ww), (bbb), and (ccc) in the scope of this application. These methods include the Schotten-Baumann reaction, carbodiimide coupling, use of carbonyldiimidazole, etc. (for a summary on esterification reactions, see J. March Advanced Organic Chemistry, 3rd ed., New York: John Wiley and Sons, pp. 348–351), which have been discussed previously. And again as discussed previously, the side-chain -$O_2$C-R may be acylated as a whole completed unit or piece-wise depending on whether $X^2$, $X^3$, $X^4$, and $X^5$ may be formed via condensation reactions.

Aryloxyacetylimidazoles of Formula (I) such as (150) can be prepared as exemplified in Scheme 30. Thus, methyl ketone (67) may be converted to the corresponding silyl enol ether using e.g. trimethylsilyl triflate/triethylamine. Bromination with NBS, followed by reaction with phenol (148) provides the phenoxyacetylimidazole (149), which may be converted to compounds of Formula (I) as described in Scheme 25.

Scheme 30

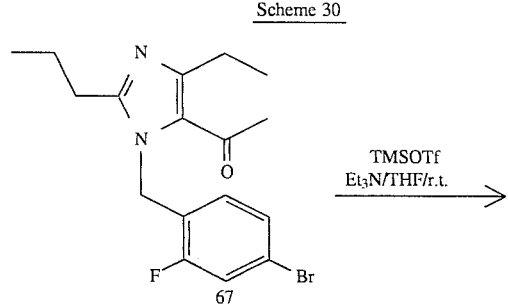

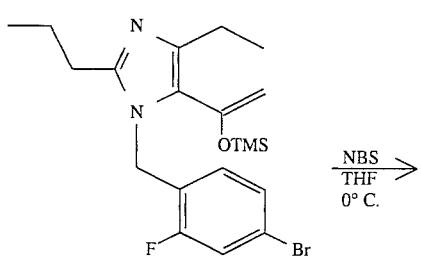

-continued
Scheme 30

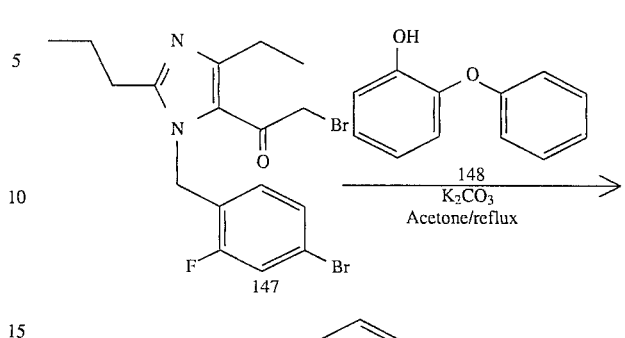

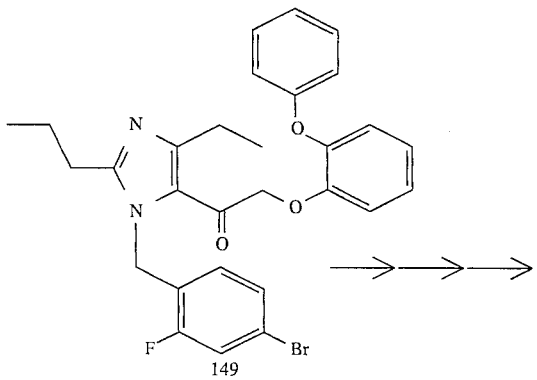

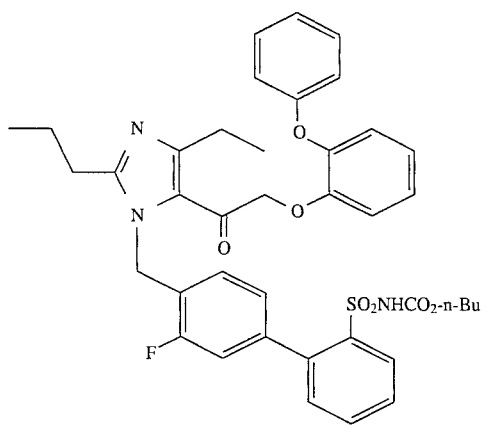

The compounds of this invention and their preparation can be understood further by the following examples which do not constitute a limitation of the invention. In these examples, unless otherwise indicated, all temperatures are in degrees centigrade and parts and percentages are by weight.

EXAMPLE 1

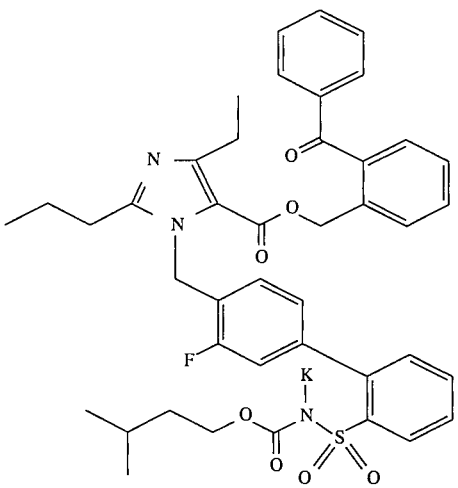

Preparation of
4-[(5-(2-benzoyl)benzyloxycarbonyl-4-
ethyl-2-n-propylimidazol-1-yl)methyl]-3-fluoro-2-
isoamyloxycarbonylaminosulfonylbipbenyl,
potassium salt.

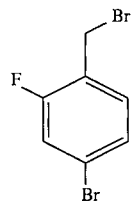

Part A. Preparation of 1-Bromo-4-bromomethyl-3-fluorobenzene.

1-Bromo-3-fluoro-4-methylbenzene (28.37 g, 0.15 mol, 1 eq), N-bromosuccinimide (26.72 g, 0.15 mol, 1 eq), azobisisobutyronitrile (1.44 g) and carbon tetrachloride (500 mL) were mixed and refluxed overnight. The mixture was filtered and washed with water (3×300 mL). The organic layer was dried (MgSO$_4$), and the solvent removed in vacuo to yield 37.88 g of an oil (75% product by NMR). NMR (CDCl$_3$) δ 4.45 (s, 2H). This material was used in the subsequent step without further purification.

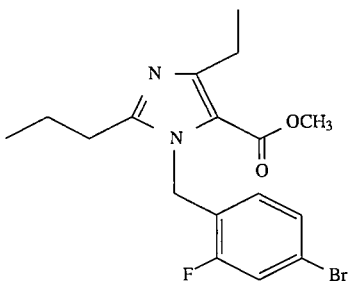

Part B. Preparation of 1-[(4-Bromo-2-fluorophenyl)methyl]-5-carbomethoxy-4-ethyl-2-n-propylimidazole.

5-Carbomethoxy-4-ethyl-2-n-propylimidazole (U.S. Pat. No. 5,137,902) (10.62 g, 54 mmol, 1 eq), 1-bromo-4-bromomethyl-3-fluorobenzene (19.58 g, 54 mmol, 1 eq), potassium carbonate (7.48 g, 54 mmol, 1 eq), and DMF (200 mL) were mixed and stirred overnight at room temperature. Ethyl acetate was added (500 mL) and the mixture was washed with water (3×300 mL). The ethyl acetate layer was dried (MgSO$_4$), and the solvent removed in vacuo to yield 25.42 g of an oil. Flash chromatography in 75:25 to 65:35 hexanes/ethyl acetate yielded 13.65 g of product as an amber oil. NMR (CDCl$_3$) δ 7.35–7.22 (m, 1H); 7.22–7.10 (m, 1H); 6.45 (t, 1H, J=7Hz); 5.49 (s, 2H); 3.78 (s, 3H); 2.90 (q, 2H, J=7Hz); 2.59 (t, 2H, J=7Hz); 1.70 (t of q, 2H, J=7,7Hz); 1.35–1.15 (m, 3H); 0.95 (t, 3H, J=7Hz).

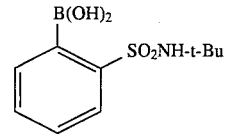

Part C. Preparation of 2-(t-butylamino)sulfonylphenyl boronic acid

To a 0° C. solution of 34.0 g (0.16 mol) of benzene-N-(t-butyl)sulfonamide in 500 mL of THF under N$_2$ was added 160 mL (0.36 mol) of 2.25M n-butyllithium in hexane over 35 min., keeping the temperature between 0°–2° C. The reaction mixture was allowed to warm to room temperature over 1.5 h, during which time a thick precipitate formed. Triisopropylborate (46 mL, 0.20 mol) was added, keeping the temperature below 35° C. After 1 h, the reaction mixture was cooled, 1N HCl (260 mL) was added, and the mixture was stirred 30 min. After diluting with 520 mL of water, the mixture was extracted with 3× 400 mL of ether. The combined organic extracts were extracted with 3× 200 mL of 1N NaOH, and the aqueous extracts were acidified to pH 1 with 6N HCl, then extracted with 3× 250 mL of ether. The ether extracts were washed with 250 mL of brine, dried over MgSO$_4$ and the solvents were removed in vacuo to yield 45 g of a thick oil. After addition of toluene (45 mL), the mixture was agitated for 1 h on the rotary evaporator. A small quantity of solid formed, which was used to induce partial solidification of the remaining crude product. Additional toluene (150 mL) was added, and the mixture was reduced to ½ volume in vacuo, keeping the temperature from 0°–10° C. The resulting precipitate was collected and washed with hexane, then dried under vacuum to give 24.6 g (60%) of the title compound as white crystals, m.p. 118°–119° C. $^1$H NMR (CDCl$_3$): δ 1.18 (s, 9H, CH$_3$); 5.13 (s, 1 H, NH), 6.29 (br s, 2H, OH); 7.53 (m, 2H, ArH); 7.82 (d, 1H, ArH); 8.00 ( d, 1H, ArH).

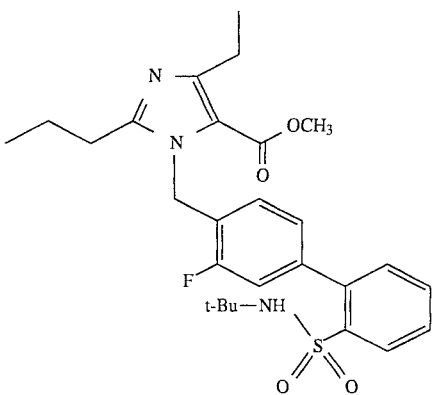

Part D. Preparation of 2'-(N-t-butyl)sulfonamido-4-[(5-carbomethoxy-4-ethyl-2-n-propylimidazol-1-yl)methyl]-3-fluorobiphenyl.

1-[(4-Bromo-2-fluorophenyl)methyl]-5-carbomethoxy-4-ethyl-2-n-propylimidazole (5.00 g, 13 mmol, 1 eq) was dissolved in toluene (25 mL) and added to a suspension of potassium carbonate (3.61 g, 26 mmol, 2 eq), tetrabutylammonium bromide (0.42 g, 1.3 mmol, 0.1 eq), 2-(t-butylamino)sulfonylphenyl boronic acid (5.03 g, 20 mmol, 1.5 eq) in toluene (25 mL). Water (10 mL) was then added followed tetrakistriphenylphosphine palladium (0) (0.75 g, 0.65 mmol, 0.05 eq). The mixture was slowly warmed to reflux temperature. After 16 hours, the reaction was worked up by adding water and extracting with methylene chloride (3×). The methylene chloride layers were combined and rinsed with brine (1×). The organic layer was dried (MgSO$_4$), and the solvent removed in vacuo to yield 9.69 g of an amber oil Flash chromatography in 75:25 to 1:1 hexanes/ethyl acetate yielded 5.89 g of an amber oil. NMR (CDCl$_3$) δ8.06 (d, 1H, J=8Hz); 7.47 (t, 1H, J=8Hz); 7.40 (t, 1H, J=8Hz) 7.30–7.15 (m, 2H); 7.08 (d, 1H, J=8Hz); 6.58 (t, 1H, J=7Hz); 5.53 (s, 2H); 3.70 (s, 3H); 3.60 (s, 1H); 2.83 (q, 2H, J=7Hz); 2.57 (t, 2H, J=7Hz); 1.65 (t of q, 2H, J=7,7 Hz); 1.20–1.10 (m, 3H); 0.91 (s, 9H); 0.87 (t, 3H, J=7Hz).

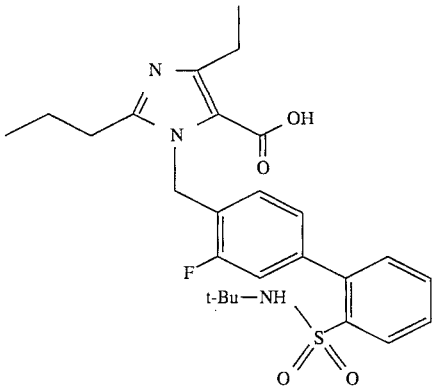

Part E. Preparation of 2'-(N-t-butyl)sulfonamido-4-[(5-carboxy-4-ethyl-2-n-propylimidazol-1-yl)methyl]-3-fluorobiphenyl.

2'-(N-t-butyl)sulfonamido-4-[(5-carbomethoxy-4-ethyl-2-n-propylimidazol-1-yl)methyl]-3-fluorobiphenyl (5.89 g, 11.4 mmol, 1 eq), 10 N NaOH (11.42 mL, 114 mmol, 10 eq), THF (25 mL), and methanol (enough to make a solution) were mixed and heated at 50° C. overnight. The reaction was worked up by adding water and removing the organic solvents in vacuo on a rotary evaporator. Methanol was added and the pH was adjusted to about 2 with concentrated HCl. The methanol was removed in vacuo and solids precipitated from the water. These solids were filtered, rinsed with ether and pumped under high vacuum to yield 4.45 g of a light yellow product: m.p. 223.5°–224.5° C. The solvent was further reduced from the filtrate yielding more product as a second crop: 1.13 g, m.p. 223.0°–224.0° C. NMR (DMSO-d$_6$) δ 8.01 (d, 1H, J=7Hz); 7.58 (m, 2H); 7.35–7.20 (m, 2H); 7.14 (d, 1H, J=7Hz); 6.94 (t, 1H, J=7Hz); 6.80 (s, 1H): 5.79 (s, 2H); 3.05–2.80 (m, 4H): 1.66 (t of q, 2H, J=7,7 Hz); 1⁄23 (t, 3H, J=7Hz); 0.95 (s, 9H); 0.88 (t, 3H, J=7Hz).

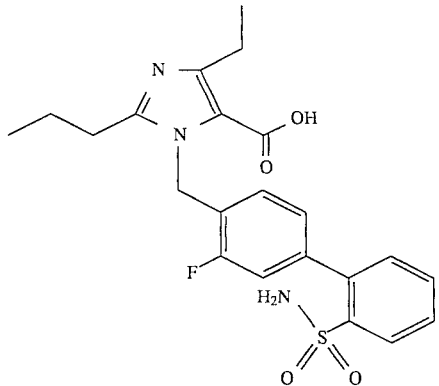

Part F. Preparation of 4-[(5-Carboxy-4-ethyl-2-n-propylimidazol-1-yl)methyl]-3-fluoro-2'-sulfonamidobiphenyl.

2'-(N-t-Butyl)sulfonamido-4-[(5-carboxy-4-ethyl-2-n-propylimidazol-1-yl)methyl]-3-fluorobiphenyl (5.58 g) and trifluoroacetic acid (TFA) (75 mL) were mixed and stirred at room temperature overnight. The TFA was removed in vacuo and the residue was dissolved in toluene. The toluene was removed in vacuo on a rotary evaporator and this procedure was repeated again to remove all traces of TFA. The residue was dissolved in ethyl acetate, dried (MgSO$_4$), and the solvent removed in vacuo to yield 6.92 g of an amber glass. NMR (DMSO-d$_6$) δ 8.10–7.95 (m, 1H): 7.70–7.50 (m, 2H); 7.37 (s, 2H); 7.45–7.10 (m, 3H); 6.96 (t, 1H, J=7Hz); 5.84 (s, 2H); 3.10–2.80 (m, 4H); 1.80–1.55 (m, 2H); 1.25 (t, 3H, J=7Hz); 0.91 (t, 3H, J=7Hz). The material was used without additional purification in the next step.

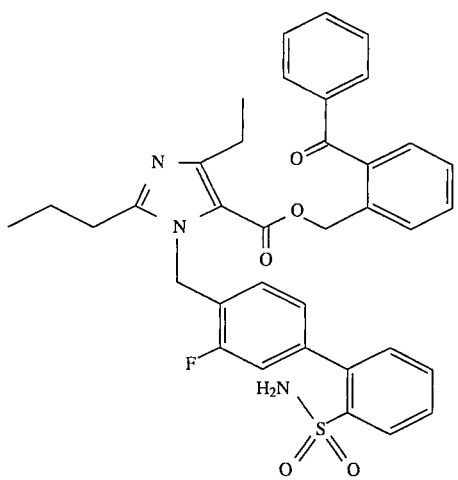

Part G. Preparation of 4-[(5-(2-benzoyl)benzyloxycarbonyl-4-ethyl-2-n-propylimidazol-1-yl)methyl]-3-fluoro-2'-sulfonamidobiphenyl.

4-[(5-Carboxy-4-ethyl-2-n-propylimidazol-1-yl)methyl]-3-fluoro-2'-sulfonamidobiphenyl (6.92 g, 11 mmol, 1 eq), 2-benzoylbenzyl bromide (obtained through bromination of 2-methylbenzophenone by the procedure described in part A, except that the reaction was terminated after 1 h, and after work up, the unstable product was stored at 0° C.) (7.57 g, 22 mmol, 2 eq), potassium carbonate (1.52 g, 11 mmol, 1 eq) and DMF (75 mL) were mixed and stirred overnight. The reaction was worked up as described in Part B. Flash chromatography in 75:25 to 0:100 hexanes/ethyl acetate yielded 2.41 g of an amber glass. FAB MS detects M$^+$+H= 446.

Part H. Preparation of 4-[(5-(2-benzoyl)benzyloxycarbonyl-4-ethyl-2-n-propylimidazol-1-yl)methyl]-3-fluoro-2'-isoamyloxycarbonylaminosulfonylbiphenyl, potassium salt.

4-[(5-(2-Benzoyl)benzyloxycarbonyl-4-ethyl-2-n-propylimidazol-1-yl)methyl]-3-fluoro-2'-sulfonamidobiphenyl (2.41 g, 3.77 mmol, 1 eq), 4-N,N-dimethylaminopyridine (1.84 g, 15.1 mmol, 4 eq), isoamyl chloroformate (9.87 g, 15.1 mmol, 4 eq), pyridine (11 mL) and methylene chloride (50 mL) were mixed and stirred at room temperature. After 48 h, the reaction was complete. Methylene chloride was added and the mixture was rinsed with water (1×), 10% citric acid (2×), and brine (1×). The organic layer was seperated, dried (MgSO$_4$), and the solvent removed in vacuo to yield an amber oil. Flash chromatography in 1:1 hexanes/ethyl acetate to 100% ethyl acetate yielded 1.26 g of product as a tan colored glass. The product was further titrated with 0.09M KOH and the water removed in vacuo followed by azeotroping with isopropanol to yield 1.20 g of an amber glass. NMR (CDCl$_3$) δ 8.07 (d, 1H, J=8Hz); 7.72 (d, 2H, J=8Hz); 7.60–7.00 (m, 12H0; 6.36 (t, 1H, J=8Hz); 5.40 (s, 2H); 5.34 (s, 2H); 3.71 (t, 2H, J=7Hz); 2.64 (q, 2H, J=7Hz); 2.56 (t, 2H, J=7Hz); 1.66 (t of q, 2H, J=7,7Hz); 1.40 (m, 1H); 1.22 (q, 2H, J=7Hz); 1.07 (t, 3H, J=7Hz); 0.91 (t, 3H, J=7Hz); 0.71 (d, 6H, J=7Hz). Anal. calcd. for C$_{42}$H$_{44}$FN$_3$OS.(H$_2$O)$_{0.5}$: C, 62.98; H, 5.54; F, 2.37; N, 5.25; S, 4.00. Found: C, 62.85; H, 5.54; F, 2.33; N, 5.09; S, 3.79.

EXAMPLE 2

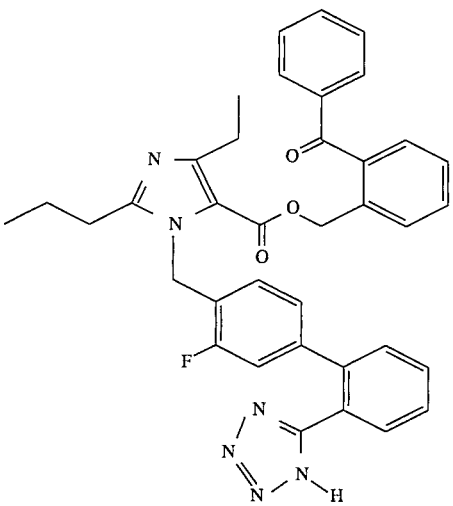

Preparation of 4-[(5-(2-benzoyl)benzyloxycarbonyl-4-ethyl-2-n-propylimidazol-1-yl)methyl]-3-fluoro-2'-(1H-tetrazol-5-yl)biphenyl.

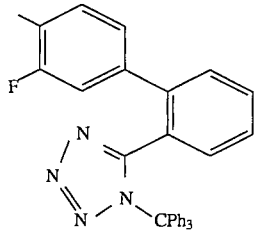

Part A. Preparation of 3-fluoro-4-methyl-2'-(N-triphenylmethyl-1H-tetrazol-5-yl)biphenyl.

4-Bromo-2-fluorotoluene (5.00 g, 26 mmol, 1 eq), 2-(N-triphenylmethyl-1H-tetrazol-5-yl)benzeneboronic acid (U.S. Pat. No. 5,130,439) (14.29 g, 26 mmol, 1 eq), tetrakistriphenylphosphinepalladium (0) (1.53 g, 1.3 mmol, 0.05 eq), tetrabutylammonium bromide (0.42 g, 1.3 mmol, 0.05 eq), 2M sodium carbonate (28.99 mL, 58 mmol, 2.23 eq) and toluene (200 mL) were mixed and refluxed for 4 hours. The reaction was worked up as in example 1, part D to yield 11.98 g of an amber glass. The glass was dissolved in ethyl acetate (25 mL) and triturated with ether to yield 6.04 g of white solid product. The filtrate was concentrated and flash chromatographed in 9:1 hexanes/ethyl acetate to yield a further 3.72 g of white solid product. NMR (CDCl$_3$) δ 8.00–7.85 (m, 1H); 7.55–7.40 (m, 2H); 7.40–7.10 (m, 10H); 7.00–6.70 (m, 9H); 2.18 (s, 3H).

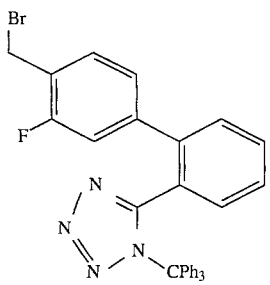

Part B. Preparation of 4-bromomethyl-3-fluoro-2'-(N-triphenylmethyl-1H-tetrazol-5-yl)biphenyl.

3-Fluoro-4-methyl-2'-(N-triphenylmethyl-1H-tetrazol-5-yl)biphenyl (6.00 g, 12 mmol) was brominated by the procedure described in example 1, part A to yield 7.45 g of an amber glass. NMR (CDCl$_3$) δ 4.39 (-CH$_2$Br).

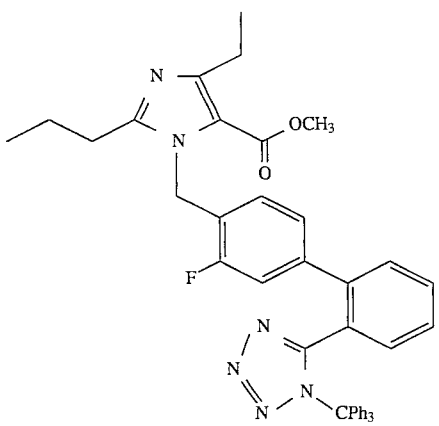

Part C. Preparation of 1-[(3-fluoro-2'-(N-triphenylmethyl-1H-tetrazol-5-yl)biphenyl)methyl]-5-carbomethoxy-4-ethyl-2-n-propylimidazole.

4-bromomethyl-3-fluoro-2'-(N-triphenylmethyl- 1H-tetrazol-5-yl)biphenyl (7.45 g, 11.0 mmol, 1 eq) was alkylated onto 5-carbomethoxy- 4-ethyl-2-n-propylimidazole (2/16 g, 11.0 mmol, 1 eq) by the procedure described in Example 1, part B to yield after chromatography 2.53 g of an amber glass. NMR (CDCl$_3$) δ 8.00–7.80 (m, 1H); 7.60–7.40 (m, 2H); 7.40–7.15 (m, 10H); 7.05–6.70 (m, 8H); 6.43 (t, 1H, J=8Hz); 5.47 (s, 2H); 3.71 (s, 3H); 2.91 (q, 2H, J=7Hz); 2.48 (t, 2H, J=7Hz); 1.75–1.55 (m, 2H); 1.26 (t, 3H, J=7Hz); 0.87 (t, 3H, J=7Hz).

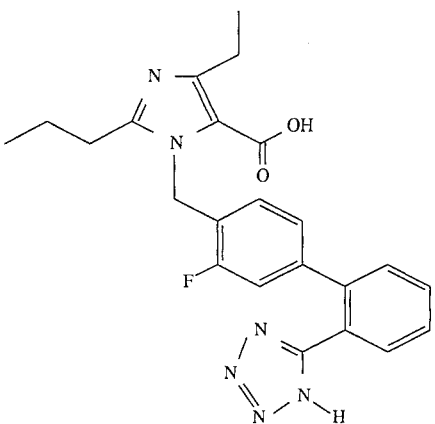

Part D. Preparation of 1-[(3-fluoro-2'-(1H-tetrazol-5-yl)biphenyl)methyl]-5-carboxy-4-ethyl-2-n-propylimidazole.

1-[(3-Fluoro-2'-(N-triphenylmethyl-1H-tetrazol-5-yl)biphenyl)methyl]- 5-carbomethoxy-4-ethyl-2-n-propylimidazole (2.02 g, 2.92 mmol, 1 eq), 1.000N NaOH (5.85 mL, 5.85 mmol, 2 eq), THF (10 mL) and methanol (enough to solublize the mixture) were mixed and stirred at room temperature overnight. The reaction was incomplete and so another 2 equivalents of 1.000N NaOH were added and the mixture stirred for an additional 4 hours. The reaction was istill ncomplete and so another 4 equivalents of 10N NaOH were added and the mixture stirred overnight at room temperature. The reaction was worked up by adding water and removing the organic solvents in vacuo. The remaining aqueous mixture was rinsed with ether (3×). Ethyl acetate was added to the aqueous mixture and the pH was adjusted to 2–3 with conc. HCl. The layers were seperated and the aqueous layer was extracted (2×) with ethyl acetate. The ethyl acetate layers were combined, dried (MgSO$_4$), and the solvent removed in vacuo to yield a yellow glass. The glass was stirred in ether to triturate 1.19 g of solid product. NMR shows that both the triphenylmethyl group and the methyl ester had been cleaved. NMR (DMSO-d$_6$) δ 7.80–7.40 (m, 4H); 7.00 (d, 1H, J=10 Hz); 6.87 (d, 1H, J=8Hz); 6.62 (t, 1H, J=8Hz); 5.64 (s, 2H); 2.83 (q, 2H, J=7Hz); 2.67 (t, 2H, J=7Hz); 1.56 (t of q, 2H, J=7,7Hz); 1.15 (t, 3H, J=7Hz); 0.84 (t, 3H, J=7Hz). FAB MS: (M$^+$+H)=435.

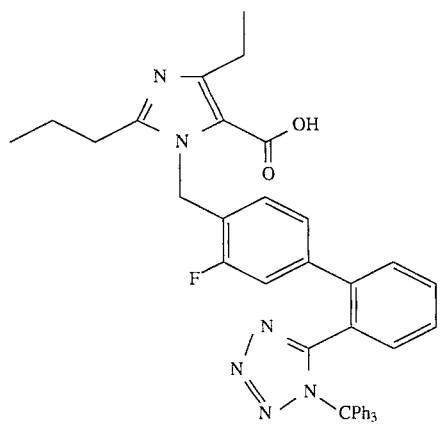

Part E. Preparation of 1-[(3-fluoro-2'-(N-triphenylmethyl-1H-tetrazol-5-yl)biphenyl)methyl]-5-carboxy-4-ethyl-2-n-propylimidazole.

1-[(3-Fluoro-2'-(1H-tetrazol-5-yl)biphenyl)methyl]-5-carboxy-4-ethyl- 2-n-propylimidazole (960 mg, 2.21 mmol, 1 eq), triethylamine (0.34 mL, 2.43 mmol, 1.1 eq), triphenylmethyl chloride (678 mg, 2.43 mmol, 1.1 eq), and methylene chloride (10 mL) were mixed and stirred at room temperature. After 4 hours, the reaction was worked up by adding water and seperating the layers, The organic layer was dried (MgSO$_4$), and the solvent removed in vacuo to yield 1.48 g of a white glass. Flash chromatography in 1:1 hexanes/ethyl acetate to 100% ethyl acetate to 75:25 ethyl acetate/isopropanol to yield 1.01 g of product as a white glass. NMR (CDCl$_3$) δ 7.80–7.60 (m, 1H); 7.50–7.05 (m, 12H); 6.94 (d, 6H, J=8Hz); 6.80–6.40 (m, 3H); 5.70–5.30 (m, 2H); 2.90–2.70 (m, 2H); 2.40–2.10 (m, 2H); 1.50 (m, 2H); 1.10–0.80 (m, 3H); 0.75–0.40 (m, 3H).

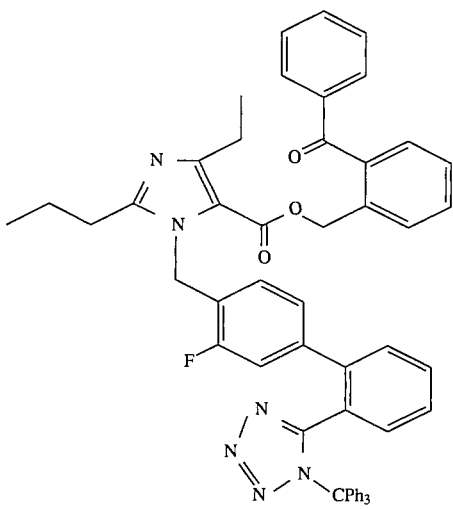

Part F. Preparation of 4-[(5-(2-benzoyl)benzyloxycarbonyl-4-ethyl-2-n-propylimidazol-1-yl)methyl]-3-fluoro-2'-(N-triphenylmethyl-1H-tetrazol-5-yl)biphenyl.

1-[(3-Fluoro-2'-(N-triphenylmethyl-1H-tetrazol-5-yl)biphenyl)methyl]- 5-carboxy-4-ethyl-2-n-propylimidazole (0.47 g, 0.694 mmol) was alkylated with 2-benzoylbenzyl bromide by the procedure described in example 1, part G to yield after flash chromatography in 75:25 to 1:1 to 0:100 hexanes/ethyl acetate 440 mg of an amorphous white product. NMR (CDCl$_3$) δ 7.95–7.85 (m, 1H); 7.75 (d, 2H, J=8Hz); 7.60–7.15 (m, 19 H); 6.94 (d, 6H, J=8Hz); 6.90–6.70 (m, 2H); 6.39 (t, 1H, J=8Hz); 5.38 (s, 2H); 5.35 (s, 2H); 2.77 (q, 2H, J=7Hz); 2.41 (t, 2H, J=7Hz); 1.75–1.50 (m, 2H); 1.14 (t, 3H, J=7Hz); 0.84 (t, 3H, J=7Hz).

Part G. Preparation of 4-[(5-(2-benzoyl)benzyloxycarbonyl-4-ethyl-2-n-propylimidazol-1-yl)methyl]-3-fluoro-2'-(1H-tetrazol-5-yl)biphenyl.

4-[(5-(2-Benzoyl)benzyloxycarbonyl-4-ethyl-2-n-propylimidazol-1-yl)methyl]- 3-fluoro-2'-(N-triphenylmethyl-1H-tetrazol-5-yl)biphenyl (440 mg) and methanol (25 mL) were mixed and refluxed under nitrogen for 3 hours. Silica gel was added and the solvent removed in vacuo. The residue was added to a flash chromatography column and quickly chromatographed in 1:1 hexanes/ethyl acetate to 80:20 chloroform/methanol to yield 280 mg of product as an off-white glass. NMR (CDCl$_3$) δ 7.83 (d, 1H, J=7Hz); 7.68 (d, 2H, J=7Hz); 7.60–7.10 (m, 10H); 6.80–6.60 (m, 2H); 6.27 (t, 1H, J=7Hz); 5.30 (s, 4H); 2.50 (m, 2H); 2.33 (t, 2H, J=7Hz); 1.54 (t of q, 2H, J=7,7 Hz); 0.95–0.60 (m, 6H). Anal. calcd. for C$_{37}$H$_{33}$FN$_6$O$_3$: C, 67.77; H, 5.53; F, 2.90; N, 12.82. Found: C, 67.73; H, 5.15; F, 2.76; N, 12.62.

EXAMPLE 3

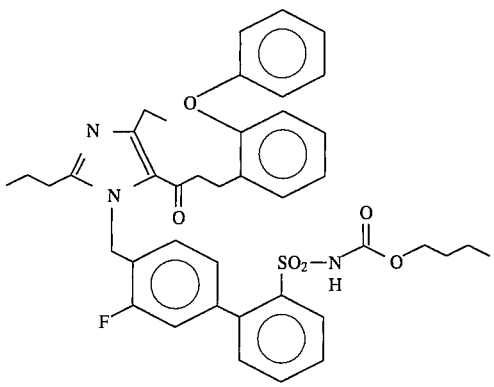

Preparation of 1-((2'-((n-Butyloxycarbonyl-amino)sulfonyl)-3-fluoro-(1,1'-biphenyl)-4-yl)methyl)-4-ethyl-5-(2-(2-phenoxyphenyl)ethylcarbonyl)-2-propyl-1H-imidazole.

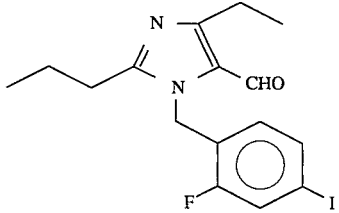

Part A: Preparation of 1-(2-fluoro-4-iodobenzyl)-4-ethyl-2-propyl-1H-imidazole-5-carboxaldehyde A solution of 2-fluoro-4-iodotoluene (47.28 g, 0.20 mol), N-bromosuccinamide (37.64 g, 0.21 mol) and azobisisobutyronitrile (3.65 g, 0.02 mol) in CCl$_4$ (200 mL) was refluxed under N$_2$ overnight. The mixture was cooled, the solid was filtered off and washed with CCl$_4$. The filtrate was concentrated. The precipitated formed was filtered and washed with hexane to give 13.92 g of 86% pure benzyl bromide. The mother liquid was concentrated to give 48.88 g of 60% pure benzyl bromide. Both fractions were used without further purification in the next step.

4-Ethyl-2-propyl-1H-imidazole-5-carboxaldehyde (6.32 g, 38.0 mmol), potassium carbonate (10.57 g, 76.5 mmol), and 2-fluoro-4-iodobenzyl bromide (13.90 g of 86%, 38.0 mmol) were added together with 50 mL of DMF. The reaction mixture was stirred at room temperature overnight under N$_2$. The solvent was removed in vacuo and the residue was partitioned between EtOAc and H$_2$O. The two layers were separated. The aqueous layer was extracted with EtOAc. The combined organic mixture was washed with H₂O and brine, dried over MgSO₄ and concentrated. The crude product mixture was purified by flash chromatography (silica gel, 30–50% EtOAc/hexane) to yield 10.63 g orange oil (70%). MS m/e 401.0, [M+H]⁺; ¹H NMR (300 MHz, CDCl₃): δ 0.95 (t, 3H, CH₃), 1.32 (t, 3H, CH₃), 1.70 (m, 2H, CH₂), 2.60 (m, 2H, CH₂), 2.82 (q, 2H, CH₂), 5.52 (s, 2H, CH2Ar), 6.42 (t, 1H, ArH), 7.38 (d, 1H, ArH), 7.42 (d, 1H, ArH), 9.73 (s, 1H, CHO).

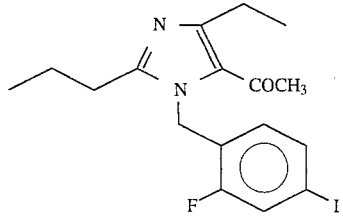

Part B: Preparation of 1-(2-fluoro-4-iodobenzyl)-5-acetyl-4-ethyl-2-propyl-1H-imidazole To a solution of 1-(2-fluoro-4-iodobenzyl)-4-ethyl-2-propyl-1H-imidazole-5-carboxaldehyde (16.52 g, 41.3 mmol) in THF (100 mL) was added methylmagnesium bromide (44.0 mL of 1.4/M in toluene/THF, 61.6 mmol) over 30 minutes. The reaction mixture was stirred at room temperature for 1.5 h. It was then quenched with 100 mL of 1N aqueous HCl. The mixture was extracted with CH₂Cl₂, the organic solution was washed with H₂O and brine, dried over MgSO₄, and concentrated to a yellow oil (16.87 g). The yellow oil was dissolved in 400 mL of CH₂Cl₂, and Manganese(IV) oxide (70.50 g, 811 mmol) was added. The mixture was refluxed under N₂ overnight. The mixture was cooled. It was then filtered through celite and washed with CH₂Cl₂. The CH₂Cl₂ solution was concentrated and chromatographed on silica gel with 50% EtOAc/hexane and 10% MeOH/CH₂Cl₂ to give 4.70 g of the desired product and 6.87 g of the alcohol. MS m/e 415.0, [M+H]⁺; ¹H NMR (300 MHz, CDCl₃): δ 0.98 (t, 3H, CH₃), 1.35 (t, 3H, CH₃), 1.68 (m, 2H, CH₂), 2.42 (s, 3H, CH₃) 2.58 (m, 2H, CH₂), 2.92 (q, 2H, CH₂), 5.45 (s, 2H, CH₂Ar), 6.28 (t, 1H, ArH), 7.35 (d, 1H, ArH), 7.42 (d, 1H, ArH).

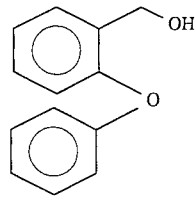

Part C: Preparation of o-phenoxybenzyl alcohol

To a solution of o-phenoxybenzoic acid (19.0 g, 88.7 mmol) in THF (100 mL) at 0° C. under N₂ was added BH₃.THF (133 mL, 1.0M in THF) over a period of 1 h, keeping the temperature below 5° C. The reaction mixture was then stirred at room temperature for 2 h. It was quenched with H₂O, then 1N aqueous HCl. The two layers were separated. The aqueous layer was extracted with EtOAc. The combined organic mixture was washed with brine, dried over MgSO, and concentrated to a light yellow oil (16.9 g). The crude product was used in the next step without further purification. MS m/e 183.1, [M+H-H₂O]⁺; ¹H NMR (300 MHz, CDCl₃): δ 2.08 (t, 1H, OH), 4.76 (d, 2H, CH₂Ar), 6.82–7.48 (m, 9H, ArH).

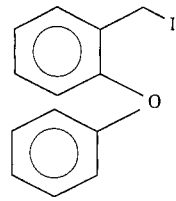

Part D: Preparation of o-phenoxybenzyl iodide

To a solution of o-phenoxybenzyl alcohol (5.0 g, 25 mmol) and triethylamine (10.4 mL, 75 mmol) in CH₂Cl₂ (50 mL) at 0° C. was added methanesulfonyl chloride (3.9 mL, 50 mmol). The reaction mixture was stirred at 0° C. for 1 h and then at room temperature for 3.5 h. The mixture was washed H₂O and brine. It was filtered through phase separator paper and concentrated to a yellow oil. The oil was then dissolved in 50 mL of acetone, and sodium iodide (7.5 g, 50 mmol) was then added. The mixture was stirred at more temperature overnight. Hexane was added to the mixture. The solid was filtered off. The filtrate was concentrated and chromatographed on silica gel with hexane to give 5.22 g of yellow oil. MS m/e 183.1, [M+H-HI]⁺; ¹H NMR (300 MHz, CDCl₃): δ 4.52 (s, 2H, CH₂Ar), 6.82–7.48 (m, 9H, ArH).

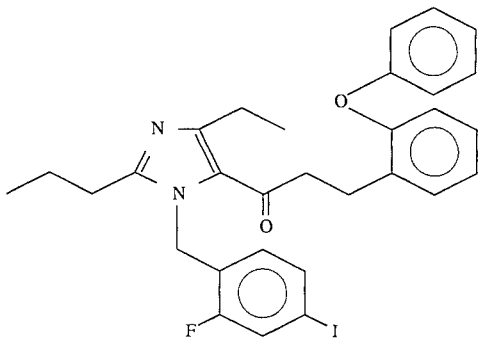

Part E: Preparation of 1-(2-fluoro-4-iodobenzyl)-4-ethyl-5-(2-(2-phenoxy phenyl)ethylcarbonyl)-2-propyl- 1H-imidazole 1-(2-fluoro-4-iodobenzyl)-5-acetyl-4-ethyl-2-propyl-1H-imidazole (5.52 g, 13.3 mmol) was dissolved in 50 mL of THF. The mixture was cooled at 0° C. under N₂ and lithium diisopropylamide (7.3 mL of 2M in THF, 14.6 mmol) was added. After stirred at 0° C. for 15 minutes, a solution of o-phenoxybenzyl iodide (5.22 g, 16.8 mmol) in THF (15 mL) was added. The reaction mixture was warmed up to room temperature and stirred for 2 h. The mixture was partitioned between EtOAc and H₂O. The two layers were separated. The aqueous layer was extracted with EtOAc. The combined organic solution was washed with brine, dried over MgSO₄. It was concentrated and chromatographed on silica gel with 10–50% EtOAc/hexane to yield 2.35 g of the desired product. MS m/e 597.2, [M+H]⁺; IR (KBr): 1646 cm⁻¹ for CO; ¹H NMR (300 MHz, CDCl₃): δ 0.95 (t, 3H, CH₃), 1.22 (t, 3H, CH₃), 1.65 (m, 2H, CH₂), 2.57 (m, 2H, CH₂), 2.82 (q, 2H, CH₂), 2.98 (m, 2H, CH₂), 3.10 (m, 2H, CH₂) 5.42 (s, 2H, CH₂Ar), 6.22 (t, 1H, ArH), 6.82 (d, 1H, ArH), 6.90 (d, 2H, ArH), 7.02 (m, 2H, ArH), 7.18 (d, 1H, ArH), 7.22 (m, 2H, ArH), 7.30 (m, 2H, ArH), 7.40 (d, 1H, ArH).

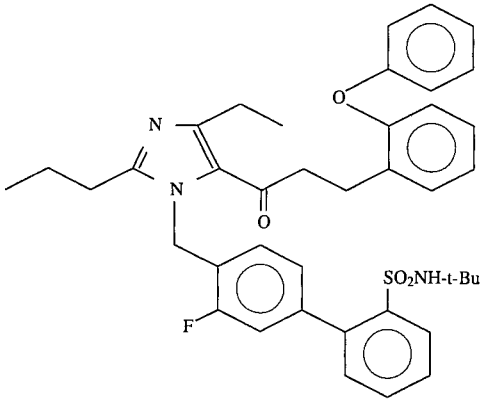

Part F: Preparation of 1-((2'-((t-butylamino)sulfonyl)-3-fluoro-(1,1'-biphenyl)-4-yl)methyl)-4-ethyl-5-(2-(2-phenoxyphenyl)ethylcarbonyl)-2-propyl-1H-imidazole 1-(2-fluoro-4-iodobenzyl)-4-ethyl-2-propyl-1H-imidazole-5-phenoxyphenethyl ketone (2.35 g, 3.90 mmol), 2-(t-butylamino)sulfonylphenyl boronic acid (1.52 g, 5.85 mmol), and soduim carbonate (10 mL of 2M aqueous solution), and tetrabutylammonium bromide (65 mg, o.20 mmol) were added together with 50 mL of toluene. Tetrakis(triphenylphosphine) palladium(O) (0.23 g, 0.20 mmol) was added. The mixture was refluxed under $N_2$ overnight. The solvent was removed in vacuo and the residue was partitioned between $H_2O$ and $CH_2Cl_2$. The aqueous layer was extracted with $CH_2Cl_2$, and the combined organic solution was washed with brine, dried over $MgSO_4$ and concentrated. The crude product was purified by flash column chromatography ( silica gel, 30% EtOAc/hexane) to give 1.92 g of light yellow foam (72%). MS m/e 682.5, [M+H]$^+$; $^1$H NMR (300 MHz, CDCl$_3$): δ 0.96 (t, 3H, CH$_3$), 0.98 (t, 9H, CH$_3$), 1.27 (t, 3H, CH$_3$), 1.69 (m, 2H, CH$_2$), 2.60 (t, 2H, CH$_2$), 2.85 (q, 2H, CH$_2$), 2.97 (m, 2H, CH$_2$), 3.13 (m, 2H, CH$_2$), 3.58 (s, 1H, NH), 5.57 (s, 2H, CH$_2$Ar), 6.60 (t, 1H, ArH), 6.86 (d, 1H, ArH), 6.92 (d, 2H, ArH), 7.05 (d, 2H, ArH), 7.16 (m, 2H, ArH), 7.26 (m,5H, ArH), 7.55 (m, 2H, ArH), 8.16 (m, 1H, ArH).

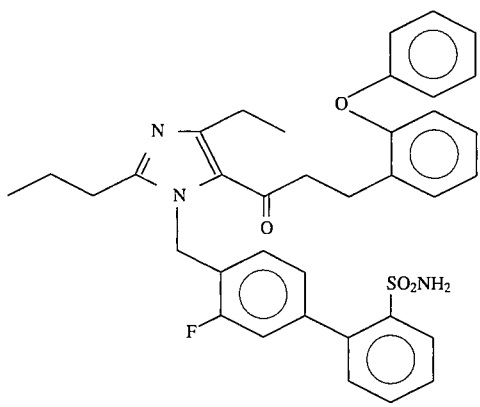

Part G: Preparation of 1-((2'-(aminosulfonyl)-3-fluoro-(1,1'-biphenyl)-4-yl)methyl)-4-ethyl-5-(2-(2-phenoxyphenyl)ethylcarbonyl)-2-propyl- 1H-imidazole 1-((2'-((t-butylamino)sulfonyl)-3-fluoro-(1,1'-biphenyl)-4-yl)methyl)-4-ethyl- 2-propyl-1H-imidazole-5-phenoxyphenethyl ketone (1.92 g, 2.8 mmol) was refluxed with 15 mL of trifluoroacetic acid under $N_2$ for 2 h. The solvent was removed in vacuo. The residue was dissolved in $CH_2Cl_2$, and washed with aqueous $NaHCO_3$ and brine. The organic solution was filtered through phase separator paper and then concentrated to a light yellow foam (1.84 g). MS m/e 626.0, [M+H]$^+$; $^1$H NMR (300 MHz, CDCl$_3$): δ 0.95 (t, 3H, CH$_3$), 1.26 (t, 3H, CH$_3$), 1.69 (m, 2H, CH$_2$), 2.60 (t, 2H, CH$_2$), 2.84 (q, 2H, CH$_2$), 2.97 (m, 2H, CH$_2$), 3.12 (m, 2H, CH$_2$), 4.20 (s, 2H, NH$_2$), 5.57 (s, 2H, CH$_2$Ar), 6.65 (t, 1H, ArH), 6.85 (d, 1H, ArH), 6.92 (d, 2H, ArH), 7.01–7.37 (m, 9H, ArH), 7.58 (m, 2H, ArH), 8.15 (d, 1H, ArH).

Part H: Preparation of 1-((2'-((n-Butyloxycarbonylamino) sulfonyl)-3-fluoro-( 1,1'-biphenyl)-4-yl)methyl)-4-ethyl-5-(2-(2-phenoxyphenyl)ethylcarbonyl)- 2-propyl-1H-imidazole 1-((2'-(aminosulfonyl)-3-fluoro-(1,1'-biphenyl)-4-yl)methyl)-4-ethyl-2-propyl- 1H-imidazole-5-phenoxyphenethyl ketone (1.84 g, 2.90 mmol) was dissolved in 50 mL of $CH_2Cl_2$. To the mixture was added 4-N,N-dimethylaminopyridine (0.40 g, 3.19 mmol), pyridine (2 mL), and n-Butyl chloroformate (1.48 mL, 11.60 mmol). The reaction mixture was allowed to stir at room temperature under $N_2$ for 98 h.. The mixture was washed with 10% aqueous citric acid and brine. The organic solution was filtered through phase separator paper and concentrated. It was then chromatographed on silica gel (eluted with 25–100% EtOAc/ $CH_2Cl_2$ ) to give 1.48 g light yellow foam. MS m/e 725.0, [M+H]$^+$; $^1$H NMR (300 MHz, CDCl$_3$) δ 0.84 (t, 3H, CH$_3$), 0.97 (t, 3H, CH$_3$), 1.10–1.32 (m, 5H, CH$_3$,CH$_2$), 1.47 (m, 2H, CH$_2$), 1.71 (m, 2H, CH$_2$), 2.63 (t, 2H, CH$_2$), 2.83 (q, 2H, CH$_2$), 2.99 (m, 2H, CH$_2$), 3.12 (m, 2H, CH$_2$), 3.98 (t, 2H, OCH$_2$), 5.58 (s, 2H, CH$_2$Ar), 6.62 (t, 1H, ArH), 6.81–7.37 (m, 12H, ArH), 7.60 (m, 2H, ArH), 8.25 (d, 1H, ArH).

EXAMPLE 4

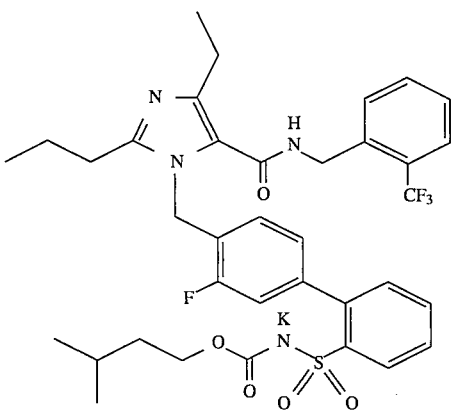

89

Preparation of 4-[(5-(2-trifluoromethylphenyl)
methylaminocarbonyl-4-ethyl-
2-n-propylimidazol-1-yl)methyl]-3-
fluoro-2'-
isoamyloxycarbonylaminosuifonylbiphenyl,
potassium salt

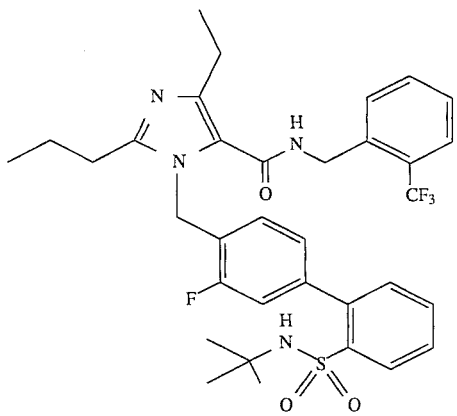

Part A. Preparation of 4-[(5-(2-trifluoromethylphenylmethyl)aminocarbonyl-4-ethyl-2-n-propylimidazol-1-yl)methyl]-3-fluoro-2'-(N-t-butyl)sulfonamidobiphenyl.

A solution of (2-trifluoromethyl)benzylamine (0.22 mL, 1.6 mmol), dicyclohexylcarbodiimide (0.33 g, 1.6 mmol), and 1-hydroxybenzotriazole hydrate (0.22 g, 1.6 mmol) in acetonitrile (30 mL) was stirred under $N_2$ for 15 minutes. 2'-(N-t-butyl)sulfonamido-4-[(5-carboxy-4-ethyl-2-n-propylimidazol- 1-yl)methyl]-3-fluorobiphenyl (0.75 g, 1.6 mmol) was then added and the reaction stirred at room temperature overnight. The reaction was filtered and the filtrate then evaporated. The residue was taken up in $CH_2Cl_2$, washed with water, dried over $MgSO_4$, filtered and evaporated. The residue was then chromatographed with 50% ethyl acetate in hexane to yield 0.95 g of a white product. NMR ($CDCl_3$) δ 8.09 (d, 1H), 7.60–7.10 (m, 9H), 6.75 (t, 1H), 6.04 (m, 1H), 5.51 (m, 1H), 4.67 (d, 2H), 2.63 (m, 2H), 2.53 (m, 2H), 1.60 (m, 2H), 1,18 (m, 3H), 0.90 (m, 12H)

Part B. Preparation of 4-[(5-(2-trifluoromethylphenyl)methylaminocarbonyl-4-ethyl-2-n-propylimidazol-1-yl)methyl]-3-fluoro-2'-isoamyloxycarbonylaminosulfonylbiphenyl, potassium salt.

4-[(5-(2-trifluoromethylphenyl)methylaminocarbonyl-4-ethyl-2-n-propylimidazol- 1-yl)methyl]-3-fluoro-2'-(N-t-butyl)sulfonamidobiphenyl was converted to product by using the methods of Example 1, parts G and H. The reactions yielded 0.33 g of product. NMR ($CDCl_3$) δ 8.02 (d, 1H), 7.64–7.05 (m, 9H), 6.56 (t, 1H), 6.20 (m, 1H), 5.33 (s, 2H), 4.65 (d, 2H), 3.77 (t, 2H), 2.67 (q, 2H), 2.54 (m, 2H), 1.65 (m, 2H), 1.40 (m, 1H), 1.21 (m, 3H), 0.95 (t, 3H), 0.76 (d, 6H).

90

EXAMPLE 5

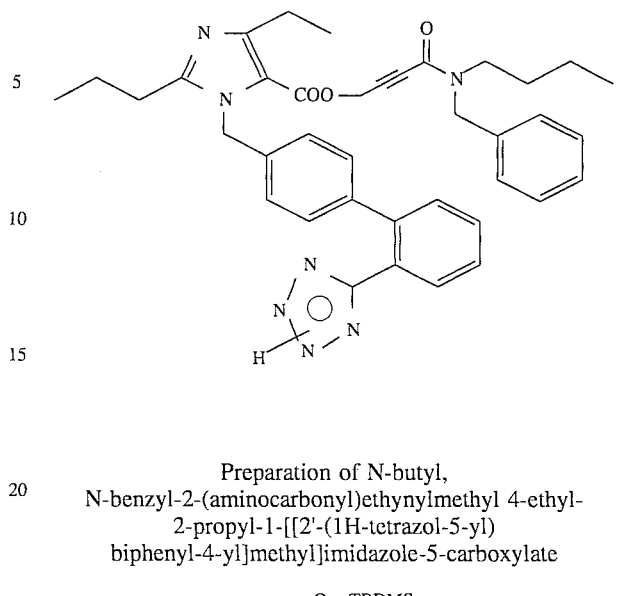

Preparation of N-butyl,
N-benzyl-2-(aminocarbonyl)ethynylmethyl 4-ethyl-
2-propyl-1-[[2'-(1H-tetrazol-5-yl)
biphenyl-4-yl]methyl]imidazole-5-carboxylate

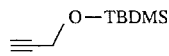

Part A. Preparation of t-Butyldimethylsilyl propargyl ether

To a solution of 5.82 mL of propargyl alcohol in 20 mL of pyridine and 30 mL of $CH_2Cl_2$ was added 0.122 g of DMAP and 16.88 g of TBDMSCl in a $N_2$ atmosphere. After stirring 3 days, the reaction was poured into 100 mL of 1N HCl, and diluted with $CH_2Cl_2$. The layers were separated and the organic layer washed with 100 mL of 1N HCl (2×), 10% $NaHCO_3$, $H_2O$ and brine and dried ($MgSO_4$). Filtration and concentration provided 15.07 g of an oil which was used without purification.

$^1$H-NMR ($CDCl_3$) δ 4.19 (s, 2H), 2.25 (s, 1H), 0.80 (s, 9H), 0.03 (s, H).

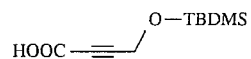

Part B. Preparation of 4-(t-Butyldimethylsilyloxy)-2-butynoic acid

To an ice-cold solution of 13.71 g t-butyldimethylsilyl propargyl ether in 160 mL anhydrous THF was added dropwise 35 mL EtMgBr (3M in $Et_2O$) in a $N_2$ atmosphere. After completing the addition, the reaction was stirred 45 minutes at room temperature. Pellets of dry ice were then added slowly until the reaction became cold and carboxylate salt precipitated. Stirring at room temperature was continued overnight. The reaction was concentrated to dryness and the residue partitioned between $H_2O$ and $Et_2O$ and the organic extract discarded. The aqueous solution was acidified to pH 2 with 6N HCl and immediately extracted with EtOAc. The organic layer was washed with 10% $NaHCO_3$, $H_2O$, and brine and dried ($MgSO_4$). Filtration and concentration provided 13.56 g of product which was used without purification. $^1$H-NMR ($CDCl_3$) δ 10.6 (s, 1H), 4.3 (s, 2H), 0.80 (s, 9H), 0.03 (s, 6H).

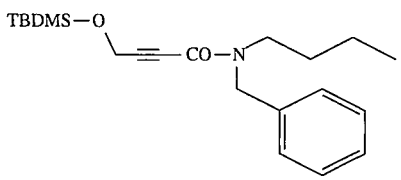

Part C. Preparation of N-butyl, N-benzyl-4-(t-butyldimethylsilyloxy)-2-butynamide In a flame-dried flask, 0.279 g NaH (80% dispersion in mineral oil) was washed with 5 mL pentane (3×) while maintaining a $N_2$ atmosphere. The NaH was then suspended in 50 mL anhydrous benzene to which was added dropwise at room temperature a solution of 2.0 g 4-(t-butyldimethylsilyloxy)-2-butynoic acid in 45 mL benzene. After 45 minutes 4.05 mL $(COCl)_2$ was added and the reaction stirred overnight. The mixture was filtered through glass fiber paper to remove NaCl and the clear filtrate concentrated. The residue was dissolved in 95 mL benzene and concentrated again. The crude residual acid chloride was used immediately as described below.

To an ice-cold solution of 0.350 g butylbenzylamine and 0.447 mL diisopropylethylamine in 11 mL dry benzene under $N_2$ was added a solution of the above acid chloride in 11 mL benzene. After stirring overnight with gradual warming to room temperature, the reaction was poured into $H_2O$ and extracted with $Et_2O$ (3×). The combined organic extracts were washed with brine and dried ($MgSO_4$). Filtration and concentration provide crude product which was purified by flash chromatography with a 10%–15% $Et_2O$/hexanes gradient to give 0.39 g of product.

$^1$H-NMR ($CDCl_3$) δ 7.30–7.15 (m, 5H), 4.7 and 4.55 (s, 2H), 4.4 and 4.38 (s, 2H), 3.40 and 3.22 (t, 2H), 1.6–1.4 (m, 2H), 1.30–1.18 (m, 2H), 0.90–0.75 (m, 12H), 0.03 and 0.01 (s, 6H). [product is a mixture of rotamers]

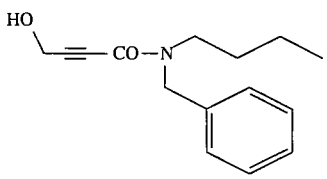

Part D. Preparation of N-butyl, N-benzyl-4-hydroxy-2-butynamide

To an ice-cold solution of 0.61 g N-butyl, N-benzyl-4-(t-butyldimethylsilyl-oxy)-2-butynamide in 17 mL $CH_3CN$ under $N_2$ was added dropwise 0.61 mL 48% HF. The reaction was stirred 2 hours at ice bath temperature, then neutralized by the careful addition of 10% $NaHCO_3$. The reaction was transferred to a separatory funnel, diluted with $H_2O$ and extracted with $Et_2O$. The combined organics were washed with 10% $NaHCO_3$, $H_2O$, and brine and dried ($MgSO_4$). Filtration and concentration provided 0.27 g of product which was used as is.

$^1$H-NMR ($CDCl_3$) δ 7.40–7.20 (m, 5H), 4.80 (s, 1H), 4.60 (s, 1H), 4.43–4.37 (dd, 2H), 4.20–4.05 (bs, 1H), 3.50–3.40 (t, 2H), 3.30–3.20 (t, 2H), 1.60–1.40 (m, 2H), 1.40–1.20 (m, 2H), 0.95–0.80 (2t, 3H). [product is a mixture of rotamers]

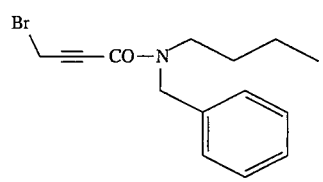

Part E. Preparation of N-butyl, N-benzyl-4-bromo-2-butynamide

To an ice-cold solution of 0.27 g N-butyl, N-benzyl-4-hydroxy-2-butynamide in 11 mL $CH_2Cl_2$ in a $N_2$ atmosphere was added 0.582 g $CBr_4$. After stirring 10 min, 0.345 g $Ph_3P$ was added and the reaction stirred overnight with gradual warming to room temperature. The reaction was diluted with $H_2O$ and extracted with $CH_2Cl_2$. The combined organics were washed with brine and dried ($Na_2SO_4$). Filtration, concentration, and flash chromatography using a 20%–40% $Et_2O$/hexanes gradient gave 0.26 g of product.

$^1$H-NMR ($CDCl_3$) δ 7.40–7.20 (m, 5H), 4.75 and 4.60 (s, 2H), 4.21 and 4.00 (d, 1H), 3.42 and 3.26 (t, 2H), 1.50 amd 1.30 (m, 2H), 0.98–0.83 (2t, 3H). [product is a mixture of rotamers]

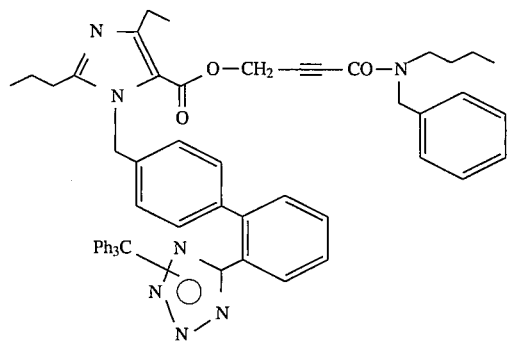

Part F. Preparation of N-butyl, N-benzyl-2-(aminocarbonyl)ethynylmethyl 4-ethyl-2-propyl-1-[[2'-(N-triphenylmethyl(tetrazol-5-yl)) biphenyl-4-yl] methyl]imidazole-5-carboxylate To a solution/suspension of 0.55 g 4-ethyl-2-propyl-1-[ [2'-(N-triphenylmethyl(tetrazol- 5-yl))biphenyl-4-yl-]methyl]imidazole-5-carboxylic acid, 0.26 g N-butyl, N-benzyl-4-bromo-2-butynamide, and 0.12 g powdered $K_2CO_3$ in 3 mL DMF was added in one portion 0.14 g KI. The reaction was stirred 3 h at room temperature under $N_2$, then partitioned between 8 mL $H_2O$ and 40 mL EtOAc. The organic extract was washed once with ice-cold 0.1N $Na_2S_2O_3$, $H_2O$, and brine, and dried ($MgSO_4$). Filtration, evaporation and flash chromatography using a 30%–50% EtOAc/hexanes gradient provided 0.65 g of product.

$^1$H-NMR ($CDCl_3$) δ 7.87 (br d, 1H), 7.50–7.40 (m, 2H), 7.38–7.16 (m, 15 H), 7.10–7.00 (m, 2H), 7.00–6.90 (m, 6H), 6.78–6.65 (m, 2H), 5.41 and 5.35 (s, 2H), 4.81 and 4.79 (s, 2H), 4.70 and 4.60 (s, 2H), 3.40 and 3.25 (t, 2H), 2.95 and 2.83 (q, 2H), 1.75–1.60 (m, 2H), 1.57–1.40 (m, 2H), 1.35–1.14 (m, 5H), 0.95–0.80 (2t, 6H). [product is a mixture of rotamers]

Part G. Preparation of N-butyl, N-benzyl-2-(aminocarbonyl)ethynylmethyl 4-ethyl-2-propyl-1-[[2'-(1H-tetrazol-5-yl)biphenyl-4-yl]methyl]imidazole-5-carboxylate To a solution of 0.55 g N-butyl, N-benzyl-3-carboxamido-2-propynyl 4-ethyl-2-propyl-1-[[2'-(N-triphenylmethyl(tetrazol-5-yl))biphenyl-4-yl]methyl]imidazole-5-carboxylate in 14 mL MeOH at room temperature was added 5 drops of 6N HCl. After stirring overnight, the reaction was evaporated to dryness and the residue purified by flash chromatography using a 0%–5% MeOH/CHCl₃ gradient to provide 0.36 g of product.

MS (NH₃-CI) 644.4 (M+H)⁺, 680.4 (M+NH₄)⁺.

EXAMPLE 6

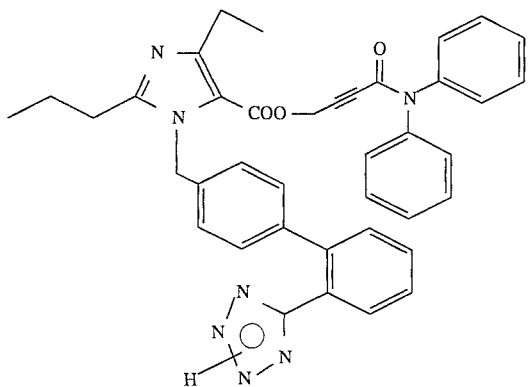

Preparation of N,N-diphenyl-2-(aminocarbonyl)ethynylmethyl 4-ethyl-2-propyl-1-[[2'-(1H-tetrazol-5-yl)biphenyl-4-yl]methyl]imidazole-5-carboxylate

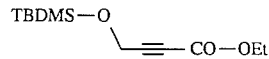

Part A. Preparation of Ethyl 4-(t-butyldimethylsilyloxy)-2-butynoate

To a solution/suspension of 2.0 g of 4-(t-butyldimethylsilyloxy)-2-butynoic acid and 1.48 g Na₂CO₃ in 37 mL DMF under N₂ was added slowly 1.58 mL Et₂SO₄. After stirring overnight, the reaction was diluted with EtOAc and washed several times with H₂O. The organic extract was then washed with brine and dried over MgSO₄. Filtration, evaporation and flash chromatography with a 5%–10% Et₂O/hexanes gradient provided 1.58 g of pure product.

¹H-NMR (CDCl₃) δ 4.3 (s, 2H), 4.10 (q, 2H), 1.20 (t, 3H), 0.80 (s, 9H), 0.03 (s, 6H).

Part B. Preparation of N, N-diphenyl-4-(t-butyldimethylsilyloxy)-2-butynamide To a solution of 1.4 mL Me₃Al (2.0M in hexanes) in 3.6 mL anhydrous CH₂Cl₂ under N₂ was added 0.49 g of diphenylamine in one portion. After stirring 30 min, 0.35 g ethyl 4-(t-butyldimethylsilyloxy)-2-butynoate in 0.4 mL CH₂Cl₂ was added dropwise. The reaction was stirred overnight at room temperature, then heated in an oil bath at 35° overnight. The reaction was quenched by the addition of a few drops of 1N HCl, diluted with H₂O, and extracted with CH₂Cl₂. The combined organics were with H₂O and brine and dried over Na₂SO₄. Filtration, evaporation, and flash chromatography with a 10–15% Et₂O/hexanes gradient provided 0.31 g of product.

¹H-NMR (CDCl₃) δ 7.50–7.20 (m, 10H), 4.25 (s, 2H), 0.84 (s, 9H), 0.02 (s, 6H).

Part C. Preparation of N, N-diphenyl-4-hydroxy-2-butynamide

By employing the procedure described in Example 5, Part D, there was obtained from 0.91 g N, N-diphenyl-4-(t-butyldimethylsilyloxy)-2-butynamide 0.45 g of pure product.

¹H-NMR (CDCl₃) δ 7.43–7.15 (m, 10H), 4.10 (s, 2H), 3.05 (br s, 1H).

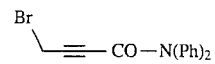

Part D. Preparation of N, N-diphenyl-4-bromo-2-butynamide

By employing the procedure described in Example 5, Part E, there was obtained from 0.45 g N, N-diphenyl-4-hydroxy-2-butynamide 0.54 g of product.

¹H-NMR (CDCl₃) δ 7.43–7.2 (m, 10H), 4.0 and 3.78 (s, 2H). [product is a mixture of rotamers]

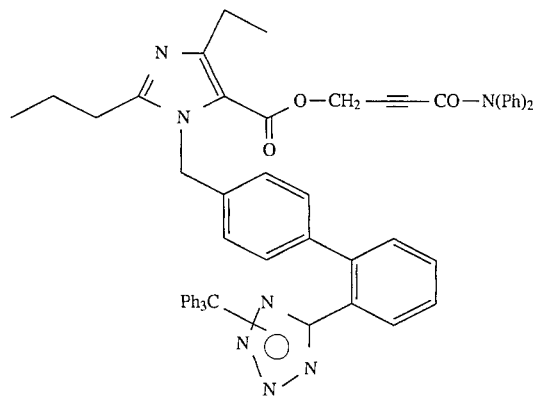

Part E. Preparation of N-butyl, N-benzyl-2-(aminocarbonyl)ethynylmethyl 4-ethyl-2-propyl-1-[[2'-(N-triphenylmethyl(tetrazol-5-yl))biphenyl-4-yl]methyl]imidazole-5-carboxylate By employing the procedure described in Example 5, Part F, there was obtained from 0.56 g N, N-diphenyl-4-bromo-2-butynamide 1.16 g of pure product.

¹H-NMR (CDCl₃) δ 7.90–7.85 (m, 1H), 7.44–7.39 (m, 2H), 7.37–7.17 (m, 20H), 7.15–7.02 (m, 2H), 6.95–6.85 (m, 6H), 6.80–6.78 (m, 2H), 5.40 (s, 2H), 4.60 (s, 2H), 2.79 (q, 2H), 2.58 (t, 2H), 1.65 (m, 2H), 1.22 (t, 3H), 0.90 (t, 3H).

Part F. Preparation of N-butyl, N-benzyl-2-(aminocarbonyl)ethynylmethyl 4-ethyl-2-propyl-1-[[2'-(1H-tetrazol-5-yl)biphenyl-4-yl]methyl]imidazole- 5-carboxylate By employing the procedure described in Example 5, Part G, there was obtained from 1.16 g N, N-diphenyl-3-carboxamido-2-propynyl 4-ethyl- 2-propyl-1-[[2'-(N-triphenylmethyl(tetrazol-5-yl))biphenyl-4-yl]methyl]imidazole-5-carboxylate 0.60 g of pure product.

¹H-NMR (CDCl₃) δ 7.83 7.80 (m, 1H), 7.60–7.50 (m, 2H), 7.44–7.40 (m, 1H), 7.40–7.20 (m, 8H), 7.20–7.06 (m, 4H), 6.82–6.78 (m, 2H), 5.40 (s, 2H), 4.61 (s, 2H), 2.63 (q, 2H), 2.42 (t, 2H), 1.75–1.60 (m, 2H), 1.05 (t, 3H), 0.91 (t, 3H).

EXAMPLE 7

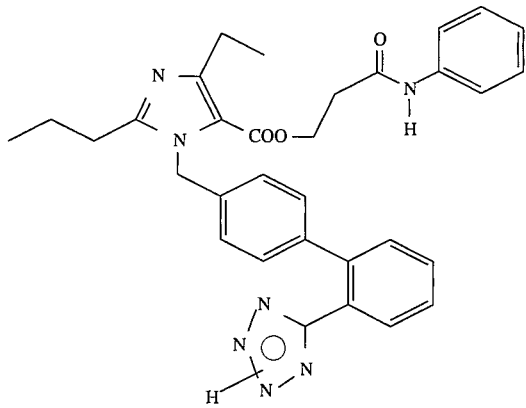

Preparation of N-phenyl-2-(aminocarbonyl)ethyl 4-ethyl-2-propyl-1-[[2'-(1H-tetrazol-5-yl)biphenyl-4-yl]methyl]imidazole-5-carboxylate

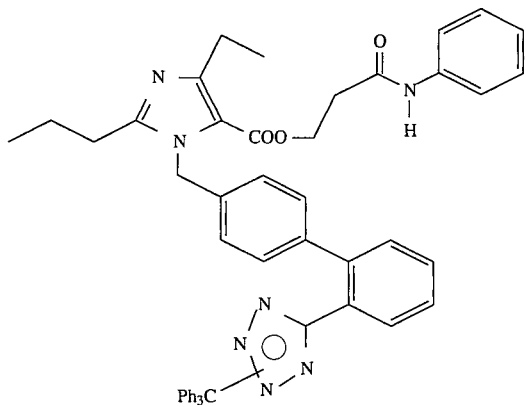

Part A. Preparation of N-phenyl-2-(aminocarbonyl)ethyl 4-ethyl-2-propyl-1-[[2'-(N-triphenylmethyl(tetrazol-5-yl))biphenyl-4-yl]methyl]imidazole-5-carboxylate To a solution/suspension of 0.66 g 4-ethyl-2-propyl-1-[[2'-(N-triphenylmethyl(tetrazol- 5-yl))biphenyl-4-yl]methyl]imidazole-5-carboxylic acid, 0.23 g 2-bromo-N-phenylpropionamide, and 0.15 g K₂CO₃ in 7 mL of DMF was added 0.17 g of KI. The reaction was stirred 10 minutes at room temperature, then heated in a N₂ atmosphere at 70° C. overnight. The reaction was partitioned between H₂O and EtOAc, and the organic extract washed with brine and dried with MgSO₄. Filtration, concentration, and flash chromatography with a 10–60% EtOAc/hexanes gradient provided 0.35 g of pure product.

¹H-NMR (CDCl₃) δ 8.70 and 7.98 (br s, 1H), 7.85 (m, 1H), 7.50–7.40 (m, 4H), 7.37–7.20 (m, 13H), 7.11–7.00 (m, 3H), 6.99–6.91 (m, 5H), 6.80–6.77 (m, 2H), 5.40 (s, 2H), 5.35 and 4.28 (q, 1H), 2.99 (q, 2H), 2.55 (t, 2H), 1.78–1.60 (m, 2H), 1.53 and 1.48 (d, 3H), 1.37 (t, 3H), 0.87 (t, 3H).

Part B. Preparation of N-phenyl-2-(aminocarbonyl)ethyl 4-ethyl-2-propyl-1-[[2'-(1H-tetrazol-5-yl)biphenyl-4-yl]methyl]imidazole-5-carboxylate A solution of 0.05 g N-phenyl-2-(aminocarbonyl)ethyl 4-ethyl-2-propyl- 1-[[2'-(N-triphenylmethyl(tetrazol-5-yl))biphenyl-4-yl]methyl]imidazole-5-carboxylate in 2.5 mL MeOH was refluxed overnight under N₂. The reaction was evaporated to dryness and the residue immediately purified by flash chromatography with 0–5% MeOH/CHCl₃ gradient to give 0.0226 g of pure product.

¹H-NMR (CDCl₃) δ 8.10 (br s, 1H), 7.88 (m, 1H), 7.60–7.45 (m, 2H), 7.40–7.23 (m, 3H), 7.20–7.10 (m, 2H), 7.09–6.96 (m, 3H), 6.81–6.75 (m, 2H), 5.40 (s, 2H), 5.27 (q, 1H), 2.72 (q, 2H), 2.40 (t, 2H), 1.68–1.60 (m, 2H), 1.52 (d, 3H), 1.08 (t, 3H), 0.88 (t, 3H).

EXAMPLE 8

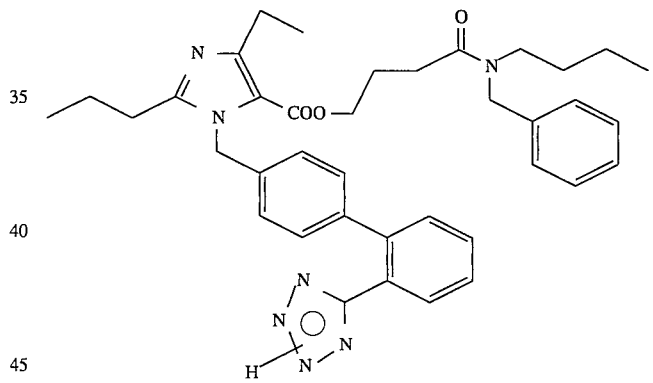

Preparation of N-butyl, N-benzyl-4-(aminocarbonyl)propyl 4-ethyl-2-propyl-1-[[2'-(1H-tetrazol-5-yl)biphenyl-4-yl]methyl]imidazole-5-carboxylate

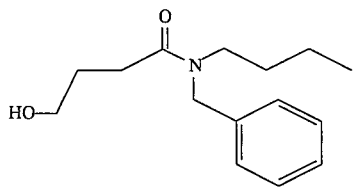

Part A. Preparation of N-butyl, N-benzyl-4-hydroxy-butanamide

To a solution of 23 mL of Me₃Al (2.0M in hexanes) in 24 mL of CH₂Cl₂ was added in a N₂ atmosphere 8.33 mL butylbenzylamine. The mixture was stirred 30 minutes at room temperature before adding 0.89 mL of g-butyrolactone. The reaction was stirred overnight at room temperature, then quenched with 1N HCl to pH 2–3, and extracted with $CH_2Cl_2$. The combined organics were washed with $H_2O$ and brine, and dried over $Na_2SO_4$. Filtration, evaporation, and flash chromatography with a 0–5% MeOH/$CHCl_3$ gradient provided 2.07 g of product.

$^1$H-NMR ($CDCl_3$) δ 7.40–7.17 (m, 5H), 4.61 and 4.59 (s, 2H), 3.75 and 3.65 (t, 2H), 3.38 and 3.21 (t, 2H), 2.58 and 2.47 (t, 2H), 2.00–1.80 (m, 2H), 1.60–1.43 (m, 2H), 1.38–1.22 (m, 2H), 0.97–0.85 (2t, 3H).

Part B. Preparation of N-butyl, N-benzyl-4-(aminocarbonyl)propyl 4-ethyl-2-propyl-1-[[2'-(tetrazol-5-yl)biphenyl-4-yl]methyl]imidazole-5-carboxylate To a solution of 0.40 g 4-ethyl-2-propyl-1-[[2'-(1H-tetrazol-5-yl)biphenyl- 4-yl]methyl]imidazole-5-carboxylic acid in 50 mL anhydrous THF was added 0.27 g CDI in one portion. After stirring overnight at room temperature under $N_2$, there was added a solution of the sodium alkoxide of N-butyl, N-benzyl-4-hydroxy-butanamide (prepared from 0.48 g of the alcohol with NaH) in 5 mL THF. After 24 hours at room temperature, the reaction was poured into cold brine and extracted with $CH_2Cl_2$/i-PrOH (4:1). The organic extract was dried ($MgSO_4$), filtered, evaporated, and purified by flash chromatography using 0–15% MeOH/$CH_2Cl_2$ to give 0.16 g of product.

$^1$H-NMR ($CDCl_3$) δ 13.5 (br s, 1H), 7.8 (m, 1H), 7.51–7.4 (m, 3H), 7.38–7.10 (m, 4H), 7.10–7.08 (m, 1H), 7.08–7.00 (m, 2H), 6.82–6.77 (m, 2H), 5.41 and 5.39 (s, 2H), 4.60 and 4.49 (s, 2H), 4.25 and 4.15 (t, 2H), 3.37 and 3.18 (t, 2H), 2.85–2.68 (m, 2H), 2.55–2.45 (m, 2H), 2.40 (t, 2H), 2.01–1.90 (2t, 2H), 1.65–1.40 (m, 2H), 1.28–1.20 (m, 4H), 0.92–0.80 (2t, 6H).

EXAMPLE 9

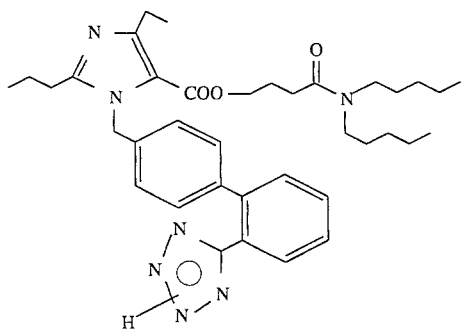

Preparation of Preparation of N, N-dipentyl-4-(aminocarbonyl)propyl 4-ethyl-2-propyl-1-[[2'-(tetrazol-5-yl)biphenyl-4-yl]methyl]imidazole-5-carboxylate

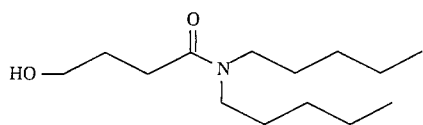

Part A. Preparation of N, N-dipentyl-4-hydroxy-butanamide

By employing the method described in Example 8, Part A, there was obtained from 0.89 mL g-butyrolactone and 9.41 mL dipentylamine 2.51 g of pure product.

$^1$H-NMR ($CDCl_3$) δ 3.99 (br s, 1H), 3.65 (t, 2H), 3.37–3.20 (m, 4H), 2.43 (t, 2H), 1.95–1.83 (m, 2H), 1.62–1.43 (m, 4H), 1.40–1.20 (m, 8H), 0.97–0.80 (2t, 6H).

Part B. Preparation of N, N-dipentyl-4-aminocarbonylpropyl 4-ethyl-2-propyl-1-[[2'-(1H-tetrazol-5-yl)biphenyl-4-yl]methyl]imidazole-5-carboxylate By employing the method described in Example 8, Part B, there was obtained from 0.47 g N, N-dipentyl-4-hydroxy-butanamide, 0.40 g 4-ethyl- 2-propyl- 1-[[2'-(tetrazol-5-yl)biphenyl-4-yl]methyl]imidazole-5-carboxylic acid, and 0.27 g CDI 0.12 g of pure product.

$^1$H-NMR ($CDCl_3$) δ 13.3 (br s, 1H), 7.81 (m, 1H), 7.55–7.38 (m, 3H), 7.10–7.00 (m, 2H), 6.82–6.80 (m, 2H), 5.40 (s, 2H), 4.22 (t, 2H), 3.25 (t, H), 3.19 (t, 2H), 2.84 (m, 2H), 2.50 (t, 2H), 2.40 (t, 2H), 2.01 (m, 2H), 1.70–1.40 (m, 6H), 1.37–1.18 (m, 11H), 0.95–0.80 (m, 9H).

EXAMPLE 10

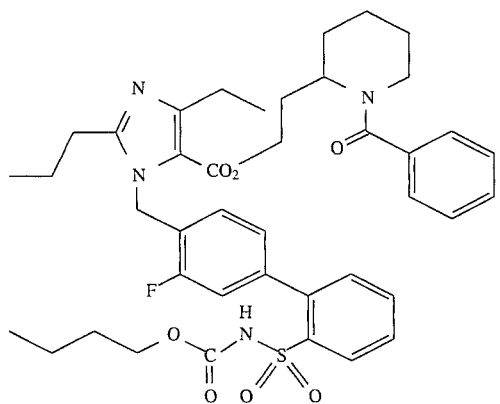

Preparation of 2-(N-Benzoylpiperidin-2-yl)ethyl 1-[(2'-(n-butoxycarbonylaminosulfonyl)-3-fluorobiphenyl)methyl]-4-ethyl-2-propylimidazolecarboxylate.

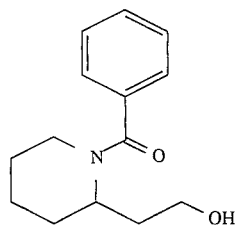

Part A. Preparation of N-benzoyl-2-piperidineethanol

To a solution of benzoic anhydride (16.6 g, 73.5 mmol) and triethylamine (8.2 g, 81.1 mmol) in 150 mL of methylene chloride, was added 2-piperidine-ethanol (10.0 g, 77.5 mmol). A slight exotherm was observed and the reaction mixture was stirred at ambient temperature overnight. The reaction mixture was washed in turn with 200 mL of 1N hydrochloric acid, 200 mL of saturated sodium bicarbonate, and 100 mL brine. The organic phase was dried over anhydrous magnesium sulfate, filtered and concentrated under vacuum to give 14.0 g of a crude product. This was purified by flash chromatography (silica gel, 100% ethyl acetate) to yield 9.47 g (55%) of product as a light amber oil. MS: m/e 234, [M+H]$^+$; $^1$H NMR (300 MHz, CDCl$_3$): δ 1.50–1.75 (br m, 6H); 1.84–2.03 (br m, 1H); 2.06 (complex t, 1H); 2.91 (br t, J=13 Hz, 1H); 3.47 (t, J=11.7 Hz, 1H); 3.60–3.71 (br m, 2H); 4.15 (br s, 2H); 4.96 (br d, J=12 Hz, 1H); 7.41 (br s, 5H).

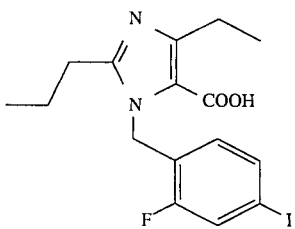

Part B. Preparation of
1-(2-fluoro-4-iodobenzyl)-4-ethyl-2-propyl,
1H-imidazole-5-carboxylic acid.

A solution of 30% hydrogen peroxide (5.2 mL, 50.9 mmol) in 80 mL of tetrahydrofuran was chilled in an ice bath. To this was added a solution of sodium dihydrogen phosphate monohydrate (5.2 g, 37.7 mmol) in 50 mL of water followed by a solution of 1-(2-fluoro-4-iodobenzyl)-4-ethyl-2-propyl- 1H-imidazole-5-carboxaldehyde (10 g, 25 mmol) in 80 mL of tetrahydrofuran. To this reaction mixture, was slowly added over a 30 minute period, a solution of 80% sodium chlorite (5.65 g, 50 mmol) in 130 mL of water, maintaining the reaction temperature between +5° and 10° C. The yellow reaction mixture was then stirred at room temperature overnight. By the next day, the reaction mixture had become a turbid white solution, to which was added solid sodium sulfite (6.25 g, 49.6 mmol) followed by a solution of sodium sulfite (23.4 g, 186 mmol) in 100 mL of water. The reaction mixture was stirred for 30 minutes and its pH was adjusted to pH 12 with 3N sodium hydroxide, dissolving any precipitated solids. The tetrahydrofuran was stripped under vacuum and the aqueous residue was extracted with 250 mL of methylene chloride. The aqueous phase was stripped of any residual methylene chloride under vacuum and filtered through celite. The filtrate was chilled in ice and the product precipitated with the addition of 6N hydrochloric acid. The product was filtered, washed with ice cold water, and dried overnight, yielding 6.88 g (66%) of product as a white solid. MS: m/e 417 [M+H]$^+$; $^1$H NMR (300 MHz, DMSO-d$_6$): δ 0.87 (t, J=7.3 Hz, 3H); 1.16 (t, J=7.3 Hz, 3H); 1.63 (m, 2H); 2.61 (t, J=7.7 Hz, 2H); 2.81 (q, J=7.3 Hz, 2H); 5.52 (s, 2H); 6.33 (t, J=8.1 Hz, 1H); 7.51 (d, J=8.1 Hz, 1H); 7.69 (d, J=9.5 Hz, 1H).

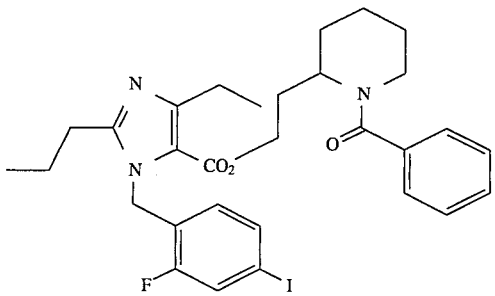

Part C. Preparation of
2-(N-Benzoylpiperidin-2-yl)ethyl
1-[2-fluoro-4-iodophenyl)methyl]-
4-ethyl-2-propylimidazolecarboxylate.

Oxalyl chloride (15 mL, 21.8 g, 172 mmol) was cautiously added to a flask containing the product from part B (1.5 g, 3.6, mmol), chilled in a ice bath. The cooling bath was removed and the reaction mixture was heated to reflux under nitrogen for 30 minutes. The excess oxalyl chloride was stripped under vacuum and the solid residue was dissolved in 15 mL dry methylene chloride. To the resulting solution was added a solution containing N-benzoyl-2-piperidineethanol (1.3 g, 5.5 mmol) and pyridine (1 mL, 0.98 g, 12 mmol) in 5 mL dry methylene chloride. The reaction was refluxed under nitrogen for two hours and then stirred at room temperature overnight. The reaction mixture was washed twice with 40 mL of 1N hydrochloric acid, then four times with 25 mL saturated sodium bicarbonate, and finally with 25 mL of brine. The organic layer was dried over anhydrous magnesium sulfate, filtered and concentrated under vacuum to give 2.56 g of crude product. This was purified by flash chromatography (silica gel, gradient: 50% hexane/50% ethyl acetyate- 25% hexane/75% ethyl acetate) to yield 1.77 g (78%) of product as a glass. MS: m/e 632, [M+H]$^+$.

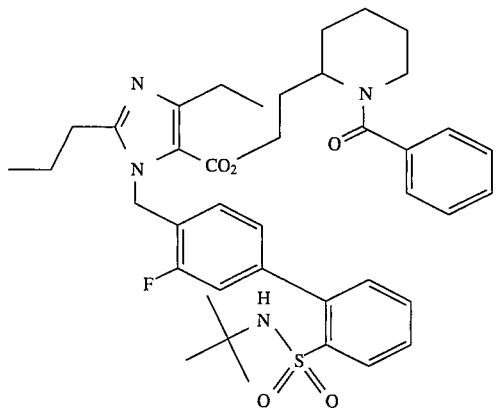

Part D. Preparation of
2-(N-Benzoylpiperidin-2-yl)ethyl
1-[(2'-(t-butylaminosulfonyl)-
3-fluorobiphenyl)methyl]-4-ethyl-2-
propylimidazolecarboxylate.

A mixture of the product from part C (1.0 g, 1.6 mmol), 2-(t-butylamino)sulfonyl-phenyl boronic acid (0.55 g, 2.1 mmol), tetrabutylammonium bromide (0.05 g, 0.16 mmol), and potassium carbonate (0.60 g, 4.3 mmol) was suspended in 6 mL of toluene and 2 mL of water. The reaction mixture was degassed by evacuating and refilling with nitrogen. Tetrakistriphenylphosphine palladium(0) (0.1 g, 0.087 mmol) was added and the degassing procedure repeated. The reaction mixture was refluxed with efficient stirring overnight. The reaction mixture was poured into a separatory funnel containing 25 mL of ethyl acetate and the aqueous layer drained and discarded. The organic phase was washed in turn with 25 mL of water, two 25 mL portions of saturated sodium bicarbonate, and 25 mL of brine. The organic phase was then dried over anhydrous magnesium sulfate, filtered and stripped under vacuum to give 1.32 g of crude product. This was purified by flash chromatography (silica gel, gradient: 10% acetone/30% ethyl acetate/60% hexane- 20% acetone/30% ethyl acetate/50% hexane) to yield 0.82 g (72%) of product as a glass. MS: m/e 703, [M+H]⁺.

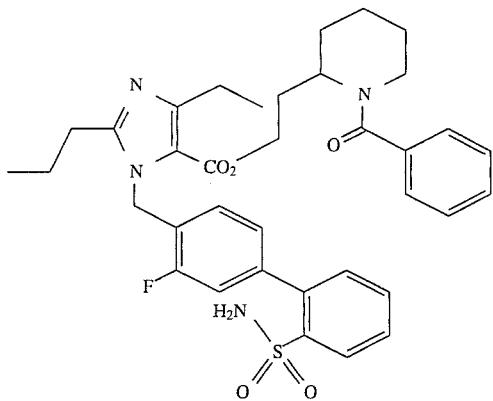

Part E. Preparation of 2-(N-Benzoylpiperidin-2-yl)ethyl 1-[(2'-aminosulfonyl)-3-fluorobiphenyl)methyl]-4-ethyl-2propylimidazolecarboxylate.

A solution of the product from part D (0.82 g, 1.1 mmol) in 35 mL of trifluoroacetic acid was refluxed protected from moisture for 3 h. The trifluoroacetic acid was stripped under vacuum and the residue dissolved in 50 mL of methylene chloride. This solution was washed with two portions of 50 mL of saturated sodium bicarbonate and then with brine. The organic phase was dried over anhydrous magnesium sulfate, filtered, and stripped under vacuum to give 0.74 g (98%) of crude product as a glass. MS: m/e 661, [M+H]⁺. This product was sufficiently pure to use in the next reaction.

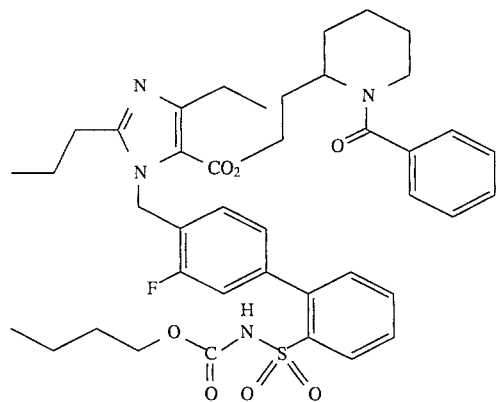

Part F. Preparation of 2-(N-Benzoylpiperidin-2-yl)ethyl 1-[(2'-(n-butoxycarbonylaminosulfonyl)-3-fluorobiphenyl)methyl]-4-ethyl-2-propylimidazolecarboxylate.

To a solution containing the product from part E (0.74 g, 1.1 mmol) and 4-dimethylaminopyridine (0.63 g, 5.1 mmol) in a mixture of 5 mL of pyridine and 50 mL of methylene chloride, was added n-butyl chloroformate (0.65 g, 4.74 mmol) under a nitrogen atmosphere. The reaction mixture was stirred overnight at room temperature, and then washed in turn with four 100 mL portions of 1N hydrochloric acid, 100 mL of saturated sodium bicarbonate, and 100 mL of brine. The organic phase was dried over anhydrous magnesium sulfate, filtered and stripped under vacuum to give 0.88 g of crude product. This was purified by flash chromatography (silica gel, 0.5% acetic acid, 20% acetone, 30% ethyl acetate, 50% hexane) to give 0.61 g (72%) of product as a white solid foam. MS: m/e 761, [M+H]⁺.

EXAMPLE 11

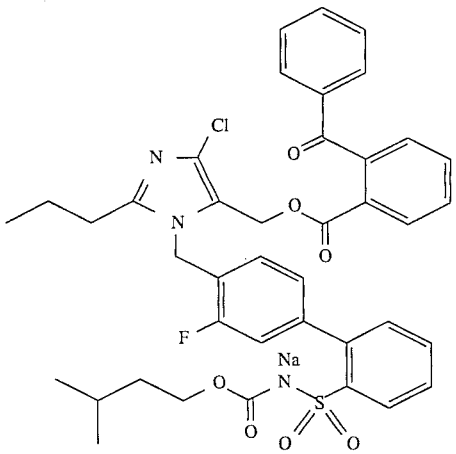

Preparation of 4-[(5-((2-benzoyl)phenylcarbonyloxymethyl)-4-chloro-2-n-propylimidazol-1-yl)methyl]-3-fluoro-2'-isoamyloxycarbonylaminosulfonylbiphenyl, sodium salt.

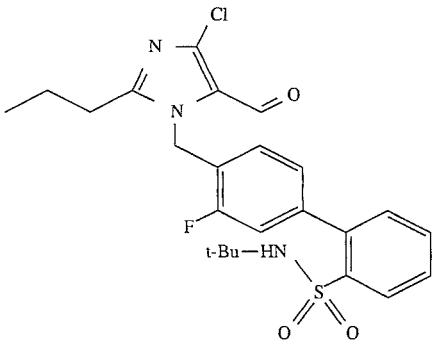

Part A. Preparation of 1-[2'-(t-butylaminosulfonyl)-3-fluorobiphenyl-4-yl]methyl-4-chloro-2-n-propylimidazole-5-carboxaldehyde.

4-Chloro-2-n-propyl-imidazole-5-carboxaldehyde was prepared as described in U.S. Pat. No. 4,760,083. The imidazole can then be converted to the title compound by using the methods of Example 1, Parts A, B, and C. NMR (CDCl$_3$) δ 9.77 (s,1H), 8.16 (d, 1H), 7.50 (m, 2H), 7.30 (m, 3H), 6.86 (t, 1H), 5.63 (s, 2H), 3.55 (s, 1H), 2.65 (m, 2H), 1.79 (m, 2H), 1.00 (m 12H).

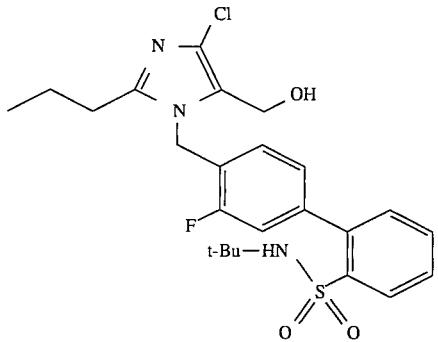

Part B. Preparation of 2'-(N-t-butyl)sulfonamido-4-[(4-chloro-5-hydroxymethyl-2-n-propylimidazol-1-yl)methyl]-3-fluorobiphenyl.

1-[2'-(t-Butylaminosulfonyl)-3-fluorobiphenyl-4-yl]methyl-4-chloro-2-n-propylimidazole- 5-carboxaldehyde (3.49 g, 7.10 mmol) was dissolved in methanol (30 mL). Sodium borohydride (0.32 g, 8.5 mmol) was added over 5 minutes. The reaction was complete within minutes. The reaction was poured into water and extracted with ethyl acetate (3×). The solvent was dried (MgSO$_4$) and the solvent removed in vacuo to yield 3.20 g of a tan powder. NMR (CDCl$_3$) δ 8.18 (d, 1H), 7.55 (m, 2H), 7.30 (m, 3H), 6.78 (t, 1H), 5.49 (s, 2H), 4.56 (d, 2H), 3.76 (s, 1H), 2.59 (m, 2H), 1.75 (m, 2H), 1.02 (s, 9H), 0.98 (t, 3H).

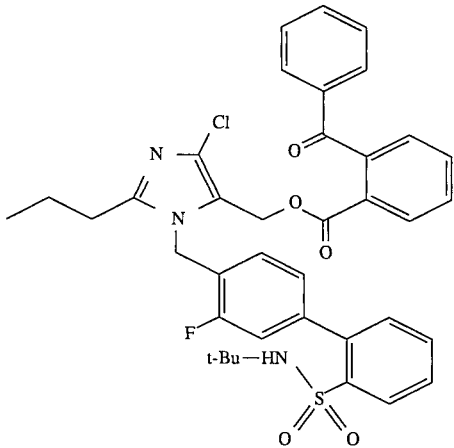

Part C. Preparation of 4-[(5-((2-benzoyl)phenylcarbonyloxy)methyl-4-chloro-2-n-propylimidazol-1-yl)methyl]-2'-(N-t-butyl)sulfonamido-3-fluorobiphenyl.

2-Benzoylbenzoic acid (0.23 g, 1.0 mmol), dicyclohexylcarbodiimide (0.21 g, 1.0 mmol), dimethylaminopyridine (0.01 g, 0.1 mmol), and 2'-(N-t-butyl)sulfonamido- 4-[(4-chloro-5-hydroxymethyl-2-n-propylimidazol-1-yl)methyl]-3-fluorobiphenyl (0.50 g, 1.0 mmol) were all added to CH$_2$Cl$_2$ (25 mL). The reaction was stirred at room temperature for 72 h. The reaction was filtered. The filtrate was washed with water, 10% citric acid, water, dried (MgSO$_4$) and the solvent removed in vacuo to yield 0.72 g. NMR (CDCl$_3$) δ 8.16 (d, 1H), 8.02 (d, 1H), 7.6–7.3 (m, 11H), 7.15 (t, 2H), 6.63 (t, 1H), 5.04 (s, 2H), 4.93 (s, 2H), 3.67 (s, 1H), 2.55 (m, 2H), 1.70 (m 2H), 1.00 (m, 12H).

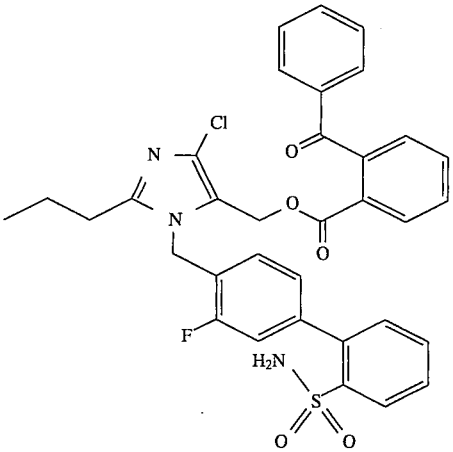

Part D. Preparation of 4-[(5-((2-benzoyl)phenylcarbonyloxy)methyl-4-chloro-2-n-propylimidazol-1-yl)methyl]-3-fluoro-2'-sulfonamidobiphenyl.

4[(5-((2-Benzoyl)phenylcarbonyloxy)methyl-4-chloro-2-n-propylimidazol-1-yl)methyl]- 2'-(N-t-butyl)sulfonamido-3-fluorobiphenyl (0.72 g, 1.0 mmol) was dissolved in trifluoroacetic acid (20 mL). The reaction was heated to reflux for 2 hours. It then was stirred at room temperature overnight. The solvent was removed in vacuo. The residue was taken up in CH$_2$Cl$_2$. 10% Sodium bicarbonate was added until the aqueous was neutral. The CH$_2$Cl$_2$ layer was separated, dried, and the solvent removed in vacuo. Column chromatography using 50% ethyl acetate in hexane yielded 0.48 g. NMR (CDCl$_3$) δ 8.15 (d, 1H), 8.03 (d, 1H), 7.7–7.1 (m, 13H), 6.67 (t, 1H), 5.03 (s, 2H), 4.91 (s, 2H), 4.48 (s, 2H), 2.55 (m, 2H), 1.75 (m, 2H), 0.98 (t, 3H).

Part E. Preparation of 4-[(5-((2-benzoyl)phenylcarbonyloxy)methyl-4-chloro-2-n-propylimidazol-1-yl)methyl]-3-fluoro-2'-isoamyloxycarbonylaminosulfonylbiphenyl, sodium salt.

4-[(5-(2-Benzoyl)phenylcarbonyloxy)methyl-4-chloro-2-n-propylimidazol-1-yl)methyl]- 3-fluoro-2'-sulfonamidobiphenyl (0.24 g, 0.37 mmol) and dimethylaminopyridine (0.28 g, 2.3 mmol) were added to a mixture of CH$_2$Cl$_2$ (25 mL) and pyridine (1 mL). i-Amylchloroformate solution (2.25M in toluene, 1.0 mL, 2.3 mmol) was added to the reaction and it was stirred at room temperature for 48 h. The reaction was diluted with additional CH$_2$Cl$_2$ and washed with 10% citric acid solution (3×). The solution was dried (MgSO$_4$) and the solvent removed in vacuo. The material was then washed with hexane to yield 0.22 g of a solid. The product was titrated with 0.09M KOH and the water was removed in vacuo. NMR (CDCl$_3$) δ 8.03 (m, 2H), 7.7–7.0 (m, 13H), 6.65 (m, 1H), 4.91 (s, 2H), 4.79 (s, 2H), 3.49 (m, 2H), 2.57 (m, 2H), 1.75 (m, 2H), 0.98 (t, 3H), 0.64 (d, 6H).

EXAMPLE 12

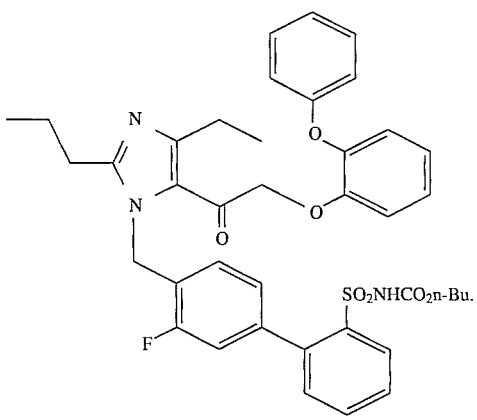

Preparation of
1-((2'-((n-butyloxycarbonylamino)sulfonyl)-
3-fluoro-(1,1'-biphenyl)-
4-yl)methyl)-2-(n-propyl)-4-ethyl-5-
(2-(phenoxy)phenoxy)acetyl-1H-imidazole

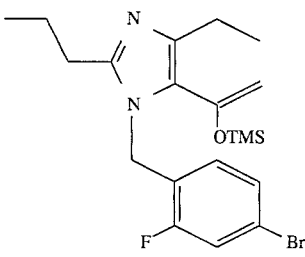

Part A. Preparation of 1-(4-bromo-2-fluorobenzyl)-2-(n-propyl)-4-ethyl-5-(1-(trimethylsilyloxy)ethenyl)-1H-imidazole To a solution of 2.50 g (6.81 mmol) of 1-(4-bromo-2-fluorobenzyl)- 2-(n-propyl)-4-ethyl-5-acetyl-1H-imidazole (67 $R^1$=2-F, $R^2$=4-Br, n=0; prepared using the procedures of Example 3, Parts A and B) in 80 mL anhydrous THF was added 7.59 mL trimethylsilyl triflate (40.8 mmol) under nitrogen at 22° C., followed by 11.38 mL (81.9 mmol) triethylamine. The mixture was stirred at 22° C. for 2.5 hours and then diluted with 100 mL of anhydrous ethyl ether and quenched with 10 mL of saturated NaHCO₃ solution. The organic layer was washed with saturated NaHCO₃ solution, dried over Na₂SO₄, and filtered. Solvents were then removed under reduced pressure yield 2.69 g (90%) of the title compound as a brown oil, which was used without further purification. ¹H NMR (300 MHz, CDCl₃): δ 0.14 (s, 9H); 0.84 (t, 3H); 1.16 (t, 3H); 1.68 (m, 2H); 2.41 (t, 2H); 2.56 (q, 2H); 4.30 (s, 1H); 4.43 (s, 1H); 5.03 (s, 2H); 6.44 (t, 1H); 7.10 (m, 2H).

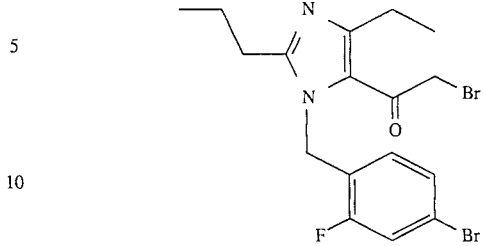

Part B. Preparation of 1-(4-bromo-2-fluorobenzyl)-2-(n-propyl)-4-ethyl-5-bromoacetyl- 1H-imidazole To 2.69 g (6.13 mmol) of 1-(4-bromo-2-fluorobenzyl)-2-(n-propyl)-4-ethyl- 5-(1-(trimethylsilyloxy)ethenyl)-1H-imidazole in 100 mL THF at 0° C. was added 1.09 g (6.13 mmol) of NBS. After stirring for 30 min, the solution was poured into saturated NaHCO₃ solution. The mixture was extracted with anhydrous ethyl ether, dried over Na₂SO₄ and filtered. The filtrate was evaporated under reduced pressure to give 2.32 g (85%) of the title compound as a brown oil, which was used without further purification. ¹H NMR (300 MHz, CDCl₃): δ 0.96 (t, 3H); 1.42 (t, 3H); 1.76 (m, 2H); 2.46 (t, 2H); 3.02 (q, 2H); 5.30 (s, 2H); 5.50 (s, 2H); 6.59 (t, 1H); 7.14 (m H).

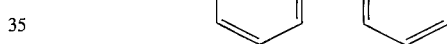

Part C. Preparation of 2-phenoxyphenol

A solution of 23.4 g (74.9 mmol) of boron tribromide-dimethyl sulfide complex in 150 mL of 1,2-dichloroethane was added dropwise to 3.00 g (15.0 mmol) of 2-methoxyphenyl phenyl ether in 50 mL dichloroethane at room temperature. The mixture was stirred at reflux overnight. 50 mL 3M NaOH was added to quench the reaction. After separation of layers, the organic layer was extracted with 3×100 mL 3M NaOH. The combined aqueous layer was acidified with conc. HCl, and the precipitated product was extracted with 3×150 mL ethyl ether. After washing with brine solution, drying over MgSO₄, and filtering, solvents were evaporated under reduced pressure to give 2.30 g (82.4%) of an off-white solid, which was used without further purification. ¹H NMR (300 MHz, CDCl₃): δ 5.57 (s, 1H); 6.81–6.90 (m, 2H); 7.01–7.07 (m, 4H); 7.12 (t, 1H, J=7.3 Hz); 7.31–7.38 (m, 2H).

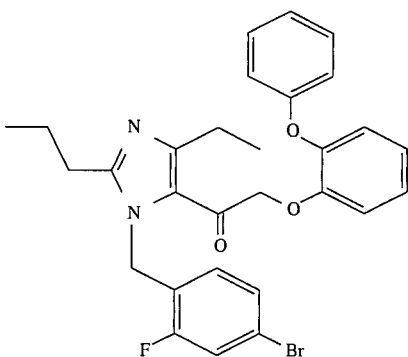

Part D. Preparation of 1-(4-bromo-2-fluorobenzyl)-2-(n-propyl)-4-ethyl-5-(2-(phenoxy)phenoxy)acetyl-1H-imidazole To a solution of 0.63 g (3.36 mmol) of 2-phenoxyphenol and 0.62 g (4.48 mmol) of $K_2CO_3$ in 75 mL acetone at ambient temperature was added 1.00 g (2.24 mmol) of 1-(4-bromo-2-fluorobenzyl)-2-(n-propyl)-4-ethyl-5-bromoacetyl-1H-imidazole obtained from Part B of Example 11 in 25 mL acetone. After stirring at reflux overnight, the reaction mixture was poured into water and extracted with 3×100 mL ethyl acetate. The combined organic layers were washed with brine, dried over $MgSO_4$, filtered, and the solvents evaporated under reduced pressure. The crude product was purified by flash column chromatography using 10–40% ethyl acetate in hexane, which provided 0.16 g (6.3%) of a clear oil after evaporation of solvents under reduced pressure. $^1H$ NMR (300 MHz, $CDCl_3$): δ 0.95 (t, 3H, J=7.3 Hz); 1.29 (t, 3H, J =7.3 Hz); 1.66 (m, 2H); 2.60 (m, 2H); 2.81 (q, 2H, J=7.3 Hz); 5.00 (s, 2H); 6.38 (t, 1H, J=7.8 Hz); 6.89–7.29 (m, 10H).

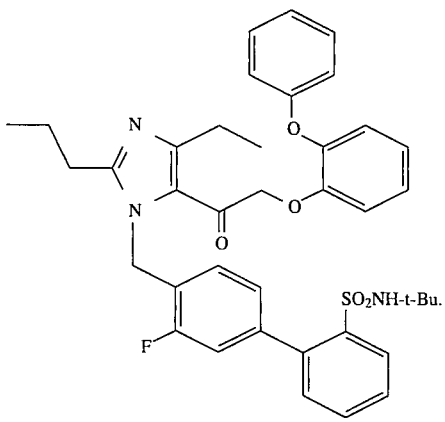

Part E. Preparation of 1-((2'-(t-butylaminosulfonyl)-3-fluoro-(1,1'-biphenyl)-4-yl)methyl)-2-(n-propyl)-4-ethyl-5-(2-(phenoxy)phenoxy)acetyl-1H-imidazole From 0.16 g (0.29 mmol) of 1-(4-bromo-2-fluorobenzyl)-2-(n-propyl)-4-ethyl-5-(2-(phenoxy)phenoxy)acetyl-1H-imidazole, using 0.12 g (0.47 mmol) of 2-(t-butylamino)sulfonylphenyl boronic acid, 0.12 g (0.86 mmol)potassium carbonate, 0.016 g (0.05 mmol) tetrabutylammonium bromide, 0.02 g (0.02 mmol) tetrakis(triphenylphosphine)palladium(0), with 1 mL of water and 2 mL of toluene as solvent, 0.08 g (40%) of the title compound was obtained following the procedure of Example 3, Part F, after purification by preparative TLC (silica gel; 20% acetone, 30% ethyl acetate, 50% hexane). $^1H$ NMR (300 MHz, $CDCl_3$): δ 0.97 (m, 12H, overlapping t-butyl singlet and methyl triplet); 1.32 (t, 3H, J=7.3 Hz); 1.72 (m, 2H); 2.63 (t, 2H, J=7.3 Hz); 2.83 (q, 2H, J=7.3 Hz); 3.57 (s, 1H); 5.06 (s, 2H); 5.58 (s,2H); 6.61 (t, 1H, J=8.1 Hz); 6.87–7.09 (m, 7H); 7.12 (d, 1H, J=8.1 Hz); 7.23–7.29 (m,5H); 7.51 (m, 2H); 8.15 (d, 1H, J=7.7 Hz).

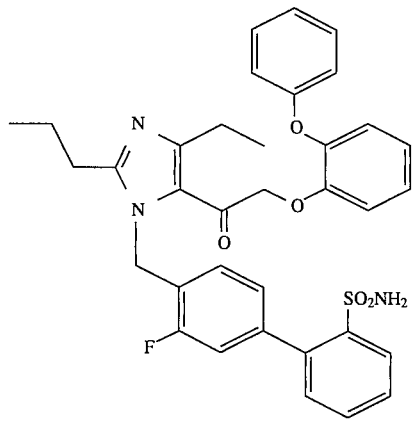

Part F. Preparation of 1-((2'-(aminosulfonyl)-3-fluoro-(1,1'-biphenyl)-4-yl)methyl)-2-(n-propyl)-4-ethyl-5-(2-(phenoxy)phenoxy)acetyl-1H-imidazole From 0.08 g (0.12 mmol) of 1-((2'-(t-butylaminosulfonyl)-3-fluoro-( 1,1'-biphenyl)-4-yl)methyl)-2-(n-propyl)-4-ethyl-5-(2-(phenoxy)phenoxy)acetyl- 1H-imidazole in 6 mL of trifluoroacetic acid, 0.08 g (100%) of the title compound was obtained, following the precedure of Example 3, Part G, with a 5 hr reflux period. MS m/e=628, $[M=H]^+$; $^1H$ NMR (300 MHz, $CDCl_3$): δ 0.98 (t, 3H, J =7.3 Hz); 1.33 (t, 3H, J=7.3 Hz); 2.66 (t, 2H, J=7.3 Hz); 2.83 (q, 2H, J=7.3 Hz); 4.20 (br s, 2H); 5.04 (s, 2H); 5.56 (s,2H); 6.63 (t, 1H, J=7.8 Hz); 6.84–7.09 (m, 9H); 7.18 –7.29 (m,4H); 7.48–7.61 (m, 2H); 8.14 (d, 1H, J=7.8 Hz).

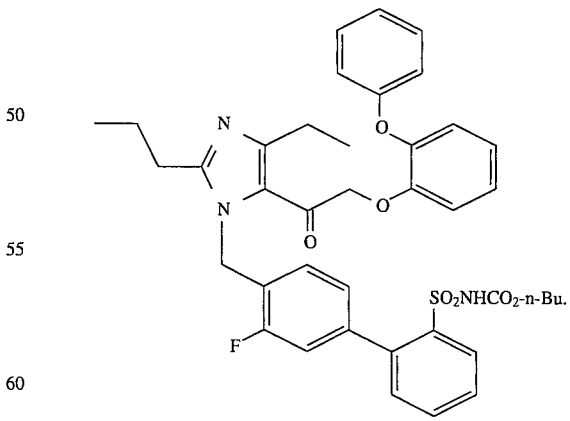

Part G. Preparation of 1-((2'-((n-butyloxycarbonylamino)sulfonyl)-3-fluoro-(1,1'-biphenyl)-4-yl)methyl)-2-(n-proply)-4-ethyl-5-( 2-(phenoxy)acetyl-1H-imidazole.

From 0.08 g (0.13 mmol) of 1-((2'-(aminosulfonyl)-3-fluoro-(1,1'- biphenyl)-4-yl)methyl)-2-(n-propyl)-4-ethyl-5-

(2-(phenoxy)phenoxy)acetyl- 1H-imidazole and using 0.10 g (0.82 mmol) of 4-N,N-dimehtylaminopyreidine, 100 ml, 0.11 g (0.73 mmol) of n-butyl chloroformate, with 1 mL pyridine and 10 mL methylene chloride as solvent, 0.05 g (54%) of title was obtained following the procedure of Example 3, Part H, with a 16 hr reaction time and after purification by prep TLC (silica gel; 20% acetone, 30% ethyl acetate, 50% hexane). MS m/e=728, [M=H]+; 1H NMR (300 MHz, CDCl₃)δ0.83 (t, 3H, J=7.3 Hz); 0.98 (t, 3H, J=7.3 Hz); 1.18 (m.2H); 1.32 (t, 3H, J=7.3 Hz); 1.43 (m,2H); 1.73 (m,2H) 2.67 (t, 2H, J=7.7 Hz);2.82 (q, 2H, j=7.3 Hz); 3.98 (t, 2H, J=6.6 Hz);5.05 (s, 2H); 5.57 (s, 2H); 6.59 (t, 1H, j=7.7 Hz); 6.86–7.10 (m, 6H);7.16–7.33 (m,6H);7.54–7.66 (m,2H); 8.25(d, 1H, J=7.7 Hz).

Compounds 13–488 in tables 1–5 can be prepared by the procedures described in examples 1–12 employing the approximately substituted starting materials.

TABLE 1

| Ex. No. | R⁶ | R⁸ | Rᵃ | R¹³ | R² | m.p. |
|---|---|---|---|---|---|---|
| 13 | n-propyl | ethyl | a (CH₂-2-benzoylphenyl) | CH₃O₂C—NHSO₂— | H | |
| 13a | n-propyl | ethyl | b (CH₂-2-benzoylphenyl) | Ph—(CH₂)₂O₂C—NHSO₂— | H | |
| 13b | n-propyl | ethyl | c (CH₂-2-benzoylphenyl) | (CH₃)₂CH(CH₂)₂O₂C—NHSO₂— | H | |
| 14 | n-propyl | ethyl | d (CH₂-2-benzoylphenyl) | Ph—(CH₂)₂O₂C—NHSO₂— | 2-F | |
| 15 | n-propyl | ethyl | e (CH₂-2-benzoylphenyl) | CH₃(CH₂)₂O₂C—NHSO₂— | 2-F | |
| 16 | n-propyl | ethyl | f (CH₂-2-benzoylphenyl) | (CH₃)₂CHCH₂O₂C—NHSO₂— | 2-F | |

TABLE 1-continued

| Ex. No. | R[6] | R[8] | R[a] | R[13] | R[2] | m.p. |
|---|---|---|---|---|---|---|
| 17 | n-propyl g | ethyl | -CH2-C6H4(2-C(O)C6H5) | CH3(CH2)3O2C—NHSO2— | 2-F | |
| 18 | n-propyl (M+H)+=756.3 | ethyl | -CH2-C6H4(2-C(O)C6H5) | CH3(CH2)3O2C—NHSO2— | 2-Cl | |
| 19 | n-propyl h | ethyl | -CH2-C6H4(2-OC6H5) | CH3(CH2)3O2C—NHSO2— | 2-F | |
| 20 | n-propyl (M+H)+=744.2 | ethyl | -CH2-C6H4(2-OC6H5) | CH3(CH2)3O2C—NHSO2— | 2-Cl | |
| 21 | n-propyl (M+H)+=710.3 | ethyl | -CH2-C6H4(2-O-iPr) | CH3(CH2)3O2C—NHSO2— | 2-Cl | |
| 22 | n-propyl i | ethyl | -CH2-C6H4(2-SO2C6H5) | CH3(CH2)2O2C—NHSO2— | 2-F | |
| 23 | n-propyl j | ethyl | -CH2-C6H4(2-SO2C6H5) | (CH3)2CH(CH2)2O2C—NHSO2— | 2-F | |
| 24 | n-propyl k | ethyl | -CH2-C6H4(2-(2-thienyl)) | CH3(CH2)2O2C—NHSO2— | 2-F | |

TABLE 1-continued

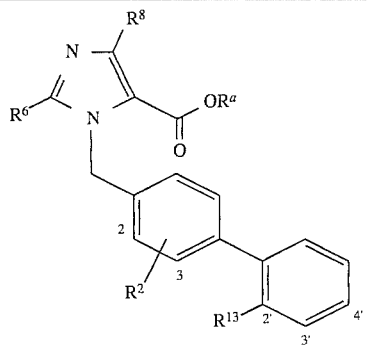

| Ex. No. | R⁶ | R⁸ | Rᵃ | R¹³ | R² | m.p. |
|---|---|---|---|---|---|---|
| 25 | n-propyl l | ethyl | —CH₂—(phenyl)—(2-thienyl) | $(CH_3)_2CH(CH_2)_2O_2C-NHSO_2-$ | 2-F | |
| 26 | n-propyl m | ethyl | —CH₂—(phenyl)—(3-thienyl) | $CH_3(CH_2)_2O_2C-NHSO_2-$ | 2-F | |
| 27 | n-propyl n | ethyl | —CH₂—(phenyl)—(3-thienyl) | $(CH_3)_2CH(CH_2)_2O_2C-NHSO_2-$ | 2-F | |
| 28 | n-propyl o | ethyl | —CH₂—(biphenyl) | $CH_3(CH_2)_2O_2C-NHSO_2-$ | 2-F | |
| 29 | n-propyl p | ethyl | —CH₂—(biphenyl) | $(CH_3)_2CH(CH_2)_2O_2C-NHSO_2-$ | 2-F | |
| 30 | n-propyl q | ethyl | —CH₂—(phenyl)—(pyrimidinyl) | $CH_3(CH_2)_2O_2C-NHSO_2-$ | 2-F | |
| 31 | n-propyl r | ethyl | —(CH₂)₄—O—phenyl | $(CH_3)_2CH(CH_2)_2O_2C-NHSO_2-$ | 2-F | |
| 32 | n-propyl s | ethyl | —(CH₂)₂—O—phenyl | $(CH_3)_2CH(CH_2)_2O_2C-NHSO_2-$ | 2-F | |

TABLE 1-continued

| Ex. No. | R⁶ | R⁸ | Rᵃ | R¹³ | R² | m.p. |
|---|---|---|---|---|---|---|
| 33 | n-propyl | ethyl | t (-(CH₂)₃-O-CH₂-C₆H₅) | $(CH_3)_2CH(CH_2)_2O_2C-NHSO_2-$ | 2-F | |
| 34 | n-propyl | ethyl | u (-CH₂-(2-benzoylphenyl)) | $(CH_3(CH_2)_3-NH-CO-NHSO_2-$ | 2-F | |
| 35 | n-propyl | Cl | v (-CH₂-(2-benzoylphenyl)) | $(CH_3)_2CH(CH_2)_2O_2C-NHSO_2-$ | 2-F | |
| 36 | n-propyl (M+H)⁺=733.3 | ethyl | -CH₂CH₂-N(phthalimido) | $(CH_3)_2CH(CH_2)_2O_2C-NHSO_2-$ | 2-F | |
| 37 | n-propyl (M+H)⁺=719.2 | ethyl | -CH₂CH₂-N(phthalimido) | $CH_3(CH_2)_3O_2C-NHSO_2-$ | 2-F | |
| 38 | n-propyl (M+H)⁺=747.3 | ethyl | -CH₂CH₂CH₂-N(phthalimido) | $(CH_3)_2CH(CH_2)_2O_2C-NHSO_2-$ | 2-F | |
| 39 | n-propyl | ethyl | -CH₂-(2-phenylthiophenyl) | $(CH_3)_2CH(CH_2)_2O_2C-NHSO_2-$ | 2-F | w |

TABLE 1-continued

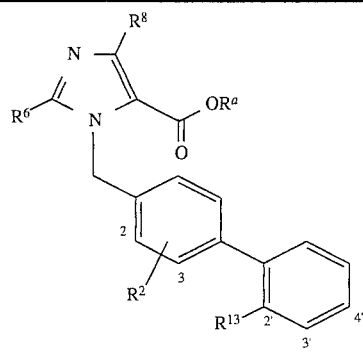

| Ex. No. | R⁶ | R⁸ | Rᵃ | R¹³ | R² | m.p. |
|---|---|---|---|---|---|---|
| 40 | n-propyl | ethyl | —CH₂-(2-(phenylsulfinyl)phenyl) | (CH₃(CH₂)₃NH—CO—NHSO₂— | 2-F | |
| 41 | n-propyl | ethyl | —CH₂-(2-(phenylsulfinyl)phenyl) | (CH₃)₂CH(CH₂)₂O₂C—NHSO₂— | 2-F (M+H)⁺=744 | |
| 42 | n-propyl | ethyl | —CH₂-(2-(phenylsulfinyl)phenyl) | (CH₃)₂CH(CH₂)₂O₂C—NHSO₂— | 2-F | |
| 43 | n-propyl | ethyl | —CH₂-(2-(phenylsulfinyl)phenyl) | (CH₃)(CH₂)₃O₂C—NHSO₂— | 2-F | |
| 44 | n-propyl | ethyl | —CH₂-(2-(phenylsulfinyl)phenyl) | (CH₃)(CH₂)₂O₂C—NHSO₂— | 2-F | |
| 45 | n-propyl | ethyl | —CH₂-(2-(phenylsulfinyl)phenyl) | (CH₃)₂CHO₂C—NHSO₂— | 2-F | |
| 46 | n-propyl | ethyl | —CH₂-(2-(phenylsulfinyl)phenyl) | PhCH₂O₂C—NHSO₂— | 2-F | |
| 47 | n-propyl | ethyl | —CH₂-(2-(phenylsulfinyl)phenyl) | Ph(CH₂)₂O₂C—NHSO₂— | 2-F | |

TABLE 1-continued
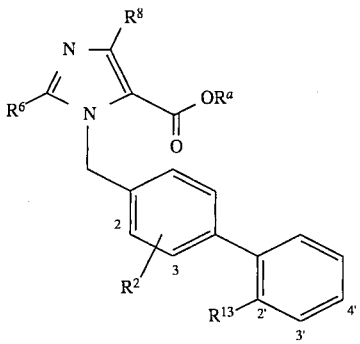
| Ex. No. | R⁶ | R⁸ | Rᵃ | R¹³ | R² | m.p. |
|---|---|---|---|---|---|---|
| 48 | n-propyl | ethyl | 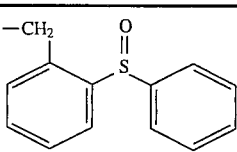 | Ph(CH₂)₃O₂C—NHSO₂— | 2-F | |
| 49 | n-propyl | ethyl | 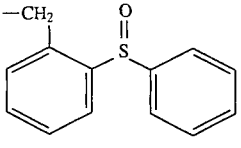 | Ph(CH₂)₄O₂C—NHSO₂— | 2-F | |
| 50 | n-propyl | ethyl | 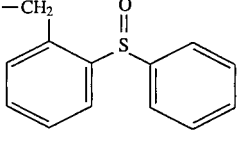 | (CH₃)₂CH(CH₂)₂O₂C—NHSO₂— | H | |
| 51 | n-propyl | ethyl | 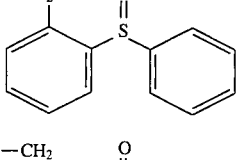 | (CH₃)₂CH(CH₂)O₂C—NHSO₂— | H | |
| 52 | n-propyl | ethyl | 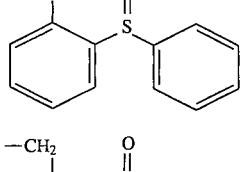 | (CH₃)(CH₂)₃O₂C—NHSO₂— | H | |
| 53 | n-propyl | ethyl | 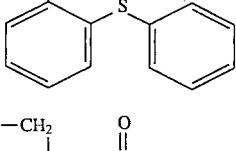 | (CH₃)(CH₂)₂O₂C—NHSO₂— | H | |
| 54 | n-propyl | ethyl | 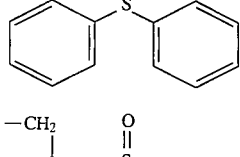 | (CH₃)₂CHO₂C—NHSO₂— | H | |
| 55 | n-propyl | ethyl | 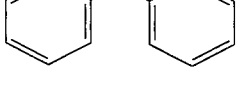 | PhCH₂O₂C—NHSO₂— | H | |

TABLE 1-continued

[Structure diagram showing the general formula with R⁸, R⁶, ORᵃ, R², R¹³ substituents on a biphenyl scaffold]

| Ex. No. | $R^6$ | $R^8$ | $R^a$ | $R^{13}$ | $R^2$ | m.p. |
|---|---|---|---|---|---|---|
| 56 | n-propyl | ethyl | -CH₂-(2-pyrimidinyl)phenyl | $(CH_3(CH_2)_3NH-CO-NHSO_2-$ | 2-F | |
| 57 | n-propyl | ethyl | -CH₂-(2-pyrimidinyl)phenyl | $(CH_3)_2CH(CH_2)_2O_2C-NHSO_2-$ | 2-F | |
| 58 | n-propyl | ethyl | -CH₂-(2-pyrimidinyl)phenyl | $(CH_3)_2CH(CH_2)O_2C-NHSO_2-$ | 2-F | |
| 59 | n-propyl | ethyl | -CH₂-(2-pyrimidinyl)phenyl | $(CH_3)(CH_2)_3O_2C-NHSO_2-$ | 2-F | |
| 60 | n-propyl | ethyl | -CH₂-(2-pyrimidinyl)phenyl | $(CH_3)(CH_2)_2O_2C-NHSO_2-$ | 2-F | |
| 61 | n-propyl | ethyl | -CH₂-(2-pyrimidinyl)phenyl | $(CH_3)_2CHO_2C-NHSO_2-$ | 2-F | |
| 62 | n-propyl | ethyl | -CH₂-(2-pyrimidinyl)phenyl | $PhCH_2O_2C-NHSO_2-$ | 2-F | |

TABLE 1-continued
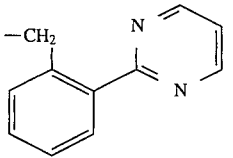
| Ex. No. | R⁶ | R⁸ | Rᵃ | R¹³ | R² | m.p. |
|---|---|---|---|---|---|---|
| 63 | n-propyl | ethyl | 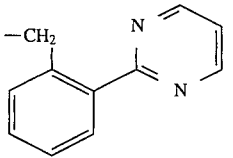 | Ph(CH₂)₂O₂C—NHSO₂— | 2-F | |
| 64 | n-propyl | ethyl | 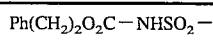 | Ph(CH₂)₃O₂C—NHSO₂— | 2-F | |
| 65 | n-propyl | ethyl |  | Ph(CH₂)₄O₂C—NHSO₂— | 2-F | |
| 66 | n-propyl | ethyl |  | (CH₃)₂CH(CH₂)₂O₂C—NHSO₂— | H | |
| 67 | n-propyl | ethyl | 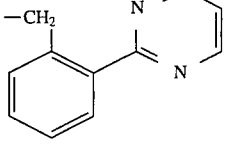 | (CH₃)₂CH(CH₂)₂O₂C—NHSO₂— | 2-F | |
| 68 | n-propyl | ethyl | 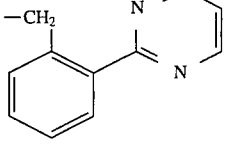 | (CH₃)₂CH(CH₂)O₂C—NHSO₂— | 2-F | |
| 69 | n-propyl | ethyl | 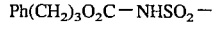 | (CH₃)(CH₂)₃O₂C—NHSO₂— | 2-F | |

TABLE 1-continued

[Structure: biphenyl core with CH2-N linked to N=CR6 and C(=NR8)... with CO2Ra substituent; R2 on ring, R13 on 2' position]

| Ex. No. | $R^6$ | $R^8$ | $R^a$ | $R^{13}$ | $R^2$ | m.p. |
|---|---|---|---|---|---|---|
| 70 | n-propyl | ethyl | -CH2CH2-N(phthalimide-3,6-dichloro) | $(CH_3)_2CH(CH_2)_2O_2C-NHSO_2-$ | 2-F | |
| 71 | n-propyl | ethyl | -CH2-(3-benzoylphenyl) | $-CN_4H$ | H | x |
| 72 | n-propyl | ethyl | -CH2-(3-(N,N-diphenylcarbamoyl)phenyl) | $-CN_4H$ | H | 112.5–117.0 |
| 73 | n-propyl | ethyl | -CH2-(4-(N,N-diphenylcarbamoyl)phenyl) | $-CN_4H$ | 2-F | y |
| 74 | n-propyl | ethyl | -CH2-(4-benzoylphenyl) | $-CN_4H$ | H | (M+H)+ = 611 |
| 75 | n-propyl | ethyl | -CH2-(2-benzoylphenyl) | $-CN_4H$ | H | z |

TABLE 1-continued
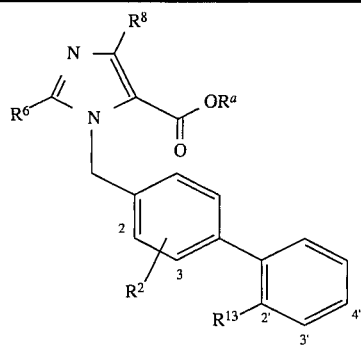
| Ex. No. | $R^6$ | $R^8$ | $R^a$ | $R^{13}$ | $R^2$ | m.p. |
|---|---|---|---|---|---|---|
| 76 | n-propyl | ethyl | 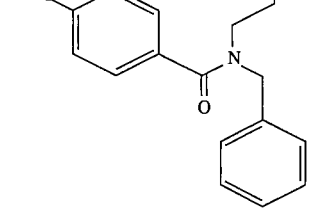 | —CN$_4$H | H | aa |
| 77 | n-propyl | ethyl | 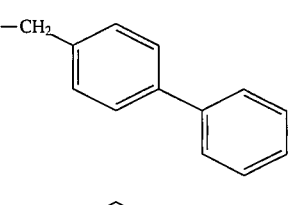 | —CN$_4$H | H | bb |
| 78 | n-propyl | ethyl | 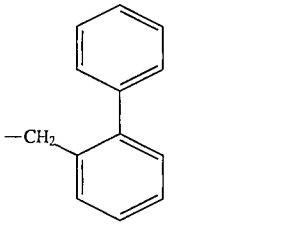 | —CN$_4$H | H | bb |
| 79 | n-propyl | ethyl | 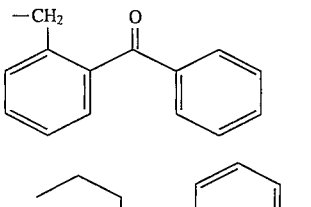 | —CN$_4$H | 2-F | dd |
| 80 | n-propyl | ethyl | 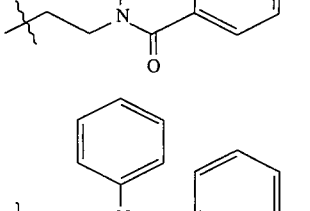 | PhCH$_2$O$_2$C—NHSO$_2$— | 2-F | |
| 81 | n-propyl | ethyl | 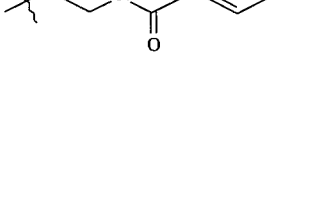 | Ph(CH$_2$)$_2$O$_2$C—NHSO$_2$— | 2-F | |

TABLE 1-continued

| Ex. No. | R⁶ | R⁸ | Rᵃ | R¹³ | R² | m.p. |
|---|---|---|---|---|---|---|
| 82 | n-propyl | ethyl | N-benzyl-N-butanoyl aminoethyl | $Ph(CH_2)_3O_2C-NHSO_2-$ | 2-F | |
| 83 | n-propyl | ethyl | N-isobutyl-N-butanoyl aminoethyl | $Ph(CH_2)_4O_2C-NHSO_2-$ | 2-F | |
| 84 | n-propyl | ethyl | N-phenyl-N-butanoyl aminoethyl | $(CH_3(CH_2)_3.NH-CO-NHSO_2-$ | 2-F | |
| 85 | n-propyl | ethyl | N-isobutyl-N-benzoyl aminoethyl | $(CH_3)_2CH(CH_2)_2O_2C-NHSO_2-$ | 2-F | |
| 86 | n-propyl | ethyl | N-benzyl-N-benzoyl aminoethyl | $(CH_3)_2CH(CH_2)O_2C-NHSO_2-$ | 2-F | |
| 87 | n-propyl | ethyl | N-(phenylacetyl) aminoethyl | $(CH_3)(CH_2)_2O_2C-NHSO_2-$ | 2-F | |
| 88 | n-propyl | ethyl | 2-benzoylbenzyl | $(CH_3)_2CH(CH_2)_2O_2C-NHSO_2-$ | 3-F (M+H)⁺ = 754 | |

TABLE 1-continued

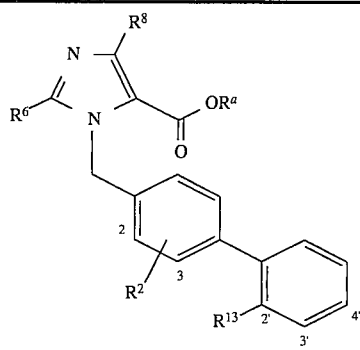

| Ex. No. | R⁶ | R⁸ | Rᵃ | R¹³ | R² | m.p. |
|---|---|---|---|---|---|---|
| 89 | n-propyl | ethyl | —CH₂-(2-benzylphenyl) | (CH₃)₂CH(CH₂)₂O₂C—NHSO₂— | 2-CH₃O— | |
| 90 | n-propyl | ethyl | —CH₂-(2-(NH—CO—NH—Ph)phenyl) | Ph(CH₂)₂O₂C—NHSO₂— | 2-CH₃ | |
| 91 | n-propyl | ethyl | —CH₂-(2-(CO—NH—Ph)phenyl) | (CH₃)₂CH(CH₂)₂O₂C—NHSO₂— | 3-CH₃O— | |
| 92 | n-propyl | ethyl | —CH₂-(2-(NH—CO—Ph)phenyl) | (CH₃)₂CH(CH₂)₂O₂C—NHSO₂— | 2-NO₂— | |
| 93 | n-propyl | ethyl | —CH₂-(2-(SO₂—NH—Ph)phenyl) | (CH₃(CH₂)₃NH—CO—NHSO₂— | 2-CN | |
| 94 | n-propyl | ethyl | —CH₂-(2-(NH—SO₂—Ph)phenyl) | (CH₃)₂CH(CH₂)₂O₂C—NHSO₂— | 3-CH₃S— | |
| 95 | n-propyl | ethyl | —CH₂-(2-(CO—NH—SO₂—Ph)phenyl) | (CH₃)₂CH(CH₂)O₂C—NHSO₂— | 3-CH₃SO₂— | |
| 96 | n-propyl | ethyl | —CH₂-(2-(SO₂—NH—CO—Ph)phenyl) | (CH₃)(CH₂)₃O₂C—NHSO₂— | 3-CH₃SO— | |

TABLE 1-continued

| Ex. No. | $R^6$ | $R^8$ | $R^a$ | $R^{13}$ | $R^2$ | m.p. |
|---|---|---|---|---|---|---|
| 97 | n-propyl | ethyl | —CH$_2$—(2-SO$_2$—NH—CO$_2$—Ph)phenyl | (CH$_3$)(CH$_2$)$_2$O$_2$C—NHSO$_2$— | 2-Br | |
| 98 | n-propyl | ethyl | —CH$_2$—(2-OCO—NH—SO$_2$—Ph)phenyl | (CH$_3$)$_2$CHO$_2$C—NHSO$_2$— | 3-I | |
| 99 | n-propyl | ethyl | —CH$_2$—(2-SO$_2$—NH—CO—NH—Ph)phenyl | PhCH$_2$O$_2$C—NHSO$_2$— | 2-F | |
| 100 | n-propyl | ethyl | —CH$_2$—(2-NH—CO—NH—SO$_2$—Ph)phenyl | Ph(CH$_2$)$_2$O$_2$C—NHSO$_2$— | H | |
| 101 | n-propyl | ethyl | —CH$_2$—(2-SO$_2$—NH—SO$_2$—Ph)phenyl | Ph(CH$_2$)$_3$O$_2$C—NHSO$_2$— | 3-F | |
| 102 | n-propyl | ethyl | —CH$_2$—(2-NH—SO$_2$—NH—CO—Ph)phenyl | Ph(CH$_2$)$_4$O$_2$C—NHSO$_2$— | 3-F | |
| 103 | n-propyl | ethyl | —CH$_2$—(2-CO—NH—SO$_2$—NH—Ph)phenyl | (CH$_3$(CH$_2$)$_3$NH—CO—NHSO$_2$— | 2-F | |
| 104 | n-propyl | ethyl | —CH$_2$—(2-benzoyl)phenyl | 2'-(CH$_3$)$_2$CH(CH$_2$)$_2$O$_2$C—NHSO$_2$— | 2-Cl | (M+H)$^+$= 796.6 |

TABLE 1-continued

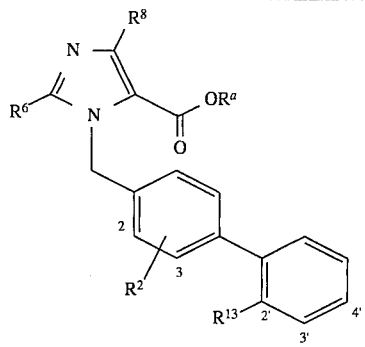

| Ex. No. | R⁶ | R⁸ | Rᵃ | R¹³ | R² | m.p. |
|---|---|---|---|---|---|---|
| 105 | n-propyl | ethyl | —CH₂CH₂CH₂—O—(phenyl) | 2'-(CH₃)₂CH(CH₂)₂O₂C—NHSO₂— | 2-Cl | |
| 106 | n-propyl | ethyl | —CH₂CH₂CH₂—O—CH₂—(phenyl) | 2'-(CH₃)₂CH(CH₂)₂O₂C—NHSO₂— | 2-Cl | |
| 107 | n-propyl | ethyl | —CH₂—(2-benzoylphenyl) | 2'-(CH₃)₂CH(CH₂)₂O₂C—NHSO₂— | 2-Cl | |
| 108 | n-propyl | ethyl | —CH₂CH₂CH₂—O—(phenyl) | 2'-(CH₃)₂CH(CH₂)₂O₂C—NHSO₂— | 2-Cl | |
| 109 | n-propyl | ethyl | —CH₂—(2-(phenylsulfinyl)phenyl) | 2'-(CH₃)₂CH(CH₂)₂O₂C—NHSO₂— | 2-Cl | |
| 110 | n-propyl | ethyl | (t-butyl-(CH₂)₃-C(O)-phenyl) | 2'-(CH₃)₂CH(CH₂)₂O₂C—NHSO₂— | 2-Br | |
| 111 | n-propyl | ethyl | (t-butyl-CH₂-C(O)-phenyl) | 2'-(CH₃)₂CH(CH₂)₂O₂C—NHSO₂— | 2-Br | |
| 112 | n-propyl | ethyl | (t-butyl-CH₂-C(O)-phenyl) | 2'-(CH₃)₂CH(CH₂)₂O₂C—NHSO₂— | 2-Br | |

TABLE 1-continued
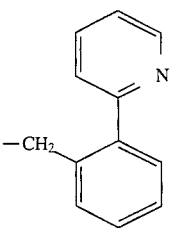
| Ex. No. | R⁶ | R⁸ | Rᵃ | R¹³ | R² | m.p. |
|---|---|---|---|---|---|---|
| 113 | n-propyl | ethyl | 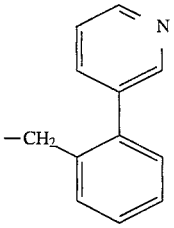 | (CH3)2CH(CH₂)₂O₂C—NHSO₂— | 2-F | |
| 114 | n-propyl | ethyl | 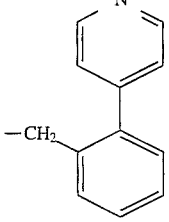 | Ph(CH₂)₂O₂C—NHSO₂— | 3-F | |
| 115 | n-propyl | ethyl | 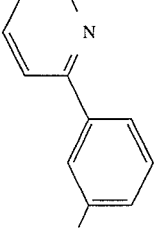 | Ph(CH₂)₃O₂C—NHSO₂— | 3-F | |
| 116 | n-propyl | ethyl | 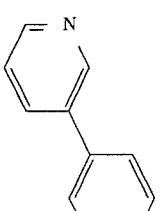 | Ph(CH₂)₄O₂C—NHSO₂— | 2-F | |
| 117 | n-propyl | ethyl |  | CH₃(CH₂)₃.NH—CO—NHSO₂— | 2-F | |

TABLE 1-continued
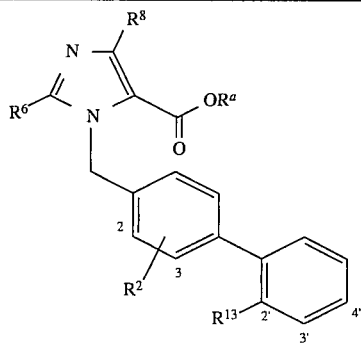
| Ex. No. | R⁶ | R⁸ | Rᵃ | R¹³ | R² | m.p. |
|---|---|---|---|---|---|---|
| 118 | n-propyl | ethyl | (4-pyridyl-phenyl)-CH₂– | $(CH_3)_2CH(CH_2)_2O_2C-NHSO_2-$ | 2-F | |
| 119 | n-propyl | ethyl | $-CH_2CH=CH-CH_2-O-$phenyl | $(CH_3)_2CH(CH_2)O_2C-NHSO_2-$ | 2-F | |
| 120 | n-propyl | ethyl | $-CH_2-C\equiv C-CH_2-O-$phenyl | $(CH_3)(CH_2)_3O_2C-NHSO_2-$ | 2-F | |
| 121 | n-propyl | ethyl | $-CH_2CH_2CH=CH-C(O)-$phenyl | $(CH_3)(CH_2)_2O_2C-NHSO_2-$ | 2-F | |
| 122 | n-propyl | ethyl | $-CH_2-C\equiv C-S(O)-$phenyl | $(CH_3)_2CHO_2C-NHSO_2-$ | 2-F | |
| 123 | n-propyl | ethyl | $-CH_2CH=CH-CH_2-S(O)-$phenyl | $PhCH_2O_2C-NHSO_2-$ | 2-F | |

TABLE 1-continued
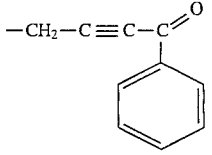
| Ex. No. | R⁶ | R⁸ | Rᵃ | R¹³ | R² | m.p. |
|---|---|---|---|---|---|---|
| 124 | n-propyl | ethyl | —CH₂—C≡C—C(=O)—Ph | Ph(CH₂)₂O₂C—NHSO₂— | 3-F | |
| 125 | n-propyl | ethyl | 3-(n-propylsulfinyl)benzyl | Ph(CH₂)₃O₂C—NHSO₂— | 3-F | |
| 126 | n-propyl | ethyl | (E)-4-(n-propylsulfinyl)-but-3-enyl | Ph(CH₂)₄O₂C—NHSO₂— | 2-F | |
| 127 | n-propyl | ethyl | 2-(phenacyl)benzyl | CH₃(CH₂)₃NH—CO—NHSO₂— | 2-F | |
| 128 | n-propyl | ethyl | 2-(benzylsulfinyl)ethyl | (CH₃)₂CH(CH₂)₂O₂C—NHSO₂— | 2-F | |

TABLE 1-continued
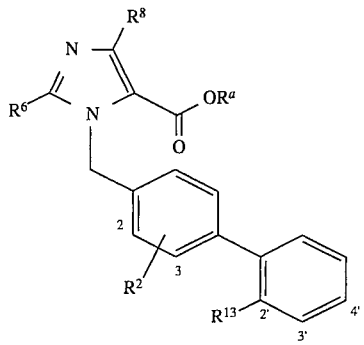
| Ex. No. | R⁶ | R⁸ | Rᵃ | R¹³ | R² | m.p. |
|---|---|---|---|---|---|---|
| 129 | n-propyl | ethyl | 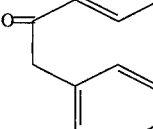 | $(CH_3)_2CH(CH_2)O_2C-NHSO_2-$ | 3-F | |
| 130 | n-propyl | ethyl | 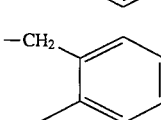 | $(CH_3)(CH_2)_3O_2C-NHSO_2-$ | 3-F | |
| 131 | n-propyl | ethyl | 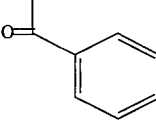 | $(CH_3)(CH_2)_2O_2C-NHSO_2-$ | 2-F | |
| 132 | n-propyl | ethyl | 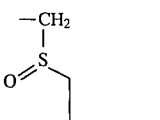 | $(CH_3)_2CHO_2C-NHSO_2-$ | 3-F | |
| 133 | n-propyl | ethyl | 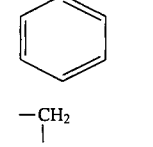 | $PhCH_2O_2C-NHSO_2-$ | H | |
| 134 | n-propyl | ethyl | 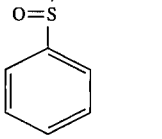 | $Ph(CH_2)_2O_2C-NHSO_2-$ | H | |

TABLE 1-continued

[Structure: biphenyl compound with imidazole ester, showing R⁶, R⁸, Rᵃ, R², R¹³ substituents, positions labeled 2, 3, 2', 3', 4']

| Ex. No. | $R^6$ | $R^8$ | $R^a$ | $R^{13}$ | $R^2$ | m.p. |
|---|---|---|---|---|---|---|
| 135 | n-propyl | ethyl | $-CH_2-CH_2-S(=O)-CH_3$ | $Ph(CH_2)_3O_2C-NHSO_2-$ | H | |
| 136 | n-propyl | ethyl | $-CH_2-C(=O)-$ | $Ph(CH_2)_4O_2C-NHSO_2-$ | H | |
| 137 | n-propyl | ethyl | $-CH_2-$(2-CHO-phenyl) | $CH_3(CH_2)_3-NH-CO-NHSO_2-$ | 2-F | |
| 138 | n-propyl | ethyl | $-CH_2-$(2-CHO-phenyl) | $(CH_3)_2CH(CH_2)_2O_2C-NHSO_2-$ | 2-F | |
| 139 | n-propyl | ethyl | $-CH_2-$(2-$CONH_2$-phenyl) | $(CH_3)_2CH(CH_2)_2O_2C-NHSO_2-$ | 2-F | |
| 140 | n-propyl | ethyl | $-CH_2-$(2-NHCHO-phenyl) | $(CH_3)(CH_2)_3O_2C-NHSO_2-$ | 2-$CH_3F$ | |
| 141 | n-propyl | ethyl | $-CH_2-$(2-$COCF_3$-phenyl) | $(CH_3)(CH_2)_2O_2C-NHSO_2-$ | 2-F | |
| 142 | n-propyl | ethyl | $-CH_2-$(2-$SO-CH_3$-phenyl) | $(CH_3)_2CHO_2C-NHSO_2-$ | 2-F | |
| 143 | n-propyl | ethyl | $-CH_2-$(2-$SO_2-CH_2CH_3$-phenyl) | $PhCH_2O_2C-NHSO_2-$ | 2-F | |
| 144 | n-propyl | ethyl | $-CH_2-$(2-$SO-CF_3$-phenyl) | $Ph(CH_2)_2O_2C-NHSO_2-$ | 2-F | |

TABLE 1-continued

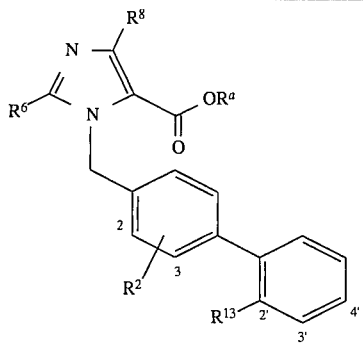

| Ex. No. | R[6] | R[8] | R[a] | R[13] | R[2] | m.p. |
|---|---|---|---|---|---|---|
| 145 | n-propyl | ethyl | 2-(SO₂—CF₂CF₃)-benzyl | Ph(CH₂)₃O₂C—NHSO₂— | 2-Cl | |
| 146 | n-propyl | ethyl | 2-(S—CH₃)-benzyl | Ph(CH₂)₄O₂C—NHSO₂— | H | |
| 147 | n-propyl | ethyl | 2-(O—CF₂CF₃)-benzyl | CH₃(CH₂)₃-NH—CO—NHSO₂— | H | |
| 148 | n-propyl | ethyl | 2-(NH—CF₃)-benzyl | (CH₃)₂CH(CH₂)₂O₂C—NHSO₂— | 2-CH₂CH₃ | |
| 149 | n-propyl | ethyl | 2-(PhCH₂CO—CH₂)-phenyl | (CH₃)₂CH(CH₂)₂O₂C—NHSO₂— | 2-F | |
| 150 | n-propyl | ethyl | 2-(PhCH₂—CO)-phenyl | (CH₃)(CH₂)₃O₂C—NHSO₂— | H | |
| 151 | n-propyl | ethyl | 2-(PhCO—CH₂)-phenyl | (CH₃)(CH₂)₂O₂C—NHSO₂— | 2-Br | |

TABLE 1-continued
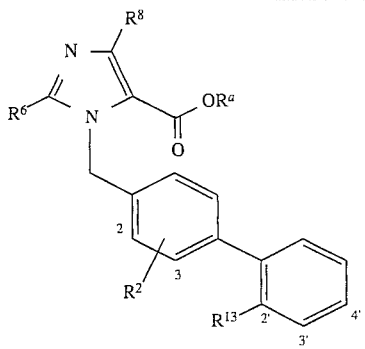
| Ex. No. | R[6] | R[8] | R[a] | R[13] | R[2] | m.p. |
|---|---|---|---|---|---|---|
| 152 | n-propyl | ethyl | (2-benzoyl-phenyl) | $(CH_3)_2CHO_2C-NHSO_2-$ | 3-CH(CH$_3$)$_2$ | |
| 153 | n-propyl | ethyl | (2-benzyl-phenyl) | $PhCH_2O_2C-NHSO_2-$ | 2-NO$_2$ | |
| 154 | n-propyl | ethyl | (3-phenyl-phenyl) | $Ph(CH_2)_2O_2C-NHSO_2-$ | H | |
| 155 | n-propyl | ethyl | $-CH_2-$(2-(3-phenyl-2-oxopropyl)styryl) | $Ph(CH_2)_3O_2C-NHSO_2-$ | H | |

TABLE 1-continued
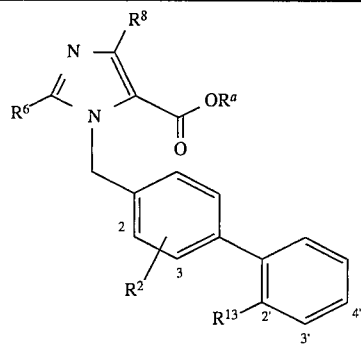
| Ex. No. | $R^6$ | $R^8$ | $R^a$ | $R^{13}$ | $R^2$ | m.p. |
|---|---|---|---|---|---|---|
| 156 | n-propyl | ethyl | ![CH2-CH=CH-CH2-C(O)-CH2-Ph] | $Ph(CH_2)_4O_2C-NHSO_2-$ | H | |
| 157 | n-propyl | ethyl | ![-CH2-(2-(PhCH2CO)-phenyl)] | $CH_3(CH_2)_3NH-CO-NHSO_2-$ | 2-I | |
| 158 | n-propyl | ethyl | ![-CH2-(2-(PhCH2CO)-phenyl)] | $(CH_3)_2CH(CH_2)_2O_2C-NHSO_2-$ | H | |
| 159 | n-propyl | ethyl | ![CH2-CH=CH-C(O)-CH2-Ph] | $(CH_3)_2CH(CH_2)O_2C-NHSO_2-$ | H | |

TABLE 1-continued

| Ex. No. | R⁶ | R⁸ | Rᵃ | R¹³ | R² | m.p. |
|---|---|---|---|---|---|---|
| 160 | n-propyl | ethyl | —CH₂—CH=CH—(2-benzoylphenyl) | $(CH_3)(CH_2)_3O_2C-NHSO_2-$ | H | |
| 161 | n-propyl | ethyl | —CH₂—C≡C—CH₂—C(O)—Ph | $(CH_3)(CH_2)_2O_2C-NHSO_2-$ | 2-F | |
| 162 | n-propyl | ethyl | —CH₂—CH=CH—C(O)—Ph | $(CH_3)_2CHO_2C-NHSO_2-$ | 2-F | |
| 163 | n-propyl | ethyl | —CH₂—CH=CH—(2-benzylphenyl) | $PhCH_2O_2C-NHSO_2-$ | 2-F | |

TABLE 1-continued
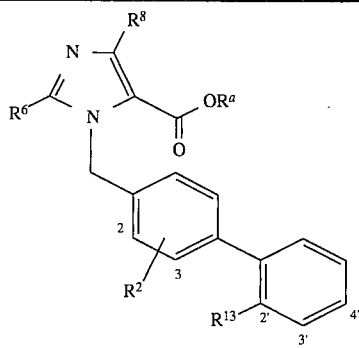
| Ex. No. | R⁶ | R⁸ | Rᵃ | R¹³ | R² | m.p. |
|---|---|---|---|---|---|---|
| 164 | n-propyl | ethyl | —CH₂-(3-biphenyl) | Ph(CH₂)₂O₂C—NHSO₂— | 2-F | |
| 165 | n-propyl | ethyl | —CH₂-(2-(2-oxopropyl)phenyl) | Ph(CH₂)₃O₂C—NHSO₂— | 2-F | |
| 166 | n-propyl | ethyl | —CH₂-(2-acetylphenyl) | Ph(CH₂)₄O₂C—NHSO₂— | H | |
| 167 | n-propyl | ethyl | —CH₂-(3-biphenyl) | CH₃(CH₂)₃.NH—CO—NHSO₂— | H | |

TABLE 1-continued

[Structure: imidazole with R⁸ at position, R⁶ group, N-CH₂ linked to biphenyl bearing R² at position 3 and R¹³ at position 2', carboxylate OR^a]

| Ex. No. | R⁶ | R⁸ | R^a | R¹³ | R² | m.p. |
|---|---|---|---|---|---|---|
| 168 | n-propyl | ethyl | CH₃-CH(-)-C(=O)-CH₂CH₂-C≡C-CH₂— | $(CH_3)_2CH(CH_2)_2O_2C-NHSO_2-$ | H | |
| 169 | n-propyl | ethyl | cyclopentyl-C(=O)-CH=CH-CH₂— | $(CH_3)_2CH(CH_2)O_2C-NHSO_2-$ | 2-F | |
| 170 | n-propyl | ethyl | 2-(OHC-CH₂-)-phenyl-CH=CH-CH₂— | $(CH_3)(CH_2)_3O_2C-NHSO_2-$ | 2-F | |
| 171 | n-propyl | ethyl | —CH₂-CH=CH-(3-NHCHO-phenyl) | $(CH_3)(CH_2)_2O_2C-NHSO_2-$ | 2-F | |

TABLE 1-continued
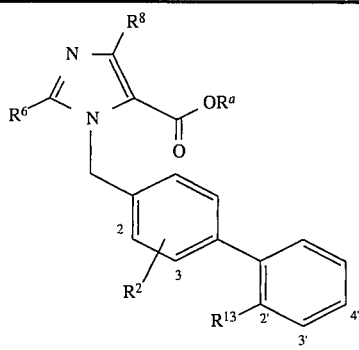
| Ex. No. | R[6] | R[8] | R[a] | R[13] | R[2] | m.p. |
|---|---|---|---|---|---|---|
| 172 | n-propyl | ethyl | —CH₂-(2-(PhNHC(O)NHCH₂)phenyl) | $(CH_3)_2CHO_2C-NHSO_2-$ | 2-F | |
| 173 | n-propyl | ethyl | —CH₂-(2-(PhCH₂C(O)NH)phenyl) | $PhCH_2O_2C-NHSO_2-$ | 2-F | |
| 174 | n-propyl | ethyl | —CH₂-(2-(PhSO₂NHCH₂)phenyl) | $Ph(CH_2)_2O_2C-NHSO_2-$ | 2-F | |

TABLE 1-continued

Structure: imidazole with R⁶ at 2-position, R⁸ at 5-position, N-CH₂-biphenyl with COOR^a group; biphenyl bears R² at position 3 and R¹³ at position 2'.

| Ex. No. | R⁶ | R⁸ | R^a | R¹³ | R² | m.p. |
|---|---|---|---|---|---|---|
| 175 | n-propyl | ethyl | —CH₂-(3-substituted phenyl)-CH=CH- linked to NH-C(O)-NH-SO₂-Ph | Ph(CH₂)₃O₂C—NHSO₂— | H | |
| 176 | n-propyl | ethyl | —CH₂-CH=CH-CH₂-NH-C(O)-CH₂-Ph | Ph(CH₂)₄O₂C—NHSO₂— | 2-F | |
| 177 | n-propyl | ethyl | —CH₂-CH=CH-CH₂-NH-C(O)-Ph | CH₃(CH₂)₃.NH—CO—NHSO₂— | 2-F | |

TABLE 1-continued

[Structure: imidazole with R8, R6, ORa/C=O, N-CH2-biphenyl with R2 at position 3, R13 at position 2']

| Ex. No. | R6 | R8 | Ra | R13 | R2 | m.p. |
|---|---|---|---|---|---|---|
| 178 | n-propyl | ethyl | —CH2-(3-styryl-phenyl with CH2-NHC(O)-n-butyl) | (CH3)2CH(CH2)2O2C—NHSO2— | 2-F | |
| 179 | n-propyl | ethyl | —CH2-(3-styryl-phenyl with NH-C(O)-NH-n-propyl) | (CH3)2CH(CH2)O2C—NHSO2— | H | |
| 180 | n-propyl | ethyl | —CH2-CH=CH-CH2-NH-SO2-cyclohexyl | (CH3)(CH2)3O2C—NHSO2— | 2-Cl | |
| 181 | ethyl | ethyl | —CH2-(2-benzoylphenyl) | (CH3)2CH(CH2)O2C—NHSO2— | 2-F | |

TABLE 1-continued
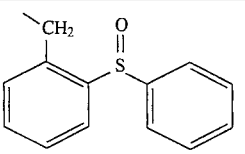
| Ex. No. | R⁶ | R⁸ | Rᵃ | R¹³ | R² | m.p. |
|---|---|---|---|---|---|---|
| 182 | ethyl | ethyl | 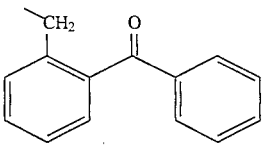 | $(CH_3)_2CH(CH_2)O_2C-NHSO_2-$ | 2-F | |
| 183 | ethyl | ethyl | 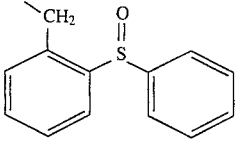 | $(CH_3)_2CH(CH_2)O_2C-NHSO_2-$ | H | |
| 184 | ethyl | ethyl | 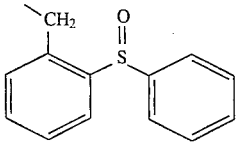 | $(CH_3)_2CH(CH_2)O_2C-NHSO_2-$ | H | |
| 185 | ethyl | ethyl | 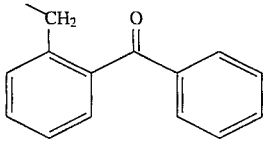 | $(CH_3)(CH_2)_3O_2C-NHSO_2-$ | 2-F | |
| 186 | ethyl | ethyl | 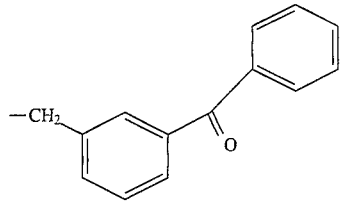 | $(CH_3)(CH_2)_3O_2C-NHSO_2-$ | 2-F | |
| 187 | n-propyl | ethyl | 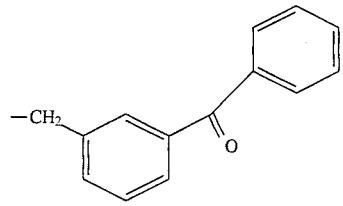 | $(CH_3)_2CH(CH_2)O_2C-NHSO_2-$ | 2-F | ee |
| 188 | n-propyl | ethyl | 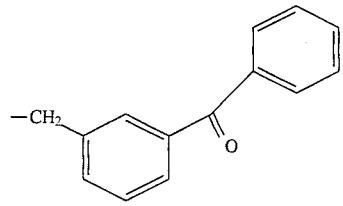 | $(CH_3)(CH_2)_2O_2C-NHSO_2-$ | 2-F | ff |

TABLE 1-continued
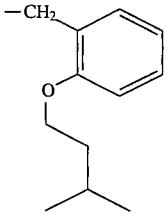
| Ex. No. | R⁶ | R⁸ | Rᵃ | R¹³ | R² | m.p. |
|---|---|---|---|---|---|---|
| 189 | n-propyl | ethyl | 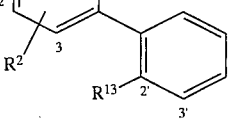 | (CH₃)₂CH(CH₂)O₂C—NHSO₂— | 2-F | gg |
| 190 | n-propyl | ethyl |  | (CH₃)₂CH(CH₂)₂O₂C—NHSO₂— | 2-F | (M+H)⁺= 678 |
| 191 | n-propyl | ethyl | 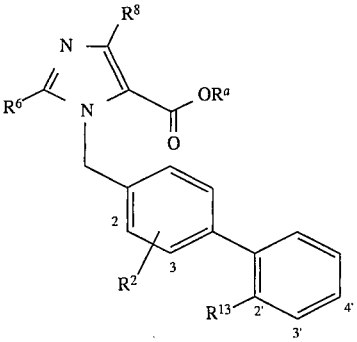 | (CH₃)₂CH(CH₂)₂O₂C—NHSO₂— | 2-F | |
| 192 | n-propyl | ethyl | 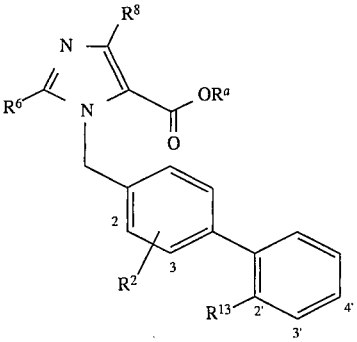 | (CH₃)₂CH(CH₂)₂O₂C—NHSO₂— | 2-F | hh |
| 193 | n-propyl | SCH₃ | 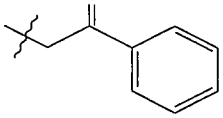 | (CH₃)₂CH(CH₂)₂O₂C—NHSO₂— | 2-F | |
| 194 | n-propyl | SOCH₃ |  | (CH₃)₂CH(CH₂)₂O₂C—NHSO₂— | 2-F | |
| 195 | n-propyl | SO₂CH₃ |  | (CH₃)₂CH(CH₂)₂O₂C—NHSO₂— | 2-F | |

TABLE 1-continued
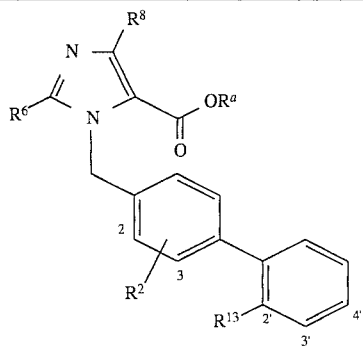
| Ex. No. | R⁶ | R⁸ | Rᵃ | R¹³ | R² | m.p. |
|---|---|---|---|---|---|---|
| 196 | n-propyl | SCH₃ | —CH₂-(2-phenylsulfinyl-phenyl) | (CH₃)₂CH(CH₂)₂O₂C—NHSO₂— | 2-F | |
| 197 | n-propyl | SOCH₃ | —CH₂-(2-phenylsulfinyl-phenyl) | (CH₃)₂CH(CH₂)₂O₂C—NHSO₂— | 2-F | |
| 198 | n-propyl | SO₂CH₃ | —CH₂-(2-phenylsulfinyl-phenyl) | (CH₃)₂CH(CH₂)₂O₂C—NHSO₂— | 2-F | |
| 199 | n-propyl | ethyl | (dipentylamide group) | (CH₃)₂CH(CH₂)₂O₂C—NHSO₂— | 2-F | |
| 200 | n-propyl | ethyl | (N-benzyl-N-alkyl amide group) | (CH₃)₂CH(CH₂)₂O₂C—NHSO₂— | 2-F | |

TABLE 1-continued
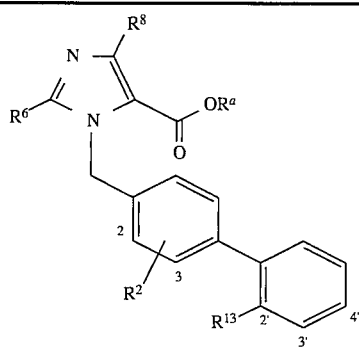
| Ex. No. | $R^6$ | $R^8$ | $R^a$ | $R^{13}$ | $R^2$ | m.p. |
|---|---|---|---|---|---|---|
| 201 | n-propyl | ethyl | 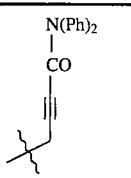 | $(CH_3)_2CH(CH_2)_2O_2C-NHSO_2-$ | 2-F | |
| 202 | n-propyl | ethyl | 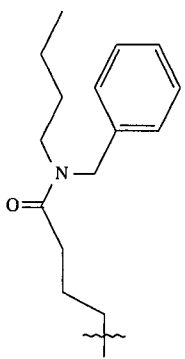 | $(CH_3)_2CH(CH_2)_2O_2C-NHSO_2-$ | 2-F $(M+H)^+=$ 791 | |
| 203 | n-propyl | ethyl | 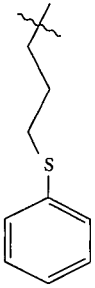 | $(CH_3)_2CH(CH_2)_2O_2C-NHSO_2-$ | 2-F | |
| 204 | n-propyl | ethyl | 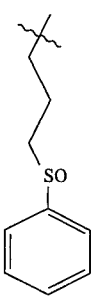 | $(CH_3)_2CH(CH_2)_2O_2C-NHSO_2-$ | 2-F | |

TABLE 1-continued

| Ex. No. | R⁶ | R⁸ | Rᵃ | R¹³ | R² | m.p. |
|---|---|---|---|---|---|---|
| 205 | n-propyl | ethyl | (branched alkyl chain with -SO₂-phenyl terminus) | $(CH_3)_2CH(CH_2)_2O_2C-NHSO_2-$ | 2-F | |
| 205 | n-propyl | ethyl | -CH₂-(phenyl)-NH-C(=O)-phenyl | $(CH_3)_2CH(CH_2)_2O_2C-NHSO_2-$ | 2-F (M+H)⁺= 769.6 | |
| 206 | n-propyl (M+H)⁺=769.5 | ethyl | -CH₂-(phenyl)-NH-C(=O)-phenyl (isomer) | $(CH_3)_2CH(CH_2)_2O_2C-NHSO_2-$ | 2-F | | a ¹H NMR (K⁺ salt) (DMSO-d₆) δ 7.97–7.30 (m, 13H); 7.04 (d, 1H, J=8Hz); 6.78 (d, 2H, J=8Hz); 5.43 (s, 2H); 5.29 (s, 2H); 3.11 (s, 3H); 2.70–2.45 (m, 4H); 1.60 (t of q, 2H, J=7,7Hz); 0.99 (t, 3H, J=7Hz); 0.87 (t, 3H, J=7Hz).
b ¹H NMR (K⁺ salt) (DMSO-d₆) δ 7.97–7.00 (m, 6H); 6.77 (d, 2H, J=8Hz); 5.41 (s, 2H); 5.28 (s, 2H); 3.74 (t, 2H, J=7Hz); 2.75–2.45 (m, 6H); 1.60 (t of q, 2H, J=7,7Hz); 0.98 (t, 3H, J=7Hz); 0.87 (t, 3H, J=7Hz).
c ¹H NMR (K⁺ salt) (DMSO-d₆) δ 8.14 (d, 1H, J=8Hz); 7.73 (d, 2H, J=8Hz); 7.60–7.42 (m, 3H); 7.42–7.20 (m, 8H); 7.08 (d, 1H, J=8Hz); 6.80 (d, 2H, J=8Hz); 5.38 (s, 4H); 3.76 (t, 2H, J=7Hz); 2.63 (q, 2H, J=7Hz); 2.57 (t, 2H, J=7Hz); 1.66 (t of q, 2H, J=7,7Hz); 1.50–1.10 (m, 3H); 1.05 (t, 3H, J=7Hz); 0.91 (t, 3H, J=7Hz).
d ¹H NMR (K⁺ salt) (CDCl₃) δ 8.07 (d, 1H, J=8Hz); 7.74 (d, 2H, J=8Hz); 7.60–7.00 (m, 14H); 7.00 (d, 3H, J=8Hz); 6.31 (t, 1H, J=8Hz); 5.38 (s, 2H); 5.31 (s, 2H); 3.89 (t, 2H, J=7Hz); 2.75 (q, 4H, J=7Hz); 2.45 (t, 2H, J=7Hz); 1.65 (t of q, 2H, J=7,7Hz); 1.06 (t, 3H, J=7Hz); 0.90 (t, 3H, J=Hz).
e ¹H NMR (K⁺ salt) (CDCl₃) δ 8.08 (d, 1H, J=8Hz); 7.75 (d, 2H, J=8Hz); 7.60–7.43 (, 3H); 7.43–6.95 (m, 9H); 6.36 (t, 1H, J=8Hz); 5.40 (s, 2H); 5.37 (s, 2H); 3.63 (t, 2H, J=7Hz); 2.66 (q, 2H, J=7Hz); 2.56 (t, 2H, J=7Hz); 1.64 (t of q, 2H, J=7,7Hz); 1.50–1.20 (m, 2H); 1.07 (t, 3H, J=7Hz); 0.91 (t, 3H, J=7Hz); 0.67 (t, 3H, J=7Hz).
f ¹H NMR (CDCl₃) δ 8.27 (d, 1H, J=8Hz); 7.77 (d, 2H, J=8Hz); 7.70–7.00 (m, 2H); 6.73 (t, 1H, J=8Hz); 5.57 (s, 2H); 5.46 (s, 2H); 3.78 (d, 2H, J=7Hz); 3.00–2.75 (m, 4H); 1.90 (m, 3H); 1.20 (t, 3H, J=7Hz); 1.00 (t, 3H, J=7Hz); 0.77 (d, 6H, J=7Hz).
g ¹H NMR (K⁺ salt) (CDCl₃) δ 8.08 (d, 1H, J=8Hz); 7.75 (d, 2H, J=8Hz); 7.65–7.00 (m, 12H); 6.36 (t, 1H, J=8Hz); 5.41 (s, 2H); 5.36 (s, 2H); 3.68 (t, 2H, J=7Hz); 2.65 (q, 2H, J=7Hz); 2.56 (t, 2H, J=7Hz); 1.66 (t of q, 2H, J=7,7Hz); 1.45–0.95 (m, 7H); 0.91 (t, 3H, J=& Hz)

TABLE 1-continued

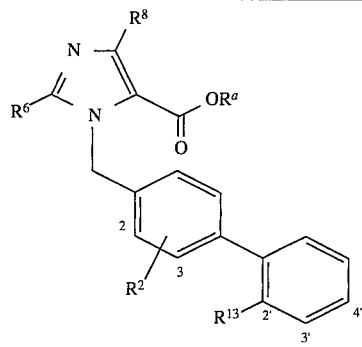

| Ex. No. | R⁶ | R⁸ | Rᵃ | R¹³ | R² | m.p. |
|---|---|---|---|---|---|---| h ¹H NMR (K⁺ salt) (CDCl₃) δ 8.04 (d, 1H, J=8Hz); 7.41 (d, 1H, J=8Hz); 7.40–6.95 (m, 10H); 6.91 (d, 2H, J=8Hz); 6.84 (d, 1H, J=8Hz); 6.47 (t, 1H, J=8Hz); 5.38 (s, 2H); 5.28 (s, 2H); 3.68 (t, 2H, J=7Hz); 2.82 (q, 2H, J=7Hz); 2.59 (t, 2H, J=7Hz); 1.71 (t of q, 2H, J=7, & Hz); 1.32 (t of t, 2H, J=7,7Hz); 1.25–1.00 (m, 5H); 0.94 (t, 3H, J=7Hz); 0.74 (t, 3H, J=7Hz).

i ¹H NMR (K⁺ salt) (CDCl₃) δ 8.07 (d, 2H, J=8Hz); 7.85 (d, 2H, J=8Hz); 7.65–7.15 (m, 10H); 7.10 (d, 1H, J=8Hz); 7.05–6.90 (m, 1H); 6.50–6.35 (m, 1H); 5.51 (s, 2H); 5.37 (s, 2H); 3.70–3.55 (m, 2H); 2.74 (q, 2H, J=7Hz); 2.62 (t, 2H, J=7Hz); 1.73 (t of q, 2H, J=7,7Hz); 1.45–1.20 (m, 2H); 1.15 (t, 3H, J=7Hz); 0.96 (t, 3H, J=7Hz); 0.68 (t, 3H, J=7Hz).

j ¹H NMR (K⁺ salt) (CDCl₃) δ 8.07 (d, 2H, J=8Hz); 7.85 (d, 2H, J=8Hz); 7.60–7.10 (m, 9H); 7.07 (d, 1H, J=8Hz); 6.96 (d, 1H, J=8Hz); 6.41 (t, 1H, J=8Hz); 5.52 (s, 2H); 5.37 (s, 2H); 3.69 (t, 2H, J=7Hz); 2.72 (q, 2H, J=7Hz); 2.62 (t, 2H, J=7Hz); 1.71 (t of q, 2H, J=7,7Hz); 1.50–1.30 (m, 1H); 1.30–1.10 (m, 2H); 1.13 (t, 3H, J=7Hz); 0.96 (t, 3H, J=7Hz); 0.71 (t, 3H, J=7Hz).

k ¹H NMR (K⁺ salt) (CDCl₃) δ 8.05–7.90 (m, 1H); 7.50–6.90 (m, 12H); 6.46 (t, 1H, J=8Hz); 5.37 (s, 2H); 5.18 (s, 2H); 3.75–3.40 (m, 2H); 2.72 (q, 2H, J=7Hz); 2.60–2.40 (m, 2H); 1.75–1.50 (m, 2H); 1.50–1.20 (m, 2H); 1.20–1.00 (m, 3H); 0.95–0.75 (m, 3H); 0.75–0.60 (m, 3H).

l ¹H NMR (K⁺ salt) (CDCl₃) δ 8.05–7.90 (m, 1H); 7.50–6.90 (m, 12H); 6.60–6.40 (m, 1H); 5.42 (s, 2H); 5.25 (s, 2H); 3.90–3.60 (m, 2H); 2.77 (q, 2H, J=7Hz); 2.70–2.50 (m, 2H); 1.80–1.55 (m, 2H); 1.55–1.30 (m, 1H); 1.35–1.10 (m, 5H); 1.00–0.80 (m, 3H); 0.76 (d, 6H, J=7Hz).

m ¹H NMR (K⁺ salt) (CDCl₃) δ 8.00 (d, 1H, J=8Hz); 7.50–6.95 (m, 12H); 6.60–6.40 (m, 1H); 5.41 (s, 2H); 5.20 (s, 2H); 3.70–3.50 (m, 2H); 2.77 (q, 2H, J=7Hz); 2.59 (t, 2H, J=7Hz); 1.70 (m, 2H); 1.45–1.00 (m, 2H); 1.13 (t, 3H, J=7Hz); 0.94 (t, 3H, J=7Hz); 0.80–0.50 (m, 3H).

n ¹H NMR (K⁺ salt) (CDCl₃) δ 7.97 (d, 1H, J=8Hz); 7.50–6.90 (m, 12H); 6.55–6.40 (m, 1H); 5.40 (s, 2H); 5.21 (s, 2H); 3.80–3.60 (m, 2H); 2.77 (q, 2H, J=7Hz); 2.60 (t, 2H, J=7Hz); 1.71–1.30 (m, 1H); 1.30–1.00 (m, 2H); 1.13 (t, 3H, J=7Hz); 0.96 (t, 3H, J=7Hz); 0.75 (d, 6H, J=7Hz).

o ¹H NMR (K⁺ salt) (CDCl₃) δ 7.98 (d, 1H, J=8Hz); 7.46 (d, 1H, J=8Hz); 7.45–7.10 (m, 11H); 7.07 (d, 1H, J=8Hz); 6.98 (d, 1H, J=8Hz); 6.46 (t, 1H, J=8Hz); 5.38 (s, 2H); 5.15 (s, 2H); 3.60 (t, 2H, J=7Hz); 2.77 (q, 2H, J=7Hz); 2.59 (t, 2H, J=7Hz); 1.71 (t of q, 2H, J=7,7Hz); 1.34 (t of q, 2H, J=7,7Hz); 1.15 (t, 3H, J=7Hz); 0.95 (t, 3H, J=7Hz); 0.67 (t, 3H, J=7Hz).

p ¹H NMR (K⁺ salt) (CDCl₃) δ 7.98 (d, 1H, J=8Hz); 7.46 (d, 1H, J=8Hz); 7.45–7.10 (m, 11H); 7.08 (d, 1H, J=8Hz); 7.01 (d, 1H, J=8Hz); 6.47 (t, 1H, J=8Hz); 5.38 (s, 2H); 5.17 (s, 2H); 3.73 (t, 2H, J=7Hz); 2.77 (q, 2H, J=7Hz); 2.59 (t, 2H, J=7Hz); 1.80–1.60 (m, 2H); 1.50–1.30 (m, 1H); 1.30–1.10 (m, 2H); 1.15 (t, 3H, J=7Hz); 0.90 (t, 3H, J=7Hz); 0.74 (d, 6H, J=7Hz).

q ¹H NMR (K⁺ salt) (CDCl₃) δ 9.13 (s, 1H); 8.69 (s, 2H); 7.98 (s, 1H, J=8Hz); 7.60–7.40 (m, 3H); 7.34 (t, 1H, J=8Hz); 7.30–7.10 (m, 4H); 7.09 (d, 1H, J=8Hz); 7.02 (d, 1H, J=Hz); 6.45 (t, 1H, J=8Hz); 6.45 (t, 1H, J=8Hz); 5.36 (s, 2H); 5.18 (s, 2H); 3.56 (t, 2H, J=7Hz); 2.73 (q, 2H, J=7Hz); 2.60 (t, 2H, J=7Hz); 1.71 (t of q, 2H, J=7,7Hz); 1.32 (t of q, 2H, J=7,7Hz); 1.13 (t, 3H, J=7Hz); 0.94 (t, 3H, J=7Hz); 0.67 (t, 3H, J=7Hz).

r ¹H NMR (K⁺ salt) (CDCl₃) δ 8.07 (d, 1H, J=8Hz); 7.45–7.15 (m, 5H); 7.14 (d, 1H, J=8Hz); 7.03 (d, 1H, J=8Hz); 6.93 (d, 1H, J=8Hz); 6.86 (d, 2H, J=8Hz); 6.47 (t, 1H, J=8Hz); 5.40 (s, 2H); 4.30–4.15 (m, 2H); 4.00–3.85 (m, 2H); 3.76 (t, 2H, J=7Hz); 2.89 (q, 2H, J=7Hz); 2.64 (t, 2H, J=7Hz); 1.90–1.60 (m, 4H); 1.60–1.30 (m, 1H); 1.35–1.20 (m, 5H); 0.97 (t, 3H, J=7Hz); 0.77 (d, 6H, J=7Hz).

s ¹H NMR (CDCl₃) δ 8.26 (d, 1H, J=8Hz); 7.64 (t, 1H, J=8Hz); 7.57 (t, 1H, J=8Hz); 7.40–7.20 (m, 4H); 7.10 (d, 1H, J=11Hz); 7.05–6.80 (m, 4H); 6.64 (t, 1H, J=8Hz); 5.57 (s, 2H); 4.40 (t, 2H, J=7Hz); 4.15–3.95 (m, 4H); 2.91 (q, 2H, J=7Hz); 2.66 (t, 2H, J=7Hz); 2.17 (t of t, 2H, J=7,7Hz); 1.74 (t of q, 2H, J=7,7Hz); 1.55–1.25 (m, 3H); 1.27 (t, 3H, J=7Hz); 0.98 (t, 3H, J=7Hz); 0.82 (d, 6H, J=Hz).

t ¹H NMR (CDCl₃) δ 8.19 (d, 1H. J=8Hz); 7.60–7.40 (m, 2H); 7.30–7.10 (m, 6H); 7.04 (d, 1H, J=11Hz); 6.90 (d, 1H, J=8Hz); 6.53 (t, 1H, J=8Hz); 5.48 (s, 2H); 4.43 (s, 2H); 4.21 (t, 2H, J=7Hz); 3.93 (t, 2H, J=7Hz); 3.46 (t, 2H, J=7Hz); 2.82 (q, 2H, J=7Hz); 2.59 (t, 2H, J=7Hz); 1.97 (t of t, 2H, J=7Hz); 1.66 (t of q, 2H, J=7,7Hz); 1.50–1.00 (m, 6H); 0.89 (t, 3H, J=7Hz); 0.74 (d, 6H, J=7Hz).

u ¹H NMR (CDCl₃) δ 8.16 (d, 1H, J=8Hz); 7.77 (d, 2H, J=8Hz); 7.70–7.20 (m, 13H); 6.93 (d, 2H, J=8Hz); 5.96 (t, 1H, J=8Hz); 5.41 (s, 2H); 5.37 (s, 2H); 3.03 (q, 2H, J=7Hz); 2.74 (q, 2H, J=7Hz); 2.63 (t, 2H, J=7Hz); 1.69 (t of q, 2H, J=7,7Hz); 1.40–1.00 (m, 7H); 0.95 (t, 3H, J=7Hz); 0.81 (t, 3H, J=7Hz).

v ¹H NMR (K⁺ salt) (CDCl₃) δ 8.07 (d, 1H, J=8Hz); 7.77 (d, 2H, J=8Hz); 7.59 (d, 2H, J=8Hz); 7.60–7.00 (m, 11H); 6.37 (t, 1H, J=8Hz); 5.46 (s, 2H); 5.38 (s, 2H); 3.67 (t, 2H, J=7Hz); 2.56 (t, 2H, J=7Hz); 1.63 (t of t, 2H, J=7,7Hz); 1.50–1.10 (m, 5H); 0.86 (t, 3H, J=7Hz); 0.70 (d, 6H, J=7Hz).

w ¹H NMR (CDCl₃) δ 8.18 (d, 1H, J=8Hz); 7.65–7.05 (m, 12H); 7.01 (d, 1H, J=10Hz); 6.91 (d, 1H, J=8Hz); 6.57 (t, 1H, J=8Hz); 5.51 (s, 2H); 5.33 (s, 2H); 3.96 (t, 2H, J=7Hz); 2.84 (q, 2H, J=7Hz); 2.58 (t, 2H, J=7Hz); 1.66 (q, 2H, J=7Hz); 1.50–1.20 (m, 3H); 1.16 (T, 3H, J=7HZ); 0.90 (T, 3H, J=7HZ); 0.74 (d, 6H, J=7Hz).

x ¹H NMR (DMSO-d₆) δ 7.74 (s, 1H); 7.80–7.35 (m, 12H); 6.98 (d, 2H, J-8Hz); 6.83 (d, 2H, J=8Hz); 5.48 (s, 2H); 5.29 (s, 2H); 2.72 (q 2H, J=7Hz); 2.52 (t, 2H, J=7Hz); 1.54 (t of q, 2H, J=7,7Hz); 1.05 (t, 3H, J=7Hz); 0.83 (t, 3H, J=7Hz).

y ¹H NMR (CDCl₃) δ 7.77 (d, 1H, J8Hz); 7.60 (t, 1H, J=8Hz); 7.51 (t, 1H, J=8Hz); 7.45–7.00 (m, 6H); 7.09 (d, 6H, J=8Hz); 6.83 (d, 1H, J=11Hz); 6.72 (d, 1H, J=8Hz); 6.30 (d, 1H, J=8Hz); 5.41 (s, 2H); 5.12 (s, 2H); 2.70 (q, 2H, J=7Hz); 2.44 (t, 2H, J=7Hz); 1.60 (t of q, 2H, J=7,7Hz); 1.04 (t, 3H, J=7Hz); 0.86 (t, 3H, J=8Hz).

z ¹H NMR (CDCl₃) δ 7.85 (d, 1H, J=7Hz); 7.67 (d, 2H, J=7Hz); 7.65–7.20 (m, 10H); 6.91 (d, 2H, J=7Hz); 6.55 (d, 2H, J=7Hz); 5.26 (s, 2H); 5.21 (s, 2H); 2.50–2.25 (m, 2H); 2.20–2.00 (m, 2H); 1.65–1.40 (m, 2H); 0.90–0.60 (m, 6H).

aa ¹H NMR (CDCl₃) δ 7.85–7.70 (m, 1H); 7.65–7.40 (m, 2H); 7.41 (d, 1H, J=8Hz); 7.40–6.80 (m, 11H); 6.75–6.60 (m, 2H); 5.38 (bs, 2H); 5.25–5.10 (m, 2H); 4.37 (s, 1H); 4.41 (s, 1H); 3.50–3.30 (m, 1H); 3.20–3.00 (m, 1H); 2.70–2.55 (m, 2H); 2.40–2.25 (m, 2H); 1.70–0.60 (m, 15H).

bb ¹H NMR (CDCl₃) δ 7.95–7.80 (m, 1H); 7.60–7.20 (m, 12H); 7.04 (d, 2H, J=8Hz); 6.67 (d, 2H, J=8Hz); 5.38 (s, 2H); 5.16 (s, 2H); 2.45 (q, 2H, J=7Hz); 2.15 (t, 2H, J=7Hz); 1.57 (t of q, 2H, J=7,7Hz); 0.90–0.70 (m, 6H).

cc ¹H NMR (CDCl₃) δ 7.85 (d, 1H, J=8Hz); 7.70–7.50 (m, 2H); 7.45–7.10 (m, 10H); 6.97 (d, 2H, J=8Hz); 6.54 (d, 2H, J=8Hz); 5.30 (s, 2H); 5.07 (s, 2H); 2.45–2.25 (m, 2H); 2.20–2.00 (m, 2H); 1.54 (t of q, 2H, J=7,7Hz); 0.83 (t, 3H, J=7Hz); 0.73 (t, 3H, J=7Hz).

dd ¹H NMR (CDCl₃) δ 7.83 (d, 1H, J=7Hz); 7.68 (d, 2H, J=7Hz); 7.60–7.10 (m, 10H); 6.80–6.60 (m, 2H); 6.27 (t, 1H, J=8Hz); 5.30 (s, 4H); 2.50 (m, 2H); 2.33 (t, 2H, J=7Hz); 1.54 (t of q, 2H, J=7,7Hz); 0.95–0.60 (m, 6H).

ee ¹H NMR (K⁺ salt) (CDCl₃) δ 8.01 (d, 1H, J=8Hz); 7.85–7.65 (m, 4H); 7.65–7.50 (m, 2H); 7.50–7.12 (m, 6H); 7.09 (d, 1H, J=8Hz); 7.00 (d, 1H, J=8Hz); 6.48 (t, 1H, J=8Hz); 5.42 (s, 2H); 5.27 (s, 2H); 3.70 (t, 2H, J=7Hz); 2.84 (q, 2H, J=7Hz); 2.63 (t, 2H, J=7Hz); 1.73 (t of q, 2H, J=7,7Hz); 1.50–1.30 (m, 1H); 1.30–1.10 (m, 5H); 0.96 (t, 3H, J=7Hz); 0.71 (d, 6H, J=7Hz).

ff ¹H NMR (K⁺ salt) (CDCl₃) δ 7.93 (d, 1H, J=8Hz); 7.80–7.60 (m, 4H); 7.47 (t, 2H, J=8Hz); 7.45–7.05 (m, 6H); 7.01 (d, 1H, J=8Hz); 6.93 (d, 1H, J=8Hz); 6.40 (t, 1H, J=8Hz); 5.34 (s, 2H); 5.19 (s, 2H); 3.53 (t, 2H, J=7Hz); 2.77 (q, 2H, J=7Hz); 2.57 (t, 2H, J=7Hz); 1.80–1.50 (m, 2H); 1.35–1.10 (m, 2H); 1.08 (t, 3H, J=7Hz); 0.88 (t, 3H, J=7Hz); 0.60 (t, 3H, J=7Hz).

TABLE 1-continued

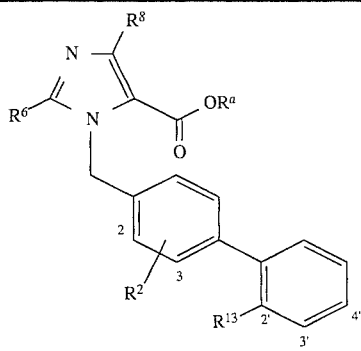

| Ex. No. | R⁶ | R⁸ | Rᵃ | R¹³ | R² | m.p. |
|---|---|---|---|---|---|---| gg ¹H NMR (K⁺ salt) (CDCl₃) δ 8.03 (d, 1H, J=8Hz); 7.40–7.15 (m, 5H); 7.10 (d, 1H, J=8Hz); 7.06 (d, 1H, J=8Hz); 6.95–6.80 (m, 2H); 6.51 (t, 1H, J=8Hz); 5.44 (s, 2H); 5.25 (s, 2H); 3.97 (t, 2H, J=7Hz); 3.76 (t, 2H, J=7Hz); 2.82 (q, 2H, J=7Hz); 2.61 (t, 2H, J=7Hz); 1.90–1.55 (m, 5H); 1.55–1.35 (m, 1H); 1.28 (q, 2H, J=7Hz); 1.14 (t, 3H, J=7Hz); 0.94 (t, 3H, J=7Hz); 0.92 (d, 6H, J=7Hz); 0.77 (d, 6H, J=7Hz).

hh ¹H NMR (K⁺ salt) (CDCl₃) δ 8.00 (d, 1H, J=8Hz); 7.80 (d, 2H, J=8Hz); 7.45 (t, 1H, J=8Hz); 7.40–7.05 (m, 5H); 7.05 (d, 1H, J=8Hz); 7.00 (d, 1H, J=8Hz); 6.47 (t, 1H, J=8Hz); 5.37 (s, 2H); 4.18 (t, 2H, J=7Hz); 3.63 (t, 2H, J=7Hz); 2.97 (t, 2H, J=7Hz); 2.81 (q, 2H, J=7Hz); 2.55 (t, 2H, J=7Hz); 2.10–1.90 (m, 2H); 1.80–1.50 (m, 2H); 1.50–1.20 (m, 1H); 1.25–1.10 (m, 5H); 0.87 (t, 3H, J=7Hz); 0.66 (d, 6H, J=7Hz).

The following examples in Table 2 can be synthesized by the procedures described in examples 1–12 and by methods familiar to one skilled in the art.

TABLE 2

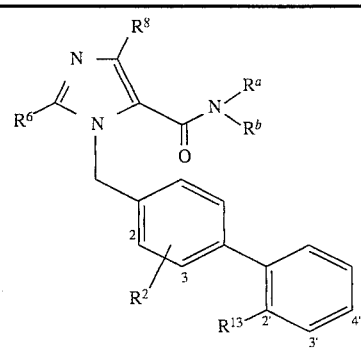

| Ex No. | R⁶ | R⁸ | Rᵃ | Rᵇ | R¹³ | R² | m.p. |
|---|---|---|---|---|---|---|---|
| 208 | n-propyl | ethyl | -CH₂-(2-benzoylphenyl) | H | CH₃O₂C—NHSO₂— | H | |
| 209 | n-propyl | ethyl | -CH₂-(2-benzoylphenyl) | H | Ph—(CH₂)₂O₂C—NHSO₂— | H | |
| 210 | n-propyl | ethyl | -CH₂-(2-benzoylphenyl) | H | (CH₃)₂CH(CH₂)₂O₂C—NHSO₂— | H | |

TABLE 2-continued

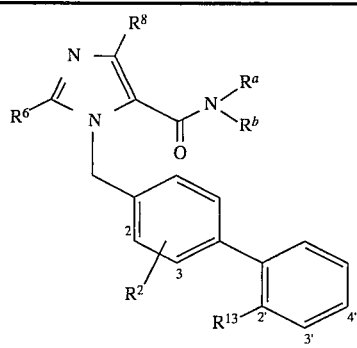

| Ex No. | R⁶ | R⁸ | Rᵃ | Rᵇ | R¹³ | R² | m.p. |
|---|---|---|---|---|---|---|---|
| 211 | n-propyl | ethyl | (2-benzoylbenzyl) | H | Ph—(CH₂)₂O₂C—NHSO₂— | 2-F | |
| 212 | n-propyl | ethyl | (2-benzoylbenzyl) | H | CH₃(CH₂)₂O₂C—NHSO₂— | 2-F | |
| 213 | n-propyl | ethyl | (2-benzoylbenzyl) | H | (CH₃)₂CHCH₂O₂C—NHSO₂— | 2-F | |
| 214 | n-propyl | ethyl | (2-benzoylbenzyl) | H | CH₃(CH₂)₃O₂C—NHSO₂— | 2-F | |
| 215 | n-propyl | ethyl | (2-benzoylbenzyl) | H | CH₃(CH₂)₃O₂C—NHSO₂— | 2-Cl | |
| 216 | n-propyl | ethyl | —CH₂-(2-phenoxyphenyl) | H | CH₃(CH₂)₃O₂C—NHSO₂— | 2-F | |
| 217 | n-propyl | ethyl | —CH₂-(2-phenoxyphenyl) | H | CH₃(CH₂)₃O₂C—NHSO₂— | 2-Cl | |

TABLE 2-continued
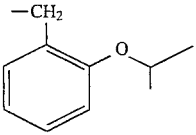
| Ex No. | R⁶ | R⁸ | Rᵃ | Rᵇ | R¹³ | R2 m.p. |
|---|---|---|---|---|---|---|
| 218 | n-propyl | ethyl | 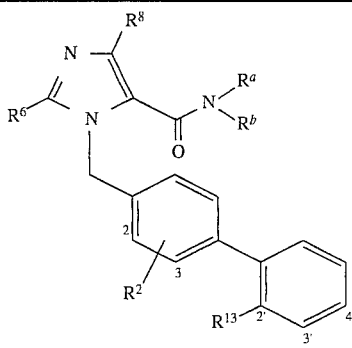 | H | $CH_3(CH_2)_3O_2C-NHSO_2-$ | 2-Cl |
| 219 | n-propyl | ethyl | 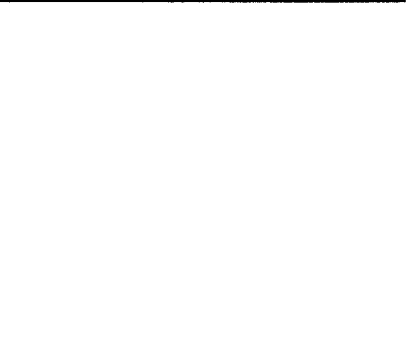 | H | $CH_3(CH_2)_2O_2C-NHSO_2-$ | 2-F |
| 220 | n-propyl | ethyl | 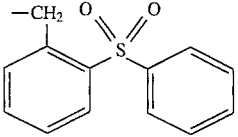 | H | $(CH_3)_2CH(CH_2)_2O_2C-NHSO_2-$ | 2-F |
| 221 | n-propyl | ethyl | 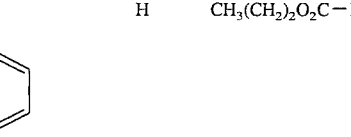 | H | $CH_3(CH_2)_2O_2C-NHSO_2-$ | 2-F |
| 222 | n-propyl | ethyl |  | H | $(CH_3)_2CH(CH_2)_2O_2C-NHSO_2-$ | 2-F |
| 223 | n-propyl | ethyl | 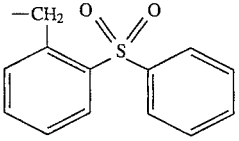 | H | $CH_3(CH_2)_2O_2C-NHSO_2-$ | 2-F |
| 224 | n-propyl | ethyl | 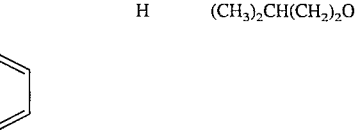 | H | $CH_3(CH_2)_2O_2C-NHSO_2-$ | 2-F (M + H)⁺ = 757 |
| 225 | n-propyl | ethyl |  | H | $CH_3(CH_2)_2O_2C-NHSO_2-$ | 2-F |

TABLE 2-continued
| Ex No. | R⁶ | R⁸ | Rᵃ | Rᵇ | R¹³ | R2 m.p. |
|---|---|---|---|---|---|---|
| 226 | n-propyl | ethyl | 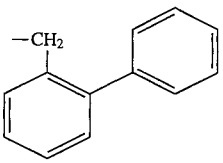 | H | $(CH_3)_2CH(CH_2)_2O_2C-NHSO_2-$ | 2-F |
| 227 | n-propyl | ethyl | 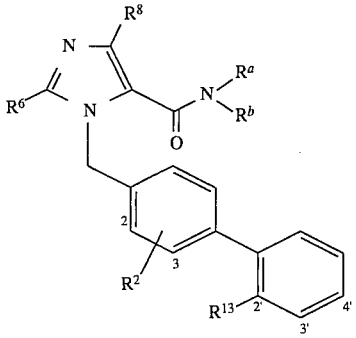 | H | $CH_3(CH_2)_2O_2C-NHSO_2-$ | 2-F |
| 228 | n-propyl | ethyl | 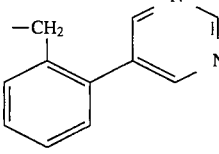 | H | $(CH_3)_2CH(CH_2)_2O_2C-NHSO_2-$ | 2-F |
| 229 | n-propyl | ethyl | 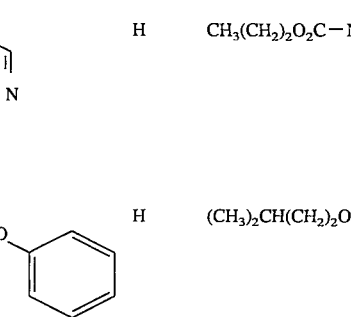 | H | $(CH_3)_2CH(CH_2)_2O_2C-NHSO_2-$ | 2-F |
| 230 | n-propyl | ethyl | 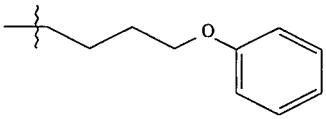 | H | $(CH_3)_2CH(CH_2)_2O_2C-NHSO_2-$ | 2-F |
| 231 | n-propyl | ethyl | 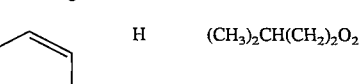 | H | $(CH_3(CH_2)_3-NH-CO-NHSO_2-$ | 2-F |
| 232 | n-propyl | Cl | 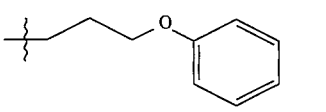 | H | $(CH_3)_2CH(CH_2)_2O_2C-NHSO_2-$ | 2-F |
| 233 | n-propyl | ethyl | 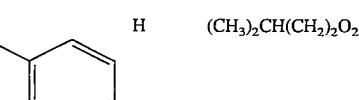 | H | $(CH_3)_2CH(CH_2)_2O_2C-NHSO_2-$ | 2-F |

TABLE 2-continued

Structure with R⁸, Rᵃ, Rᵇ, R⁶, R², R¹³ substituents on a biphenyl system.

| Ex No. | R⁶ | R⁸ | Rᵃ | Rᵇ | R¹³ | R2 m.p. |
|---|---|---|---|---|---|---|
| 234 | n-propyl | ethyl | —CH₂—(2-(phenylsulfinyl)phenyl) | H | CH₃(CH₂)₃—NH—CO—NHSO₂— | 2-F |
| 235 | n-propyl | ethyl | —CH₂—(2-(phenylsulfinyl)phenyl) | H | (CH₃)₂CH(CH₂)₂O₂C—NHSO₂— | 2-F |
| 236 | n-propyl | ethyl | —CH₂—(2-(phenylsulfinyl)phenyl) | H | (CH₃)₂CH(CH₂)₂O₂C—NHSO₂— | 2-F |
| 237 | n-propyl | ethyl | —CH₂—(2-(phenylsulfinyl)phenyl) | H | (CH₃)(CH₂)₃O₂C—NHSO₂— | 2-F |
| 238 | n-propyl | ethyl | —CH₂—(2-(phenylsulfinyl)phenyl) | H | (CH₃)(CH₂)₂O₂C—NHSO₂— | 2-F |
| 239 | n-propyl | ethyl | —CH₂—(2-(phenylsulfinyl)phenyl) | H | (CH₃)₂CHO₂C—NHSO₂— | 2-F |
| 240 | n-propyl | ethyl | —CH₂—(2-(phenylsulfinyl)phenyl) | H | PhCH₂O₂C—NHSO₂— | 2-F |
| 241 | n-propyl | ethyl | —CH₂—(2-(phenylsulfinyl)phenyl) | H | Ph(CH₂)₂O₂C—NHSO₂— | 2-F |

TABLE 2-continued
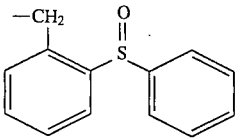
| Ex No. | $R^6$ | $R^8$ | $R^a$ | $R^b$ | $R^{13}$ | $R^2$ m.p. |
|---|---|---|---|---|---|---|
| 242 | n-propyl | ethyl | 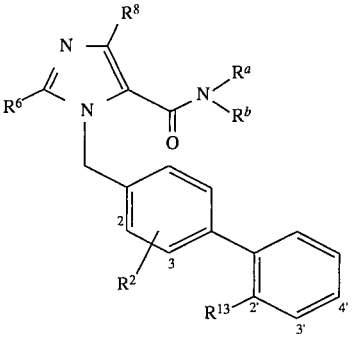 | H | $Ph(CH_2)_3O_2C-NHSO_2-$ | 2-F |
| 243 | n-propyl | ethyl | 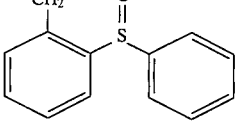 | H | $Ph(CH_2)_4O_2C-NHSO_2-$ | 2-F |
| 244 | n-propyl | ethyl | 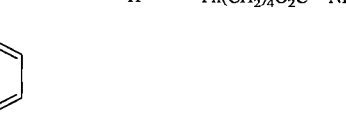 | H | $(CH_3)_2CH(CH_2)_2O_2C-NHSO_2-$ | H |
| 245 | n-propyl | ethyl | 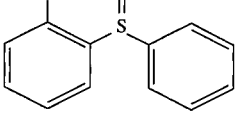 | H | $(CH_3)_2CH(CH_2)O_2C-NHSO_2-$ | H |
| 246 | n-propyl | ethyl |  | H | $(CH_3)(CH_2)_3O_2C-NHSO_2-$ | H |
| 247 | n-propyl | ethyl | 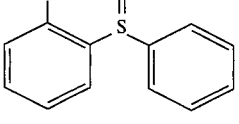 | H | $(CH_3)(CH_2)_2O_2C-NHSO_2-$ | H |
| 248 | n-propyl | ethyl |  | H | $(CH_3)_2CHO_2C-NHSO_2-$ | H |
| 249 | n-propyl | ethyl | 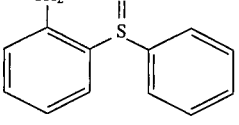 | H | $PhCH_2O_2C-NHSO_2-$ | H |

TABLE 2-continued

| Ex No. | R⁶ | R⁸ | Rᵃ | Rᵇ | R¹³ | R2 m.p. |
|---|---|---|---|---|---|---|
| 250 | n-propyl | ethyl | −CH₂-(2-pyrimidinyl)phenyl | H | CH₃(CH₂)₃−NH−CO−NHSO₂− | 2-F |
| 251 | n-propyl | ethyl | −CH₂-(2-pyrimidinyl)phenyl | H | (CH₃)₂CH(CH₂)₂O₂C−NHSO₂− | 2-F |
| 252 | n-propyl | ethyl | −CH₂-(2-pyrimidinyl)phenyl | H | (CH₃)₂CH(CH₂)O₂C−NHSO₂− | 2-F |
| 253 | ethyl | ethyl | −CH₂-(2-(phenylsulfonyl))phenyl | H | CH₃(CH₂)₂O₂C−NHSO₂− | 2-F |
| 254 | ethyl | ethyl | −CH₂-(2-(phenylsulfonyl))phenyl | H | (CH₃)₂CH(CH₂)₂O₂C−NHSO₂− | 2-F |
| 255 | ethyl | Cl | −CH₂-(2-(phenylsulfonyl))phenyl | H | CH₃(CH₂)₂O₂C−NHSO₂− | 2-F |
| 256 | ethyl | Br | −CH₂-(2-(phenylsulfonyl))phenyl | H | (CH₃)₂CH(CH₂)₂O₂C−NHSO₂− | 2-F |

TABLE 2-continued

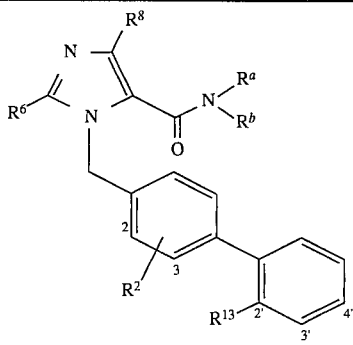

| Ex No. | $R^6$ | $R^8$ | $R^a$ | $R^b$ | $R^{13}$ | $R^2$ m.p. |
|---|---|---|---|---|---|---|
| 257 | ethyl | $C_2F_6$ | —CH$_2$-(2-(phenylsulfonyl)phenyl) | CH$_3$ | CH$_3$(CH$_2$)$_2$O$_2$C—NHSO$_2$— | 2-F |
| 258 | ethyl | ethyl | —CH$_2$-(2-(phenylsulfonyl)phenyl) | n-butyl | (CH$_3$)$_2$CH(CH$_2$)$_2$O$_2$C—NHSO$_2$— | H |
| 259 | n-propyl | ethyl | —CH$_2$-(2-(phenylsulfonyl)phenyl) | H | CN$_4$H | 2-F |
| 260 | ethyl | ethyl | —CH$_2$-(2-(phenylsulfonyl)phenyl) | H | (CH$_3$)$_2$CH(CH$_2$)$_2$—NH—CO—NHSO$_2$— | 2-F |
| 261 | n-propyl | ethyl | —CH$_2$CH$_2$N-phthalimido | H | (CH$_3$)$_2$CH(CH$_2$)$_2$O$_2$C—NHSO$_2$— | 2-F |
| 262 | n-propyl | ethyl | —CH$_2$CH$_2$N-phthalimido | H | (CH$_3$)$_2$CH(CH$_2$)O$_2$C—NHSO$_2$— | 2-F |
| 263 | n-propyl | ethyl | —CH$_2$CH$_2$N-(3-methylphthalimido) | H | (CH$_3$)(CH$_2$)$_2$O$_2$C—NHSO$_2$— | 2-F |

TABLE 2-continued

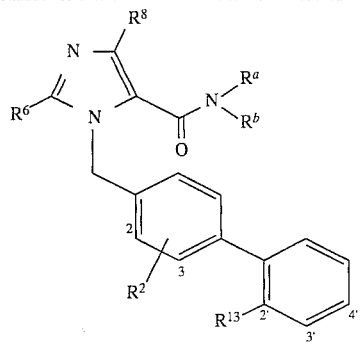

| Ex No. | R⁶ | R⁸ | Rᵃ | Rᵇ | R¹³ | R2 | m.p. |
|---|---|---|---|---|---|---|---|
| 264 | n-propyl | ethyl | —CH₂CH₂N(CO)₂C₆H₃(CH₃) (phthalimide with CH₃) | H | $(CH_3)_2CH(CH_2)_2O_2C-NHSO_2-$ | 2-F | |
| 265 | n-propyl | ethyl | —CH₂CH₂N(CO)₂C₆H₃(CH₃) (phthalimide with CH₃) | H | $(CH_3)_2CH(CH_2)O_2C-NHSO_2-$ | 2-F | |
| 266 | n-propyl | ethyl | —CH₂CH₂N(CO)₂C₆H₃(OCH₃) (phthalimide with OCH₃) | H | $(CH_3)(CH_2)_2O_2C-NHSO_2-$ | 2-F | |
| 267 | n-propyl | ethyl | —CH₂CH₂N(CO)₂C₆H₃(OCH₃) (phthalimide with OCH₃) | H | $(CH_3)_2CH(CH_2)_2O_2C-NHSO_2-$ | 2-F | |
| 268 | n-propyl | ethyl | —CH₂CH₂N(CO)₂C₆H₃(OCH₃) (phthalimide with OCH₃) | H | $(CH_3)_2CH(CH_2)O_2C-NHSO_2-$ | 2-F | |
| 269 | n-propyl | ethyl | —CH₂CH₂N(CO)₂C₆H₃(OCH₃) (phthalimide with OCH₃) | H | $(CH_3)(CH_2)_2O_2C-NHSO_2-$ | 2-F | |

TABLE 2-continued

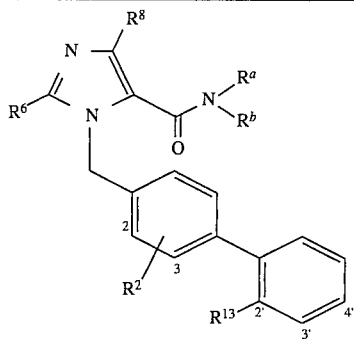

| Ex No. | R⁶ | R⁸ | Rᵃ | Rᵇ | R¹³ | R2 m.p. |
|---|---|---|---|---|---|---|
| 270 | n-propyl | ethyl | —CH₂CH₂N(CO)₂C₆H₃(NO₂) (phthalimido, 3-NO₂) | H | $(CH_3)_2CH(CH_2)_2O_2C-NHSO_2-$ | 2-F |
| 271 | n-propyl | ethyl | —CH₂CH₂N(CO)₂C₆H₃(NO₂) (phthalimido, 3-NO₂) | H | $(CH_3)_2CH(CH_2)O_2C-NHSO_2-$ | 2-F |
| 272 | n-propyl | ethyl | —CH₂CH₂N(CO)₂C₆H₃(NO₂) (phthalimido, 3-NO₂) | H | $(CH_3)(CH_2)_2O_2C-NHSO_2-$ | 2-F |
| 273 | n-propyl | ethyl | —CH₂CH₂N(CO)₂C₆H₂(Cl)₂ (phthalimido, 3,6-Cl₂) | H | $(CH_3)_2CH(CH_2)_2O_2C-NHSO_2-$ | 2-F |
| 274 | n-propyl | ethyl | —CH₂CH₂N(CO)₂C₆H₂(Cl)₂ (phthalimido, 3,6-Cl₂) | H | $(CH_3)_2CH(CH_2)O_2C-NHSO_2-$ | 2-F |
| 275 | n-propyl | ethyl | —CH₂CH₂N(CO)₂C₆H₂(Cl)₂ (phthalimido, 3,6-Cl₂) | H | $(CH_3)(CH_2)_2O_2C-NHSO_2-$ | 2-F |

TABLE 2-continued

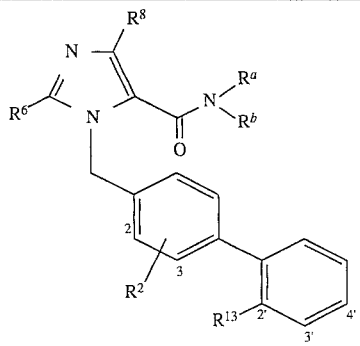

| Ex No. | R[6] | R[8] | R[a] | R[b] | R[13] | R2 | m.p. |
|---|---|---|---|---|---|---|---|
| 276 | n-propyl | ethyl | —(CH$_2$)$_3$N(phthalimido) | H | (CH$_3$)$_2$CH(CH$_2$)$_2$O$_2$C—NHSO$_2$— | 2-F | |
| 277 | n-propyl | ethyl | —(CH$_2$)$_3$N(phthalimido) | H | (CH$_3$)$_2$CH(CH$_2$)$_2$O$_2$C—NHSO$_2$— | 2-F | |
| 278 | n-propyl | ethyl | —(CH$_2$)$_3$N(phthalimido) | H | (CH$_3$(CH$_2$)$_2$O$_2$C—NHSO$_2$— | 2-F | |
| 279 | n-propyl | ethyl | —(CH$_2$)$_4$N(phthalimido) | H | (CH$_3$)$_2$CH(CH$_2$)$_2$O$_2$C—NHSO$_2$— | 2-F | |
| 280 | n-propyl | ethyl | —(CH$_2$)$_4$N(phthalimido) | H | (CH$_3$)$_2$CH(CH$_2$)O$_2$C—NHSO$_2$— | 2-F | |
| 281 | n-propyl | ethyl | —(CH$_2$)$_4$N(phthalimido) | H | (CH$_3$)(CH$_2$)$_2$O$_2$C—NHSO$_2$— | 2-F | |

TABLE 2-continued

[Structure: imidazole core with R⁶, R⁸, Rᵃ, Rᵇ substituents, N-CH₂-biphenyl with R², R¹³ groups]

| Ex No. | R⁶ | R⁸ | Rᵃ | Rᵇ | R¹³ | R2 m.p. |
|---|---|---|---|---|---|---|
| 282 | n-propyl | ethyl | -CH₂CH₂N(phthalimido) | H | CN₄H | 2-F |
| 283 | n-propyl | ethyl | -CH₂CH₂N(phthalimido) | CH₃ | $(CH_3)_2CH(CH_2)_2O_2C-NHSO_2-$ | 2-F |
| 284 | n-propyl | ethyl | -CH₂CH₂N(phthalimido) | n-C₃H₇ | $(CH_3)_2CH(CH_2)_2O_2C-NHSO_2-$ | 2-F |
| 285 | n-propyl | ethyl | -CH₂-(2-CF₃-phenyl) | H | $(CH_3)_2CH(CH_2)_2O_2C-NHSO_2-$ | 2-F (M+H)⁺ = 717.4 |
| 286 | n-propyl | ethyl | -CH₂-(2-CF₃-phenyl) | H | $(CH_3)_2CH(CH_2)O_2C-NHSO_2-$ | 2-F |
| 287 | n-propyl | ethyl | -CH₂-(2-CF₃-phenyl) | H | $(CH_3)(CH_2)_3O_2C-NHSO_2-$ | 2-F (M+H)⁺ = 703.4 |
| 288 | n-propyl | ethyl | -CH₂-(2-CF₃-phenyl) | H | CN₄H | 2-F |

TABLE 2-continued

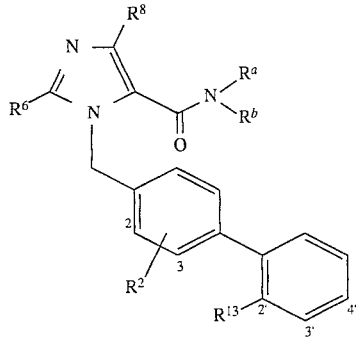

| Ex No. | $R^6$ | $R^8$ | $R^a$ | $R^b$ | $R^{13}$ | $R^2$ | m.p. |
|---|---|---|---|---|---|---|---|
| 289 | n-propyl | ethyl | —CH$_2$—(2-NO$_2$-phenyl) | H | $(CH_3)_2CH(CH_2)_2O_2C-NHSO_2-$ | 2-F | |
| 290 | n-propyl | ethyl | —CH$_2$—(2-NO$_2$-phenyl) | H | $(CH_3)_2CH(CH_2)_2O_2C-NHSO_2-$ | 2-F | |
| 291 | n-propyl | ethyl | —CH$_2$—(2-NO$_2$-phenyl) | H | $(CH_3)(CH_2)_2O_2C-NHSO_2-$ | 2-F | |
| 292 | n-propyl | ethyl | —CH$_2$—(2-NO$_2$-phenyl) | H | $CN_4H$ | 2-F | |
| 293 | n-propyl | ethyl | —CH$_2$—(2-SO—CH$_3$-phenyl) | H | $(CH_3)_2CH(CH_2)_2O_2C-NHSO_2-$ | 2-F | |
| 294 | n-propyl | ethyl | —CH$_2$—(2-SO—CH$_3$-phenyl) | H | $(CH_3)_2CH(CH_2)O_2C-NHSO_2-$ | 2-F | |
| 295 | n-propyl | ethyl | —CH$_2$—(2-SO—CH$_3$-phenyl) | H | $(CH_3)(CH_2)_2O_2C-NHSO_2-$ | 2-F | |
| 296 | n-propyl | ethyl | —CH$_2$—(2-SO—CH$_3$-phenyl) | H | $CN_4H$ | 2-F | |

TABLE 2-continued

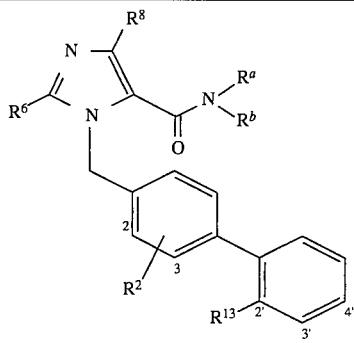

| Ex No. | R⁶ | R⁸ | Rᵃ | Rᵇ | R¹³ | R2 m.p. |
|---|---|---|---|---|---|---|
| 297 | N-propyl | ethyl | -CH₂-（2-COOCH₃-phenyl） | H | $(CH_3)_2CH(CH_2)_2O_2C-NHSO_2-$ | 2-F |
| 298 | n-propyl | ethyl | -CH₂-（2-COOCH₃-phenyl） | H | $(CH_3)_2CH(CH_2)O_2C-NHSO_2-$ | 2-F |
| 299 | n-propyl | ethyl | -CH₂-（2-COOCH₃-phenyl） | H | $(CH_3)(CH_2)_2O_2C-NHSO_2-$ | 2-F |
| 300 | n-propyl | ethyl | -CH₂-（2-COOCH₃-phenyl） | H | $CN_4H$ | 2-F |
| 301 | n-propyl | ethyl | -CH₂-（2-CO(CH₂)₃CH₃-phenyl） | H | $(CH_3)_2CH(CH_2)_2O_2C-NHSO_2-$ | 2-F |
| 302 | n-propyl | ethyl | -CH₂-（2-CO(CH₂)₃CH₃-phenyl） | H | $(CH_3)_2CH(CH_2)O_2C-NHSO_2-$ | 2-F |
| 303 | n-propyl | ethyl | -CH₂-（2-CO(CH₂)₃CH₃-phenyl） | H | $(CH_3)(CH_2)_2O_2C-NHSO_2-$ | 2-F |
| 304 | n-propyl | ethyl | -CH₂-（2-CO(CH₂)₃CH₃-phenyl） | H | $CN_4H$ | 2-F |

TABLE 2-continued

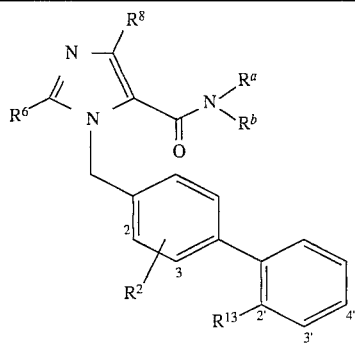

| Ex No. | R⁶ | R⁸ | Rᵃ | Rᵇ | R¹³ | R2 | m.p. |
|---|---|---|---|---|---|---|---|
| 305 | n-propyl | ethyl | —CH₂—(3-CF₃-phenyl) | H | (CH₃)₂CH(CH₂)₂O₂C—NHSO₂— | 2-F | |
| 306 | n-propyl | ethyl | —CH₂—(3-CF₃-phenyl) | H | (CH₃)₂CH(CH₂)O₂C—NHSO₂— | 2-F | |
| 307 | n-propyl | ethyl | —CH₂—(3-CF₃-phenyl) | H | (CH₃)(CH₂)₂O₂C—NHSO₂— | 2-F | |
| 308 | n-propyl | ethyl | —CH₂—(3-CF₃-phenyl) | H | CN₄H | 2-F | |
| 309 | n-propyl | ethyl | —CH₂—(3-COCH₃-phenyl) | H | (CH₃)₂CH(CH₂)₂O₂C—NHSO₂— | 2-F | |
| 310 | n-propyl | ethyl | —CH₂—(3-COCH₃-phenyl) | H | (CH₃)₂CH(CH₂)O₂C—NHSO₂— | 2-F | |
| 311 | n-propyl | ethyl | —CH₂—(3-COCH₃-phenyl) | H | (CH₃)(CH₂)₂O₂C—NHSO₂— | 2-F | |
| 312 | n-propyl | ethyl | —CH₂—(3-COCH₃-phenyl) | H | CN₄H | 2-F | |
| 313 | n-propyl | ethyl | —CH₂—(3-NO₂-phenyl) | H | (CH₃)₂CH(CH₂)₂O₂C—NHSO₂— | 2-F | |
| 314 | n-propyl | ethyl | —CH₂—(3-NO₂-phenyl) | H | (CH₃)₂CH(CH₂)O₂C—NHSO₂— | 2-F | |
| 315 | n-propyl | ethyl | —CH₂—(3-NO₂-phenyl) | H | (CH₃)(CH₂)₂O₂C—NHSO₂— | 2-F | |

TABLE 2-continued

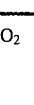

| Ex No. | R⁶ | R⁸ | Rᵃ | Rᵇ | R¹³ | R2 m.p. |
|---|---|---|---|---|---|---|
| 316 | n-propyl | ethyl | —CH₂–(3-NO₂-phenyl) | H | CN₄H | 2-F |
| 317 | n-propyl | ethyl | —CH₂–(3-SO—CH₃-phenyl) | H | (CH₃)₂CH(CH₂)₂O₂C—NHSO₂— | 2-F |
| 318 | n-propyl | ethyl | —CH₂–(3-SO—CH₃-phenyl) | H | (CH₃)₂CH(CH₂)O₂C—NHSO₂— | 2-F |
| 319 | n-propyl | ethyl | —CH₂–(3-SO—CH₃-phenyl) | H | (CH₃)(CH₂)₂O₂C—NHSO₂— | 2-F |
| 320 | n-propyl | ethyl | —CH₂–(3-SO—CH₃-phenyl) | H | CN₄H | 2-F |
| 321 | n-propyl | ethyl | —CH₂–(2-phenoxyphenyl) | H | (CH₃)₂CH(CH₂)₂O₂C—NHSO₂— | 2-F (M + H)⁺ = 741 |
| 322 | n-propyl | ethyl | —CH₂–(2-methoxyphenyl) | H | (CH₃)(CH₂)₃O₂C—NHSO₂— | 2-F (M + H)⁺ = 665.3 |
| 323 | n-propyl | ethyl | —CH(CH₃)(CH₂)₃O–phenyl | H | (CH₃)₂CH(CH₂)₂O₂C—NHSO₂— | 2-F (M + H)⁺ = 707 |

TABLE 2-continued

| Ex No. | R⁶ | R⁸ | Rᵃ | Rᵇ | R¹³ | R2 | m.p. |
|---|---|---|---|---|---|---|---|
| 324 | n-propyl | ethyl | (4-phenoxybutyl) | H | $(CH_3)(CH_2)_3O_2C-NHSO_2-$ | 2-F | $(M+H)^+ = 693$ |
| 325 | n-propyl | ethyl | $-CH_2CH_2-$(2-pyridyl) | H | $(CH_3)_2CH(CH_2)_2O_2C-NHSO_2-$ | 2-F | |
| 326 | n-propyl | ethyl | $-NH-$(2-pyrazinyl) | H | $(CH_3)_2CH(CH_2)_2O_2C-NHSO_2-$ | 2-F | |

The following examples in Table 3 can be synthesized by the procedures described in examples 1–12 and by methods familiar to one skilled in the art.

TABLE 3

| Ex No. | R⁶ | R⁸ | Rᵃ | R¹³ | R² | m.p. |
|---|---|---|---|---|---|---|
| 327 | n-propyl | ethyl | $-CH_2CH_2-$(2-benzoylphenyl) | $(CH_3)_2CH(CH_2)_2O_2C-NHSO_2-$ | 2-F | |

TABLE 3-continued (structure shown: imidazole with R⁶, R⁸, Rᵃ substituents, N-CH₂ linked to biphenyl with R², R¹³ substituents at positions 2, 3, 2', 3', 4')

| Ex No. | R⁶ | R⁸ | Rᵃ | R¹³ | R² | m.p. |
|---|---|---|---|---|---|---|
| 328 | n-propyl | ethyl | —CH₂CH₂—C(O)—(2-benzoylphenyl) | $(CH_3)_2CH(CH_2)O_2C-NHSO_2-$ | 2-F | |
| 329 | n-propyl | ethyl | —CH₂CH₂—C(O)—(2-benzoylphenyl) | $(CH_3)(CH_2)_3O_2C-NHSO_2-$ | 2-F | |
| 330 | n-propyl | ethyl | —CH₂CH₂—C(O)—(2-benzoylphenyl) | $(CH_3)(CH_2)_4O_2C-NHSO_2-$ | 2-F | |
| 331 | n-propyl | ethyl | —CH₂CH₂—(2-(phenylsulfinyl)phenyl) | $(CH_3)_2CH(CH_2)_2O_2C-NHSO_2-$ | 2-F | |
| 332 | n-propyl | ethyl | —CH₂CH₂—(2-(phenylsulfinyl)phenyl) | $(CH_3)_2CH(CH_2)O_2C-NHSO_2-$ | 2-F | |
| 333 | n-propyl | ethyl | —CH₂CH₂—(2-(phenylsulfinyl)phenyl) | $Ph-(CH_2)_2O_2C-NHSO_2-$ | 2-F | |
| 334 | n-propyl | ethyl | —CH₂CH₂—(2-(phenylsulfinyl)phenyl) | $2'-(CH_3)(CH_2)_3O_2C-NHSO_2-$ 5'-Cl | 2-F | |
| 335 | n-propyl | ethyl | —CH₂CH₂—(2-(phenylsulfinyl)phenyl) | $(CH_3)(CH_2)_3O_2C-NHSO_2-$ | 2-F | |

TABLE 3-continued

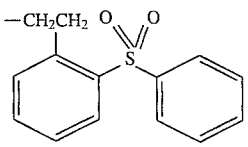

| Ex No. | R6 | R8 | Ra | R13 | R2 | m.p. |
|---|---|---|---|---|---|---|
| 336 | n-propyl | ethyl | 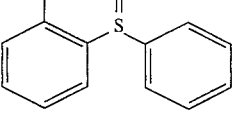 —CH$_2$CH$_2$- (2-PhSO$_2$-phenyl) | (CH$_3$)$_2$CH(CH$_2$)$_2$O$_2$C—NHSO$_2$— | 2-F | |
| 337 | n-propyl | ethyl | 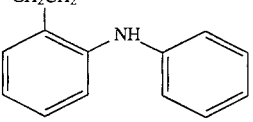 —CH$_2$CH$_2$- (2-PhS(O)-phenyl) | (CH$_3$)$_2$CH(CH$_2$)$_2$O$_2$C—NHSO$_2$— | 2-F | |
| 338 | n-propyl | ethyl | 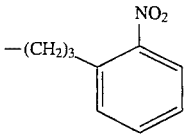 —CH$_2$CH$_2$- (2-PhNH-phenyl) | (CH$_3$)$_2$CH(CH$_2$)$_2$O$_2$C—NHSO$_2$— | 2-F | |
| 339 | n-propyl | ethyl | —(CH$_2$)$_3$- (2-NO$_2$-phenyl) | (CH$_3$)$_2$CH(CH$_2$)$_2$O$_2$C—NHSO$_2$— | 2-F | |
| 340 | n-propyl | ethyl | —(CH$_2$)$_3$- (2-CO$_2$CH$_3$-phenyl) | (CH$_3$)$_2$CH(CH$_2$)$_2$O$_2$C—NHSO$_2$— | 2-F | |
| 341 | n-propyl | ethyl | —(CH$_2$)$_3$- (2-SO$_2$CH$_3$-phenyl) | (CH$_3$)$_2$CH(CH$_2$)$_2$O$_2$C—NHSO$_2$— | 2-F | |
| 342 | n-propyl | ethyl | —(CH$_2$)$_3$- (2-OCH$_3$-phenyl) | (CH$_3$)$_2$CH(CH$_2$)$_2$O$_2$C—NHSO$_2$— | 2-F | |
| 343 | n-propyl | ethyl | —(CH$_2$)$_3$- (2-NHCOCH$_3$-phenyl) | (CH$_3$)$_2$CH(CH$_2$)$_2$O$_2$C—NHSO$_2$— | 2-F | |

TABLE 3-continued

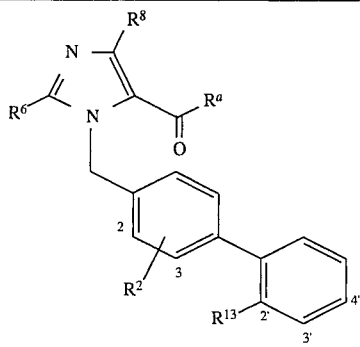

| Ex No. | R⁶ | R⁸ | Rᵃ | R¹³ | R² | m.p. |
|---|---|---|---|---|---|---|
| 345 | n-propyl | ethyl | —(CH₂)₃-(2-pyridin-2-yl-phenyl) | $(CH_3)_2CH(CH_2)_2O_2C-NHSO_2-$ | 2-F | |
| 346 | n-propyl | ethyl | —(CH₂)₃-(2-pyrimidin-2-yl-phenyl) | $(CH_3)_2CH(CH_2)_2O_2C-NHSO_2-$ | 2-F | |
| 347 | n-propyl | ethyl | —(CH₂)₄-(2-NO₂-phenyl) | $(CH_3)_2CH(CH_2)_2O_2C-NHSO_2-$ | 2-F | |
| 348 | n-propyl | ethyl | —(CH₂)₆-(2-CO₂—CH(CH₃)₂-phenyl) | $(CH_3)_2CH(CH_2)_2O_2C-NHSO_2-$ | 2-F | |
| 349 | n-propyl | ethyl | —(CH₂)₅-(2-(1-methylimidazol-2-yl)-phenyl) | $(CH_3)_2CH(CH_2)_2O_2C-NHSO_2-$ | 2-F | |
| 350 | n-propyl | ethyl | —(CH₂)₄-(2-CO₂CH₃-phenyl) | $(CH_3)_2CH(CH_2)_2O_2C-NHSO_2-$ | 2-F | |

TABLE 3-continued

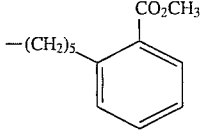

| Ex No. | R⁶ | R⁸ | Rᵃ | R¹³ | R² | m.p. |
|---|---|---|---|---|---|---|
| 351 | n-propyl | ethyl | 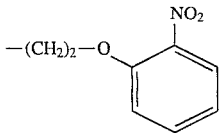 —(CH₂)₅— (2-CO₂CH₃-phenyl) | $(CH_3)_2CH(CH_2)_2O_2C-NHSO_2-$ | 2-F | |
| 352 | n-propyl | ethyl | —(CH₂)₂—O— (2-NO₂-phenyl) | $(CH_3)_2CH(CH_2)_2O_2C-NHSO_2-$ | 2-F | |
| 353 | n-propyl | ethyl | —(CH₂)₂—O— (2-CO₂CH₃-phenyl) | $(CH_3)_2CH(CH_2)_2O_2C-NHSO_2-$ | 2-F | |
| 354 | n-propyl | ethyl | —(CH₂)₂—O—CH₂— (2-SO₂CH₃-phenyl) | $(CH_3)_2CH(CH_2)_2O_2C-NHSO_2-$ | 2-F | |
| 355 | n-propyl | ethyl | —(CH₂)₂—S— (2-OCH₃-phenyl) | $(CH_3)_2CH(CH_2)_2O_2C-NHSO_2-$ | 2-F | |
| 356 | n-propyl | ethyl | —(CH₂)₂—S—CH₂— (2-NHCOCH₃-phenyl) | $(CH_3)_2CH(CH_2)_2C-NHSO_2-$ | 2-F | |
| 357 | n-propyl | ethyl | —(CH₂)₂—NH—CH₂CH₂— (2-(2-pyridyl)-phenyl) | $(CH_3)_2CH(CH_2)_2O_2C-NHSO_2-$ | 2-F | |

TABLE 3-continued

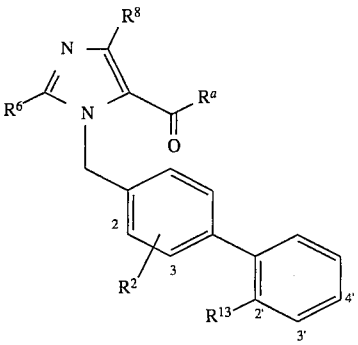

| Ex No. | R⁶ | R⁸ | Rᵃ | R¹³ | R² | m.p. |
|---|---|---|---|---|---|---|
| 358 | n-propyl | ethyl | —(CH₂)₂—N(CH₂)—CH₂CH₂CH₂— (with 2-pyrimidinyl-phenyl) | (CH₃)₂CH(CH₂)₂O₂C—NHSO₂— | 2-F | |
| 359 | n-propyl | ethyl | —(CH₂)₄— (2-NO₂-phenyl) | (CH₃)₂CH(CH₂)₂O₂C—NHSO₂— | 2-F | |
| 360 | n-propyl | ethyl | —(CH₂)₅— (2-CO₂—CH(CH₃)₂-phenyl) | (CH₃)₂CH(CH₂)₂O₂C—NHSO₂— | 2-F | |
| 361 | n-propyl | ethyl | —(CH₂)₅— (2-CO₂CH₃-phenyl) | (CH₃)₂CH(CH₂)₂O₂C—NHSO₂— | 2-F | |
| 362 | n-propyl | ethyl | —CH₂CH₂— (2-benzyl-phenyl) | (CH₃)₂CH(CH₂)₂O₂C—NHSO₂— | 2-F | |
| 363 | n-propyl | ethyl | —CH₂CH₂— (2-(2-CH₃—CO-phenethyl)-phenyl) | (CH₃)₂CH(CH₂)₂O₂C—NHSO₂— | 2-F | |
| 364 | n-propyl | ethyl | —CH₂CH₂— (2-phenoxy-phenyl) | (CH₃)₂CH(CH₂)₂O₂C—NHSO₂— | 2-F | |

TABLE 3-continued

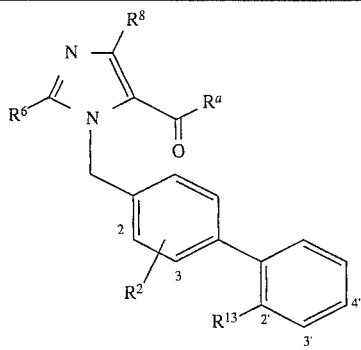

| Ex No. | R⁶ | R⁸ | Rᵃ | R¹³ | R² | m.p. |
|---|---|---|---|---|---|---|
| 365 | n-propyl (M + H)⁺ | ethyl | —CH₂CH₂— (2-isobutoxyphenyl) | (CH₃)(CH₂)₃O₂C—NHSO₂— M + H⁺ = 720.3 | 2-F | |
| 366 | n-propyl | ethyl | —CH₂CH₂— (2-methoxyphenyl) | (CH₃)₂CH(CH₂)₂O₂C—NHSO₂— | 2-F | |
| 367 | n-propyl | ethyl | —CH₂CH₂— (3-phenoxyphenyl) | (CH₃)₂CH(CH₂)₂O₂C—NHSO₂— | 2-F | |
| 368 | n-propyl | ethyl | —CH₂CH₂— (3-benzoylphenyl) | (CH₃)₂CH(CH₂)₂O₂C—NHSO₂— | 2-F | |
| 369 | n-propyl | ethyl | —CH₂CH₂— (3-phenylsulfinylphenyl) | (CH₃)₂CH(CH₂)₂O₂C—NHSO₂— | 2-F | |
| 370 | n-propyl | ethyl | —CH₂CH₂— (3-phenylsulfonylphenyl) | (CH₃)₂CH(CH₂)₂O₂C—NHSO₂— | 2-F | |
| 371 | n-propyl | ethyl | —CH₂CH₂— (3-phenylthiophenyl) | (CH₃)₂CH(CH₂)₂O₂C—NHSO₂— | 2-F | |

TABLE 3-continued

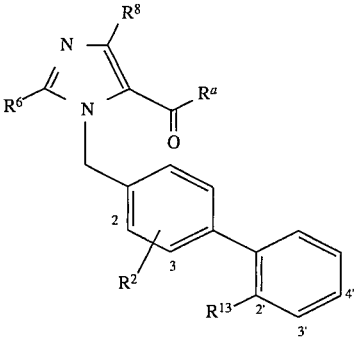

| Ex No. | R⁶ | R⁸ | Rᵃ | R¹³ | R² | m.p. |
|---|---|---|---|---|---|---|
| 372 | n-propyl | ethyl | —CH₂CH₂—N(Ph)(CO—CH₂CH₂CH₃) | CH₃(CH₂)₃OC—NHSO₂— | 2-F | |
| 373 | n-propyl | ethyl | —CH₂CH₂—N(Ph)(CO—Ph) | (CH₃)₂CH(CH₂)₂OC—NHSO₂— | 2-F | |
| 374 | n-propyl | ethyl | —CH₂CH₂—N(Ph)(CO—Ph) | CH₃(CH₂)₃O₂C—NHSO₂— | 2-F | |
| 375 | n-propyl | ethyl | —CH₂CH₂—N(Ph)(CO—Ph) | CH₃(CH₂)₂OC—NHSO₂— | 2-F | |
| 376 | n-propyl | ethyl | —CH₂CH₂—N(CH₂CH₂CH₃)(CO—CH₂Ph) | CH₃(CH₂)₃OC—NHSO₂— | 2-F | |
| 377 | n-propyl | ethyl | —CH₂CH₂—N(CH₂CH₂CH₃)(CO—CH₂CH(CH₃)₂) | (CH₃)₂CH(CH₂)₂OC—NHSO₂— | 2-F | |
| 378 | n-propyl | ethyl | —CH₂CH₂—N(CH₂CH₂CH₃)(CO—Ph) | CH₃(CH₂)₃OC—NHSO₂— | 2-F | |
| 379 | n-propyl | ethyl | —CH₂CH₂—N(Ph)(CO—CH₂CH(CH₃)₂) | (CH₃)₂CH(CH₂)₂O₂C—NHSO₂— | 2-F | |
| 380 | n-propyl | ethyl | —CH₂CH₂—N(Ph)(CHO) | (CH₃)₂CH(CH₂)₂OC—NHSO₂— | 2-F | |
| 381 | n-Propyl | ethyl | —CH₂CH₂—N(CH₂—Ph)(CHO) | (CH₃)₂CH(CH₂)₂OC—NHSO₂— | 2-F | |

TABLE 3-continued

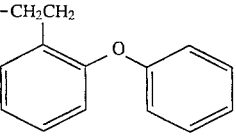

| Ex No. | R⁶ | R⁸ | Rᵃ | R¹³ | R² | m.p. |
|---|---|---|---|---|---|---|
| 382 | n-propyl (M + H)⁺ = 726.5 | ethyl | —CH₂CH₂— 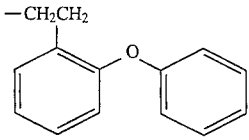 | (CH₃)(CH₂)₃O₂C—NHSO₂— | 2-F | |
| 383 | n-propyl (M + H)⁺ = 740.3 | ethyl | —CH₂CH₂— 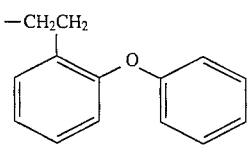 | (CH₃)₂CH(CH₂)₂O₂C—NHSO₂— | 2-F | |
| 384 | n-propyl | ethyl | —CH₂CH₂— 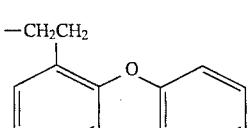 | (CH₃)₂CH(CH₂)O₂C—NHSO₂— (M + H)⁺ = 726.2 | 2-F | |
| 385 | n-propyl (M + H)⁺ = 712.3 | ethyl | —CH₂CH₂— 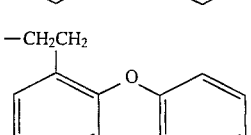 | (CH₃)(CH₂)₂O₂C—NHSO₂— | 2-F | |
| 386 | ethyl | ethyl | —CH₂CH₂— 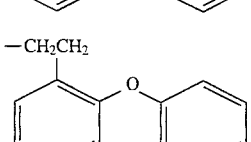 | (CH₃)(CH₂)₂O₂C—NHSO₂— | 2-F | |
| 387 | n-butyl | Cl | —CH₂CH₂— 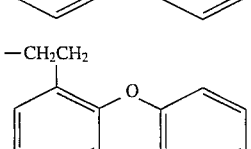 | (CH₃)(CH₂)₂O₂C—NHSO₂— | 2-F | |
| 388 | n-propyl | Br | —CH₂CH₂— 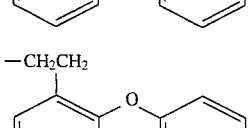 | (CH₃)(CH₂)₂O₂C—NHSO₂— | 2-F | |
| 389 | n-propyl | NO₂ | —CH₂CH₂— | (CH₃)(CH₂)₂O₂C—NHSO₂— | 2-F | |

TABLE 3-continued

| Ex No. | R6 | R8 | Ra | R13 | R2 | m.p. |
|---|---|---|---|---|---|---|
| 390 | n-propyl | CF2CF3 | —CH2CH2—(2-phenoxyphenyl) | (CH3)(CH2)2O2C—NHSO2— | 2-F | |
| 391 | n-propyl | CH3 | —CH2CH2—(2-phenoxyphenyl) | (CH3)(CH2)2O2C—NHSO2— | 2-F | |
| 392 | n-propyl | ethyl | —CH2CH2—N(CO—Ph)(CH2CH2CH2CH3) | (CH3)(CH2)3OC—NHSO2— | 2-F | |
| 393 | n-propyl | ethyl | —CH2CH2—N(CO—CH2CH2CH3)(CH2CH2CH3) | (CH3)(CH2)3OC—NHSO2— | 2-F | |
| 394 | n-propyl | ethyl | —CH2CH2—N(CO—CH2CH2CH2CH2)(CH2CH2CH3) | (CH3)(CH2)3OC—NHSO2— | 2-F | |
| 395 | n-propyl | ethyl | —CH2CH2—N(CO—Ph)(Ph) | —CN4H | 2-F | |
| 396 | n-propyl | ethyl | —CH2CH2—N(CO—CH2CH2CH3)(Ph) | —CN4H | 2-F | |
| 397 | n-propyl | ethyl | —CH2CH2—N(pyridin-2-yl)C(O)(pyridin-3-yl) | (CH3)(CH2)3OC—NHSO2— | 2-F | |

TABLE 3-continued

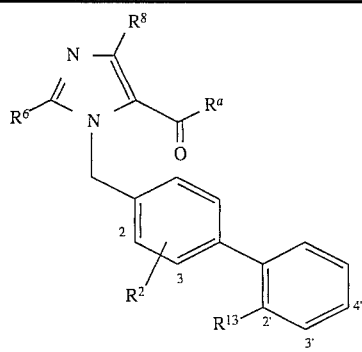

| Ex No. | $R^6$ | $R^8$ | $R^a$ | $R^{13}$ | $R^2$ | m.p. |
|---|---|---|---|---|---|---|
| 398 | n-propyl | ethyl | 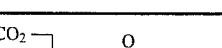 | $(CH_3)(CH_2)_3OC-NHSO_2-$ | 2-F | |

The following examples in Table 4 can be synthesized by the procedures described in examples 1–12 and by the synthetic schemes described herein and by methods familiar to one skilled in the art.

TABLE 4

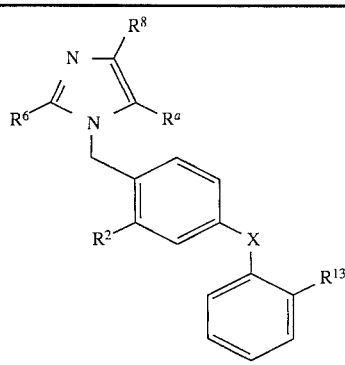

| Ex No. | $R^6$ | $R^8$ | $R^a$ | $R^{13}$ | $R^2$ | X | m.p. |
|---|---|---|---|---|---|---|---|
| 399 | n-propyl | Cl | $-NH-CO_2-$ 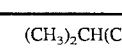 | $(CH_3)_2CH(CH_2)_2O_2C-NHSO_2-$ | 2-F | — | |
| 400 | n-propyl | Br | $-NH-CO-NH-$  | $(CH_3)_2CH(CH_2)_2O_2C-NHSO_2-$ | 2-F | — | |

TABLE 4-continued

| Ex m.p. No. | R⁶ | R⁸ | Rᵃ | R¹³ | R² | X |
|---|---|---|---|---|---|---|
| 401 | n-propyl | Br | —NH—CO₂—CH₂—C(O)—C(=N(Ph)₂) | $(CH_3)_2CH(CH_2)_2O_2C-NHSO_2-$ | 2-F | — |
| 402 | n-propyl | Cl | —NH—CO—NH—CH₂—C(O)—C(=N(Ph)₂) | $(CH_3)_2CH(CH_2)_2O_2C-NHSO_2-$ | 2-F | — |
| 403 | n-propyl | Cl | —NH—CO—(2-(phenylsulfinyl)phenyl) | $(CH_3)_2CH(CH_2)_2O_2C-NHSO_2-$ | 2-F | — |
| 404 | n-propyl | Cl | —NH—CO—CH₂—C(O)—C(=N(Ph)₂) | $(CH_3)_2CH(CH_2)_2O_2C-NHSO_2-$ | 2-F | — |
| 405 | n-propyl | Cl | —CH₂—SO—CH₂—(2-(phenylsulfinyl)phenyl) | $(CH_3)_2CH(CH_2)_2O_2C-NHSO_2-$ | 2-F | — |
| 406 | n-propyl | Cl | —CH₂—O—CH₂—(2-(phenylsulfinyl)phenyl) | $(CH_3)_2CH(CH_2)_2O_2C-NHSO_2-$ | 2-F | — |
| 407 | n-propyl | Cl | —CH₂—NH—CH₂—(2-(phenylsulfinyl)phenyl) | $(CH_3)_2CH(CH_2)_2O_2C-NHSO_2-$ | 2-F | — |
| 408 | n-propyl | ethyl | —CO₂—CH₂—(2-(phenylsulfinyl)phenyl) | —CN₄H | 2-F | —CO—NH— |

TABLE 4-continued
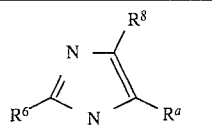
| Ex. m.p. No. | $R^6$ | $R^8$ | $R^a$ | $R^{13}$ | $R^2$ | X |
|---|---|---|---|---|---|---|
| 409 | n-propyl | ethyl | —CO—NH—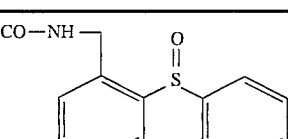 | —CN$_4$H | 2-F | —O— |
| 410 | n-propyl | ethyl | —CO$_2$—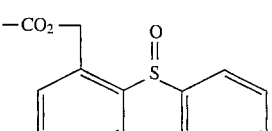 | $(CH_3)_2CH(CH_2)_2O_2C$—NHSO$_2$— | 2-F | —S— |
| 411 | n-propyl | ethyl | —CO$_2$—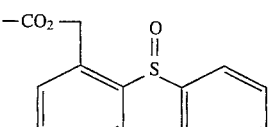 | $(CH_3)_2CH(CH_2)_2O_2C$—NHSO$_2$— | 2-F | CH$_2$— |
| 412 | n-propyl | ethyl | —CO$_2$—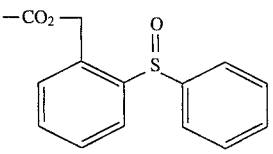 | $(CH_3)_2CH(CH_2)_2O_2C$—NHSO$_2$— | 2-F | —CO— |
| 413 | n-propyl | ethyl | —CO$_2$—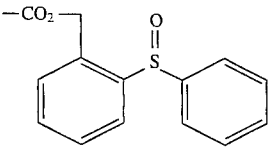 | $(CH_3)_2CH(CH_2)_2O_2C$—NHSO$_2$— | 2-F | —NMe— |
| 414 | n-propyl | ethyl | —CO$_2$—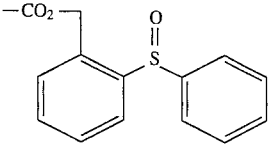 | $(CH_3)_2CH(CH_2)_2O_2C$—NHSO$_2$— | 2-F | —SO$_2$— |
| 415 | n-propyl | ethyl | —CO$_2$— | $(CH_3)_2CH(CH_2)_2O_2C$—NHSO$_2$— | 2-F | —SO— |

TABLE 4-continued

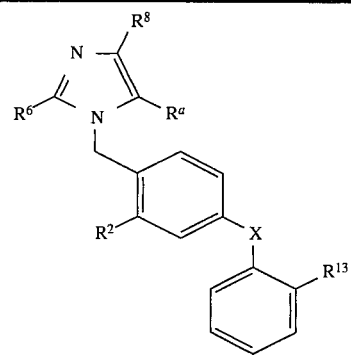

| Ex m.p. No. | R⁶ | R⁸ | Rᵃ | R¹³ | R² | X |
|---|---|---|---|---|---|---|
| 416 NHCO— | n-propyl | ethyl | —CO₂— [2-(phenylsulfinyl)benzyl] | $(CH_3)_2CH(CH_2)_2O_2C-NHSO_2-$ | 2-F | — |
| 417 OCH₂— | n-propyl | ethyl | —CO₂— [2-(phenylsulfinyl)benzyl] | $(CH_3)_2CH(CH_2)_2O_2C-NHSO_2-$ | 2-F | — |
| 418 CH₂O— | n-propyl | ethyl | —CO₂— [2-(phenylsulfinyl)benzyl] | $(CH_3)_2CH(CH_2)_2O_2C-NHSO_2-$ | 2-F | — |
| 419 SCH₂— | n-propyl | ethyl | —CO₂— [2-(phenylsulfinyl)benzyl] | $(CH_3)_2CH(CH_2)_2O_2C-NHSO_2-$ | 2-F | — |
| 420 CH₂S— | n-propyl | ethyl | —CO₂— [2-(phenylsulfinyl)benzyl] | $(CH_3)_2CH(CH_2)_2O_2C-NHSO_2-$ | 2-F | — |
| 421 NMeCH₂— | n-propyl | ethyl | —CO₂— [2-(phenylsulfinyl)benzyl] | $(CH_3)_2CH(CH_2)_2O_2C-NHSO_2-$ | 2-F | — |
| 422 NHSO₂— | n-propyl | ethyl | —CO₂— [2-(phenylsulfinyl)benzyl] | $(CH_3)_2CH(CH_2)_2O_2C-NHSO_2-$ | 2-F | — |

TABLE 4-continued

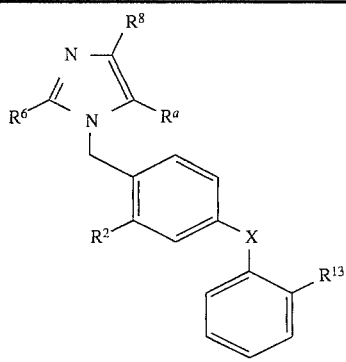

| Ex. No. m.p. | R⁶ | R⁸ | Rᵃ | R¹³ | R² | X |
|---|---|---|---|---|---|---|
| 423 SO₂NH— | n-propyl | ethyl | —CO₂—[2-(phenylsulfinyl)benzyl] | $(CH_3)_2CH(CH_2)_2O_2C-NHSO_2-$ | 2-F | — |
| 424 CH=CH— | n-propyl | ethyl | —CO₂—[2-(phenylsulfinyl)benzyl] | $(CH_3)_2CH(CH_2)_2O_2C-NHSO_2-$ | 2-F | — |
| 425 CH(OPh)— | n-propyl | ethyl | —CO₂—[2-(phenylsulfinyl)benzyl] | $(CH_3)_2CH(CH_2)_2O_2C-NHSO_2-$ | 2-F | — |
| 426 [gem-dimethylcyclopropyl] | n-propyl | ethyl | —CO₂—[2-(phenylsulfinyl)benzyl] | $(CH_3)_2CH(CH_2)_2O_2C-NHSO_2-$ | 2-F | — |
| 427 | n-propyl | ethyl | —CO₂—[2-benzoylbenzyl] | $(CH_3)_2CH(CH_2)_2O_2C-NHSO_2-$ | 2-F | —O— |
| 428 | n-propyl | ethyl | —CO₂—[2-benzoylbenzyl] | $(CH_3)_2CH(CH_2)_2O_2C-NHSO_2-$ | 2-F | —CO— |

TABLE 4-continued
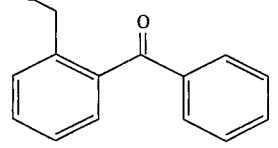
| Ex m.p. No. | $R^6$ | $R^8$ | $R^a$ | $R^{13}$ | $R^2$ | X |
|---|---|---|---|---|---|---|
| 429 | n-propyl | ethyl | —CO$_2$— 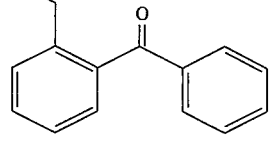 | $(CH_3)_2CH(CH_2)_2O_2C$—NHSO$_2$— | 2-F | — |
| C(CH$_3$)$_2$— | | | | | | |
| 430 | n-propyl | ethyl | —CH$_2$CO$_2$— 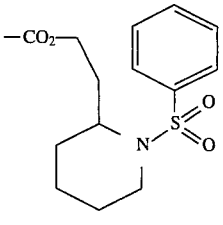 | $(CH_3)_2CH(CH_2)_2O_2C$—NHSO$_2$— | 2-F | — |
| 431 | n-propyl | ethyl | —CO$_2$— 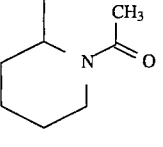 | $(CH_3)_2CH(CH_2)_2O_2C$—NHSO$_2$— | 2-F | — |
| 432 | n-propyl | ethyl | —CO$_2$— 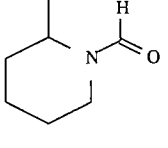 | $(CH_3)_2CH(CH_2)_2O_2C$—NHSO$_2$— | 2-F | — |
| 433 | n-propyl | ethyl | —CO$_2$— 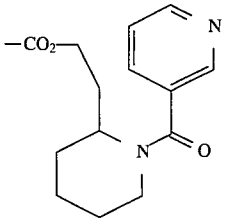 | $(CH_3)_2CH(CH_2)_2O_2C$—NHSO$_2$— | 2-F | — |
| 434 | n-propyl | ethyl | —CO$_2$—  | $(CH_3)_2CH(CH_2)_2O_2C$—NHSO$_2$— | 2-F | — |

TABLE 4-continued

[Structure: core scaffold with R⁶, R⁸, Rᵃ, R², R¹³, X substituents on imidazole/benzyl/diphenyl ether system]

| Ex m.p. No. | R⁶ | R⁸ | Rᵃ | R¹³ | R² | X |
|---|---|---|---|---|---|---|
| 435 | n-propyl | ethyl | —CO₂—[CH₂CH₂-piperidinyl-N-C(=O)-O-Ph] | (CH₃)₂CH(CH₂)₂O₂C—NHSO₂— | 2-F | — |
| 436 | n-propyl | ethyl | —CO₂—[CH₂CH₂-piperidinyl-N-C(=O)-NH-Ph] | (CH₃)₂CH(CH₂)₂O₂C—NHSO₂— | 2-F | — |
| 437 | n-propyl | ethyl | —CO₂—[CH₂CH₂-piperidinyl-N-COCF₂CF₂CF₃] | (CH₃)₂CH(CH₂)₂O₂C—NHSO₂— | 2-F | — |
| 438 | n-propyl | ethyl | —CO₂—CH₂—CH=CH—[piperidinyl-N-C(=O)-Ph] | (CH₃)₂CH(CH₂)₂O₂C—NHSO₂— | 2-F | — |
| 439 | n-propyl | ethyl | —CO₂—CH₂—CH=CH—[piperidinyl-N-SO₂CF₃] | (CH₃)₂CH(CH₂)₂O₂C—NHSO₂— | 2-F | — |
| 440 | n-propyl | ethyl | —CO₂(CH₂)₂NHCOPh | (CH₃)₂CH(CH₂)₂O₂C—NHSO₂— | 2-F | — |
| 441 | n-propyl | ethyl | —CO₂(CH₂)₃NHCOPh | (CH₃)₂CH(CH₂)₂O₂C—NHSO₂— | 2-F | — |
| 442 | n-propyl | ethyl | —CO₂(CH₂)₄NHCOPh | (CH₃)₂CH(CH₂)₂O₂C—NHSO₂— | 2-F | — |
| 443 | n-propyl | ethyl | —CO₂CH₂CONHPh | (CH₃)₂CH(CH₂)₂O₂C—NHSO₂— | 2-F | — |
| 444 | n-propyl | ethyl | —CO₂(CH₂)₂CONHPh | (CH₃)₂CH(CH₂)₂O₂C—NHSO₂— | 2-F | — |

TABLE 4-continued

| Ex m.p. No. | R⁶ | R⁸ | Rᵃ | R¹³ | R² | X |
|---|---|---|---|---|---|---|
| 445 | n-propyl | ethyl | —CO₂(CH₂)₃CONHPh | (CH₃)₂CH(CH₂)₂O₂C—NHSO₂— | 2-F | — |
| 446 | n-propyl | ethyl | —CO₂(CH₂)₄CONHPh | (CH₃)₂CH(CH₂)₂O₂C—NHSO₂— | 2-F | — |
| 447 | n-propyl | ethyl | —CO₂(CH₂)₂NHCOPh | (CH₃)₂CH(CH₂)₂O₂C—NHSO₂— | H | — |
| 448 | n-propyl | ethyl | —CO₂(CH₂)₃NHCOPh | (CH₃)₂CH(CH₂)₂O₂C—NHSO₂— | H | — |
| 449 | n-propyl | ethyl | —CO₂(CH₂)₄NHCOPh | (CH₃)₂CH(CH₂)₂O₂C—NHSO₂— | H | — |
| 450 | n-propyl | ethyl | —CO₂CH₂CONHPh | (CH₃)₂CH(CH₂)₂O₂C—NHSO₂— | H | — |
| 451 | n-propyl | ethyl | —CO₂(CH₂)₂CONHPh | (CH₃)₂CH(CH₂)₂O₂C—NHSO₂— | H | — |
| 452 | n-propyl | ethyl | —CO₂(CH₂)₃CONHPh | (CH₃)₂CH(CH₂)₂O₂C—NHSO₂— | H | — |
| 453 | n-propyl | ethyl | —CO₂(CH₂)₄CONHPh | (CH₃)₂CH(CH₂)₂O₂C—NHSO₂— | H | — |
| 454 | n-propyl | ethyl | —CO₂(CH₂)₂NHCOPh | 2'-(CH₃)₂CH(CH₂)₂O₂C—NHSO₂— | 2-Cl | — |
| 455 | n-propyl | ethyl | —CO₂(CH₂)₃NHCOPh | 2'-(CH₃)₂CH(CH₂)₂O₂C—NHSO₂— | 2-Cl | — |
| 456 | n-propyl | ethyl | —CO₂(CH₂)₄NHCOPh | 2'-(CH₃)₂CH(CH₂)₂O₂C—NHSO₂— | 2-Cl | — |
| 457 | n-propyl | ethyl | —CO₂CH₂CONHPh | 2'-(CH₃)₂CH(CH₂)₂O₂C—NHSO₂— | 2-Cl | — |
| 458 | n-propyl | ethyl | —CO₂(CH₂)₂CONHPh | 2'-(CH₃)₂CH(CH₂)₂O₂C—NHSO₂— | 2-Cl | — |
| 459 | n-propyl | ethyl | —CO₂(CH₂)₃CONHPh | 2'-(CH₃)₂CH(CH₂)₂O₂C—NHSO₂— | 2-Cl | — |
| 460 | n-propyl | ethyl | —CO₂(CH₂)₄CONHPh | 2'-(CH₃)₂CH(CH₂)₂O₂C—NHSO₂— | 2-Cl | — |
| 461 | n-propyl | ethyl | —CO₂(CH₂)₂NHCOPh | 2'-(CH₃)₂CH(CH₂)₂O₂C—NHSO₂— | 2-Br | — |
| 462 | n-propyl | ethyl | —CO₂(CH₂)₃NHCOPh | 2'-(CH₃)₂CH(CH₂)₂O₂C—NHSO₂— | 2-Br | — |
| 463 | n-propyl | ethyl | —CO₂(CH₂)₄NHCOPh | 2'-(CH₃)₂CH(CH₂)₂O₂C—NHSO₂— | 2-Br | — |
| 464 | n-propyl | ethyl | —CO₂CH₂CONHPh | 2'-(CH₃)₂CH(CH₂)₂O₂C—NHSO₂— | 2-Br | — |
| 465 | n-propyl | ethyl | —CO₂(CH₂)₂CONHPh | 2'-(CH₃)₂CH(CH₂)₂O₂C—NHSO₂— | 2-Br | — |
| 466 | n-propyl | ethyl | —CO₂(CH₂)₃CONHPh | 2'-(CH₃)₂CH(CH₂)₂O₂C—NHSO₂— | 2-Br | — |
| 467 | n-propyl | ethyl | —CO₂(CH₂)₄CONHPh | 2'-(CH₃)₂CH(CH₂)₂O₂C—NHSO₂— | 2-Br | — |
| 468 | n-propyl | cyclpropyl | —CH₂-(2-benzoylphenyl) | 2'-(CH₃)₂CH(CH₂)₂O₂C—NHSO₂— | 2-Cl | — |
| 469 | n-propyl | Cl | —CH₂O-C(O)-(2-benzoylphenyl) | (CH₃)₂CH(CH₂)₂O₂C—NHSO₂— | 2-F | — |
| 470 | n-propyl | Cl | —CH₂NH-C(O)-(2-benzoylphenyl) | (CH₃)₂CH(CH₂)₂O₂C—NHSO₂— | 2-F | — |

TABLE 4-continued
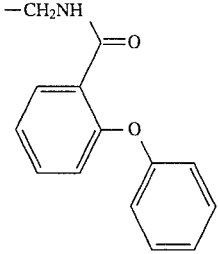
| Ex m.p. No. | R⁶ | R⁸ | Rᵃ | R¹³ | R² | X |
|---|---|---|---|---|---|---|
| 471 | n-propyl | Cl | —CH₂NH—C(=O)—(2-phenoxyphenyl) | (CH₃)₂CH(CH₂)₂O₂C—NHSO₂— | 2-F | — |
| 472 | n-propyl | Cl | —CH₂NH—C(=O)—N(CH₂Ph)₂ | (CH₃)₂CH(CH₂)₂O₂C—NHSO₂— | 2-F | — |
| 473 | n-propyl | Cl | —CH₂NH—C(=O)—N(Ph)₂ | (CH₃)₂CH(CH₂)₂O₂C—NHSO₂— | 2-F | — |
| 474 | n-propyl | Cl | —CH₂O—C(=O)—(2-benzoylphenyl) | CH₃(CH₂)₃O₂C—NHSO₂— | 2-F | — |
| 475 | n-propyl | Cl | —CH₂NH—C(=O)—(2-benzoylphenyl) | CH₃(CH₂)₃O₂C—NHSO₂— | 2-F | — |

TABLE 4-continued
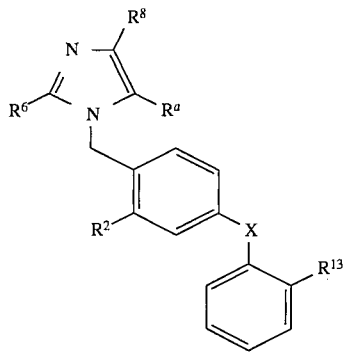
| Ex. No. | m.p. | R⁶ | R⁸ | Rᵃ | R¹³ | R² | X |
|---|---|---|---|---|---|---|---|
| 476 | | n-propyl | Cl | —CH₂NH—C(=O)—(2-phenoxyphenyl) | CH₃(CH₂)₃O₂C—NHSO₂— | 2-F | — |
| 477 | | n-propyl | Cl | —CH₂NH—C(=O)—N(CH₂Ph)₂ | CH₃(CH₂)₃O₂C—NHSO₂— | 2-F | — |
| 478 | | n-propyl | Cl | —CH₂NH—C(=O)—N(Ph)₂ | CH₃(CH₂)₃O₂C—NHSO₂— | 2-F | — |
| 479 | | n-propyl | Cl | —CH₂O—C(=O)—(2-benzoylphenyl) | (CH₃)₂CH(CH₂)₂O₂C—NHSO₂— | 2-F | — |
| 480 | | n-propyl | Cl | —CH₂NH—C(=O)—(2-benzoylphenyl) | (CH₃)₂CH(CH₂)₂O₂C—NHSO₂— | 2-F | — |

TABLE 4-continued
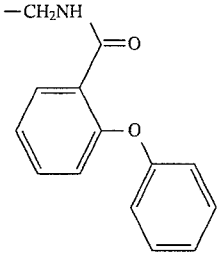
| Ex m.p. No. | $R^6$ | $R^8$ | $R^a$ | $R^{13}$ | $R^2$ | X |
|---|---|---|---|---|---|---|
| 481 | n-propyl | Cl | 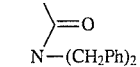 | $(CH_3)_2CH(CH_2)_2O_2C-NHSO_2-$ | 2-F | — |
| 482 | n-propyl | Cl | —CH$_2$NH—C(=O)—N—(CH$_2$Ph)$_2$ | $(CH_3)_2CH(CH_2)_2O_2C-NHSO_2-$ | 2-F | — |
| 483 | n-propyl | Cl | —CH$_2$NH—C(=O)—N—(Ph)$_2$ | $(CH_3)_2CH(CH_2)_2O_2C-NHSO_2-$ | 2-F | — |
| 484 | n-propyl | Cl | 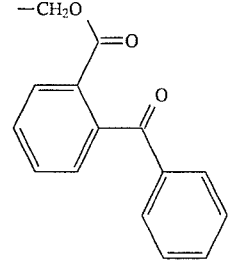 | $CH_3(CH_2)_3O_2C-NHSO_2-$ | 2-F | — |
| 485 | n-propyl | Cl | 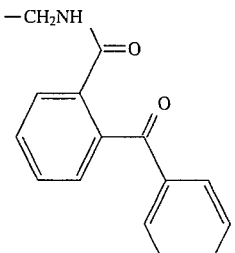 | $CH_3(CH_2)_3O_2C-NHSO_2-$ | 2-F | — |

TABLE 4-continued

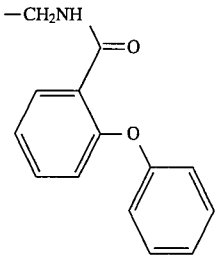

| Ex m.p. No. | R⁶ | R⁸ | Rᵃ | R¹³ | R² | X |
|---|---|---|---|---|---|---|
| 486 | n-propyl | Cl | 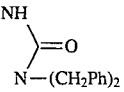 —CH₂NH, =O, (phenoxyphenyl) | $CH_3(CH_2)_3O_2C-NHSO_2-$ | 2-F | — |
| 487 | n-propyl | Cl | —CH₂NH, =O, N—(CH₂Ph)₂ | $CH_3(CH_2)_3O_2C-NHSO_2-$ | 2-F | — |
| 488 | n-propyl | Cl | —CH₂NH, =O, N—(Ph)₂ | $CH_3(CH_2)_3O_2C-NHSO_2-$ | 2-F | — |

EXAMPLE 489

Preparation of 1-(2'-((i-amyloxycarbonyl-amino)sulfonyl)-3-fluoro-(1,1'-biphenyl) '4-yl)methyl)-5-[2-(N-benzoyl-N-phenylamino)ethylcarbonyl-4-ethyl-2-propyl-1H-imidazole Part A: Preparation of 1-(2-fluoro-4-bromobenzyl)-4-ethyl-2-propyl-1H-imidazole-5-carboxaldehyde

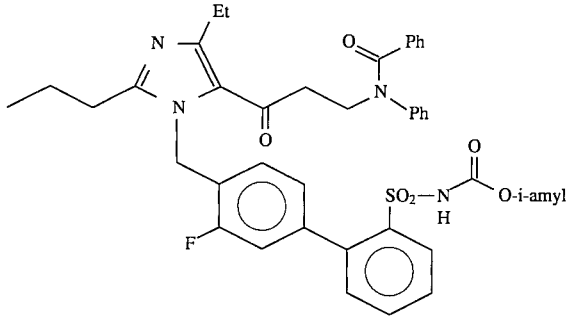

this compound was prepared following the same method described in part A of Example 3 (60% yield). ¹HNMR (300 MHz, CDCl₃): δ0.95 (t, 3H, CH₃), 1.32 (t, 3H, CH₃), 1.70 (m, 2H, CH₂), 2.60 (m, 2H, CH₂), 2.85 (q, H, CH₂), 5.52 (s, 2H, ArCH₂), 6.60 (t, 1H, ArH), 7.18 (d, 1H, ArH), 7.25 (d, 1H, ArH), 9.75 (s, 1H, CHO).

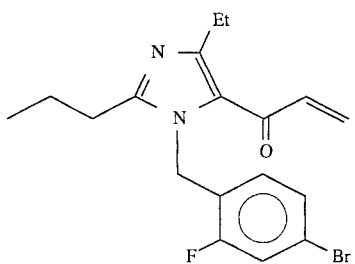

Part B: Preparation of 1-(2-fluoro-4-bromobenzyl)-4-ethyl-2-propyl- 1H-imidazole-5-vinyl ketone To a solution of 1-(2-fluoro-4-bromobenzyl)-4-ethyl-2-propyl- 1H-imidazole-5-carboxaldehyde (21.58 g, 61.1 mmol) in THF (150 mL) was added vinylmagnesium bromide (92 mL of 1.0M solution in THF, 92.0 mmol) over 30 min. The reaction mixture was stirred at room temperature under $N_2$ for 1 h. It was then quenched with 100 mL of 1N aqueous HCl. The mixture was extracted with $CH_2Cl_2$, the organic solution was washed with $H_2O$ and brine, dried over $MgSO_4$ and concentrated to an orange oil. The resulting oil was dissolved in $CH_2Cl_2$ and manganese (IV) oxide (79.97 g, 920 mmol) was added. The resulting mixture was stirred at room temperature under $N_2$ overnight. The mixture was filtered through celite and washed with $CH_2Cl_2$. The $CH_2Cl_2$ solution was concentrated and chromatographed on silica gel with 1/1 ethyl acetate/hexane to yield 20.4 g yellow oil. $^1$HNMR (300 MHz, $CDCl_3$): δ0.95 (t, 3H, $CH_3$), 1.30 (t, 3H, $CH_3$), 1.70 (m, 2H, $CH_2$), 2.60 (m, 2H, $CH_2$), 2.88 (q, 2H, $CH_2$), 5.48 (s, 2H, $ArCH_2$), 5.80 (d, 1H, CH=), 6.30 & 6.62 (d, 2H, =$CH_2$), 6.90 (t, 1H, ArH), 7.15 (d, 1H, ArH), 7.25 (d, 1H, ArH).

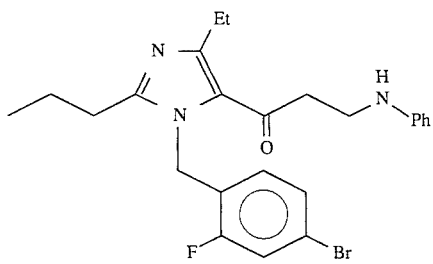

Part C: Preparation of 1-(2-fluoro-4-bromobenzyl)-5-[2-(N-phenylamino)ethylcarbonyl-4-ethyl-2-propyl-1H-imidazole To a solution of 1-(2-fluoro-4-bromobenzyl)-4-ethyl-2-propyl- 1H-imidazole-5-vinyl ketone (2.06 g, 5.41 mmol) and triethylamine (2.50 mL, 16.5 mmol) in THF (100 mL) was added aniline (1.50 mL, 16.5 mmol). The mixture was refluxed under $N_2$ for 7 h. The solvent was removed in vacuo. The residue was dissolved in EtOAc, and washed with $H_2O$ and brine. The organic solution was then dried over $MgSO_4$ and concentrated. the crude mixture was chromatographed on silica gel with 30–50% EtOAc/hexane to yield 2.03 g off-white solid (83%). $^1$HNMR (300 MHz, $CDCl_3$): δ0.97 (t, 3H, $CH_3$), 1.32 (t, 3H, $CH_3$), 1.68 (m, 2H, $CH_2$), 2.58 (t, 2H, $CH_2$), 2.90 (q, 2H, $CH_2$), 3.04 (t, 2H, $CH_2$), 3.49 (t, 2H, $CH_2$), 3.92 (s, 1H, NH), 5.49 (s, 2H, $ArCH_2$), 6.41 (t, 1H, ArH),6.57 (d, 2H, ArH), 6.71 (t, 1H, ArH), 7.15 (m, 3H, ArH), 7.26 (m, 1H, ArH).

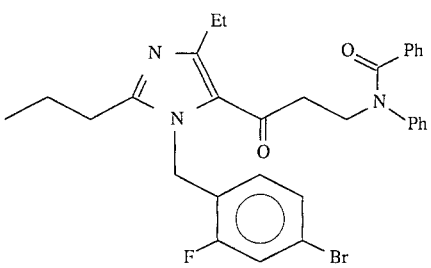

Part D: Preparation of 1-(2-fluoro-4-bromobenzyl)-5-[2-(N-benzoyl-N-phenylamino)ethylcarbonyl-4-ethyl-2-propyl-1H-imidazole To a solution of 1-(2-fluoro-4-bromobenzyl)-5-[2-(N-phenylamino)ethylcarbonyl-4-ethyl-2-propyl-1H-imidazole (2.16 g, 4.96 mmol) and triethylamine (1.50 mL, 10.8 mmol) in THF (100 mL) was added benzoyl chloride (1.20 mL, 10.3 mmol). The mixture was refluxed under $N_2$ for 1 h. The solvent was removed in vacuo. The residue was dissolved in EtOAc, and washed with $H_2O$, and then 1N NaOH and brine. The organic solution was then dried over $MgSO_4$ and concentrated to a yellow oil (2.70 g, 94% yield). MS m/e 578.2,[M+H]$^+$; $^1$HNMR (300 MHz, $CDCl_3$): δ0.95 (t, 3H, $CH_3$), 1.27 (t, 3H, $CH_3$), 1.66 (m, 2H, $CH_2$), 2.55 (t, 2H, $CH_2$), 2.90 (q, 2H, $CH_2$), 3.18 (t, 2H, $CH_2$), 4.22 (t, 2H, $CH_2$), 5.38 (s, 2H, $ArCH_2$), 6.40 (t, 1H, ArH),6.98 (d, 2H, ArH), 7.10–7.30 (m, 5H, ArH), 7.55 (t, 2H, ArH), 7.70 (t, 1H, ArH), 8.15 (d, 2H, ArH).

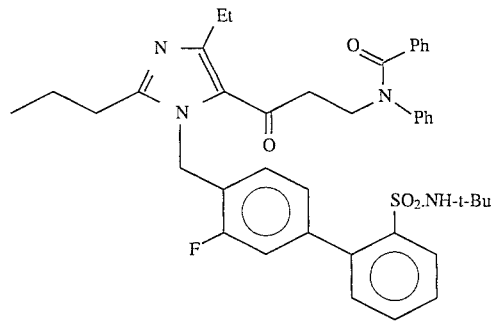

Part E: Preparation of 1-((2'-((t-butylamino)sulfonyl)-3-fluoro-( 1,1'-biphenyl)-4-yl)methyl)-5-[2-(N-phenylamino)ethylcarbonyl-4-ethyl- 2-propyl-1H-imidazole 1-(2-fluoro-4-bromobenzyl)-5-[2-(N-phenylamino)ethylcarbonyl- 4-ethyl-2-propyl-1H-imidazole (2.20 g, 3.82 mmol), 2-(t-butylamino)sulfonylphenyl boronic acid (1.23 g, 4.78 mmol), and soduim carbonate (5 mL of 2M aqueous solution), and tetrabutylammonium bromide (60 mg, 5%) were added together with 25 mL of toluene. Tetrakis(triphenylphosphine) palladium(0) (0.22 g, 5%) was added. The mixture was refluxed under $N_2$ for 4 h. The solvent was removed in vacuo and the residue was partitioned between $H_2O$ and $CH_2Cl_2$. The aqueous layer was extracted with $CH_2Cl_2$, and the combined organic solution was washed with brine, dried over $MgSO_4$ and concentrated. The crude product was purified by flash column chromatography (silica gel, 50% EtOAc/hexane) to give 1.66 g of pale yellow foam (61%). MS m/e 709.3, [M+H]$^+$; $^1$H NMR (300 MHz, $CDCl_3$): δ0.95 (t, 3H, $CH_3$), 0.99 (t, 9H, $CH_3$), 1.30 (t, 3H, $CH_3$), 1.70 (m, 2H, $CH_2$), 2.60 (t, 2H, $CH_2$), 2.90 (q, 2H, $CH_2$), 3.22 (t, 2H, $CH_2$), 3.57 (s, 1H, NH), 4.22 (t, 2H, $CH_2$), 5.50 (s, 2H, $CH_2Ar$), 6.60 (t, 1H, ArH), 7.02 (d, 3H, ArH), 7.10–7.30 (m, 10H, ArH), 7.50 (m, 2H, ArH), 8.15 (d, 1H, ArH).

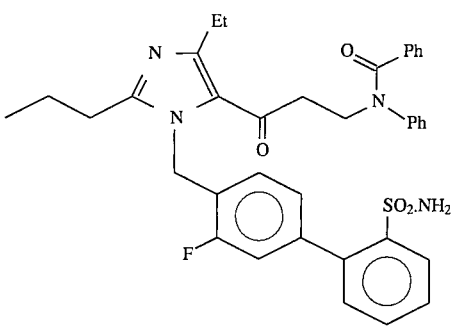

Part F: Preparation of 1-((2'-(aminosulfonyl)-3-fluoro-(1,1'-biphenyl)- 4-yl)methyl)-5-[2-(N-phenylamino)ethylcarbonyl-4-ethyl-2-propyl-1H-imidazole 1-((2'-((t-butylamino)sulfonyl)-3-fluoro-(1,1'-biphenyl)-4-yl)methyl)-5-[2-(N-phenylamino)ethylcarbonyl-4-ethyl-2-propyl-1H-imidazole (1.66 g, 2.34 mmol) was refluxed with 25 mL of trifluoroacetic acid under N$_2$ for 2.5 h. The solvent was removed in vacuo. The residue was dissolved in CH$_2$Cl$_2$, and washed with aqueous NaHCO$_3$ and brine. The organic solution was filtered through phase separator paper and then concentrated to a light yellow foam (1.39 g). MS m/e 695.2, [M+H]$^+$; $^1$H NMR (300 MHz, CDCl$_3$): δ0.98 (t, 3H, CH$_3$), 1.27 (t, 3H, CH$_3$), 1.72 (m, 2H, CH$_2$), 2.68 (t, 2H, CH$_2$), 2.88 (q, 2H, CH$_2$), 3.12 (t, 2H, CH$_2$), 4.20 (t, 2H, CH$_2$), 4.40 (s, 2H, NH$_2$), 5.50 (s, 2H, CH$_2$Ar), 6.63 (t, 1H, ArH), 7.00 (d, 3H, ArH), 7.10–7.30 (m, 11H, ArH), 7.50–7.60 (dd, 2H, ArH), 8.15 (d, 1H, ArH).

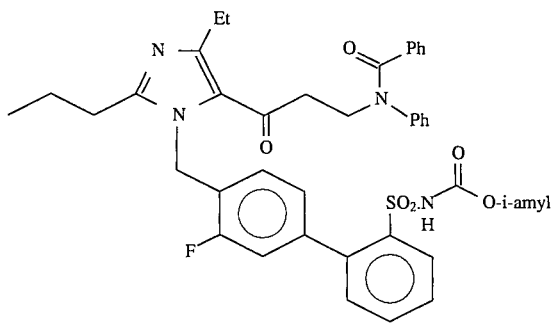

Part G: Preparation of 1-((2'-((i-amyloxycarbonyl-amino)sulfonyl)-3-fluoro-( 1,1'-biphenyl)-4-yl)methyl)-5-[2-(N-phenylamino)ethylcarbonyl-4-ethyl- 2-propyl-1H-imidazole 1-((2'-(aminosulfonyl)-3-fluoro-(1,1'-biphenyl)-4-yl)methyl)-5-[2-(N-phenylamino)ethylcarbonyl-4-ethyl-2-propyl-1H-imidazole (0.45 g, 0.69 mmol) was dissolved in 10 mL of CH$_2$Cl$_2$. To the mixture was added 4-N,N-dimethylaminopyridine (0.14 g, 1.15 mmol), pyridine (2 mL), and isoamyl chloroformate (0.50 mL of 34% in toluene, 1.13 mmol). The reaction mixture was allowed to stir at room temperature under N$_2$ overnight. The mixture was diluted with CH$_2$Cl$_2$, and then washed with 10% aqueous citric acid and brine. The organic solution was filtered through phase separator paper and concentrated. It was then chromatographed on silica gel (eluted with 6:3:1 hexane/ethyl acetate/acetone containing 0.1% HOAc) to give 0.29 g white foam.. MS m/e 767.5, [M+H]$^+$; $^1$H NMR (300 MHz, CDCl$_3$): δ0.77 (d, 6H, CH$_3$), 0.97 (t, 3H, CH$_3$), 1.20 (t, 3H, CH$_3$), 1.31 (m, 2H, CH$_2$), 1.48 (m, 1H, CH), 1.70 (m, 2H, CH$_2$), 2.59 (t, 2H, CH$_2$), 2.77 (q, 2H, CH$_2$), 3.06 (t, 2H, CH$_2$), 3.79 (t, 2H, CH$_2$), 4.29 (t, 2H, CH$_2$), 5.24 (s, 2H, CH$_2$Ar), 6.40 (t, 1H, ArH), 6.97 (d, 3H, ArH), 7.02 (m, 2H, ArH), 7.07–7.25 (m, 9H, ArH), 7.37 (m, 2H, ArH), 8.16 (d, 1H, ArH).

EXAMPLE 490

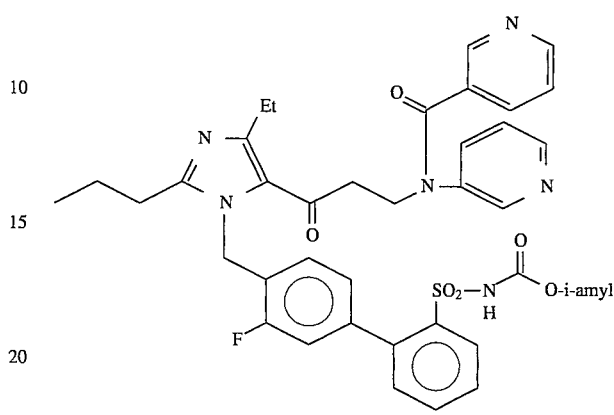

Preparation of 1-((2'-((i-amloxycarbonyl-amino)sulfonyl)-3-fluoro-( 1,1'-biphenyl)-4-yl)methyl)-5-[2-(N-nicotinoyl-N-3-pyridinoamino)ethylcarbonyl-4-ethyl-2-propyl-1H-imidazole The title compound was prepared by the same methods described in Example 489 from the appropriate starting materials. MS (NH$_3$DCl) 769, [M+H]$^+$; $^1$H NMR (300 MHz, CDCl$_3$): δ0.86 (d, 6H, CH$_3$), 0.97 (t, 3H, CH), 1.72 (m,3H, CH$_3$), 2.52 (t, 3H, CH$_3$), 1.38 (m, 2H, CH$_2$), 1.50 (m, 1H, CH) 1.72 (m, 2H, CH$_2$), 2.52 (t, 2H, CH$_2$), 2.98 (q, 2H, CH$_2$), 3.34 (br.s, 2H, CH$_2$), 4.00 (t, 2H, CH$_2$), 4.38 (br.s, 2H, CH$_2$), 5.40 (br.s, 2H, CH$_2$AR), 6.10 (t, 1H, ArH), 6.92 (d, 3H, ArH), 7.03–7.20 (m, 3H, ArH), 7.38 (dd, 2H, ArH), 7.48–7.61 (m, 4H, ArH), 7.78 (d, 1H, ArH), 8.28 (m, 2H, ArH), 8.33 (s, 1H, ArH), 83.45 (d, 1H, ArH).

EXAMPLE 491

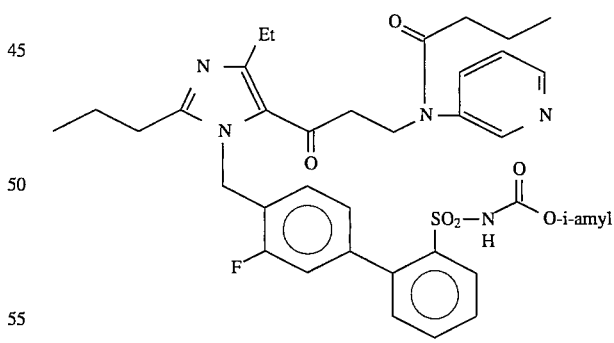

Preparation of 1-((2'-((i-amyloxycarbonyl-amino)sulfonyl)-3-fluoro-( 1,1'-biphenyl)-4-yl)methyl)-5-[2-(N-butyryl-N-3-pyridinoamino)ethylcarbonyl-4-ethyl-2-propyl-1H-imidazole The title compound was prepared by the same methods described in Example 489 from the appropriate starting materials MS (FAB) 734.6, [M+H]$^+$; $^1$H NMR (300 MHz, CDCl$_3$): δ0.77 (t, 3H, CH$_3$), 0.85 (d, 6H, CH$_3$), 0.94 (t, 3H, CH₃), 1.34 (t, 3H, CH₃), 1.38–1.60 (m, 5H, CH & CH₂), 2.93 (q, 2H, CH₂), 3.21 (br.s, 2H, CH₂), 4.08 (t, 4H, CH₂), 5.50 (br.s, 2H, CH₂Ar), 6.19 (t, 1H, ArH), 7.03 (dd, 1H, ArH), 7.09 (dd, 3H, ArH), 7.22 (dd, 1H, ArH), 7.42 (m, 1H, ArH), 7.53–7.68 (m,3H, ArH), 7.71 (d, 1H, ArH), 8.31 (dd, 1H, ArH), 8.44 (dd, 1H, ArH).

Compounds 489–696 in table 5 can be prepared by the procedure described in Examples 489–491 employing appropriately substituted starting materials.

TABLE 5

| | W | R² | R¹¹ᵃ | R¹¹ᵇ | R¹⁰ | [M + H]⁺ |
|---|---|---|---|---|---|---|
| 489 | F | Ph | Ph | i-amyl | 767 | |
| 490 | F | 3-pyridine | 3-pyridine | i-amyl | 769 | |
| 491 | F | 3-pyridine | n-Pr | i-amyl | 734 | |
| 492 | F | nPr | Ph | i-amyl | | |
| 493 | F | n-Bu | Ph | n-Pr | | |
| 494 | F | n-Bu | Ph | n-Bu | 733 | |
| 495 | F | n-Bu | Ph | i-Bu | | |
| 496 | F | n-Bu | Ph | i-amyl | | |
| 497 | F | nPr | nPr | n-Pr | | |
| 498 | F | nPr | nPr | n-Bu | 685 | |
| 499 | F | nPr | nPr | i-Bu | | |
| 500 | F | nPr | nPr | i-amyl | | |
| 501 | F | Ph | Ph | n-Pr | 739 | |
| 502 | F | Ph | Ph | n-Bu | 753 | |
| 503 | F | Ph | Ph | i-Bu | | |
| 504 | F | nPr | Ph | n-pentyl | | |
| 505 | F | Ph | n-Pr | n-Pr | | |
| 506 | F | Ph | n-Pr | n-Bu | 719 | |
| 507 | F | Ph | n-Pr | i-Bu | | |
| 508 | F | Ph | n-Pr | i-amyl | 733 | |
| 509 | F | 2-pyridine | 3-pyridine | n-Pr | | |
| 510 | F | 2-pyridine | 3-pyridine | n-Bu | | |
| 511 | F | 2-pyridine | 3-pyridine | i-Bu | | |
| 512 | F | 2-pyridine | 3-pyridine | i-amyl | 769 | |
| 513 | F | 2-pyridine | 4-pyridine | n-Pr | | |
| 514 | F | 2-pyridine | 4-pyridine | n-Bu | | |
| 515 | F | 2-pyridine | 4-pyridine | i-Bu | | |
| 516 | F | 2-pyridine | 4-pyridine | i-amyl | | |
| 517 | F | 3-pyridine | 3-pyridine | n-Pr | | |
| 518 | F | 3-pyridine | 3-pyridine | n-Bu | 765 | |
| 519 | F | 3-pyridine | 3-pyridine | i-Bu | | |
| 520 | F | nPr | Ph | n-Bu | 719 | |
| 521 | F | 3-pyridine | 4-pyridine | n-Pr | | |
| 522 | F | 3-pyridine | 4-pyridine | n-Bu | 755 | |
| 523 | F | 3-pyridine | 4-pyridine | i-Bu | | |
| 524 | F | 3-pyridine | 4-pyridine | i-amyl | 769 | |
| 525 | F | 4-pyridine | 3-pyridine | n-Pr | | |
| 526 | F | 4-pyridine | 3-pyridine | n-Bu | | |
| 527 | F | 4-pyridine | 3-pyridine | i-Bu | | |
| 528 | F | 4-pyridine | 3-pyridine | i-amyl | | |
| 529 | F | 4-pyridine | 4-pyridine | n-Pr | | |
| 530 | F | 4-pyridine | 4-pyridine | n-Bu | | |
| 531 | F | 4-pyridine | 4-pyridine | i-Bu | | |
| 532 | F | 4-pyridine | 4-pyridine | i-amyl | | |
| 533 | F | Ph | 3-pyridine | n-Pr | | |
| 534 | F | Ph | 3-pyridine | n-Bu | | |
| 535 | F | Ph | 3-pyridine | i-Bu | | |
| 536 | F | Ph | 3-pyridine | i-amyl | | |
| 537 | F | Ph | 4-pyridine | n-Pr | | |
| 538 | F | Ph | 4-pyridine | n-Bu | | |
| 539 | F | Ph | 4-pyridine | i-Bu | | |
| 540 | F | Ph | 4-pyridine | i-amyl | 768 | |
| 541 | F | 2-pyridine | Ph | n-Pr | | |
| 542 | F | 2-pyridine | Ph | n-Bu | | |
| 543 | F | 2-pyridine | Ph | i-Bu | | |
| 544 | F | 2-pyridine | Ph | i-amyl | | |
| 545 | F | 2-pyridine | n-Pr | n-Pr | | |
| 546 | F | 2-pyridine | n-Pr | n-Bu | | |
| 547 | F | 2-pyridine | n-Pr | i-Bu | | |
| 548 | F | 2-pyridine | n-Pr | i-amyl | 733 | |
| 549 | F | 3-pyridine | Ph | n-Pr | | |
| 550 | F | 3-pyridine | Ph | n-Bu | | |
| 551 | F | 3-pyridine | Ph | i-Bu | | |
| 552 | F | 3-pyridine | Ph | i-amyl | | |
| 553 | F | 3-pyridine | n-Pr | n-Pr | | |
| 554 | F | 3-pyridine | n-Pr | n-Bu | | |
| 555 | F | 3-pyridine | n-Pr | i-Bu | | |
| 556 | F | 3-pyridine | i-Pr | i-amyl | 734 | |
| 557 | F | 4-pyridine | Ph | n-Pr | | |
| 558 | F | 4-pyridine | Ph | n-BU | | |
| 559 | F | 4-pyridine | Ph | i-BU | | |
| 560 | F | 4-pyridine | Ph | i-amyl | | |
| 561 | F | 4-pyridine | n-Pr | n-Pr | | |
| 562 | F | 4-pyridine | n-Pr | n-Bu | | |
| 563 | F | 4-pyridine | n-Pr | i-Bu | | |
| 564 | F | 4-pyridine | n-Pr | 1-amyl | | |
| 565 | H | nPr | Ph | n-Pr | | |
| 566 | F | nPr | Ph | i-Bu | | |
| 567 | H | nPr | Ph | i-Bu | | |
| 568 | H | nPr | Ph | i-amyl | | |
| 569 | H | n-Bu | Ph | n-Pr | | |
| 570 | H | n-Bu | Ph | n-Bu | | |
| 571 | H | n-Bu | Ph | i-Bu | | |
| 572 | H | n-Bu | Ph | i-amyl | | |
| 573 | H | nPr | nPr | n-Pr | | |
| 574 | H | nPr | nPr | n-Bu | | |
| 575 | H | nPr | nPr | i-Bu | | |
| 576 | H | nPr | nPr | i-amyl | | |
| 577 | H | Ph | Ph | n-Pr | | |
| 578 | H | Ph | Ph | n-Bu | | |
| 579 | H | Ph | Ph | i-Bu | | |
| 580 | H | Ph | Ph | i-amyl | | |
| 581 | H | nPr | n-Bu | n-Pr | | |
| 582 | H | nPr | n-Bu | n-Bu | | |
| 583 | H | nPr | n-Bu | i-Bu | | |
| 584 | H | nPr | n-Bu | i-amyl | | |
| 585 | H | 2-pyridine | 3-pyridine | n-Pr | | |
| 586 | H | 2-pyridine | 3-pyridine | n-Bu | | |
| 587 | H | 2-pyridine | 3-pyridine | i-Bu | | |
| 588 | H | 2-pyridine | 3-pyridine | i-amyl | | |
| 589 | H | 2-pyridine | 4-pyridine | n-Pr | | |
| 590 | H | 2-pyridine | 4-pyridine | n-Bu | | |
| 591 | H | 2-pyridine | 4-pyridine | i-Bu | | |
| 592 | H | 2-pyridine | 4-pyridine | i-amyl | | |
| 593 | H | 3-pyridine | 3-pyridine | n-Pr | | |
| 594 | H | 3-pyridine | 3-pyridine | n-Bu | | |
| 595 | H | 3-pyridine | 3-pyridine | i-Bu | | |
| 596 | H | 3-pyridine | 3-pyridine | i-amyl | 751 | |
| 597 | H | 3-pyridine | 4-pyridine | n-Pr | | |

TABLE 5-continued

| W | R² | R¹¹ᵃ | R¹¹ᵇ | R¹⁰ | [M + H]⁺ |
|---|---|---|---|---|---|
| 598 | H | 3-pyridine | 4-pyridine | n-Bu | |
| 599 | H | 3-pyridine | 4-pyridine | i-Bu | |
| 600 | H | 3-pyridine | 4-pyridine | i-amyl | |
| 601 | H | 4-pyridine | 3-pyridine | n-Pr | |
| 602 | H | 4-pyridine | 3-pyridine | n-Bu | |
| 603 | H | 4-pyridine | 3-pyridine | i-Bu | |
| 604 | H | 4-pyridine | 3-pyridine | i-amyl | |
| 605 | H | 4-pyridine | 4-pyridine | n-Pr | |
| 606 | H | 4-pyridine | 4-pyridine | n-Bu | |
| 607 | H | 4-pyridine | 4-pyridine | i-Bu | |
| 608 | H | 4-pyridine | 4-pyridine | i-amyl | |
| 609 | H | Ph | 3-pyridine | n-Pr | |
| 610 | H | Ph | 3-pyridine | n-Bu | |
| 611 | H | Ph | 3-pyridine | i-Bu | |
| 612 | H | Ph | 3-pyridine | i-amyl | |
| 613 | H | Ph | 4-pyridine | n-Pr | |
| 614 | H | Ph | 4-pyridine | n-Bu | |
| 615 | H | Ph | 4-pyridine | i-Bu | |
| 616 | H | Ph | 4-pyridine | i-amyl | |
| 617 | H | 2-pyridine | Ph | n-Pr | |
| 618 | H | 2-pyridine | Ph | n-Bu | |
| 619 | H | 2-pyridine | Ph | i-Bu | |
| 620 | H | 2-pyridine | Ph | i-amyl | |
| 621 | H | 2-pyridine | n-Pr | n-Pr | |
| 622 | H | 2-pyridine | n-Pr | n-Bu | |
| 623 | H | 2-pyridine | n-Pr | i-Bu | |
| 624 | H | 2-pyridine | n-Pr | i-amyl | |
| 625 | H | 3-pyridine | Ph | n-Pr | |
| 626 | H | 3-pyridine | Ph | n-Bu | |
| 627 | H | 3-pyridine | Ph | i-Bu | |
| 628 | H | 3-pyridine | Ph | i-amyl | |
| 629 | H | 3-pyridine | n-Pr | n-Pr | |
| 630 | H | 3-pyridine | n-Pr | n-Bu | |
| 631 | H | 3-pyridine | n-Pr | i-Bu | |
| 632 | H | 3-pyridine | n-Pr | i-amyl | 716 |
| 633 | H | 4-pyridine | Ph | n-Pr | |
| 634 | H | 4-pyridine | Ph | n-Bu | |
| 635 | H | 4-pyridine | Ph | i-Bu | |
| 636 | H | 4-pyridine | Ph | i-amyl | |
| 637 | H | 4-pyridine | n-Pr | n-Pr | |
| 638 | H | 4-pyridine | n-Pr | n-Bu | |
| 639 | H | 4-pyridine | n-Pr | i-Bu | |
| 640 | H | 4-pyridine | n-Pr | i-amyl | |
| 641 | F | 2-pyridine | n-Bu | n-Pr | |
| 642 | F | 2-pyridine | n-Bu | n-Bu | |
| 643 | F | 2-pyridine | n-Bu | i-Bu | |
| 644 | F | 2-pyridine | n-Bu | i-amyl | |
| 645 | F | 2-pyridine | i-Pr | n-Pr | |
| 646 | F | 2-pyridine | i-Pr | n-Bu | |
| 647 | F | 2-pyridine | i-Pr | i-Bu | |
| 648 | F | 2-pyridine | i-Pr | i-amyl | |
| 649 | F | 3-pyridine | n-Bu | n-Pr | |
| 650 | F | 3-pyridine | n-Bu | n-Bu | |
| 651 | F | 3-pyridine | n-Bu | i-Bu | |
| 652 | F | 3-pyridine | n-Bu | i-amyl | |
| 653 | F | 3-pyridine | i-Pr | n-Pr | |
| 654 | F | 3-pyridine | i-Pr | n-Bu | |
| 655 | F | 3-pyridine | i-Pr | i-Bu | |
| 656 | F | 3-pyridine | i-Pr | i-amyl | |
| 657 | F | 4-pyridine | n-Bu | n-Pr | |
| 658 | F | 4-pyridine | n-Bu | n-Bu | |
| 659 | F | 4-pyridine | n-Bu | i-Bu | |
| 660 | F | 4-pyridine | n-Bu | i-amyl | |
| 661 | F | 4-pyridine | i-Pr | n-Pr | |
| 662 | F | 4-pyridine | i-Pr | n-Bu | |
| 663 | F | 4-pyridine | i-Pr | i-Bu | |
| 664 | F | 4-pyridine | i-Pr | i-amyl | |
| 665 | F | Ph | Me | n-Pr | |
| 666 | F | Ph | Me | n-Bu | |
| 667 | F | Ph | Me | i-Bu | |
| 668 | F | Ph | Me | i-amyl | |
| 669 | F | Ph | Et | n-Pr | |
| 670 | F | Ph | Et | n-Bu | |
| 671 | F | Ph | Et | i-Bu | |
| 672 | F | Ph | Et | i-amyl | |
| 673 | F | 2-pyridine | Me | n-Pr | |
| 674 | F | 2-pyridine | Me | n-Bu | |
| 675 | F | 2-pyridine | Me | i-Bu | |
| 676 | F | 2-pyridine | Me | i-amyl | |
| 677 | F | 2-pyridine | Et | n-Pr | |
| 678 | F | 2-pyridine | Et | n-Bu | |
| 679 | F | 2-pyridine | Et | i-Bu | |
| 680 | F | 2-pyridine | Et | i-amyl | |
| 681 | F | 3-pyridine | Me | n-Pr | |
| 682 | F | 3-pyridine | Me | n-Bu | |
| 683 | F | 3-pyridine | Me | i-Bu | |
| 684 | F | 3-pyridine | Me | i-amyl | |
| 685 | F | 3-pyridine | Et | n-Pr | |
| 686 | F | 3-pyridine | Et | n-Bu | |
| 687 | F | 3-pyridine | Et | i-Bu | |
| 688 | F | 3-pyridine | Et | i-amyl | 720 |
| 689 | F | 4-pyridine | Me | n-Pr | |
| 690 | F | 4-pyridine | Me | n-Bu | |
| 691 | F | 4-pyridine | Me | i-Bu | |
| 692 | F | 4-pyridine | Me | i-amyl | |
| 693 | F | 4-pyridine | Et | n-Pr | |
| 694 | F | 4-pyridine | Et | n-Bu | |
| 695 | F | 4-pyridine | Et | i-Bu | |
| 696 | F | 4-pyridine | Et | i-amyl | |

Utility

Angiotensin II (AII) produces numerous biological responses (e.g. vasoconstriction) through stimulation of its receptors on cell membranes. For the purpose of identifying compounds such as AII antagonists which am capable of interacting with AII receptors, a ligand-receptor binding assay was utilized.

DuP 753 and PD123177 were used as standards, and to block Angiotensin II binding to the $AT_1$ and $AT_2$ sites, respectively. DuP 753 was synthesized according to the procedures described by Carini and Duncia (U.S. Pat. No. 5,138,069). PD123177 was prepared using the methods described by Blankely et al. (U.S. Pat. No. 4,812,462).

$AT_1$ site binding was determined in a rat adrenal cortical microsome preparation or in a rat liver membrane preparation. Results for $AT_1$ binding were similar in both assays. $AT_2$ site binding was determined using a rat adrenal medulla preparation. For the adrenal cortical microsome and adrenal medulla preparations, the method of Chiu, et al. (*Receptor*, 1, 33, 1990) was employed. For the liver membrane preparation, the method of Bauer et al. (*Molecular Pharmacology*, 39, 579–585, 1991) was used, with the following changes: male Charles River CD rats were employed; the homogenation buffer consisted of a solution of Trizma base (10 mM) and EDTA (5.0 mM) adjusted to pH 7.5 with 1N HCl; the binding buffer consisted of a solution of Trizma base (50 mM) and $MgCl_2$ $6H_2O$ (5 mM) adjusted to pH 7.20 with 6N HCl; and the binding was assessed using a 96 well plate format at 22° C. To illustrate the adrenal cortex assay, in brief, aliquots of a freshly prepared particulate fraction of rat adrenal cortex were incubated with 0.15 nM [$^{125}$I] AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by gamma counting. The inhibitory concentration ($IC_{50}$) of potential AII antagonists which gives 50% displacement of the total specifically bound [$^{125}$I] AII is presented as a measure of the affinity of such compound for the AII receptor. $AT_1$ site binding was determined in the presence of $10^{-6}$M PD123177. $AT_2$ site binding was determined in the presence of $10^{-6}$M DuP 753. $IC_{50}$ was determined by displacement of [$^{125}$I] AII from the receptor by the test compound.

Using the assay method described above, the compounds of this invention am found to exhibit an activity of at least $IC_{50}$ <100 nanomolar at both the $AT_1$ and $AT_2$ receptors, thereby demonstrating and confirming the activity of these compounds as effective $AT_1/AT_2$ AII receptor antagonists.

The potential antihypertensive effects of the compounds of this invention may be demonstrated by administering the compounds to awake rats made hypertensive by ligation of the left renal artery (Cangiano, et al., *J. Pharmacol. Exp. Ther.*, 208, 310, 1979). This procedure increases blood pressure by increasing renin production with consequent elevation of AII levels. Compounds are administered intravenously via cannula in the jugular vein to give a cumulative dose of 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure.

The compounds of this invention are useful in treating hypertension, and for the treatment of hyperuricemia, primary and secondary hyperaldosteronism, psoriasis, cardiac disorders such as acute and chronic congestive heart failure, angina pectoris, myocardial infarction, systolic and diastolic dysfunction, cardiac myopathy, and cardiac hypertrophy and hyperplasia, esp. left ventricular hypertrophy; pulmonary disorders such as primary and secondary pulmonary hypertension; vascular disorders such as atherosclerosis, restenosis after vascular injury associated with e.g. angioplasty or bypass surgery, vascular hypertrophy and hyperplasia, atheroma and Raynaud's disease; cerebrovascular disorders such as migraine, and ischemic and hemorragic stroke; renal disorders such as renal vascular hypertension, proteinuria of primary renal disease, end stage renal disease and renal transplant therapy, glomerulonephritis, nephrotic syndrome, scleroderma and glomerular sclerosis, and for enhancing renal blood flow; CNS disorders such as impairment of cognitive function and memory loss, addiction, anxiety, bulimia, depression, epilepsy, pain, Parkinson's disease, psychosis, sleep disorders and tardive dyskinesia; ocular disorders such as macular degeneration and elevated intraocular pressure; gastrointestinal and bladder disorders; disorders associated with diabetes, such as diabetic angiopathy, nephropathy and retinopathy, and for delaying the onset of type II diabetes. The application of the compounds of this invention for these and similar disorders will be apparent to those skilled in the art. The compounds of this invention are also useful as diagnostic agents, to test the renin angiotensin system.

Patients in need of treatment for elevated intraocular pressure can be treated with compounds of this invention administered in the form of typical pharmaceutical formulations such as tablets, capsules, injectables and the like as well as topical ocular formulations in the form of solutions, ointments, inserts, gels and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, beta-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized with a pharmaceutical carrier in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

Administration of a compound of this invention with a NSAID can prevent renal failure which sometimes results from administration of a NSAID. The compounds of this invention can also be administered in combination with other antihypertensives and/or diuretics. Administration of a compound of this invention with a diuretic, either as a stepwise combined therapy (diuretic first) or as a physical mixture, enhances the antihypertensive effect of the compound. For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amLodipine, nimodipine, isradipine, nitrendipine and verapamil; b-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; a-adrenergic antagonists such as prazosin, doxazosin, and terazosin; sympatholytic agents such as methyldopa, clonidine and guanabenz; atriopeptidase inhibitors (alone or with ANP) such as UK-79300; serotonin antagonists such as ketanserin; $A_2$-adrenosine receptor agonists such as CGS 22492C; potassium channel agonists such as pinacidil and cromakalim; and various other antihypertensive drugs including reserpine, minoxidil, guanethidine, hydralazine hydrochloride and sodium nitroprusside as well as combinations of the above-named drugs. Combinations useful in the management of congestive heart failure include, in addition, compounds of this invention with cardiac stimulants such as dobutamine and xamoterol and phosphodiesterase inhibitors including atarinone and milrinone.

What is claimed is:

1. A compound of formula II:

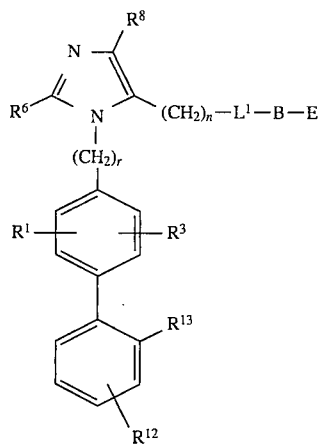

(II)

wherein:

$R^2$ is independently
(a) H,
(b) halo,
(c) $C_1$–$C_4$-alkyl;

$R^3$ is
(a) H, or
(b) halo;

$R^6$ is
(a) $C_1$–$C_{10}$ alkyl,
(b) $C_3$–$C_{10}$ alkenyl, or
(c) $C_3$–$C_{10}$ alkynyl;

$R^7$ is
(a) $C_1$–$C_6$-alkyl,
(b) $C_3$–$C_6$-cycloalkyl,
(c) aryl, or
(d) benzyl, optionally substituted on the phenyl ring with 1–2 substituents selected from the group consisting of halo, $C_1$–$C_4$-alkyl, $C_1$–$C_4$-alkoxy or —$NO_2$;

$R^8$ is
(a) H,
(b) halogen
(c) aryl
(d) $C_1$–$C_6$-alkyl, optionally substituted with
  i) $OR^{25}$,
  ii) $S(O)_xR^{10}$,
  iii) $NR^{23}R^{24}$,
  iv) $NR^{26}COR^{11}$,
  v) $NR^{26}CO_2R^7$,
  vi) $NR^{26}CONR^{23}R^{24}$,
  vii) $OCONR^{23}R^{24}$,
  viii) $OCOR^{11}$,
  ix) aryl
(e) $C_2$–$C_6$-alkenyl,
(f) —$C_1$–$C_4$-alkyl-aryl,
(h) $C_1$–$C_4$-alkoxy,
(i) $C_vF_w$ where v=1 to 3 and w=1 to (2v+1),
(j) —$S(O)_xR^{10}$,
(k) —$S(O)_2NR^{23}R^{24}$,
(l) —$CONR^{23}R^{24}$,
(m) —$COR^7$, or
(n) —$CO_2R^{12}$;

$R^{25}$ is
(a) H,
(b) $C_1$–$C_6$ alkyl,
(c) aryl,
(d) —($C_1$–$C_4$-alkyl)-aryl,
(e) $C_3$–$C_6$alkenyl, or
(f) —($C_3$–$C_6$alkenyl)-aryl;

$R^9$ is
(a) H,
(b) $C_1$–$C_5$-alkyl,
(c) aryl
(d) —($C_1$–$C_4$-alkyl)-aryl, or
(e) heteroaryl;

$R^{10}$ is
(a) aryl,
(b) $C_3$–$C_7$-cycloalkyl,
(c) $C_1$–$C_4$-perfluoroalkyl,
(d) $C_1$–$C_4$-alkyl, optionally substituted with a substituent selected from the group consisting of aryl as defined below, heteroaryl as defined below, —OH, —SH, $C_1$–$C_4$-alkyl, $C_1$–$C_4$-alkoxy, $C_1$–$C_4$-alkylthio, —$CF_3$, halo, —$NO_2$, —$CO_2R^{12}$, —$NH_2$, $C_1$–$C_4$-alkylamino, $C_1$–$C_4$-dialkylamino, —$PO_3H_2$, or
(e) heteroaryl;

$R^{11}$, $R^{11a}$ and $R^{11b}$ are independently
(a) H,
(b) $C_1$–$C_6$-alkyl,
(c) $C_3$–$C_6$-cycloalkyl,
(d) aryl,
(e) —($C_1$–$C_5$-alkyl)-aryl, or
(f) heteroaryl;

$R^{12}$ is
(a) H,
(b) methyl, or
(c) benzyl, optionally substituted on the phenyl ring with 1–2 substituents selected from the group consisting of halo, $C_1$–$C_4$-alkyl, $C_1$–$C_4$-alkoxy or —$NO_2$;

$R^{13}$ is
(a) —$CO_2H$,
(b) —$CH_2CO_2H$,
(c) —$C(CF_3)_2OH$,
(d) —$CONHNHSO_2CF_3$,
(e) —$CONHOR^{12}$,
(f) —$CONHSO_2R^{10}$,
(g) —$CONHSO_2NHR^9$,
(h) —$C(OH)R^9PO_3H_2$,
(i) —$NHCOCF_3$,
(j) —$NHCONHSO_2R^{10}$,
(k) —$NHPO_3H_2$,
(l) —$NHSO_2R^{10}$,
(m) —$NHSO_2NHCOR^{10}$,
(n) —$OPO_3H_2$,
(o) —$OSO_3H$,
(p) —$PO(OH)R^9$, (q) —PO$_3$H$_2$,
(r) —SO$_3$H,
(s) —SO$_2$NHR$^9$,
(t) —SO$_2$NHCOR$^{10}$,
(u) —SO$_2$NHCONHR$^9$,
(v) —SO$_2$NHCO$_2$R$^{10}$,

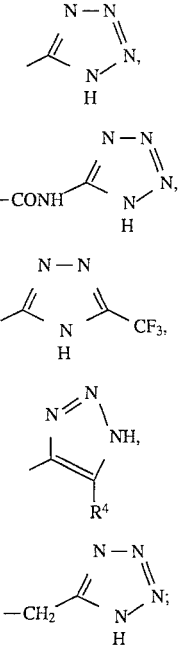

(w)

(x)

(y)

(z)

(aa)

R$^4$ is
(a) CN,
(b) NO$_2$, or
(c) C$_2$R$^{11}$;

R$^{16}$ is
(a) H,
(b) C$_1$–C$_6$-alkyl, or
(c) benzyl, optionally substituted on the phenyl ring with 1–2 substituents selected from the group consisting of halo, C$_1$–C$_4$-alkyl, C$_1$–C$_4$-alkoxy or —NO$_2$;

R$^{23}$ and R$^{24}$ are, independently
(a) H,
(b) C$_1$–C$_6$-alkyl,
(c) aryl, or
(d) —(C$_1$–C$_4$-alkyl)-aryl, or R$^{23}$ and R$^{24}$ when taken together constitute a pyrrolidine, piperidine or morpholine ring;

R$^{26}$ is
(a) H,
(b) C$_1$–C$_4$-alkyl,
(c) aryl, or
(d) arylmethyl;

R$^{28}$ is
(a) aryl, or
(b) heteroaryl;

R$^{29}$ is
(a) —CHO,
(b) —CONH$_2$,
(c) —NHCHO,
(d) —CO—(C$_1$–C$_6$ perfluoroalkyl),
(e) —S(O)$_r$—(C$_1$–C$_6$ perfluoroalkyl),
(f) —O—(C$_1$–C$_6$ perfluoroalkyl), or
(g) —NR$^{11a}$—(C$_1$–C$_6$ perfluoroalkyl);

E is (a) —(T)$_y$—(B)$_y$—X$^2$—(B)$_y$—R$^{28}$
(b) —T—(B)$_y$—R$^{28}$
(c) —(T)$_y$—(B)$_y$—X$^2$—B, or
(d) —T—(B)$_y$—R$^{29}$;

L$^1$ is
(a) —CO$_2$—
(b) —CONR$^{11a}$—
(c) —NR$^{11a}$CO$_2$—
(d) —NR$^{11a}$CONR$^{11b}$—;

B is C$_1$–C$_6$ alkyl;

T is arylene or heteroarylene;

X$^2$ is
(a) —CO—,
(b) —O—,
(c) —S(O)$_r$—,
(d) —(C$_1$–C$_4$-alkylene)—,
(e) —NR$^{11a}$CONR$^{11b}$—,
(f) —CONR$^{11a}$—,
(g) —NR$^{11a}$CO—,
(h) —SO$_2$NR$^{16}$—,
(i) —NR$^{16}$SO$_2$—,
(j) —CONR$^{11a}$SO$_2$—,
(k) —SO$_2$NR$^{11a}$CO—,
(l) —SO$_2$NR$^{11a}$CO$_2$—,
(m) —OCONR$^{11a}$SO$_2$—,
(n) —SO$_2$NR$^{11a}$CONR$^{11b}$—,
(o) —NR$^{11a}$CONR$^{11b}$SO$_2$—,
(p) —SO$_2$NR$^{11a}$SO$_2$—,
(q) —CONR$^{11a}$SO$_2$NR$^{11b}$—, or
(r) —NR$^{11a}$SO$_2$NR$^{11b}$CO—;

n is 0 to 2;

r is 0 to 2;

y is 0 or 1;

wherein aryl is phenyl, biphenyl, or fluorenyl optionally substituted with one to three substituents selected from the group consisting of —OH, —SH, C$_1$–C$_4$ alkyl, C$_1$–C$_4$ alkoxy, —CF$_3$, Cl, Br, F, —NO$_2$, —CO$_2$H, —CO$_2$CH$_3$, —CO$_2$-benzyl, —NH$_2$, —NH(C$_1$–C$_4$ alkyl), —N(C$_1$–C$_4$ alkyl)$_2$;

wherein heteroaryl is 2-, 3- or 4-pyridyl, 2- or 3-furyl, 2- or 3-thienyl, 2-, 3- or 4-quinolinyl, or 1-, 3- or 4-isoquinolinyl optionally substituted with one to three substituents selected from the group consisting of —OH, —SH, C$_1$–C$_4$ alkyl, C$_1$–C$_4$ alkoxy, —CF$_3$, halo, —NO$_2$, —CO$_2$H, —CO$_2$CH$_3$, —CO$_2$ - benzyl, —NH$_2$, —NH(C$_1$–C$_4$ alkyl), —N(C$_1$–C$_4$ alkyl)$_2$;

wherein arylene is 1,2-phenyl, 1,3-phenyl, 1,4-phenyl, 4,4'-biphenyl, 3,3'-biphenyl, and 2,2'-biphenyl optionally substituted with one to three substituents selected from the group consisting of —OH, —SH, C$_1$–C$_4$-alkyl, C$_1$–C$_4$-alkoxy, —CF$_3$, halo, —NO$_2$, —CO$_2$H, —CO$_2$CH$_3$, —CO$_2$-benzyl, —NH$_2$, —NH(C$_1$–C$_4$-alkyl), —N(C$_1$–C$_4$-alkyl)$_2$.

and wherein heteroarylene is 2,3-pyridyl, 3,4-pyridyl, 2,3-furyl, 3,4-furyl, 2,3-thiophenyl, 3,4-thiophenyl, 2,3-quinolinyl, 3,4-quinolinyl and 1,4-isoquinolinyl optionally substituted with one to three substituents selected from the group consisting of —OH, —SH, C$_1$–C$_4$-alkyl, C$_1$–C$_4$-alkoxy, —CF$_3$, halo, —NO$_2$, —CO$_2$H, —CO$_2$CH$_3$, —CO$_2$-benzyl, —NH$_2$, —NH(C$_1$–C$_4$-alkyl), —N(C$_1$–C$_4$-alkyl)$_2$;

or pharmaceutically acceptable salts of these compounds.

2. A compound of claim 1 selected from the group consisting of:
4-[((5-(2-Benzoylbenzyloxycarbonyl)-4-ethyl-2-n-propyl)imidazol-1-yl)methyl]-3-fluoro-2'-n-butyloxycarbonylaminosulfonyl-1,1'-biphenyl, 4-[((5-(2-Benzoylbenzyloxycarbonyl)-4-ethyl-2-n-propyl)imidazol- 1-yl)methyl]-3-fluoro-2'-((2-phenyl)ethyloxycarbonylaminosulfonyl)-1,1'-biphenyl, 4-[[[((5-(2-Benzoylbenzyloxycarbonyl)-4- ethyl-2-n-propyl)imidazol-1-yl)methyl] -2'-((2-phenyl)ethyloxycarbonylaminosulfonyl-1,1'-biphenyl, 4-[[[((5-(2-Benzoylbenzyloxycarbonyl)-4-ethyl-2-n-propyl)imidazol-1-yl)methyl] -3-fluoro2'-n-butyloxycarbonylaminosulfonyl-1,1'-biphenyl, 4-[[[((5-(2-Benzoylbenzyloxycarbonyl)-4-ethyl-2-n-propyl)imidazol-1-yl)methyl] -3-fluoro-2'-n-isoamyloxycarbonylaminosulfonyl-1,1'-biphenyl, 4-[[[((5-(2-Benzoylbenzyloxycarbonyl)-4-ethyl-2-n-propyl)imidazol-1-yl)methyl] -2'-n-isoamyloxycarbonylaminosulfonyl-1,1'-biphenyl, 4-[[[((5-2(2-Benzoylbenzyloxycarbonyl)-4-ethyl-2-n-propyl)imidazol-1-yl)methyl]-3-fluoro-2'-n-propyloxycarbonylaminosulfonyl-1,1'-biphenyl, 4-[[[((5-(2-Isoamyloxybenzyloxycarbonyl)-4-ethyl-2-n-propyl)imidazol-1-yl)methyl]-3-fluoro-2'-n-butyloxycarbonylaminosulfonyl-1,1'-biphenyl, 4-[[[((5-(2-Phenylaminocarbonyl)benzyloxycarbonyl-4-ethyl- 2-n-propyl)imidazol-1-yl)methyl]-3-fluoro-2'-n-butyloxycarbonylaminosulfonyl-1,1'-biphenyl, 4-[[[((5-(2-Benzoylbenzyloxycarbonyl)-4-ethyl-2-n-propyl)imidazol-1-yl)methyl]-3-fluoro-2'-(1H-tetrazol-5-yl)-1,1'-biphenyl, 4-[[[((5-(2-trifluorophenyl)methylammocarbonyl)-4-ethyl-2-n-propyl)imidazol-1-yl)methyl]-3-fluoro-2'-isoamyloxycarbonylaminosulfonyl-1,1'-biphenyl, N-butyl, N-benzyl-2-(aminocarbonyl)ethynylmethyl 4-ethyl-2-propyl-1-[[2'-(1H -tetrazol- 5-yl)biphenyl-4-yl] methyl] imidazole-5-carboxylate, N, N-diphenyl-2-(aminocarbonyl)ethynylmethyl 4-3thyl-2-propyl-1-[[2'-( 1H -tetrazol-5-yl)biphenyl-4-yl]methyl] imidazole-5-carboxylate, or N-phyenyl-2-(aminocarbonyl)ethyl 4-ethyl-2-propyl-1-[[2'-(1H-tetrazol- 5-yl)biphenyl-4-yl]methyl] imidazole -5-carboxylate.

3. A pharmaceutical composition comprising a pharmaceutically suitable carrier and a compound selected from claim 1 or claim 2.

4. A method of treating hypertension in a warm-blooded animal comprising administering to said animal in need of such treatment and effective amount of a compound selected from claim 1 or claim 2.

5. A method of treating congestive heart failure in a warm-blooded animal comprising administering to said animal in need of such treatment and effective amount of a compound selected from claim 1 or claim 2.

* * * * *